(12) United States Patent
Rubin

(10) Patent No.: US 7,964,346 B2
(45) Date of Patent: Jun. 21, 2011

(54) MAMMALIAN GENES INVOLVED IN INFECTION

(76) Inventor: Donald H. Rubin, Nashville, TN (US)

( * ) Notice: Subject to any disclaimer, the term of this patent is extended or adjusted under 35 U.S.C. 154(b) by 458 days.

(21) Appl. No.: 11/666,453

(22) PCT Filed: Oct. 27, 2005

(86) PCT No.: PCT/US2005/038740
§ 371 (c)(1),
(2), (4) Date: Jun. 22, 2007

(87) PCT Pub. No.: WO2006/047673
PCT Pub. Date: May 4, 2006

(65) Prior Publication Data
US 2008/0118495 A1    May 22, 2008

Related U.S. Application Data

(60) Provisional application No. 60/622,486, filed on Oct. 27, 2004.

(51) Int. Cl.
C12Q 1/68 (2006.01)
C12Q 1/70 (2006.01)
C12N 5/00 (2006.01)
A01N 61/00 (2006.01)

(52) U.S. Cl. .............. 435/6; 435/5; 435/325; 514/1

(58) Field of Classification Search .............. 435/5, 6, 435/325; 514/1
See application file for complete search history.

(56) References Cited

OTHER PUBLICATIONS

Krishnan et al., 1997, Eur. J. Biochem., vol. 247, p. 298-305.*
Godwin et al., 1998, Genes and Development, vol. 12, p. 11-20.*
Chattopadhyay et al., 2007, Mini-Reviews in Medicinal Chemistry, vol. 7, p. 275-301.*
Ahmed R, Canning WM, Kauffman RS, Sharpe AH, Hallum JV, Fields BN: Role of the host cell in persistent viral infection: coevolution of L cells and reovoirus during persistent infection. Cell 1981, 25(2):325-332.
Altschul SF, Madden TL, Schaffer AA, Zhang J, Zhang Z, Miller W, Lipman DJ: Gapped BLAST and PSI-BLAST: a new generation of protein database search programs. Nucleic Acids Res 1997, 25(1 7):33 89-3402.
Amir RE, Iwai K, Ciechanover A: The NEDD8 pathway is essential for SCF(beta-TrCP)-mediated ubiquitination and processing of the NF-kappa B precursor p 105. J Biol Chem 2002, 277(26):23253-23259.
Arsura M, Panta GR, Bilyeu JD, Cavin LG, Sovak MA, Oliver AA, Factor V, Heuchel R, Mercurio F, Thorgeirsson SS et al: Transient activation of NFkappaB through a TAK1/IKK kinase pathway by TGF-beta1 inhibits AP1/SMAD signaling and apoptosis: implications in liver tumor formation. Oncogene 2003, 22(3):412-425.
Asano K, Vornlocher HP, Richter-Cook NJ, Merrick WC, Hinnebusch AG, Hershey JW: Structure of cDNAs encoding human eukaryotic initiation factor 3 subunits. Possible roles in RNA binding and macromolecular assembly. J Biol Chem 1997, 272(43):27042-27052.
Babiychuk EB, Monastyrskaya K, Burkhard FC, Wray S, Draeger A: Modulating signaling events in smooth muscle: cleavage of annexin 2 abolishes its binding to lipid rafts. Faseb J 2002, 16(10):1 177-1184.
Barton ES, Forrest JC, Connolly JL, Chappell JD, Liu Y, Schnell FJ, Nusrat A, Parkos CA, Dermody TS: Junction adhesion molecule is a receptor for reovirus. Cell 2001, 104(3):441-451.
Bender FC, Whitbeck JC, Ponce de Leon M, Lou H, Eisenberg RJ, Cohen GH: Specific association of glycoprotein B with lipid rafts during herpes simplex virus entry. J Virol 2003, 77(17):9542-9552.
Bhat NR, Shen Q, Fan F: TAK1-mediated induction of nitric oxide synthase gene expression in glial cells. J Neurochem 2003, 87(1):238-247.
Bonatti S, Migliaccio G, Blobel G, Walter P: Role of signal recognition particle in the membrane assembly of Sindbis viral glycoproteins. Eur J Biochem 1984, 140(3):499-502.
Breslin JJ, Mork I, Smith MK, Vogel LK, Hemmila EM, Bonavia A, Talbot PJ, Sjostrom H, Noren O, Holmes KV: Human coronavirus 229E: receptor binding domain and neutralization by soluble receptor at 37 degrees C. J Virol 2003, 77(7):4435-4438.
05814043.5, Rubin, Oct. 27, 2005, Examination Report, Jun. 16, 2008.
PCT/US05/038740, Rubin, Oct. 27, 2005, International Preliminary Report on Patentability, May 1, 2007.
PCT/US05/038740, Rubin, Oct. 27, 2005, Written Opinion, Nov. 16, 2006.
PCT/US05/038740, Rubin, Oct. 27, 2005, International Search Report, Nov. 16, 2006.
Briggs CJ, Ott DE, Coren LV, Oroszlan S, Tozser J: Comparison of the effect of FK506 and cyclosporin A on virus production in H9 cells chronically and newly infected by HIV-1. Arch Virol 1999, 144(11):2151-2160.
Brunetti CR, Burke RL, Kornfeld S, Gregory W, Masiarz FR, Dingwell KS, Johnson DC: Herpes simplex virus glycoprotein D acquires mannose 6-phosphate residues and binds to mannose 6-phosphate receptors. J Biol Chem 1994, 269(25): 17067-17074.
Brunetti CR, Dingwell KS, Wale C, Graham FL, Johnson DC: Herpes simplex virus gD and virions accumulate in endosomes by mannose 6-phosphatedependent and -independent mechanisms. J Virol 1998, 72(4):3330-3339.
Clarke P, Meintzer SM, Moffitt LA, Tyler KL: Two distinct phases of virus induced nuclear factor kappa B regulation enhance tumor necrosis factor-related apoptosis-inducing ligand-mediated apoptosis in virus-infected cells. J Biol Chem 2003, 278(20):18092-18100.
Clarke P, Meintzer SM, Widmann C, Johnson GL, Tyler KL: Reovirus infection activates JNK and the JNK-dependent transcription factor c-Jun. J Virol 2001, 75(23):1 1275-11283.
Clarke P, Tyler KL: Reovirus-induced apoptosis: A minireview. Apoptosis 2003, 8(2):141-150.

(Continued)

Primary Examiner — Shin-Lin Chen

(57) ABSTRACT

The present invention relates to nucleic acid sequences and cellular proteins encoded by these sequences that are involved in infection or are otherwise associated with the life cycle of a pathogen. The invention also relates to modulators of nucleic acid sequences and cellular proteins encoded by these sequences that are involved in infection or are otherwise associated with the life cycle of a pathogen.

2 Claims, 3 Drawing Sheets

OTHER PUBLICATIONS

De Ceuninck F, Poiraudeau S, Pagano M, Tsagris L, Blanchard O, Willeput J, Corvol M: Inhibition of chondrocyte cathepsin B and L activities by insulin-like growth factor-II (IGF-II) and its Ser29 variant in vitro: possible role of the mannose 6-phosphate/IGF-II receptor. Mol Cell Endocrinol 1995, 11 3(2):205-213.

Dermody TS, Nibert ML, Wetzel JD, Tong X, Fields BN: Cells and viruses with mutations affecting viral entry are selected during persistent infections of L cells with mammalian reoviruses. J Virol 1993, 67(4):2055-2063.

Emans N, Gorvel JP, Walter C, Gerke V, Kellner R, Griffiths G, Gruenberg J: Annexin II is a major component of fusogenic endosomal vesicles. J Cell Biol 1993, 120(6):1357-1369.

Fiedler K, Kellner R, Simons K: Mapping the protein composition of transGolgi network (TGN)-derived carrier vesicles from polarized MDCK cells. Electrophoresis 1997, 1 8(14):2613-2619.

Filipek A, Wojda U, Lesniak W: Interaction of calcyclin and its cyanogens bromide fragments with annexin II and glyceraldehyde 3-phosphate dehydrogenase. Int J Biochem Cell Biol 1995, 27(11):1 123-1131.

Finkelstein LD, Ney PA, Liu QP, Paulson RF, Correll PH: Sf-Stk kinase activity and the Grb2 binding site are required for Epo-independent growth of primary erythroblasts infected with Friend virus. Oncogene 2002, 21(22):3562-3570.

Glomb-Reinmund S, Kielian M: The role of low pH and disulfide shuffling in the entry and fusion of Semliki Forest virus and Sindbis virus. Virology 1998, 248(2):372-381.

Golitsina NL, Kordowska J, Wang CL, Lehrer SS: Ca2+-dependent binding of calcyclin to muscle tropomyosin. Biochem Biophys Res Commun 1996, 220(2): 360-365.

Guinea R, Carrasco L: Requirement for vacuolar proton-ATPase activity during entry of influenza virus into cells. J Virol 1995, 69(4):2306-2312.

Hansen J, Etchison D, Hershey JW, Ehrenfeld E: Association of cap-binding protein with eucaryotic initiation factor 3 in initiation factor preparations from uninfected and poliovirus-infected HeLa cells. J Virol 1982, 42(1):200-207.

Hansen J, Floss T, Van Sloun P, Fuchtbauer EM, Vauti F, Arnold HH, Schnutgen F, Wurst W, von Melchner H, Ruiz P: A large-scale, gene-driven mutagenesis approach for the functional analysis of the mouse genome. Proc Natl Acad Sci U S A 2003, 100(17):9918-9922.

Hawiger J: Innate immunity and inflammation: a transcriptional paradigm. Immunol Res 2001, 23(2-3):99-109.

Hicks GG, Shi EG, Li XM, Li Ch, Pawlak M, Ruley HE: Functional genomics in mice by tagged sequence mutagenesis. Nat Genet 1997, 16(4):338-344.

Hida K, Wada J, Zhang H, Hiragushi K, Tsuchiyama Y, Shikata K, Makino H: Identification of genes specifically expressed in the accumulated visceral adipose tissue of OLETF rats. J Lipid Res 2000, 41(10):1615-1622.

Higaki S, Gebhardt BM, Lukiw WJ, Thompson HW, Hill JM: Effect of immunosuppression on gene expression in the HSV-1 latently infected mouse trigeminal ganglion. Invest Ophthalmol Vis Sci 2002, 43(6):1862-1869.

Hirose Y, Manley JL: Creatine phosphate, not ATP, is required for 3' end cleavage of mammalian pre-mRNA in vitro. J Biol Chem 1997, 272(47):29636-29642.

Hirst J, Futter CE, Hopkins CR: The kinetics of mannose 6-phosphate receptor trafficking in the endocytic pathway in HEp-2 cells: the receptor enters and rapidly leaves multivesicular endosomes without accumulating in a prelysosomal compartment. Mol Biol Cell 1998, 9(4):809-816.

Hugle T, Fehrmann F, Bieck E, Kohara M, Krausslich HG, Rice CM, Blum HE, Moradpour D: The hepatitis C virus nonstructural protein 4B is an integral endoplasmic reticulum membrane protein. Virology 2001, 284(1):70-81.

Huh JR, Park JM, Kim M, Carlson BA, Hatfield DL, Lee BJ: Recruitment of TBP or TFIIB to a promoter proximal position leads to stimulation of RNA polymerase II transcription without activator proteins both in vivo and in vitro. Biochem Biophys Res Commun 1999, 256(1):45-51.

Kanopka A, Muhlemann O, Petersen-Mahrt S, Estmer C, Ohrmalm C, Akusjarvi G: Regulation of adenovirus alternative RNA splicing by dephosphorylation of SR proteins. Nature 1998, 393(6681): 185-187.

Katoh M: IGSF1 1 gene, frequently up-regulated in intestinal-type gastric cancer, encodes adhesion molecule homologous to CXADR, FLJ22415 and ESAM. Int J Oncol 2003, 23(2):525-531.

Kieft JS, Zhou K, Jubin R, Murray MG, Lau JY, Doudna JA: The hepatitis C virus internal ribosome entry site adopts an ion-dependent tertiary fold. J Mol Biol 1999, 292(3):513-529.

Kim H, Lee YH, Won J, Yun Y: Through induction of juxtaposition and tyrosine kinase activity of Jak1, X-gene product of hepatitis B virus stimulates Ras and the transcriptional activation through AP-1, NF-kappaB, and SRE enhancers. Biochem Biophys Res Commun 2001, 286(5):886-894.

Koffa MD, Graham SV, Takagaki Y, Manley JL, Clements JB: The human papillomavirus type 16 negative regulatory RNA element interacts with three proteins that act at different posttranscriptional levels. Proc Natl Acad Sci U S A 2000, 97(9):4677-4682.

Korkaya H, Jameel S, Gupta D, Tyagi S, Kumar R, Zafrullah M, Mazumdar M, Lal SK, Xiaofang L, Sehgal D et al: The ORF3 protein of hepatitis E virus binds to Src homology 3 domains and activates MAPK. J Biol Chem 2001, 276(45):423 89-42400.

Kumar R, Yang J, Larsen RD, Stanley P: Cloning and expression of N acetylglucosaminyltransferase I, the medial Golgi transferase that initiates complex N-linked carbohydrate formation. Proc Natl Acad Sci U S A 1990, 87(24):9948-9952.

Lau JF, Horvath CM: Mechanisms of Type I interferon cell signaling and STAT-mediated transcriptional responses. Mt Sinai J Med 2002, 69(3):156-168.

Lee KH, Na DS, Kim JW: Calcium-dependent interaction of annexin I with annexin II and mapping of the interaction sites. FEBS Lett 1999, 442(2-3):143-146.

Li Y, Kang J, Horwitz MS: Interaction of an adenovirus 14.7-kilodalton protein inhibitor of tumor necrosis factor alpha cytolysis with a new member of the GTPase superfamily of signal transducers. J Virol 1997, 71(2): 1576-1582.

Luo T, Douglas JL, Livingston RL, Garcia JV: Infectivity enhancement by HIV-1 Nef is dependent on the pathway of virus entry: implications for HIV-based gene transfer systems. Virology 1998, 241(2):224-233.

Martinez CG, Guinea R, Benavente J, Carrasco L: The entry of reovirus into L cells is dependent on vacuolar proton-ATPase activity. J Virol 1996, 70(1):576-579.

McGregor F, Phelan A, Dunlop J, Clements JB: Regulation of herpes simplex virus poly (A) site usage and the action of immediate-early protein IE63 in the early-late switch. J Virol 1996, 70(3):1931-1940.

Melancon P, Garoff H: Reinitiation of translocation in the Semliki Forest virus structural polyprotein: identification of the signal for the E1 glycoprotein. Embo J 1986, 5(7):1551-1560.

Nakamura N, Lowe M, Levine TP, Rabouille C, Warren G: The vesicle docking protein p115 binds GM130, a cis-Golgi matrix protein, in a mitotically regulated manner. Cell 1997, 89(3):445-455.

Nezu J, Motojima K, Tamura H, Ohkuma S: Molecular cloning of a rat liver cDNA encoding the 16 kDa subunit of vacuolar H(+)-ATPases: organellar and tissue distribution of 16 kDa proteolipids. J Biochem (Tokyo) 1992, 1 12(2):212-219.

Nilsson T, Rabouille C, Hui N, Watson R, Warren G: The role of the membrane-spanning domain and stalk region of N-acetylglucosaminyltransferase I in retention, kin recognition and structural maintenance of the Golgi apparatus in HeLa cells. J Cell Sci 1996, 1 09(Pt 7): 1975-1989.

Nilsson T, Slusarewicz P, Hoe MH, Warren G: Kin recognition. A model for the retention of Golgi enzymes. FEBS Lett 1993, 330(1):1-4.

Okutsu T, Kuroiwa Y, Kagitani F, Kai M, Aisaka K, Tsutsumi O, Kaneko Y, Yokomori K, Surani MA, Kohda T et al: Expression and imprinting status of human PEG8/IGF2AS, a paternally expressed antisense transcript from the IGF2 locus, in Wilms' tumors. J Biochem (Tokyo) 2000, 127(3):475-483.

Op De Beeck A, Caillet-Fauquet P: Viruses and the cell cycle. Prog Cell Cycle Res 1997, 3:1-19.

Orci L, Perrelet A, Rothman JE: Vesicles on strings: morphological evidence for processive transport within the Golgi stack. Proc Natl Acad Sci U S A 1998, 95(5):2279-2283.

Osipovich AB, White-Grindley EK, Hicks GG, Roshon MJ, Shaffer C, Moore JH, H.E. R: Activation of cryptic 3' splice sites within introns of cellular genes following gene entrapment. Nucleic Acids Res 2004, in press.

Perkins ME, WU TW, Le Blancq SM: Cyclosporin analogs inhibit in vitro growth of Cryptosporidium parvum. Antimicrob Agents Chemother 1998, 42(4):843-848.

Pertile TL, Karaca K, Sharma JM, Walser MM: An antiviral effect of nitric oxide: inhibition of reovirus replication. Avian Dis 1996, 40(2):342-348.

Pier GB, Grout M, Zaidi T, Meluleni G, Mueschenborn SS, Banting G, Ratcliff R, Evans MJ, Colledge WH: Salmonella typhi uses CFTR to enter intestinal epithelial cells. Nature 1998, 393(6680):79-82.

Pietropaolo RL, Compton T: Direct interaction between human cytomegalovirus glycoprotein B and cellular annexin II. J Virol 1997, 71(12):9803-9807.

Pitha PM, Au WC, Lowther W, Juang YT, Schafer SL, Burysek L, Hiscott J, Moore PA: Role of the interferon regulatory factors (IRFs) in virus-mediated signaling and regulation of cell growth. Biochimie 1998, 80(8-9):651-658.

Pittis MG, Muzzolin L, Giulianini PG, Garcia RC: Mycobacteria-containing phagosomes associate less annexins I, VI, VII and XI, but not II, concomitantly with a diminished phagolysosomal fusion. Eur J Cell Biol 2003, 82(1):9-17.

Platt GM, Simpson GR, Mittnacht S, Schulz TF: Latent nuclear antigen of Kaposi's sarcoma-associated herpesvirus interacts with RING3, a homolog of the Drosophila female sterile homeotic (fsh) gene. J Virol 1999, 73(12):9789-9795.

Raynor CM, Wright JF, Waisman DM, Pryzdial EL: Annexin II enhances cytomegalovirus binding and fusion to phospholipid membranes. Biochemistry 1999, 38(16):5089-5095.

Reiss CS, Komatsu T: Does nitric oxide play a critical role in viral infections? J Virol 1998, 72(6):4547-4551.

Richardson-Burns SM, Tyler KL: Regional differences in viral growth and central nervous system injury correlate with apoptosis. J Virol 2004, 78(10):5466-5475.

Roberts PC, Kipperman T, Compans RW: Vesicular stomatitis virus G protein acquires pH-independent fusion activity during transport in a polarized endometrial cell line. J Virol 1999, 73(12):10447-10457.

Rousse S, Lallemand F, Montarras D, Pinset C, Mazars A, Prunier C, Atfi A, Dubois C: Transforming growth factor-beta inhibition of insulin-like growth factor-binding protein-5 synthesis in skeletal muscle cells involves a c-Jun N-terminal kinase-dependent pathway. J Biol Chem 2001, 276(50):46961-46967.

Rubin DH, Kornstein MJ, Anderson AO: Reovirus serotype 1 intestinal infection: a novel replicative cycle with ileal disease. J Virol 1985, 53(2): 391-398.

Rubin DH, Wetzel JD, Williams WV, Cohen JA, Dworkin C, Dermody TS: Binding of type 3 reovirus by a domain of the sigma 1 protein important for hemagglutination leads to infection of murine erythroleukemia cells. J Clin Invest 1992, 90(6):2536-2542.

Sakurai H, Shigemori N, Hasegawa K, Sugita T: TGF-beta-activated kinase 1 stimulates NF-kappa B activation by an NF-kappa B-inducing kinaseindependent mechanism. Biochem Biophys Res Commun 1998, 243(2):545-549.

Salminen M, Meyer BI, Gruss P: Efficient poly A trap approach allows the capture of genes specifically active in differentiated embryonic stem cells and in mouse embryos. Dev Dyn 1998, 212(2):326-333.

Scaplehorn N, Holmstrom A, Moreau V, Frischknecht F, Reckmann I, Way M: Grb2 and Nck act cooperatively to promote actin-based motility of vaccinia virus. Curr Biol 2002, 12(9):740-745.

Schelling JR, Gentry DJ, Dubyak GR: Annexin II inhibition of G protein-regulated inositol trisphosphate formation in rat aortic smooth muscle. Am J Physiol 1996, 270(4 Pt 2):F682-690.

Sheng J, Organ EL, Hao C, Wells KS, Ruley HE, Rubin DH: Mutations in the IGF-II pathway that confer resistance to lytic reovirus infection. BMC Cell Biol 2004, 5(1):32.

Sheng Q, Denis D, Ratnofsky M, Roberts TM, DeCaprio JA, Schaffhausen B: The DnaJ domain of polyomavirus large T antigen is required to regulate Rb family tumor suppressor function. J Virol 1997, 71(12):9410-9416.

Shibuya H, Yamaguchi K, Shirakabe K, Tonegawa A, Gotoh Y, Ueno N, Irie K, Nishida E, Matsumoto K: TAB 1: an activator of the TAK1 MAPKKK in TGFbeta signal transduction. Science 1996, 272(5265):1 179-1182.

Sizova DV, Kolupaeva VG, Pestova TV, Shatsky IN, Hellen CU: Specific interaction of eukaryotic translation initiation factor 3 with the 5' nontranslated regions of hepatitis C virus and classical swine fever virus RNAs. J Virol 1998, 72(6):4775-4782.

Spear BT, Longley T, Moulder S, Wang SL, Peterson ML: A sensitive lacZbased expression vector for analyzing transcriptional control elements in eukaryotic cells. DNA Cell Biol 1995, 14(7):635-642.

Stryke D, Kawamoto M, Huang CC, Johns SJ, King LA, Harper CA, Meng EC, Lee RE, Yee A, L'Italien L et al: BayGenomics: a resource of insertional mutations in mouse embryonic stem cells. Nucleic Acids Res 2003, 31(1):278-281.

Takekawa M, Maeda T, Saito H: Protein phosphatase 2Calpha inhibits the human stress-responsive p38 and JNK MAPK pathways. Embo J 1998, 17(16):4744-4752.

Tan SL, Nakao H, He Y, Vijaysri S, Neddermann P, Jacobs BL, Mayer BJ, Katze MG: NS5A, a nonstructural protein of hepatitis C virus, binds growth factor receptor-bound protein 2 adaptor protein in a Src homology 3 domain/ligand-dependent manner and perturbs mitogenic signaling. Proc Natl Acad Sci U S A 1999, 96(10):5533-5538.

Tanaka K, Kawakami T, Tateishi K, Yashiroda H, Chiba T: Control of IkappaBalpha proteolysis by the ubiquitin-proteasome pathway. Biochimie 2001, 83(3-4):351-356.

Taterka J, Sutcliffe M, Rubin DH: Selective reovirus infection of murine hepatocarcinoma cells during cell division. A model of viral liver infection. J Clin Invest 1994, 94(1):353-360.

Uchida K, Suzuki H, Ohashi T, Nitta K, Yumura W, Nihei H: Involvement of MAP kinase cascades in Smad7 transcriptional regulation. Biochem Biophys Res Commun 2001, 289(2):376-381.

Weiner HL, Powers ML, Fields BN: Absolute linkage of virulence and central nervous system cell tropism of reoviruses to viral hemagglutinin. J Infect Dis 1980, 141(5):609-616.

Werner-Felmayer G, Werner ER, Fuchs D, Hausen A, Reibnegger G, Schmidt K, Weiss G, Wachter H: Pteridine biosynthesis in human endothelial cells. Impact on nitric oxide-mediated formation of cyclic GMP. J Biol Chem 1993, 268(3): 1842-1846.

Wiles MV, Vauti F, Otte J, Fuchtbauer EM, Ruiz P, Fuchtbauer A, Arnold HH, Lehrach H, Metz T, von Melchner H et al: Establishment of a gene-trap sequence tag library to generate mutant mice from embryonic stem cells. Nat Genet 2000, 24(1):13-14.

Yanagisawa M, Nakashima K, Takeda K, Ochiai W, Takizawa T, Ueno M, Takizawa M, Shibuya H, Taga T: Inhibition of BMP2-induced, TAK1 kinasemediated neurite outgrowth by Smad6 and Smad7. Genes Cells 2001, 6(12):1091-1099.

Yang W, Pepperkok R, Bender P, Kreis TE, Storrie B: Modification of the cytoplasmic domain affects the subcellular localization of Golgi glycosyltransferases. Eur J Cell Biol 1996, 71(1):53-61.

Zambrowicz BP, Friedrich GA, Buxton EC, Lilleberg SL, Person C, Sands AT: Disruption and sequence identification of 2,000 genes in mouse embryonic stem cells. Nature 1998, 392(6676):608-61 1.

Zeng FY, Gerke V, Gabius HJ: Identification of annexin II, annexin VI and glyceraldehyde-3-phosphate dehydrogenase as calcyclin-binding proteins in bovine heart. Int J Biochem 1993, 25(7):1019-1027.

Zhou G, Avitabile E, Campadelli-Fiume G, Roizman B: The domains of glycoprotein D required to block apoptosis induced by herpes simplex virus 1 are largely distinct from those involved in cell-cell fusion and binding to nectin1. J Virol 2003, 77(6):3759-3767.

Zhou M, Kashanchi F, Jiang H, Ge H, Brady JN: Phosphorylation of the RAP74 subunit of TFIIF correlates with Tat-activated transcription of the HIV-1 long terminal repeat. Virology 2000, 268(2):452-460.

Radu Roxana A et al., Light exposure stimulates formation of A2E oxiranes in a mouse model of Stargardt's macular degeneration. Proceedings of the National Academy of Sciences of the United States of America. vol. 101, No. 16: pp. 5928-5933, 2004.

Paton I. R. et al., Mapping the ABCA4, IMPDH2 and TIMP3 genes in chicken. Animal Genetics. vol. 34, No. 5: pp. 395-396, 2003.

Organ Edward L. et al., Discovery of mammalian genes that participate in virus infection. BMC Cell Biology, vol. 5, No. 1: pp. 2004.

Zhang J. et al., Down-regulation of viral replication by adenoviral-mediated expression of siRNA against cellular cofactors for hepatitis C virus. Virology, Academic Press, Orlando, U.S. vol. 320, No. 1: pp. 135-143, 2004.

Sheng Jinsong et al., Mutations in the IGF-II pathway that confer resistance to lytic reovirus infection. BMC Cell Biology, vol. 5: pp. 1471-2121, 2004.

Rubin D. H. et al., A functional genomics approach to define host susceptibility to infection. Infection Genetics and Evolution, vol. 2, No. 4: pp. 273, 2003.

* cited by examiner

MAMMALIAN GENES INVOLVED IN INFECTION

This application claims priority to U.S. provisional application Ser. No. 60/622,486, filed Oct. 27, 2004, which is herein incorporated by this reference in its entirety.

ACKNOWLEDGEMENTS

This invention was made with government support under Public Health Service Grant R01CA68283. The government has certain rights in this invention.

FIELD OF THE INVENTION

The present invention relates to nucleic acid sequences and cellular proteins encoded by these sequences that are involved in infection or are otherwise associated with the life cycle of one or more pathogens, such as a virus, a bacteria, a fungus or a parasite. The invention also relates to modulators of nucleic acid sequences and cellular proteins encoded by these sequences that are involved in infection or are otherwise associated with the life cycle of a pathogen.

BACKGROUND

Traditional treatments for viral infection include pharmaceuticals aimed at specific virus derived proteins, such as HIV protease or reverse transcriptase, or recombinant (cloned) immune modulators (host derived), such as the interferons. However, the current methods have several limitations and drawbacks which include high rates of viral mutations which render anti-viral pharmaceuticals ineffective. For immune modulators, limited effectiveness, limiting side effects, a lack of specificity all limit the general applicability of these agents. Also the rate of success with current antivirals and immune-modulators has been disappointing.

The current invention focuses on genes that are not essential for cellular survival when disrupted in one or both alleles, but which are required for virus replication. This may occur with a dose effect, in which one allele knock-out may confer the phenotype of virus resistance for the cell. As targets for therapeutic intervention, inhibition of these cellular gene products, including: proteins, parts of proteins (modification enzymes that include, but are not restricted to glycosylation, lipid modifiers [myristylation, etc.]), lipids, transcription elements and RNA regulatory molecules, may be less likely to have profound toxic side effects and virus mutation is less likely to overcome the 'block' to replicate successfully.

The present invention provides a significant improvement over previous methods of attempted therapeutic intervention against viral infection by addressing the cellular genes required by the virus for growth. Therefore, the present invention also provides an innovative therapeutic approach to intervention in viral infection by providing methods to treat viruses by inhibiting the cellular genes necessary for viral infection. Inhibition of these cellular genes can also be useful in treating infection by other pathogens such as bacteria, fingi and parasites. Because these genes are nonessential to the cell's survival, these treatment methods can be used in a subject without serious detrimental effects to the subject, as has been found with previous methods.

SUMMARY OF THE INVENTION

The present invention provides nucleic acid sequences and cellular proteins encoded by these sequences that are involved in infection or are otherwise associated with the life cycle of one or more pathogens, such as a virus, a bacteria, a fungus or a parasite. The invention also provides methods of identifying modulators of nucleic acid sequences and cellular proteins encoded by these sequences that are involved in infection or are otherwise associated with the life cycle of a pathogen. Also provided are modulators of nucleic acid sequences and cellular proteins encoded by these sequences that are involved in infection or are otherwise associated with the life cycle of a pathogen.

DETAILED DESCRIPTION OF THE INVENTION

Figure 1A:
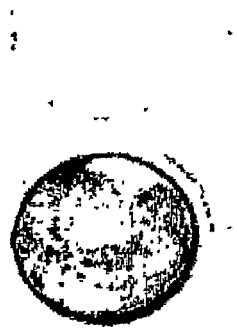
FIG. 1 shows the characterization of phenotypic properties of cloned RIE-1 cells resistant to reovirus type 1 infection. (A) Cells were stained for reovirus antigen as previously described [3]. Only the PI cells contain reovirus antigen as detected by immunohistochemistry (dark wells). Upper wells are cloned mutant RIE-1 cells from two sets of RIE-1 mutant cell lines selected for reovirus resistance. Lower wells, PI RIE-1 (left), and uninfected wild type RIE-1 (right). (B) Reovirus susceptible L-cell monolayers, maintained in 1 ml of completed medium, were used to detect the presence of virus in a 100 µl lysate obtained of mutant cells (upper two wells), PI RIE-1 cells (lower left) or uninfected parental RIE-1 cells (lower right). Note, that only L-cell monolayers exposed to a lysate from PI RIE-1 cells lysed within one week of exposure (gentian violet stain).

The present invention may be understood more readily by reference to the following detailed description of preferred embodiments of the invention and the Examples included therein.

Before the present compounds, compositions, articles, devices, and/or methods are disclosed and described, it is to be understood that this invention is not limited to specific nucleic acids, specific polypeptides, or to particular methods, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Ranges may be expressed herein as from "about" one particular value, and/or too "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally obtained prior to treatment" means obtained before treatment, after treatment, or not at all.

As used throughout, by "subject" is meant an individual. Preferably, the subject is a mammal such as a primate, and, more preferably, a human. The term "subject" includes domesticated animals, such as cats, dogs, etc., livestock (for example, cattle, horses, pigs, sheep, goats, etc.), laboratory animals (for example, mouse, rabbit, rat, gerbil, guinea pig, etc.) and avian species (for example, chickens, turkeys, ducks, pheasants, pigeons, doves, parrots, cockatoos, geese, etc.). The subjects of the present invention can also include, but are not limited to fish, amphibians and reptiles.

The present method provides several cellular genes that are necessary for viral growth in the cell but are not essential for the cell to survive. As used herein, a cellular gene "nonessential for cellular survival" means a gene for which disruption of one or both alleles results in a cell viable for at least a period of time which allows viral replication to be decreased or inhibited in a cell. Such a decrease can be utilized for preventative or therapeutic uses or used in research. A gene "necessary for viral growth" means the gene product of this gene, either protein or RNA, secreted or not, is necessary, either directly or indirectly in some way for the virus to grow, and therefore, in the absence of that gene product (i.e., a functionally available gene product), at least some of the cells containing the virus die. As utilized throughout, "gene product" is the RNA or protein resulting from the expression of a gene.

These cellular genes or host nucleic acid sequences involved in viral infection were identified using gene trap methods. These gene trap methods are set forth in the Examples as well as in U.S. Pat. Nos. 6,448,000 and 6,777,177. U.S. Pat. Nos. 6,448,000 and 6,777,177 are both incorporated herein in their entireties by this reference. For example, the host nucleic acid sequences set forth herein can be identified by a method of identifying a cellular gene necessary for viral growth in a cell and nonessential for cellular survival, comprising: (a) transferring into a cell culture a vector encoding a selective marker gene lacking a functional promoter, (b) selecting cells expressing the marker gene, (c) infecting the cell culture with the virus, and (d) isolating from the surviving cells a cellular gene within which the marker gene is inserted, thereby identifying a gene necessary for viral growth in a cell and nonessential for cellular survival. The host nucleic acid sequences can also be identified by a method of identifying a cellular gene necessary for viral growth in a cell and nonessential for cellular survival, comprising (a) transferring into a cell culture growing in serum-containing medium a vector encoding a selective marker gene lacking a functional promoter, (b) selecting cells expressing the marker gene, (c) removing serum from the culture medium, (d) infecting the cell culture with the virus, and (e) isolating from the surviving cells a cellular gene within which the marker gene is inserted, thereby identifying a gene necessary for viral growth in a cell and nonessential for cellular survival.

The identification of these host sequences and their encoded proteins permits the identification of sequences that can be targeted for modulation (for example, decreasing gene expression and/or activity of the gene product or increasing gene expression and/or activity of the gene product) and/or therapeutic intervention.

Table 1 sets forth host nucleic acid sequences that are involved in viral infection or otherwise associated with the life cycle of a virus. For example, these nucleic acids and their encoded proteins can be involved in all phases of viral life cycles including, but not limited to, viral attachment to cellular receptors, viral infection, viral entry, internalization, disassembly of the virus, viral replication, genomic integration of viral sequences, translation of mRNA, assembly of viral particles, cell lysis and egress of virus from the cells.

As used herein, a gene is a nucleic acid sequence that encodes a polypeptide under the control of a regulatory sequence, such as a promoter or operator. The coding sequence of the gene is the portion transcribed and translated into a polypeptide (in vivo, in vitro or in situ) when placed under the control of an appropriate regulatory sequence. The boundaries of the coding sequence can be determined by a start codon at the 5' (amino) terminus and a stop codon at the 3' (carboxyl) terminus. If the coding sequence is intended to be expressed in a eukaryotic cell, a polyadenylation signal and transcription termination sequence can be included 3' to the coding sequence.

Transcriptional and translational control sequences include, but are not limited to, DNA regulatory sequences such as promoters, enhancers, and terminators that provide for the expression of the coding sequence, such as expression in a host cell. A polyadenylation signal is an exemplary eukaryotic control sequence. A promoter is a regulatory region capable of binding RNA polymerase and initiating transcription of a downstream (3' direction) coding sequence. Additionally, a gene can include a signal sequence at the beginning of the coding sequence of a protein to be secreted or expressed on the surface of a cell. This sequence can encode a signal peptide, N-terminal to the mature polypeptide, which directs the host cell to translocate the polypeptide.

Table 1 (column 2) also provides the protein encoded by the genes listed in Table 1. In several instances, the gene trap vector utilized to trap the genes disrupted two genes, one of which is due to location of the vector as it resides in a gene transcribed off the negative strand. An example of such an occurrence is the disruption of the gene encoding aprataxin and the gene encoding DnaJ (Hsp40) homolog, subfamily A, member 1 by the same vector.

Table 1 also provides the chromosomal location of the gene in the rat and human genome (columns 3 and column 4, respectively). Thus, the present invention identifies the genomic loci of genes associated with viral infection. By identifying the gene and its location in the genome, the invention provides both the gene and its product(s) as targets for therapies such as antiviral, antibacterial, antifungal and antiparasitic therapies, to name a few.

Also provided in Table 1 are the GenBank Accession Nos. for the rat mRNA sequences (column 5), the GenBank Accession Nos. for the human mRNA sequences (column 6) and the GenBank Accession Nos. for the human protein sequences (column 7). The nucleic acid sequences and protein sequences provided under the GenBank Accession Nos. mentioned herein are hereby incorporated in their entireties by this reference. One of skill in the art would know that the nucleotide sequences provided under the GenBank Accession Nos. set forth herein can be readily obtained from the National Center for Biotechnology Information at the National Library of Medicine (http://www.ncbi.nlm.nih.gov/entrez/query.fcgi?db=nucleotide). Similarly, the protein sequences set forth herein can be readily obtained from the National Center for Biotechnology Information at the National Library of Medicine (http://www.ncbi.nlm.nih.gov/entrez/query.fcgi?db=protein). The nucleic acid sequences and protein sequences provided under the GenBank Accession Nos. mentioned herein are hereby incorporated in their entireties by this reference.

Table 1 also provides the GenBank Accession Nos. for the partial sequences of the rat genes obtained upon the insertion of the gene trap vector (column 9). Briefly, these genes were isolated by generating gene trap libraries by infecting cells with a retrovirus gene trap vector and selecting for cells in which a gene trap event occurred (i.e., in which the vector had inserted such that the promoterless marker gene was inserted such that a cellular promoter promotes transcription of the marker gene, i.e., inserted into a functioning gene). Genes into which the retrovirus gene trap vector inserted were then isolated from the colonies using probes specific for the retrovirus gene trap vector. Thus nucleic acids isolated by this method are isolated portions of genes. These portions were then utilized to identify the complete sequences of each gene via sequence comparisons and other bioinformatics methods.

Further provided are the Entrez Gene numbers for the rat gene and human gene (columns 10 and 11, respectively). The information provided under the Entrez Gene numbers listed in Table 1 is also hereby incorporated entirely by this reference. One of skill in the art can readily obtain this information from the National Center for Biotechnology Information at the National Library of Medicine (http://www.ncbi.nlm.nih.gov/entrez/query.fcgi?db=gene). By accessing Entrez Gene, one of skill in the art can readily obtain additional information about every gene listed in Table 1, such as the genomic location of the gene, a summary of the properties of the protein encoded by the gene, information on homologs of the gene as well as numerous reference sequences, such as the genomic, mRNA and protein sequences for each gene. Thus, in addition to the sequences set forth under the GenBank Accession Nos. in Table 1, one of skill in the art can readily obtain additional sequences, such as genomic, mRNA and protein sequences by accessing additional information available under the Entrez Gene number provided for each gene. Thus, all of the information readily obtained from the Entrez Gene Nos. set forth herein is also hereby incorporated by reference in its entirety.

Table 2 provides classification of numerous genes set forth in Table 1 according to their cellular roles. Several examples of regulatory sequences (e.g., transcription factors) are provided in Table 2 (for example, Brd2, Brd3, Ctcf, E2f2, Gtf2e1, Hnrpl, Hoxc13, Hp1-bp74, Id3, Znf207 and Zfp7). Therefore, these transcription factors control multi-gene pathways. In some cases, disruption of the transcription factor has a direct impact on viral growth. In other cases disruption of the transcription factor affects viral growth by affecting transcription or translation of the gene or genes that are under its control. Therefore, the genes that are under the control of the transcription factors set forth in Table 1 and Table 2 are also provided by the present invention as targets for therapy, such as antiviral, antibacterial, antiparasitic and antifungal therapy. Table 2 also provides examples of genes involved in other pathways such as vesicular trafficking, ubiquitination, apoptosis, metabolism etc. Thus, other genes in these pathways, either upstream or downstream of the genes set forth for these pathways in Table 2 are also provided herein as targets for therapeutic intervention (therapy). For example, a gene that produces a gene product that interacts with Ube1c either upstream or downstream in the ubiquitination pathway is considered a target for therapy against intracellular pathogens. For example, this can be a transcription factor that regulates expression of Ube1c or another protein that binds to Ube1c. These examples are merely exemplary as this applies to all of the genes set forth herein and the cellular pathways that they are involved in.

When referring to a gene(s) in Table 1, this includes any gene, nucleic acid, cDNA or RNA from any organism that can function as the gene or nucleic acid listed in Table 1. When referring to a protein(s) listed in Table 1 this includes any protein or fragment thereof from any organism that can function as the protein listed in Table 1. For example, the term ANXA1 (annexin 1) includes any ANXA1 gene, nucleic acid, cDNA or RNA, from any organism that can function as an ANXA1 gene or ANXA1 nucleic acid. The term ANXA1 also includes any protein from any organism that can function as an ANXA1 protein.

As used herein, the term "nucleic acid" refers to single or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the moieties discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides), a reduction in the AT content of AT rich regions, or replacement of non-preferred codon usage of the expression system to preferred codon usage of the expression system. The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in Sambrook et al. (2001) *Molecular Cloning—A Laboratory Manual* (3rd ed.) Vol. 1-3, Cold Spring Harbor Laboratory, Cold Spring Harbor Press, NY, (Sambrook).

Once the nucleic acid sequence is obtained, the sequence encoding the specific amino acids can be modified or changed at any particular amino acid position by techniques well known in the art. For example, PCR primers can be designed which span the amino acid position or positions and which can substitute any amino acid for another amino acid. Alternatively, one skilled in the art can introduce specific mutations at any point in a particular nucleic acid sequence through techniques for point mutagenesis. General methods are set forth in Smith, M. "In vitro mutagenesis" *Ann. Rev. Gen.,* 19:423-462 (1985) and Zoller, M. J. "New molecular biology methods for protein engineering" *Curr. Opin. Struct. Biol.,* 1:605-610 (1991), which are incorporated herein in their entirety for the methods. These techniques can be used to alter the coding sequence without altering the amino acid sequence that is encoded.

The sequences contemplated herein include fall-length wild-type (or native) sequences, as well as allelic variants, variants, fragments, homologs or fusion sequences that retain the ability to function as the cellular nucleic acid or protein involved in viral infection. In certain examples, a protein or nucleic acid sequence has at least 70% sequence identity, for example at least 750%, 80%, 85%, 90%, 95%, or 98% sequence identity to a native sequence set forth in Table 1. In other examples, a nucleic acid sequence involved in viral infection has a sequence that hybridizes to a sequence set forth in Table 1 and retains the activity of the sequence set forth in Table 1. For example, a nucleic acid that hybridizes to an ANXA1 nucleic acid sequence set forth in Table 1 (for example the nucleic acid sequence set forth under GenBank Accession No. NM_000700) and encodes a protein that retains ANXA1 activity is contemplated by the present invention. Such sequences include the genomic sequence for the genes set forth in Table 1. The examples set forth above for ANXA1 are merely illustrative and should not be limited to ANXA1 as these examples would apply to every nucleic acid and protein listed in Table 1.

Unless otherwise specified, any reference to a nucleic acid molecule includes the reverse complement of the nucleic acid. Except where single-strandedness is required by the text herein (for example, a ssRNA molecule), any nucleic acid written to depict only a single strand encompasses both strands of a corresponding double-stranded nucleic acid. For example, depiction of a plus-strand of a dsDNA also encompasses the complementary minus-strand of that dsDNA. Additionally, reference to the nucleic acid molecule that encodes a specific protein, or a fragment thereof, encompasses both the sense strand and its reverse complement. Fragments of the nucleic acids set forth in Table 1 and throughout the specification are also contemplated. These fragments can be utilized as primers and probes to amplify or detect any of the nucleic acids or genes set forth in Table 1.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

| Very High Stringency (detects sequences that share 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share 80% identity or greater) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share greater than 50% identity) | |
|---|---|
| Hybridization: | 6x SSC at RT to 55° C. for 16-20 hours |
| Wash at least twice: | 2x-3x SSC at RT to 55° C. for 20-30 minutes each. |

Also provided is a vector, comprising a nucleic acid of the present invention. The vector can direct the in vivo or in vitro synthesis of any of the proteins or polypeptides described herein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.). The vector, for example, can be a plasmid. The vectors can contain genes conferring hygromycin resistance, ampicillin resistance, gentamicin resistance, neomycin resistance or other genes or phenotypes suitable for use as selectable markers, or methotrexate resistance for gene amplification.

There are numerous other *E. coli* (*Escherichia coli*) expression vectors, known to one of ordinary skill in the art, which are useful for the expression of the nucleic acid insert. Other microbial hosts suitable for use include bacilli, such as *Bacillus subtilis*, and other enterobacteriaceae, such as *Salmonella, Serratia,* and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosorye binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures. Also, nucleic acid modifications can be made to promote amino terminal homogeneity.

Additionally, yeast expression can be used. The invention provides a nucleic acid encoding a polypeptide of the present invention, wherein the nucleic acid can be expressed by a yeast cell. More specifically, the nucleic acid can be expressed by *Pichia pastoris* or *S. cerevisiae*. There are several advantages to yeast expression systems, which include, for example, *Saccharomyces cerevisiae* and *Pichia pastoris*. First, evidence exists that proteins produced in a yeast secretion systems exhibit correct disulfide pairing. Second, efficient large scale production can be carried out using yeast expression systems. The *Saccharomyces cerevisiae* pre-pro-alpha mating factor leader region (encoded by the MFα-1 gene) can be used to direct protein secretion from yeast (Brake, et al.). The leader region of pre-pro-alpha mnating factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha mating factor leader region. This construct can be put under the control of a strong transcription promoter, such as the alcohol dehydrogenase I promoter, alcohol oxidase I promoter, a glycolytic promoter, or a promoter for the galactose utilization pathway. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, genticin or G418 resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc.

The expression vectors described herein can also include nucleic acids of the present invention under the control of an inducible promoter such as the tetracycline inducible promoter or a glucocorticoid inducible promoter. The nucleic acids of the present invention can also be under the control of a tissue-specific promoter to promote expression of the nucleic acid in specific cells, tissues or organs. Any regulatable promoter, such as a metallothionein promoter, a heat-shock promoter, and other regulatable promoters, of which many examples are well known in the art are also contemplated. Furthermore, a Cre-loxP inducible system can also be used, as well as a Flp recombinase inducible promoter system, both of which are known in the art.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice.

The invention also provides for the vectors containing the contemplated nucleic acids in a host suitable for expressing the nucleic acids. The host cell can be a prokaryotic cell, including, for example, a bacterial cell. More particularly, the bacterial cell can be an *E. coli* cell. Alternatively, the cell can be a eukaryotic cell, including, for example, a Chinese hamster ovary (CHO) cell, a COS-7 cell, a HELA cell, an avian cell, a myeloma cell, a *Pichia* cell, or an insect cell. The coding sequence for any of the polypeptides described herein can be introduced into a Chinese hamster ovary (CHO) cell line, for example, using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines have been developed and include myeloma cell lines, fibroblast cell lines, and a variety of tumor cell lines such as melanoma cell lines. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, Lipofectamine, or lipofectin mediated transfection, electroporation or any method now known or identified in the future can be used for other eukaryotic cellular hosts.

Polypeptides

The present invention provides isolated polypeptide comprising the polypeptide or protein sequences set forth under GenBank Accession Nos. in Table 1. The present invention also provides fragments of these polypeptides, for example, fragments of an annexin A1 protein, fragments of an annexin A2 protein, fragments of an annexin A3 protein, etc. These fragments can be of sufficient length to serve as antigenic peptides fox the generation of antibodies. The present invention also contemplates functional fragments of the proteins set forth in Table 1 that possess at least one activity of the protein, for ex ample, necessary for viral infection, but not necessary for survival of the cell. It will be known to one of skill in the art that the polypeptides set forth in Table 1 possess other properties. For example, ABCA4 is a member of the superfamily of ATP-binding cassette transporters. Therefore one of skill in the art could assess a ABCA4 fragment for its ability to function as an ATP-binding cassette transporter. If there is ATP-binding cassette transporter activity, one of skill in the art would know that the ABCA4 is a functional fragment of ABCA4. Fragments and variants of the polypeptides listed in Table 1 can include one or more conservative amino acid residues as compared to the amino acid sequence listed under their respective GenBank Accession Nos.

By "isolated polypeptide" or "purified polypeptide" is meant a polypeptide that is substantially free from the materials with which the polypeptide is normally associated in nature or in culture. The polypeptides of the invention can be obtained, for example, by extraction from a natural source if available (for example, a mammalian cell), by expression of a recombinant nucleic acid encoding the polypeptide (for example, in a cell or in a cell-free translation system), or by chemically synthesizing the polypeptide. In addition, polypeptide may be obtained by cleaving full length polypeptides. When the polypeptide is a fragment of a larger naturally occurring polypeptide, the isolated polypeptide is shorter than and excludes the full-length, naturally-occurring polypeptide of which it is a fragment.

The polypeptides of the invention can be prepared using any of a number of chemical polypeptide synthesis techniques well known to those of ordinary skill in the art including solution methods and solid phase methods. One method of producing the polypeptides of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the antibody of the present invention, for example, can be synthesized by standard chemical reactions. For example, a peptide or polypeptide can be synthesized and not cleaved from its synthesis resin, whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

The polypeptides of the invention can also be prepared by other means including, for example, recombinant techniques. Examples of appropriate cloning and sequencing techniques, and instructions sufficient to direct persons of skill through many cloning exercises are found in Sambrook et al. (2001) *Molecular Cloning—A Laboratory Manual* (3rd ed.) Vol. 1-3, Cold Spring Harbor Laboratory, Cold Spring Harbor Press, NY, (Sambrook).

Also provided by the present invention is a polypeptide comprising an amino acid sequence at least about 70%, 75%, 80%, 85%, 90%, 95%, 96%, 97%, 98% or 99% identical to the polypeptide sequences set forth under GenBank Accession Nos. in Table 1 or fragments of these polypeptide sequences.

It is understood that as discussed herein the use of the terms "homology" and "identity" mean the same thing as similarity. Thus, for example, if the use of the word homology is used to refer to two non-natural sequences, it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related.

In general, it is understood that one way to define any known variants and derivatives or those that might arise, of the disclosed nucleic acids and polypeptides herein, is through defining the variants and derivatives in terms of homology to specific known sequences. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/bl2seq/bl2.html)), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Also provided by the present invention are polypeptides set forth under GenBank Accession Nos. in Table 1, with one or more conservative amino acid substitutions. These conservative substitutions are such that a naturally occurring amino acid is replaced by one having similar properties. Such conservative substitutions do not alter the function of the polypeptide. For example, conservative substitutions can be made according to the following table:

TABLE 1

Amino Acid Substitutions

| Original Residue | Exemplary Substitutions |
|---|---|
| Arg | Lys |
| Asn | Gln |
| Asp | Glu |
| Cys | Ser |
| Gln | Asn |
| Glu | Asp |
| Gly | Pro |
| His | Gln |
| Ile | leu; val |
| Leu | ile; val |
| Lys | arg; gln |
| Met | leu; ile |
| Phe | met; leu; tyr |
| Ser | Thr |
| Thr | Ser |
| Trp | Tyr |
| Tyr | trp; phe |
| Val | ile; leu |

Thus, it is understood that, where desired, modifications and changes may be made in the nucleic acid encoding the polypeptides of this invention and/or amino acid sequence of the polypeptides of the present invention and still obtain a polypeptide having like or otherwise desirable characteristics. Such changes may occur in natural isolates or may be synthetically introduced using site-specific mutagenesis, the procedures for which, such as mis-match polymerase chain reaction (PCR), are well known in the art. For example, certain amino acids may be substituted for other amino acids in a polypeptide without appreciable loss of functional activity. It is thus contemplated that various changes may be made in the amino acid sequence of the polypeptides of the present invention (or underlying nucleic acid sequence) without appreciable loss of biological utility or activity and possibly with an increase in such utility or activity. Thus, it is clear that naturally occurring variations in the polypeptide sequences set forth herein as well as genetically engineered variations in the polypeptide sequences set forth herein are contemplated by the present invention. By providing the genomic location of genes that are involved in viral infection, the present invention has also provided the genomic location of any variant sequences of these genes. Thus, based on the information provided herein, it would be routine for one of skill in the art to identify and sequence the genomic region identified by applicants and identify variant sequences of the genes set forth herein. It would also be routine for one of skill in the art to utilize comparison tools and bioinformatics techniques to identify sequences from other species that are homologs of the genes set forth herein and are also necessary for infection, but not necessary for survival of the cell.

Antibodies

The present invention also provides antibodies that specifically bind to the gene products, polypeptides, proteins and fragments thereof set forth in Table 1. The antibody of the present invention can be a polyclonal antibody or a monoclonal antibody. The antibody of the invention selectively binds a polypeptide. By "selectively binds" or "specifically binds" is meant an antibody binding reaction which is determinative of the presence of the antigen (in the present case, a polypeptide set forth in Table 1 or antigenic fragment thereof among a heterogeneous population of proteins and other biologics). Thus, under designated immunoassay conditions, the specified antibodies bind preferentially to a particular peptide and do not bind in a significant amount to other proteins in the sample. Preferably, selective binding includes binding at about or above 1.5 times assay background and the absence of significant binding is less than 1.5 times assay background.

This invention also contemplates antibodies that compete for binding to natural interactors or ligands to the proteins set forth in Table 1. In other words, the present invention provides antibodies that disrupt interactions between the proteins set forth in Table 1 and their binding partners. For example, an antibody of the present invention can compete with a protein for a binding site (e.g. a receptor) on a cell or the antibody can compete with a protein for binding to another protein or biological molecule, such as a nucleic acid that is under the transcriptional control of a transcription factor set forth in Table 1. The antibody optionally can have either an antagonistic or agonistic function as compared to the antigen.

Preferably, the antibody binds a polypeptide ex vivo or in vivo. Optionally, the antibody of the invention is labeled with a detectable moiety. For example, the detectable moiety can be selected from the group consisting of a fluorescent moiety, an enzyme-linked moiety, a biotin moiety and a radiolabeled moiety. The antibody can be used in techniques or procedures such as diagnostics, screening, or imaging. Anti-idiotypic antibodies and affinity matured antibodies are also considered to be part of the invention.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

Optionally, the antibodies are generated in other species and "humanized" for administration in humans. In one embodiment of the invention, the "humanized" antibody is a human version of the antibody produced by a germ line mutant animal. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In one embodiment, the present invention provides a humanized version of an antibody, comprising at least one, two, three, four, or up to all CDRs of a monoclonal antibody that specifically binds to a protein set forth in Table 1. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Identification of Agents

A method of identifying an antiviral agent comprising a) administering the agent to a cell containing a cellular gene listed in Table 1, b) detecting the level and/or activity of the gene product produced by the cellular gene, a decrease or elimination of the gene product and/or gene product activity indicating a compound with antiviral activity.

The present invention also provides a method of identifying an antiviral agent comprising: a) administering the agent to a cell containing a cellular gene listed in Table 1, b) contacting the cell with a virus; c) detecting the level of viral infection; and d) associating the level of viral infection with the level of expression of the gene from Table 1 or the activity of the protein encoded by the gene from Table 1, a decrease or elimination of viral infection associated with a decrease or elimination of gene expression and/or activity indicating that the agent is an antiviral agent. For example, the agent can interfere with gene expression and/or the activity of the protein or polypeptide product of the gene. In the methods of the present invention, the test compounds or antiviral agents of the invention can be delivered before or after contacting a cell with a virus or simultaneously with the virus.

The methods described above can be utilized to identify any agent with an activity that decreases infection, prevents infection or promotes cell survival after infection with a pathogen(s). Therefore, in the methods of the present invention, the step of contacting the cell with the virus can be replaced with contacting the cell with any infectious pathogen. Infection includes the introduction of an infectious agent, such as a non-recombinant virus, recombinant virus, plasmid, bacteria, prion, eukaryotic microbe, or other agent capable of infecting a host, such as a cell in cell culture or a cell of a subject. Such infection can be in vitro, ex vivo or in vivo.

The test compounds used in the methods described herein can be, but are not limited to, chemicals, small molecules, drugs, proteins, cDNAs, antibodies, morpholinos, triple helix molecule, siRNAs, shRNAs, antisense RNAs, ribozymes or any other compound now known or identified in the future that interferes with the expression and/or function of the cellular genes described herein. The test compounds can also modulate the activity of the gene products of the cellular genes set forth herein.

Short interfering RNAs (siRNAs) are double-stranded RNAs that can induce sequence-specific post-transcriptional gene silencing, thereby decreasing or even inhibiting gene expression. In some examples, siRNA molecules are about 19-23 nucleotides in length, such as at least 21 nucleotides, for example at least 23 nucleotides. In one example, siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends. The direction of dsRNA processing determines whether a sense or an antisense target RNA can be cleaved by the produced siRNA endonuclease complex. Thus, siRNAs can be used to modulate transcription, for example, by silencing genes, such as one or more genes set forth in Table 1. The effects of siRNAs have been demonstrated in cells from a variety of organisms, including *Drosophila, C. elegans*, insects, frogs, plants, fungi, mice and humans (for example, WO 02/44321; Gitlin et al., *Nature* 418:430-4, 2002; Caplen et al., *Proc. Natl. Acad. Sci.* 98:9742-9747, 2001; and Elbashir et al., *Nature* 411:494-8, 2001).

In certain examples, siRNAs are directed against certain target genes, to confirm results of the gene-trap method used against the same nucleic acid sequence. Utilizing sequence analysis tools, one of skill in the art can design siRNAs to specifically target any gene set forth in Table 1 for decreased gene expression. siRNAs that inhibit or silence gene expression of any gene set forth in Table 1 can be obtained from Ambion Inc. 2130 Woodward Austin, Tex. 78744-1832 USA.

The siRNAs synthesized by Ambion Inc. can by readily obtained by providing the GenBank Accession No. for a coding sequence or the Entrez Gene number for a gene, both of which are provided for rat and human coding sequences in Table 1.

Also provided herein are examples of sequences that can be utilized to decrease gene expression of the genes listed in Table 1. Specifically, Table 3 provides sense RNA sequences and antisense RNA sequences for the genes listed in Table 1. Therefore, any of the sense or antisense sequences set forth in Table 3 can be used alone or in combination with other sequences to inhibit gene expression. These sequences can comprise a 3'TT overhang and/or additional sequences that allow efficient cloning and expression of the siRNA sequences. These sequences were obtained by analyzing the open reading frames of the genes listed in Table 3. Therefore, Table 3 provides the name of each gene analyzed, the GenBank Accession No. for the mRNA of the gene, the length of the mRNA, the ORF region of the mRNA and the Locus number for each gene. The Locus number for each gene is equivalent to the Entrez Gene number listed in Table 1. Table 3 also provides the start site of the sequence in the open reading frame of the gene that is targeted by the sense RNA sequence and/or the antisense RNA sequence set forth in Table 3. The start site for the target sequence is indicated in the Name column and in the Start column. The Name column also provides a GenBank Accession No. identifier for each target sequence. Thus, it would be clear that a row in Table 3 that had the Name NM_000350_siRNA_458 indicates that the sense and antisense sequences correspond to GenBank Accession No. NM_000350 and the start site for the target sequence is 458. For example, a target sequence for the ABCA4 gene starts at position 458. Therefore, a sequence comprising SEQ ID NO: 1 and/or a sequence comprising SEQ ID NO: 2 are two sequences that can be utilized to target ABCA4 and decrease ABCA4 gene expression. Similarly, a sequence comprising SEQ ID NO: 3 and/or a sequence comprising SEQ ID NO: 4 can be utilized to target ABCA4 expression. These examples are not meant to be limiting and pertain to every sense and antisense RNA sequence set forth in Table 3. Sequences comprising the sense and antisense RNA sequences set forth herein can be utilized to inhibit gene expression in any cell (eukaryotic or prokaryotic), animal or any other organism. These sequences can be cloned into vectors and utilized in vitro, ex vivo or in vivo to decrease gene expression.

shRNA (short hairpin RNA) is a DNA molecule that can be cloned into expression vectors to express siRNA (19-21 nt RNA duplex) for RNAi interference studies. shRNA has the following structural features: a short nucleotide sequence ranging from about 19-29 nucleotides derived from the target gene, followed by a short spacer of about 4-15 nucleotides (i.e. loop) and about a 19-29 nucleotide sequence that is the reverse complement of the initial target sequence. For example, the sense siRNa sequence for any of the genes set forth in Table 3 can be utilized to design and shRNA. As an example, a sense RNA sequence for C10orf3 (SEQ ID NO: 292) was utilized to design an shRNA with an exemplary linker sequence (CGAA). As shown below, the sense sequence is linked via the linker (CGAA) to the antisense sequence to form the top strand. The top strand and the bottom strand are annealed to make a double stranded oligonucleotide that can be cloned into an appropriate vector for expression. The double stranded oligonucleotide can have nucleotide overhangs as depicted below to facilitate cloning. These sequences can be cloned into vectors and utilized in vitro, ex vivo or in vivo to decrease gene expression.

```
Top Strand      5'-CACCG*CCAGAAGTACCAAAGATTTCGAAAAATCTTTGGTACTTCTGG-3'    (SEQ ID NO: 837)
Bottom Strand 5'-AAAACCAGAAGTACCAAAGATTTTTCGAAATCTTTGGTACTTCTGGC*-3'     (SEQ ID NO: 838)
ds Oligo for    5'-CACCGCCAGAAGTACCAAAGATTTCGAAAAATCTTTGGTACTTCTGG-3'     (SEQ ID NO: 839)
c10orf3             ||||||||||||||||||||||||||||||||||||||||||||||
shRNA            3'-CGGTCTTCATGGTTTCTAAAGCTTTTTAGAAACCATGAAGACCAAAA-5'    (SEQ ID NO: 840)
```

Therefore, any sense sequence set forth in Table 3 can be linked to its corresponding antisense sequence with a linker to make a top strand for an shRNA. The bottom strand is the reverse complement of the top strand. The "U"s in the sequence set forth in Table 3 are replaced with "T"s to make DNA strands. The top strand and the bottom strand are then annealed to form the double stranded shRNA. As mentioned above, the top and bottom strand can have overhangs or additional sequence to facilitate cloning into an expression vector.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Methods of using ribozymes to decrease or inhibit RNA expression are known in the art (for example see Kashani-Sabet, J. Investig. Dermatol. Symp. Proc., 7:76-78, 2002).

Generally, the term "antisense" refers to a nucleic acid molecule capable of hybridizing to a portion of an RNA sequence (such as mRNA) by virtue of some sequence complementarity. The antisense nucleic acids disclosed herein can be oligonucleotides that are double-stranded or single-stranded, RNA or DNA or a modification or derivative thereof, which can be directly administered to a cell (for example by administering the antisense molecule to the subject), or which can be produced intracellularly by transcription of exogenous, introduced sequences (for example by administering to the subject a vector that includes the antisense molecule under control of a promoter).

Antisense nucleic acids are polynucleotides, for example nucleic acid molecules that are at least 6 nucleotides in length, at least 10 nucleotides, at least 15 nucleotides, at least 20 nucleotides, at least 100 nucleotides, at least 200 nucleotides, such as 6 to 100 nucleotides. However, antisense molecules can be much longer. In particular examples, the nucleotide is modified at one or more base moiety, sugar moiety, or phosphate backbone (or combinations thereof), and can include other appending groups such as peptides, or agents facilitating transport across the cell membrane (Letsinger et al., Proc. Natl. Acad. Sci. USA 1989, 86:6553-6; Lemaitre et al., Proc. Natl. Acad. Sci. USA 1987, 84:648-52; WO 88/09810) or blood-brain barrier (WO 89/10134), hybridization triggered cleavage agents (Krol et al., BioTechniques 1988, 6:958-76) or intercalating agents (Zon, Pharm. Res. 5:539-49, 1988).

Examples of modified base moieties include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

Examples of modified sugar moieties include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In a particular example, an antisense molecule is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625-41, 1987). The oligonucleotide can be conjugated to another molecule, such as a peptide, hybridization triggered cross-linking agent, transport agent, or hybridization-triggered cleavage agent. Oligonucleotides can include a targeting moiety that enhances uptake of the molecule by host cells. The targeting moiety can be a specific binding molecule, such as an antibody or fragment thereof that recognizes a molecule present on the surface of the host cell.

In a specific example, antisense molecules that recognize a nucleic acid set forth herein, include a catalytic RNA or a ribozyme (for example see WO 90/11364; WO 95/06764; and Sarver et al., Science 247:1222-5, 1990). Conjugates of antisense with a metal complex, such as terpyridylCu (II), capable of mediating mRNA hydrolysis, are described in Bashkin et al. (Appl. Biochem Biotechnol. 54:43-56, 1995). In one example, the antisense nucleotide is a 2'-0-methylribonucleotide (Inoue et al., Nucl. Acids Res. 15:6131-48, 1987), or a chimeric RNA-DNA analogue (Inoue et al., FEBS Lett. 215:327-30, 1987).

The antiviral agents identified utilizing these methods can be used to inhibit viral infection in cells either in vitro, ex vivo or in vivo.

In the methods of the present invention any cell that can be infected with a virus or other pathogen, such as bacteria, parasite or fungi can be utilized. The cell can be prokaryotic or eukaryotic, such as a cell from an insect, fish, crustacean, mammal, bird, reptile, yeast or a bacterium, such as E. coli. The cell can be part of an organism, or part of a cell culture, such as a culture of mammalian cells or a bacterial culture.

The viruses of the present invention include all RNA viruses (including negative stranded RNA viruses, positive stranded RNA viruses, double stranded RNA viruses and retroviruses) and DNA viruses. Examples of viruses include, but are not limited to, HIV (including HIV-1 and HIV-2), parvovirus, papillomaviruses, measles, filovirus (for example, Marburg), SARS (severe acute respiratory syndrome) virus, hantaviruses, influenza viruses (e.g., influenza A, B and C viruses), hepatitis viruses A to G, caliciviruses, astroviruses, rotaviruses, coronaviruses, (for example, human respiratory coronavirus), picornaviruses, (for example, human rhinovirus and enterovirus), Ebola virus, human herpesvirus (such as, HSV-1-9, including zoster, Epstein-Barr, and human cytomegalovirus), foot and mouth disease virus, human adenovirus, adeno-associated virus, smallpox virus (variola), cowpox, monkey pox, vaccinia, polio, viral meningitis and hantaviruses.

For animals, viruses include, but are not limited to, the animal counterpart to any above listed human virus, avian influenza (for example, strains H5N1, H5N2, H7N1, H7N7 and H9N2), and animal retroviruses, such as simian immunodeficiency virus, avian immunodeficiency virus, pseudocowpox, bovine immunodeficiency virus, feline immunodeficiency virus, equine infectious anemia virus, caprine arthritis encephalitis virus and visna virus.

The methods of the present invention can also be used to assess bacterial infection and identify antibacterial agents. Specifically, the same methods are employed but instead of contacting a cell with a virus, the cell is contacted with a bacterium. Therefore, the present invention provides a method of identifying an antibacterial agent comprising a) administering the agent to a cell containing a cellular gene listed in Table 1, b) detecting the level and/or activity of the gene product produced by the cellular gene, a decrease or elimination of the gene product and/or gene product activity indicating a compound with antibacterial activity.

The present invention also provides a method of identifying an antibacterial agent comprising: a) administering the agent to a cell containing a cellular gene listed in Table 1, b) contacting the cell with a bacteria; c) detecting the level of bacterial infection; and d) associating the level of bacterial infection with the level of expression of the gene from Table 1 or the activity of the protein encoded by the gene from Table 1, a decrease or elimination of bacterial infection associated with a decrease or elimination of gene expression and/or activity indicating that the agent is an antibacterial agent.

Examples of bacteria include, but are not limited to, the following: *Listeria* (sp.), *Mycobacterium tuberculosis*, *Rickettsia* (all types), *Ehrlichia*, *Chylamida*. Further examples of bacteria that can be targeted by the present methods include *M. tuberculosis*, *M. bovis*, *M. bovis* strain BCG, BCG substrains, *M. avium*, *M intracellulare*, *M. africanum*, *M. kansasii*, *M. marinum*, *M. ulcerans*, *M. avium* subspecies *paratuberculosis*, *Nocardia asteroides*, other *Nocardia* species, *Legionella pneumophila*, other *Legionella* species, *Salmonella typhi*, other *Salmonella* species, *Shigella* species, *Yersinia pestis*, *Pasteurella haemolytica*, *Pasteurella multocida*, other *Pasteurella* species, *Actinobacillus pleuropneumoniae*, *Listeria monocytogenes*, *Listeria ivanovii*, *Brucella abortus*, other *Brucella* species, *Cowdria ruminantium*, *Chlamydia pneumoniae*, *Chlamydia trachomatis*, *Chlamydia psittaci*, *Coxiella burnetti*, other *Rickettsial* species, *Ehrlichia* species, *Staphylococcus aureus*, *Staphylococcus epidermidis*, *Streptococcus pyogenes*, *Streptococcus agalactiae*, *Bacillus anthracis*, *Escherichia coli*, *Vibrio choterae*, *Campylobacter* species, *Neiserria meningitidis*, *Neiserria gonorrhea*, *Pseudomonas aeruginosa*, other *Pseudomonas* species, *Haemophilus influenzae*, *Haemophilus ducreyi*, other *Hemophilus* species, *Clostridium tetani*, other *Clostridium* species, *Yersinia enterolitica*, and other *Yersinia* species.

Antibacterial agents found to be effective for one bacterium, can also be effective for other bacteria, particularly bacteria from the same family. Therefore, antibacterial agents identified for one bacteria can be tested utilizing the methods of the present invention for antibacterial activity against other bacteria.

The methods of the present invention can also be used to assess parasitic infection and identify antiparasitic agents. Specifically, the same methods are employed but instead of contacting a cell with a virus, the cell is contacted with a parasite. Therefore, the present invention provides a method of identifying an antiparasitic agent comprising a) administering the agent to a cell containing a cellular gene listed in Table 1, b) detecting the level and/or activity of the gene product produced by the cellular gene, a decrease or elimination of the gene product and/or gene product activity indicating a compound with antiparasitic activity.

The present invention also provides a method of identifying an antiparasitic agent comprising: a) administering the agent to a cell containing a cellular gene listed in Table 1, b) contacting the cell with a parasite; c) detecting the level of parasitic infection; and d) associating the level of parasitic infection with the level of expression of the gene from Table 1 or the activity of the protein encoded by the gene from Table 1, a decrease or elimination of parasitic infection associated with a decrease or elimination of gene expression and/or activity indicating that the agent is an antiparasitic agent.

Examples of parasites include, but are not limited to, the following: *Cryptosporidium*, *Plasmodium* (all species), American trypanosomes (*T. cruzi*). Furthermore, examples of protozoan and fungal species contemplated within the present methods include, but are not limited to, *Plasmodium falciparum*, other *Plasmodium* species, *Toxoplasma gondii*, *Pneumocystis carinii*, *Trypanosoma cruzi*, other trypanosomal species, *Leishmania donovani*, other *Leishmania* species, *Theileria annulata*, other *Theileria* species, *Eimeria tenella*, other *Eimeria* species, *Histoplasma capsulatum*, *Cryptococcus neoformans*, *Blastomyces dermatitidis*, *Coccidioides immitis*, *Paracoccidioides brasiliensis*, *Penicillium marneffei*, and *Candida* species.

Antiparasitic agents found to be effective for one parasite, can also be effective for other parasite, particularly parasites from the same family. Therefore, antiparasitic agents identified for one parasitic can be tested utilizing the methods of the present invention for antiparasitic activity against other parasites.

In the methods described herein, once the cell containing a cellular gene listed in Table 1 has been contacted with an agent, the level of infection can be associated with the level of gene expression and/or activity, such that a decrease or elimination of infection associated with a decrease or elimination of gene expression and/or activity indicates that the agent is effective against the pathogen. These methods can be utilized to assess the effects of an agent on bacterial infection, antiviral infection, antifungal infection, antiparasitic infection, to name a few. For example, the level of viral infection can be measured in a cell after administration of siRNA that inhibits expression of a gene set forth in Table 1. If there is a decrease in viral infection, then the siRNA is an effective antiviral agent. The level of viral infection can be assessed by measuring an antigen or other product associated with a particular viral infection (for example, p24 for HIV infection). If there is a decrease in p24 levels after administration of an siRNA directed to a gene set forth in Table 1, the siRNA targeting that gene is an effective antiviral agent against HIV. The level of viral injection can also be measured by real-time quantitative reverse transcription-polymerase chain reaction (RT-PCR) assay (See for example, Payungporn et al. "Single step multiplex real-time RT-PCR for H5N1 influenza A virus detection." *J Virol Methods*. Sep. 22, 2005; Landolt et al. "Use of real-time reverse transcriptase polymerase chain reaction assay and cell culture methods for detection of swine influenza A viruses" *Am J Vet Res.* 2005 January; 66(1): 119-24)

Similarly, the level of viral infection can be measured in a cell, utilizing the methods set forth above and known in the art, after administration of a chemical, small molecule, drug, protein, cDNA, antibody, morpholino, antisense RNA, ribozyme or any other compound. If there is a decrease in viral infection, then the chemical, small molecule, drug, protein, cDNA, antibody, morpholino, antisense RNA, ribozyme or any other compound is an effective antiviral agent. Similar methods can be utilized to measure the levels of other types of infection such as bacterial infection, fungal infection and parasitic infection.

Antiviral agents found to be effective for one virus, can also be effective for other viruses, particularly viruses from the same family. However, it is also contemplated that an agent found to be effective against HIV can also be effective against influenza or avian flu or any other virus. Therefore, antiviral agents identified for one virus can be tested utilizing the methods of the present invention for antiviral activity against other viruses. The level of the gene product can be measured by any standard means, such as by detection with an antibody specific for the protein. The nucleic acids set forth herein and fragments thereof can be utilized as primers to amplify nucleic acid sequences, such as a gene transcript of one of the genes set forth in Table 1 by standard amplification techniques. For example, expression of a gene transcript can be quantified by RT-PCR using RNA isolated from cells. A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965, 188. Each of these publications is incorporated herein by reference in its entirety for PCR methods. One of skill in the art would know how to design and synthesize primers that amplify any of the nucleic acid sequences set forth in Table 1 or a fragment thereof.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified fragment, can be analyzed by one of a number of methods known in the art. The nucleic acid can be sequenced by dideoxy or other methods. Hybridization with the sequence can also be used to determine its presence, by Southern blots, dot blots, etc.

The genes and nucleic acids of the invention can also be used in polynucleotide arrays. Polynucleotide arrays provide a high throughput technique that can assay a large number of polynucleotide sequences in a single sample. This technology can be used, for example, to identify samples with reduced expression of a nucleic acid set forth in Table 1 as compared to a control sample. This technology can also be utilized to determine the effects of reduced expression of a nucleic acid set forth in Table 1. In this way, one of skill in the art can identify genes that are upregulated or downregulated upon reduction of expression of a nucleic acid set forth in Table 1. Similarly, one of skill in the art can identify genes that are upregulated or downregulated upon increased expression of a nucleic acid set forth in Table 1. In this way, other genes can be identified as targets for therapy, such as antiviral therapy, antibacterial therapy, antiparasitic therapy or antifungal therapy.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences set forth under GenBank Accession Nos. in Table 1.

The array can also be a microarray that includes probes to different polymorphic alleles of one or more genes set forth in Table 1. A polymorphism exists when two or more versions of a nucleic acid sequence exist within a population of subjects. For example, a polymorphic nucleic acid can be one where the most common allele has a frequency of 99% or less. Different alleles can be identified according to differences in nucleic acid sequences, and genetic variations occurring in more than 1% of a population (which is the commonly accepted frequency for defining polymorphism) are useful polymorphisms for certain applications.

The allelic frequency (the proportion of all allele nucleic acids within a population that are of a specified type) can be determined by directly counting or estimating the number and type of alleles within a population. Polymorphisms and methods of determining allelic Frequencies are discussed in Hartl, D. L. and Clark, A. G., Principles of Population Genetics, Third Edition (Sinauer Associates, Inc., Sunderland Mass., 1997), particularly in chapters 1 and 2.

These microarrays can be utilized to detect polymorphic alleles in samples from subjects. Such alleles may indicate that a subject is more susceptible to viral infection or less susceptible to viral infection. For example, since the present invention shows that a disruption in any of the genes set forth in Table 1 results in decreased viral infection, such microarrays can be utilized to detect polymorphic versions of the genes set forth in Table 1 that result in decreased gene expression and/or decreased activity of the gene product to identify subjects that are less susceptible to viral infection.

The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

The level of gene product can be compared to the level of the gene product in a control cell not contacted with the compound. The level of gene product can be compared to the level of the gene product in the same cell prior to addition of the compound. Activity or function, can be measured by any standard means, such as by enzymatic assays that measure the conversion of a substrate to a product or binding assays that measure the binding of a protein to a nucleic acid, for example.

Moreover, the regulatory region of the gene can be functionally linked to a reporter gene and compounds can be screened for inhibition of the reporter gene. Such regulatory regions can be isolated from the genomic sequences and identified by any characteristics observed that are characteristic for regulatory regions of the species and by their relation to the start codon for the coding region of the gene. As used herein, a reporter gene encodes a reporter protein. A reporter protein is any protein that can be specifically detected when expressed. Reporter proteins are useful for detecting or quantitating expression from expression sequences. Many reporter proteins are known to one of skill in the art. These include, but are not limited to, β-galactosidase, luciferase, and alkaline phosphatase that produce specific detectable products. Fluorescent reporter proteins can also be used, such as green fluorescent protein (GFP), cyan fluorescent protein (CFP), red fluorescent protein (RFP) and yellow fluorescent protein (YFP).

Viral infection can also be measured via cell based assays. Briefly, cells (20,000 to 2,500,000) are infected with the desired pathogen, and the incubation continued for 3-7 days. The antiviral agent can be applied to the cells before, during, or after infection with the pathogen. The amount of virus and agent administered can be determined by skilled practitioners. In some examples, several different doses of the potential therapeutic agent can be administered, to identify optimal dose ranges. Following transfection, assays are conducted to determine the resistance of the cells to infection by various agents.

For example, if analyzing viral infection, the presence of a viral antigen can be determined by using antibody specific for the viral protein then detecting the antibody. In one example, the antibody that specifically binds to the viral protein is labeled, for example with a detectable marker such as a fluorophore. In another example, the antibody is detected by using a secondary antibody containing a label. The presence of bound antibody is then detected, for example using microscopy, flow cytometry and ELISA.

Alternatively, or in addition, the ability of the cells to survive viral infection is determined, for example, by performing a cell viability assay, such as trypan blue exclusion.

The amount of a protein listed in Table 1, in a cell, can be determines by methods standard in the art for quantitating proteins in a cell, such as Western blotting, ELISA, ELISPOT, immunoprecipitation, immunofluorescence (e.g., FACS), immunohistochemistry, immunocytochemistry, etc., as well as any other method now known or later developed for quantitating protein in or produced by a cell.

The amount of a nucleic acid listed in Table 1, in a cell, can be determined by methods standard in the art for quantitating nucleic acid in a cell, such as in situ hybridization, quantitative PCR, RT-PCR, Taqman assay, Northern blotting, ELISPOT, dot blotting, etc., as well as any other method now known or later developed for quantitating the amount of a nucleic acid in a cell.

The ability of an antiviral agent to prevent or decrease infection by a virus, such as HIV, Ebola, influenza A, SARS, smallpox, to name a few, can be assessed in animal models. Several animal models for viral infection are known in the art. For example, mouse HIV models are disclosed in Sutton et al. (*Res. Initiat Treat. Action,* 8:22-4, 2003) and Pincus et al. (*AIDS Res. Hum. Retroviruses* 19:901-8, 2003); guinea pig models for Ebola infection are disclosed in Parren et al. (*J. Virol.* 76:6408-12, 2002) and Xu et al. (*Nat. Med.* 4:37-42, 1998); and cynomolgus monkey (*Macaca fascicularis*) models for influenza infection are disclosed in Kuiken et al. (*Vet. Pathol.* 40:304-10, 2003). Such animal models can also be used to test agents for an ability to ameliorate symptoms associated with viral infection. In addition, such animal models can be used to determine the $LD_{50}$ and the $ED_{50}$ in animal subjects, and such data can be used to determine the in vivo efficacy of potential agents. Animal models can also be used to assess antibacterial, antifungal and antiparasitic agents.

Animals of any species, including, but not limited to, birds, mice, rats, rabbits, guinea pigs, pigs, micro-pigs, goats, and non-human primates, e.g., baboons, monkeys, and chimpanzees, can be used to generate an animal model of viral infection, bacterial infection, fungal infection or parasitic infection if needed.

For example, for a model of viral infection, the appropriate animal is inoculated with the desired virus, in the presence or absence of the antiviral agent. The amount of virus and agent administered can be determined by skilled practitioners. In some examples, several different doses of the potential therapeutic agent (for example, an antiviral agent) can be administered to different test subjects, to identify optimal dose ranges. The therapeutic agent can be administered before, during, or after infection with the virus. Subsequent to the treatment, animals are observed for the development of the appropriate viral infection and symptoms associated therewith. A decrease in the development of the appropriate viral infection, or symptoms associated therewith, in the presence of the agent provides evidence that the agent is a therapeutic agent that can be used to decrease or even inhibit viral infection in a subject.

The present invention also provides a method of making compound that reduces infection, comprising: a) synthesizing a compound; b) administering the compound to a cell containing a cellular gene set forth in Table 1, c) contacting the cell with an infectious pathogen; c) detecting the level of infection; d) associating the level of infection with the level of expression of the gene from Table 1 or the activity of the protein encoded by the gene from Table 1, a decrease or elimination of infection associated with a decrease or elimination of gene expression and/or activity indicating that a compound that reduces infection was made.

Also provided is a method of making compound that reduces infection, comprising: a) administering the compound to a cell containing a cellular gene set forth in Table 1, b) contacting the cell with an infectious pathogen; c) detecting the level of infection; d) associating the level of infection with the level of expression of the gene from Table 1 or the activity of the protein encoded by the gene from Table 1, a decrease or elimination of infection associated with a decrease or elimination of gene expression and/or activity indicating that a compound is a compound that reduces infection; and e) placing the compound in a pharmaceutically acceptable carrier. The compounds that reduce infection can be antiviral, antibacterial, antifungal or antiparasitic compounds or any compound that reduces infection by an infectious agent.

Transgenic Cells and Non-Human Mammals

Transgenic animal models, including recombinant and knock-out animals, can be generated from the host nucleic acids described herein. Exemplary transgenic non-human mammals include, but are not limited to, mice, rabbits, rats, chickens, cows, and pigs. The present invention provides a transgenic non-human mammal that has a knock-out of one or more genes listed in Table 1 and has a decreased susceptibility to infection by pathogens, such as viruses, bacteria, fingi and parasites. Such knock-out animals are useful for reducing the transmission of viruses from animals to humans. In the transgenic animals of the present invention one or both alleles of one or more genes set forth in Table 1 can be knocked out.

By "decreased susceptibility" is meant that the animal is less susceptible to infection or experiences decreased infection by a pathogen as compared to an animal that does not have one or both alleles of a gene of Table 1 knocked out or functionally deleted. The animal does not have to be completely resistant to the pathogen. For example, the animal can be 10%, 20%, 30%, 40%, 50%, 60%, 70%, 80%, 90%, 100% or any percentage in between less susceptible to infection by a pathogen as compared to an animal that does not have a functional deletion of a gene set forth in Table 1. Furthermore, decreasing infection or decreasing susceptibility to infection includes decreasing entry, replication, pathogenesis, insertion, lysis, or other steps in the replication strategy of a virus or other pathogen into a cell or subject, or combinations thereof.

Therefore, the present invention provides a non-human transgenic mammal comprising a functional deletion of one or more genes listed in Table 1, wherein the mammal has decreased susceptibility to infection by a pathogen, such as a virus, a bacterium, a parasite or a fungus. A functional deletion is a mutation, partial or complete deletion, insertion, or other variation made to a gene sequence that inhibits production of the gene product or renders a gene product that is not completely functional or non-functional.

Expression of the sequence used to knock-out or functionally delete the desired gene can be regulated by an appropriate promoter sequence. For example, constitutive promoters can be used to ensure that the functionally deleted gene is not expressed by the animal. In contrast, an inducible promoter can be used to control when the transgenic animal does or does not express the gene of interest. Exemplary inducible promoters include tissue-specific promoters and promoters responsive or unresponsive to a particular stimulus (such as light, oxygen, chemical concentration, such as a tetracycline inducible promoter).

For example, a transgenic mouse or other transgenic animal including a disrupted gene listed in Table 1 can be examined during exposure to various pathogens. Comparison data can provide insight into the life cycles of pathogens. Moreover, knock-out animals (such as pigs) that are otherwise susceptible to an infection (for example influenza) can be made to resist infection, conferred by disruption of the gene. If disruption of the gene in the transgenic animal results in an increased resistance to infection, these transgenic animals can be bred to establish flocks or herds that are less susceptible to infection.

Transgenic animals, including methods of making and using transgenic animals, are described in various patents and publications, such as WO 01/43540; WO 02/19811; U.S. Pub. Nos: 2001-0044937 and 2002-0066117; and U.S. Pat. Nos. 5,859,308; 6,281,408; and 6,376,743; and the references cited therein.

The transgenic animals of this invention also include conditional gene knockdown animals produced, for example, by utilizing the SIRIUS-Cre system that combines siRNA for specific gene-knockdown, Cre-loxP for tissue-specific expression and tetracycline-on for inducible expression. These animals can be generated by mating two parental lines that contain a specific siRNA of interest gene and tissue-specific recombinase under tetracycline control. See Chang et al. "Using siRNA Technique to Generate Transgenic Animals with Spatiotemporal and Conditional Gene Knockdown." American Journal of Pathology 165: 1535-1541 (2004) which is hereby incorporated in its entirety by this reference regarding production of conditional gene knockdown animals.

The present invention also provides cells including an altered or disrupted gene listed in Table 1 that are resistant to infection by a pathogen. These cells can be in vitro, ex vivo or in vivo cells and can have one or both alleles altered. Such cells therefore include cells having decreased susceptibility to HIV infection, Ebola infection, avian flu, influenza A or any of the other pathogens described herein, including bacteria, parasites and fungi.

Screening for Resistance to Infection

Also provided herein are methods of screening host subjects for resistance to infection by characterizing a nucleotide sequence of a host nucleic acid or the amino acid sequence of a host polypeptide (such as those shown in Table 1). For example, a ANXA1 nucleic acid of a subject can be isolated, sequenced, and compared to the wildtype sequence for ANXA1. The greater the similarity between that subject's ANXA1 nucleic acid and the wildtype ANXA1 sequence, the more susceptible that person is to infection, while a decrease in similarity between that subject's ANXA1 nucleic acid and the wildtype ANXA1 sequence, the more resistant that subject may be to infection. Such screens can be performed for any host nucleic acid or the amino acid sequence of a host polypeptide set forth in Table 1, in any species.

Assessing the genetic characteristics of a population can provide information about the susceptibility or resistance of that population to viral infection. For example, polymorphic analysis of alleles in a particular human population, such as the population of a particular city or geographic area, can indicate how susceptible that population is to infection. A higher percentage of alleles substantially similar to wild-type sequences listed in Table 1 indicates that the population is more susceptible to infection, while a large number of polymorphic alleles that are substantially different than wild-type sequences listed in Table 1 indicates that a population is more resistant to infection. Such information can be used, for example, in making public health decisions about vaccinating susceptible populations.

The present invention also provides a method of screening a cell for a variant form of a gene listed in Table 1. A variant can be a gene with a functional deletion, mutation or alteration in the gene such that the amount or activity of the gene pro duct is altered. These cells containing a variant form of a gene listed in Table 1 can be contacted with a pathogen to determine if cells comprising a naturally occurring variant of a gene listed in Table 1 differ in their resistance to infection. For example, cells from an animal, for example, a chicken, can be screened for a variant form of a gene listed in Table 1. If a naturally occurring variant is found and chickens possessing a variant form of the gene in their genome are less susceptible to infection, these chickens can be selectively bred to establish flocks that are resistant to infection. By utilizing these methods flocks of chickens that are resistant to avian flu can be established. Similarly, other animals can be screened for a variant form of a gene listed in Table 1. If a naturally occurring variant is found and animals possessing a variant form of the gene in their genome are less susceptible to infection, these animals can be selectively bred to establish populations that are resistant to infection. These animals include, but are not limited to, cats, dogs, livestock (for example, cattle, horses, pigs, sheep, goats, etc.), laboratory animals (for example, mouse, rabbit, rat, gerbil, guinea pig, etc.) and avian species (for example, flocks of chickens, geese, turkeys, ducks, pheasants, pigeons, doves etc.). Therefore, the present application provides populations of animals that comprise a naturally occurring variant of a gene listed in Table 1 that results in decreased susceptibility to viral infection, thus providing populations of animals that are less susceptible to viral infection. Similarly, if a naturally occurring variant is found and animals possessing a variant form of the gene in their genome are less susceptible to bacterial, parasitic or fungal infection, these animals can be selectively bred to establish populations that are resistant to bacterial, parasitic or fungal infection.

Methods of Inhibiting Infection

Also provided by the present invention is a method of inhibiting infection in a cell comprising inhibiting expression or activity of a gene or a gene product listed in Table 1. As discussed throughout, infection can be a viral infection, bacterial infection, fungal infection or a parasitic infection, to name a few. Inhibition can occur in a cell, in vitro, ex vivo or in vivo. Expression of one or more genes from Table 1 can be inhibited. Similarly, the activity of one or more gene products listed in Table 1 can be inhibited. Inhibition or a decrease in expression does not have to be complete as this can range from a slight decrease in expression to complete ablation of expression. For example, expression can be inhibited by about 5%, 10%, 20%, 30%, 40%, 50%, 60%, 70%, 80%, 90%, 95%, 99%, 100% or any percentage in between as compared to a control cell wherein the expression of a gene listed in Table 1 has not been inhibited. Similarly, inhibition or decrease in the activity of a gene product does not have to be complete as this can range from a slight decrease to complete ablation of the activity of the gene product. For example, the activity of a gene product can be inhibited by about 5%, 10%, 20%, 30%, 40%, 50%, 60%, 70%, 80%, 90%, 95%, 99%, 100% or any percentage in between as compared to a control cell wherein activity of a gene product listed in Table 1 has not been inhibited.

Antisense oligonucleotides, RNAi molecules, ribozymes and siRNA molecules can be utilized to disrupt expression and/or decrease the activity of a gene product. Small molecules, drugs, antibodies, proteins and chemicals can also be utilized to inhibit expression and/or the activity of a gene product. Antisense oligonucleotides, RNAi molecules, ribozymes, siRNA, small molecules, chemicals, antibodies proteins, cDNAs, and any other compound now known or identified in the future to decrease expression of a gene and/or activity of a gene product set forth in Table 1 can be used alone or in combination with other therapeutic agents such as antiviral compounds, antibacterial agents, antifungal agents, antiparasitic agents, anti-inflammatory agents, anti-cancer agents, etc.

Examples of antiviral compounds include, but are not limited to, amantadine, rimantadine, zanamavir and oseltamavir (Tamiflu) for the treatment of flu and its associated symptoms. Antiviral compounds useful in the treatment of HIV include Combivir® (lamivudine-zidovudine), Crixivan® (indinavir), Emtriva® (emtricitabine), Epivir® (lamivudine), Fortovase® (saquinavir-sg), Hivid® (zalcitabine), Invirase® (saquinavir-hg), Kaletra® (lopinavir-ritonavir), Lexiva™ (fosamprenavir), Norvir® (ritonavir), Retrovir® (zidovudine) Sustiva® (efavirenz), Videx EC® (didanosine), Videx® (didanosine), Viracept® (nelfinavir) Viramune® (nevirapine), Zerit® (stavudine), Ziagen® (abacavir), Fuzeon® (enfuvirtide) Rescriptor® (delavirdine), Reyataz® (atazanavir), Trizivir® (abacavir-lamivudine-zidovudine) Viread® (tenofovir disoprokil fumarate) and Agenerase® (amprenavir). Other antiviral compounds useful in the treatment of Ebola and other filoviruses include ribavirin and cyanovirin-N (CV-N). For the treatment of herpes virus, Zovirax® (acyclovir) is available. Antibacterial agents include, but are not limited to, antibiotics (for example, penicillin and ampicillin), sulfa Drugs and folic acid Analogs, Beta-Lactams, aminoglycosides, tetracyclines, macrolides, lincosamides, streptogramins, fluoroquinolones, rifampin, mupirocin, cycloserine, aminocyclitol and oxazolidinones.

Antifungal agents include, but are not limited to, amphotericin, nystatin, terbinafine, itraconazole, fluconazole, ketoconazole, griselfulvin.

Antiparasitic agents include, but are not limited to, anthelmintics, antinematodal Agents, antiplatyhelmintic agents, antiprotozoal agents, amebicides, antimalarials, antitrichomonal agents, aoccidiostats and trypanocidal agents.

The present invention provides a method of reducing or inhibiting infection in a subject comprising administering to the subject an amount of a composition that inhibits expression or activity of a gene or a gene product in Table 1. As discussed throughout, the infection can be from any pathogen, for example, a virus, a bacteria, a fungus or a parasite. The reduction or inhibition of infection does not have to be complete as this can range from a slight reduction in infection to elimination of the infection. For example, in the methods described herein, there can be a reduction of infection of 10%, 20%, 30%, 40%, 50%, 60%, 70%, 80%, 90%, 95%, 100% or any percentage in between. The reduction can result in amelioration of the symptoms associated with the infection to complete amelioration of the infection. However, complete amelioration of the infection is not necessary for a reduction or inhibition of infection in a subject to be effective in reducing the symptoms associated with the infection or effective in making the subject less susceptible to infection.

As utilized throughout, preventing infection refers to inhibiting the development of an infection. When referring to treatment, this refers to a method that ameliorates a sign or symptom of a disease or pathological condition related to a infection, such as inhibiting or decreasing viral infection and does not require a complete amelioration of symptoms or of the infection.

The present invention also provides a method of reducing or inhibiting infection in a subject comprising mutating ex vivo in a selected cell from the subject a gene listed in Table 1 to a mutated gene incapable of producing a functional gene product of the gene or to a mutated gene producing a reduced amount of a functional gene product of the gene and replacing the cell in the subject, thereby reducing infection of cells in the subject.

Any cell that can be infected with a virus or other pathogen, such as a bacterium, a fungus or a parasite is contemplated herein. A host cell can be prokaryotic or eukaryotic, such as a cell from an insect, crustacean, mammal, bird, reptile, yeast, or a bacterium such as *E. coli*. Exemplary host cells include, but are not limited to, mammalian B-lymphocyte cells, hematopoeitic cells, embryonic stem cells, embryonic germ line cells, pluripotent stem cells and totipotent stem cells.

For example, a subject susceptible to or suffering from an infection can be treated with a therapeutically effective amount of an antisense oligonucleotide, a RNAi molecule, a ribozyme or a siRNA molecule (or combinations thereof). After the antisense oligonucleotide, an RNAi molecule, a ribozyme or a siRNA molecule has taken effect (a decreased level of viral infection is observed, or symptoms associated with viral infection decrease), for example after 24-48 hours, the subject can be monitored for symptoms associated with viral infection.

Similarly, other agents, such as an antibody, polypeptide, small molecule or other drug that interacts with a host protein from Table 1 can also be used to decrease or viral infection. This interaction can be direct, such as binding to the host protein or indirect, such as binding to or modulating a protein that interacts with a host protein from Table 1. After the antibody, polypeptide, small molecule or other drug has taken effect (a decreased level of infection is observed, or symptoms associated with infection decrease), for example after 24-48 hours, the subject can be monitored for symptoms associated with infection. Other agents such as peptides and organic or inorganic molecules can also be administered to a subject in a therapeutically effective amount.

The treatments disclosed herein can also be used prophylactically, for example, to inhibit or prevent infection, such as viral infection, bacterial infection, fungal infection or parasitic infection. Such administration is indicated where the treatment is shown to have utility for treatment or prevention of the disorder. The prophylactic use is indicated in conditions known or suspected of progressing to disorders associated with infection.

In certain instances, some genes when disrupted by the present method of retrovirus insertion, resulted in overexpression of the gene product, and this overexpression inhibited viral replication. For example, upon disrupting the genomic locus comprising the sequence of CTCF this resulted in an overexpression of IGF2 which led to decreased viral replication. Therefore, the present invention provides a method of decreasing or inhibiting viral replication by overexpressing genes that lead to decreased viral replication. The present invention also provides a method of increasing the expression of genes whose overexpression decreases viral replication by disrupting the a gene, or inhibiting the gene product of a gene that results in increased expression of the gene whose overexpression decreases viral replication. For example, one could inhibit CTCF in order to increase expression of IGF2. This would be similar for any gene found to increase the expression of another gene and results in decreased viral replication.

Once a gene is found that upon disruption results in overexpression of another gene, the gene that is overexpressed can be modulated directly, i.e., via the overexpressed gene, or indirectly, i.e., via the gene that was originally disrupted (or its gene product) or via another gene (or its gene product) associated with the overexpressed gene.

Therefore, the present invention provides a method of identifying an agent that increases the expression of a gene and/or the activity of a gene product comprising contacting a cell with the agent and measuring an increase in gene expression and/or activity of the gene product.

The present invention also provides a method of identifying an agent that decreases or inhibits infection via overexpression of a gene and/or an increase in the activity of a gene product comprising administering the agent to the cell, contacting the cell with a pathogen and associating an increase in gene expression and/or activity of the gene product with the level of infection such that an increase in gene expression and/or activity of the gene product accompanied by a decrease in infection indicates that the agent inhibits infection by the pathogen via overexpression of the gene and/or an increase in the activity of the gene product.

For example, one of skill in the art can administer a compound that results in the overexpression of IGF2. This compound may interact with the IGF2 gene, IGF2 mRNA, the IGF2 protein or a fragment thereof. Information for the human IGF 2 gene and its related sequences can be found under Entrez Gene number 3481. The compound could also interact with the CTCF gene, CTCF mRNA, the CTCF protein or a fragment thereof to increase IGF2 expression. The compound can also interact with other genes, mRNAs or proteins involved in the IGF2 pathway, resulting in increased IGF2 expression.

Therefore, if disruption of gene X results in overexpression of gene Y, the gene that is overexpressed (Y) can be modulated directly, i.e. via the overexpressed gene (Y), or indirectly, i.e., via the gene that was originally disrupted (X) (or its gene product) or via another gene (or its gene product) associated with the overexpressed gene (Y). For example, one of skill in the art can administer a compound that results in the overexpression of Y. This compound may interact with the Y gene, Y mRNA or the Y protein. The compound could also interact with the X gene, X mRNA or the X protein to increase Y expression. The compound can also interact with other genes, mRNAs or proteins involved in the gene Y pathway (i.e. a cellular pathway in which gene Y is involved), resulting in increased Y expression.

Pharmaceutical Compositions and Modes of Administration

Various delivery systems for administering the therapies disclosed herein are known, and include encapsulation in liposomes, microparticles, microcapsules, expression by recombinant cells, receptor-mediated endocytosis (Wu and Wu, *J. Biol. Chem.* 1987, 262:4429-32), and construction of therapeutic nucleic acids as part of a retroviral or other vector. Methods of introduction include, but are not limited to, mucosal, topical, intradermal, intramuscular, intraperitoneal, vaginal, rectal, intravenous, subcutaneous, intranasal, and oral routes. The compounds can be administered by any convenient route, for example by infusion or bolus injection, by absorption through epithelial or mucocutaneous linings (for example, oral mucosa, rectal, vaginal and intestinal mucosa, etc.) and can be administered together with other biologically active agents. Administration can be systemic or local. Pharmaceutical compositions can be delivered locally to the area in need of treatment, for example by topical application or local injection.

Pharmaceutical compositions are disclosed that include a therapeutically effective amount of a RNA, DNA, antisense molecule, ribozyme, siRNA, molecule, drug, protein, antibody or other therapeutic agent, alone or with a pharmaceutically acceptable carrier. Furthermore, the pharmaceutical compositions or methods of treatment can be administered in combination with (such as before, during, or following) other therapeutic treatments, such as other antiviral agents, antibacterial agents, antifungal agents and antiparasitic agents.

Delivery Systems

The pharmaceutically acceptable carriers useful herein are conventional. *Remington's Pharmaceutical Sciences*, by Martin, Mack Publishing Co., Easton, Pa., 15th Edition (1975), describes compositions and formulations suitable for pharmaceutical delivery of the therapeutic agents herein disclosed. In general, the nature of the carrier will depend on the mode of administration being employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

Embodiments of the disclosure including medicaments can be prepared with conventional pharmaceutically acceptable carriers, adjuvants and counterions as would be known to those of skill in the art.

The amount of therapeutic agent effective in decreasing or inhibiting infection can depend on the nature of the pathogen and its associated disorder or condition, and can be determined by standard clinical techniques. Therefore, these amounts will vary depending on the type of virus, bacteria, fungus, parasite or other pathogen. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

In an example in which a nucleic acid is employed to reduce infection, for example, a viral infection, such as an antisense or siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). The present disclosure includes all forms of nucleic acid delivery, including synthetic oligos, naked DNA, plasmid and viral delivery, integrated into the genome or not.

As mentioned above, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell.*

*Biol.* 6:2895, 1986). The recombinant retrovirus can then be used to infect and thereby deliver to the infected cells a nucleic acid, for example an antisense molecule or siRNA. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), and pseudotyped retroviral vectors (Agrawal et al., *Exper. Hematol.* 24:738-747, 1996). Other nonpathogenic vector systems such as the foamy virus vector can also be utilized (Park et al. "Inhibition of simian immunodeficiency virus by foamy virus vectors expressing siRNAs." *Virology.* 2005 Sep. 20). It is also possible to deliver short hairpin RNAs (shRNAs) via vector delivery systems in order to inhibit gene expression (See Pichler et al. "In vivo RNA interference-mediated ablation of MDR1 P-glycoprotein." *Clin Cancer Res.* 2005 Jun. 15; 11(12):4487-94; Lee et al. "Specific inhibition of HIV-1 replication by short hairpin RNAs targeting human cyclin Ti without inducing apoptosis." *FEBS Lett.* 2005 Jun. 6; 579(14):3100-6.).

Physical transduction techniques can also be used, such as liposome delivery and receptor-mediated and other endocytosis mechanisms (see, for example, Schwartzenberger et al., *Blood* 87:472-478, 1996) to name a few examples. This invention can be used in conjunction with any of these or other commonly used gene transfer methods.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

Viruses are obligate intracellular parasites that rely upon the host cell for different steps in their life cycles. The characterization of cellular genes required for virus infection and/or cell killing will be essential for understanding viral life cycles, and can provide cellular targets for new antiviral therapies.

Candidate genes required for lytic reovirus infection were identified by tagged sequence mutagenesis, a process that permits rapid identification of genes disrupted by gene entrapment. One hundred fifty-one reovirus resistant clones were selected from cell libraries containing $2 \times 10^5$ independently disrupted genes, of which 111 contained mutations in previously characterized genes and functionally anonymous transcription units. Collectively, the genes associated with reovirus resistance differed from genes targeted by random gene entrapment in that known mutational hot spots were under represented, and a number of mutations appeared to cluster around specific cellular processes, including: IGF-II expression/signaling, vesicular transport/cytoskeletal trafficking and apoptosis.

Tagged sequence mutagenesis provides a rapid, genome-wide strategy to identify candidate cellular genes required for virus infection.

Cellular genes are likely to participate in all phases of viral life cycles including attachment to cellular receptors, internalization, disassembly, translation of mRNA, assembly and egress from the cells [1]. The susceptibility to virus infection varies greatly among different cell types, and virus-resistant cells frequently emerge post-infection [2-4]. This suggests that genetic determinants can influence host cell contributions to the virus life cycle. Despite examples of mammalian genes that influence virus infection, the identification of such genes has been hampered by the lack of practical methods for genetic analysis in cultured cells. In the present study, whether tagged sequence mutagenesis—a gene entrapment strategy widely used to mutate genes in mouse embryonic stem cells [5-10] could be used to identify candidate cellular genes required for lytic infection by reovirus, a small cytolytic RNA virus that replicates in the cytoplasm was tested. The mammalian reoviruses serve as useful models for virus-host cell interaction due to their capacity to replicate preferentially in proliferating and undifferentiated cells [3].

Gene traps are efficient mutagens as assessed by studies in mice of mutations induced originally in embryonic stem cells. In somatic cells, the approach assumes that loss-of-function mutations induced by gene entrapment may confer reovirus resistance as a result of gene dosage effects (e.g. haploinsufficiency), pre-existing heterozygosity or loss of heterozygosity. Following infection with the U3NeoSV1 retrovirus gene trap shuttle vector, libraries of mutagenized rat intestinal epithelial (RIE)-1 cell clones were isolated in which each clone contained a single gene disrupted by provirus integration [6]. The entrapment libraries were infected with reovirus type 1, and virus-resistant clones were selected under conditions that also selected against the emergence of persistently infected cells (PI) that may express virus resistance in the absence of cellular mutations [4]. Genes disrupted in a total of 151 reovirus resistant cells were identified by sequencing regions of genomic DNA adjacent to the entrapment vector [6]; of these, 111 contained mutations in previously characterized genes and anonymous transcription units.

Reovirus-resistant clones were selected at higher frequencies from entrapment libraries than from non-mutagenized cells, suggesting that reovirus-resistant phenotypes were induced by gene trap mutagenesis. However in any genetic screen, clones with the selected phenotype may arise from spontaneous mutations, and consequently, additional experiments are required to demonstrate that individual genes disrupted by gene entrapment actually contribute to the reovirus-resistant phenotype. For example, a mutation in Ctcf, a transcriptional repressor of insulin growth factor II (IGF-II), was one of 4 mutations associated with reovirus resistance that affected IGF-II expression and/or signaling. Subsequent experiments demonstrated that enforced IGF-II expression is sufficient to confer high levels of reovirus resistance [4]. In short, genes collectively identified by tagged sequence mutagenesis in a panel of reovirus resistant clones provide candidates for mechanistic studies of cellular processes that participate in the virus lifecycle. Since the disrupted genes do not adversely affect cell survival, drags that inhibit proteins encoded by the genes are not expected to be overtly toxic to cells. Hence, the candidate genes also include targets for novel anti-viral therapies.

RIE-1, L-Cells and Virus:

Reovirus type 1, strain Lang, was initially obtained from Bernard N. Fields. Virus was passaged in L-cells and a third passaged stock was purified over a CsCl gradient as previously described and was used for these experiments [59]. To develop PI cell lines, RIE-1 cells were infected with reovirus type 1, at a multiplicity of infection (MOI) of 5, and surviving cells were maintained in Dulbecco's modification of Eagle's minimum essential medium (DMEM) (Irvine Scientific, Santa Ana, Calif., USA). The herpes simplex virus (HSV)-1 clone, HSV-1 KOStk12, that expresses a reporter gene, lacZ, as an immediate-early gene [46] was a generous gift of Patricia Spear, Northwestern University, USA. For RIE-1 and L-cells, medium was supplemented with 10% fetal bovine serum, 2 mM per ml, L-Glutamine 100 units per ml, Penicillin, and 100 µg per ml Streptomycin (Irvine Scientific, Santa Ana, Calif., USA) [complete medium]. In some experiments, serum was omitted from the medium. The continuance of cell monolayers following infection with reovirus or HSV-1 was determined by staining with gentian violet.

Tagged Sequence Mutagenesis and Selection for Reovirus Resistance:

Following infection of RIE-1 cells with the U3neoSV1 vector, MOI of 0.1, mutagenized cells were selected for neomycin resistance in medium containing 1 mg/ml G418 sulfate (Clontech, Palo Alto, Calif., USA) [6]. Twenty libraries of mutant RIE-1 cells, and one library of A549 human adenocarcinoma cells, each consisting of $10^4$ gene entrapment events, were expanded until approximately $10^3$ sibling cells represented each mutant clone. These cells were plated at a sub-confluent density and incubated in serum-free media for 3 days until they became quiescent, and infected with reovirus serotype 1, MOI of 35 plaque forming units (pfu) per cell. Eighteen hours following infection, the cells were detached with trypsin, and plated in DMEM medium containing 10% fetal bovine serum (FBS) (Hyclone Laboratories, Inc., Logan, Utah, USA). After 6 hrs, the medium was removed and cells were maintained in serum-free medium until only a few cells remained attached to the flask. On average, one to ten clones were recovered from a library consisting of $10^7$ mutant cells, an enrichment for selected cells of six orders of magnitude. Cells that survived the selection were transferred to cell culture plates in media containing 10% FBS and cells were divided for extraction of DNA and cryopreservation.

Transcription and Translation of HSV-1 Immediate Early Gene Reporter:

The transcription and translation of the HSV-1 immediate early gene reporter gene, lacZ, was determined by standard northern blot techniques and β-galactosidase assay, respectively.

Generation of Libraries of Mutagenized RIE-1 Cells:

Libraries of mutagenized cells were infected with reovirus serotype-1, strain Lang, to select for clones resistant to lytic infection. Selection of virus-resistant clones was performed in serum-free medium to suppress the emergence of persistently infected (PI) cells [4]. This is important since PI cells, which arise by a process involving adaptive mutations in both the virus and the cell genomes [60], provide a means whereby RIE-1 cells can acquire virus resistance in the absence of cellular mutations. Uninfected RIE-1 cells undergo growth arrest, whereas PI RIE-1 cells are killed in serum-free medium.

DNA Sequence Analysis:

Genomic DNA immediately adjoining the 5' end of the proviral insert in each of 130 cell lines was cloned by plasmid rescue [6]. Approximately 300 to 600 base pairs of this flanking DNA were sequenced and compared with the non-redundant (nr) and expressed sequence tag (dbEST) nucleic acid databases [61]. The probability of a match with orthologous sequences in the databases varies due to interspecies variation, the amount of exon in the flanking DNA (in cases where the flanking DNA matches cDNA sequences), alternative splicing and sequencing errors. Matches with sequences in the database were considered potentially significant if probability score was <$10^{-5}$ and the sequence was non-repetitive. In most cases, the matching gene was in the same transcriptional orientation as the provirus. Moreover, matches involving cDNA sequences were co-linear across exons present in the flanking genomic DNA and diverged at splice sites. As indicated, virtually all of the genes identified had matches to murine, rat, or human gene sequences with p<$10^{-10}$.

Tagged Sequence Mutagenesis and Selection of Reovirus Resistant Clones

Twenty libraries of mutagenized RIE-1 cells, each representing approximately $10^4$ independent gene trap events, were isolated following infection with the U3NeoSV1 gene trap retrovirus. U3NeoSV1 contains coding sequences for a neomycin resistance gene in the U3 region of the viral long terminal repeat (LTR). Selection for neomycin resistance generates clones with proviruses inserted within actively transcribed genes. Cells pooled from each entrapment library were separately infected with Type 1 reovirus at a multiplicity of infection of 35, and reovirus-resistant clones were selected in serum-free media to suppress the emergence of persistently infected (PI) cells (ref). A total of 151 reovirus-resistant clones were isolated—approximately 1 mutant per $10^3$ gene trap clones or 1 mutant per $10^7$ reovirus infected cells. For comparison, the frequency of recovering resistant clones from RIE-1 cells not mutagenized by gene entrapment was less than $10^{-8}$. This suggests that reovirus-resistant phenotypes were induced by gene trap mutagenesis.

Figure 1B:
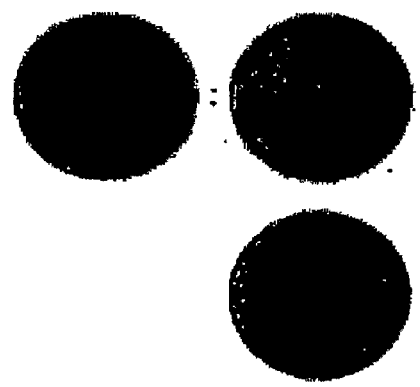
Figure 2:
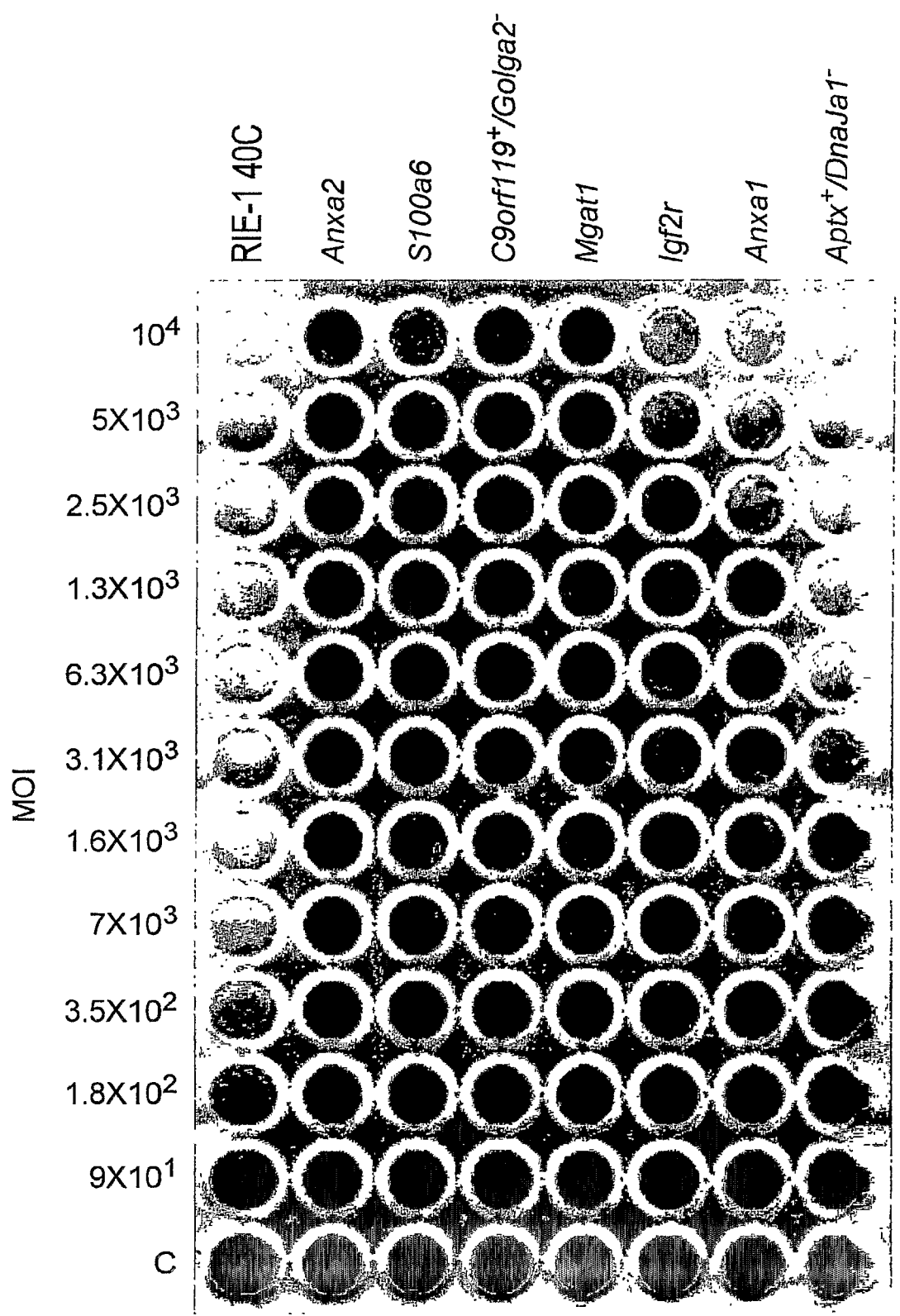
FIG. 2 shows RIE-1 mutant cells resist lytic infection by reovirus. The columns contain an unselected RIE-1 cell library, RIE-140° C., and representative reovirus resistant mutant cell clones. Serial two-fold dilutions of reovirus were made with the highest titer in the upper row, MOI=1×10$^4$. Resistance to reovirus type 1 infection was observed in the mutant cells 3 to 7 days post-infection. The bottom row of cells, denoted "C", were not infected to serve as controls for cell viability and proliferation. Cells were stained with gentian violet four days post-infection. A clear well indicates cell death following virus infection.

Reovirus-resistant cells selected in serum-free media did not express viral antigens (FIG. 1) and did not produce infectious virus as assessed by plaque assay. Most clones were resistant to infection by high titer reovirus and were further analyzed (FIG. 2). While reovirus resistance did not initially result from the establishment of a persistent infection, many clones became persistently infected upon subsequent passages, presumably because mutant cells that display virus resistance are susceptible to the establishment of a PI state [2] from residual virus used in selection.

Identification of Genes Disrupted in Reovirus-Resistant Clones

The U3NeoSV1 gene trap vector contains a plasmid origin of replication and ampicillin resistance gene; thus, regions of genomic DNA adjacent to the targeting vector were readily cloned by plasmid rescue and sequenced [6]. The flanking sequences were compared to the nucleic acid databases to identify candidate cellular genes that confer resistance to lytic infection by reovirus when altered by gene entrapment. Altogether, the 151 cloned flanking sequences matched 111 annotated gene and transcription units in the public DNA sequence databases [non-redundant (nr), high-throughput genomic sequences (htgs), and human, mouse, and rat genome sequences [6]. 40 flanking sequences were uninformative because they matched repetitive elements or regions of genomic DNA not associated with any annotated transcription unit.

Figure 3:
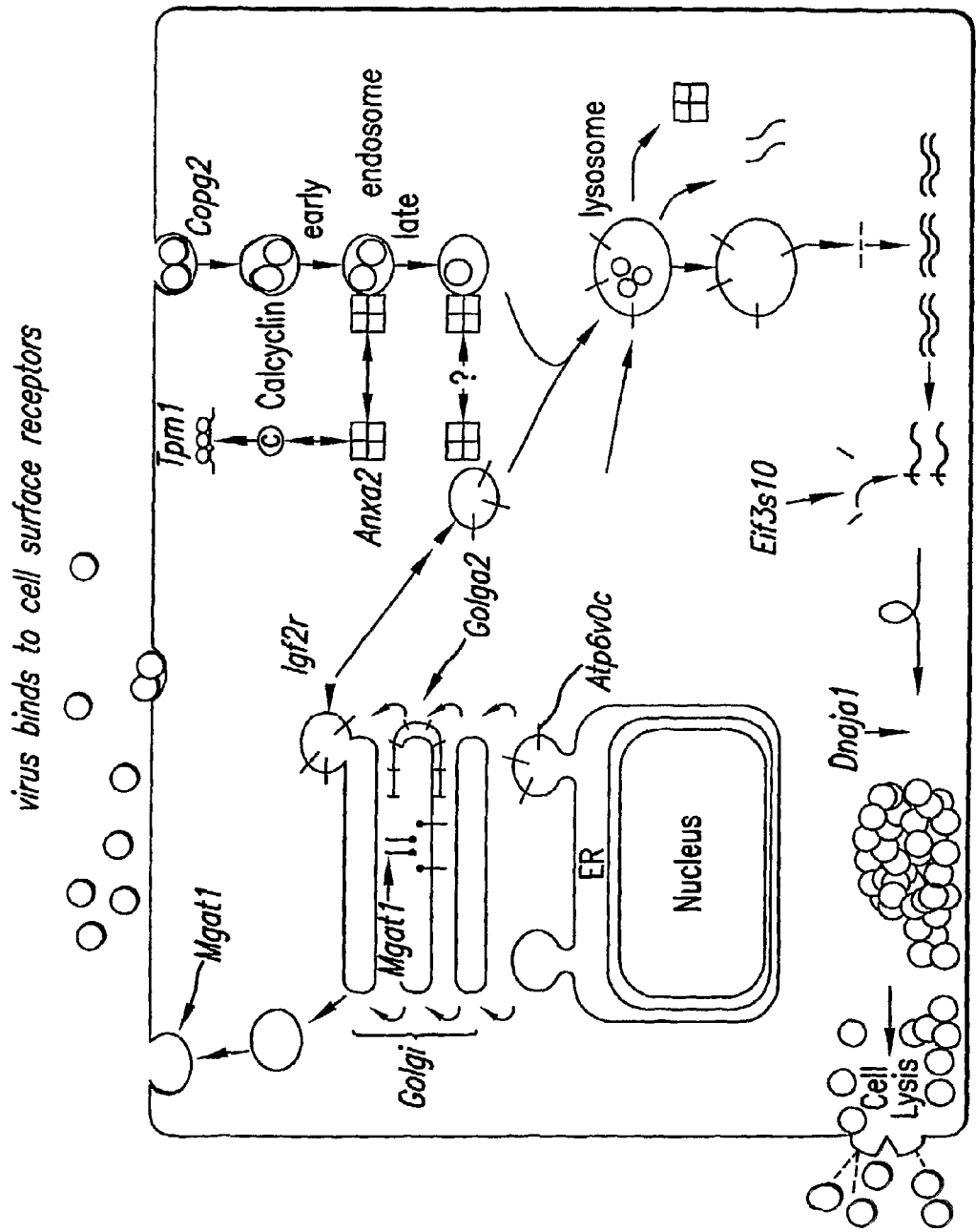
FIG. 3 shows a model of the life cycle of reovirus and proposed checkpoints based on function of the cellular genes identified by insertional mutagenesis in the present application. The virus life cycle begins (top, clockwise) with virus binding to cell surface receptor and being endocytosed into early endosomes. These endosomes then associate with annexin-II (Anax2) [85] and fuse with annexin-II-associated vesicles containing newly synthesized lysosomal enzymes migrating from the Golgi [86], which further fuse with the lysosome. The vacuolar H$^+$-ATPase acidifies the lysosome, allowing acid-dependent proteases to digest the outer coat from the virus particles and activate them [87]. These activated particles then pass through the lysosomal membrane and begin transcription of mRNA. The Golgi protein gm 130 (Golga2) is believed to mediate the docking of vesicles as they carry their newly synthesized cargo through the Golgi stack [88, 89]. N-acetylglucosaminyl transferase I (Mgat1) initiates the glycosylation of cell surface proteins (for example, receptors) and may play a major role, through kinship recognition, in helping maintain the correct assortment of lysosomal enzymes [90-94]. The Igf2r shuttles enzymes bound for the lysosome from the Golgi [95] and transfer cathepsins to the lysosome. Igf2 over expression may alter the delivery of igf2r bound cargo to the lysosome (Sheng J, Organ E L, Hao C, Wells, K S, Ruley H E, Rubin D H. 2004. Mutations in the IGF-II pathway that confer resistance to lytic reovirus infection. BMC Cell Biology, 5:32 (27 Aug. 2004). Calcyclin and the α-tropomyosins specifically bind each other, and calcyclin is known to bind Anxa2 [16, 20]. Thus, they could be involved in endosome fusion. Eif3s10 specifically binds the virus message to begin its preferential translation. The DnaJa1 protein could facilitate the proper folding of virus proteins with its chaperone function [96]. However, DnaJa1 protein and Eif3 could play additional roles in virus trafficking or apoptosis, respectively. Eventually, morphogenesis is complete when crystalline-like arrays of new virions form, cell lysis occurs, and virus is released. Many of the cellular proteins encoded by mutated genes have direct or indirect roles in trafficking of endosomes or lysosomal fusion and thus could play roles in the early disassembly or delivery of transcriptionally active virions to the appropriate cell location.

Table I lists genes disrupted in reovirus resistant clones for which some functional information is available. The Table also includes genes that encode proteins that are known to physically interact. Genes associated with particular metabolic or signaling pathways are shown in Table 2. These include gene products that could play potential roles in all aspects of virus replication: entry, disassembly, transcription, translation, and reassembly (Table 1, 2, FIG. 3). Eleven genes encoding calcyclin, insulin growth factor binding protein 5 protease (prss11), type C-like lectin protein (Clr)-f and -C, Dnaja1–/Aprataxin+ (Aprx), GATA binding protein 4 (Gata4), Bcl2 like-1 (Bcl2l1); and chromosome 10 open reading frame 3 (Chr10orf3) and myoferlin, fer-1 like protein 3 (Fer1l3), S100a6 (encoding calcyclin), and two functionally anonymous cDNAs were independently mutated in separate cell libraries (Table 1). The proviruses in these independent of mutant clones were located within 7 to over 1500 nucleotides of each other.

Resistance to HSV-1

Experiments were conducted to determine if genes were resistant to HSV-1 infection. These experiments utilized HSV-1(KOS)tk12, an infectious virus that expresses a lacZ reporter as an immediate-early gene [46]. Four clones, with mutations in the Eif3s10, AnxaI, Mgat1, and Igf2r genes, were resistant to HSV-I infection and there was a diminished capacity to express the immediate-early lacZ reporter gene. Clones with mutations in Eif3s10, Mgat1, and Ig2r also show decreases in transcription and translation of virus mRNA and cell death. Mutations in the Igf2r are known to affect HSV replication [15, 54, 58]; whereas, association of HSV replication with proteins encoded by the Eif3s10, Anxa1, and Mgat1 are novel. These data show that some of the candidate genes discovered in clones surviving reovirus infection can affect common cellular processes that are used by other viruses.

TABLE I

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Loc310836 (Abca4) | ATP-binding cassette, subfamily A (ABC1), member 4 | 2q41 | 1p22.1-p21 | XP_241525 | NM_000350 | NP_000341 | 6BE65_T7 | AR228076 BD069426 SEQ ID NO: 69 from U.S. Pat. No. 6,448,000; | 310836 | 24 |
| Anxa1 | annexin A1 | 1q51 | 9q12-q21.2 | U25159 | NM_000700 | NP_000691 | 6B37H_T7 | AR228072 BD069422 sequence 65 from U.S. Pat. No. 6,448,000; | 25380 | 301 |
| Anxa2 | annexin A2 | 8q24 | 15q21-q22 | NM_019905 | NM_001002857 NM_001002858 NM_004039 | NP_001002857 NP_001002858 NP_004030 | 7A7_rE | AR228047 BD069397 sequence 40 from U.S. Pat. No. 6,448,000; BD078939 SEQ ID NO: 19 from U.S. Pat. No. 6,777,177; | 56611 | 302 |
| Anx3 | annexin A3 | 14p22 | 4q13-q22 | NM_012823 | NM_005139 | NP_005130 | 70A-rE | BD079025 SEQ ID NO: 105 from U.S. Pat. No. 6,777,177 | 25291 | 306 |
| Aptx-/dnaja1 [Hsj2] | aprataxin/DnaJ (Hsp40) homolog, subfamily A, member 1 | 5q22 | 9p13.3 | NW_07454 | NM_017692 NM_175069 NM_175071 NM_175072/ NM_001539 | NP_060162 NP_778239 NP_778241 NP_778242/ NP_001530 | 12_3b#7-rE 12_3B#8-rE 9B27_2_rE | BD078944 SEQ ID NO: 24 U.S. Pat. No. 6,777,177 BD078943 SEQ ID NO: 23 from U.S. Pat. No. 6,777,177 BD078945 | 259271 65028 | 54840 3301 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Atp6v0c | ATPase, H+ transporting, lysosomal 16 kDa, V0 subunit c | 10q12 | 16p13.3 | NC_000016 | NM_001694 | NP_001685 | 6BE3_lac | SEQ ID NO: 25 from U.S. Pat. No. 6,777,177 AR228008, BD069358 SEQ ID NO: 1 from U.S. Pat. No. 6,448,000 | 170667 | 527 |
| Bcl2l1 | Bcl2-like1 | 3q41.2 | 20q11.21 | NP_238186 | NM_001191 NM_138578 | NP_001182 NP_612815 | L197B3E-rE L24 5-3-rE L24-4-4-rE | BD079008 SEQ ID NO: 88 from U.S. Pat. No. 6,777,177, BD079032 SEQ ID NO: 112, U.S. Pat. No. 6,777,177 | 24888 | 598 |
| Brd2 | bromodomain-containing 2 | 20p12 | 6p21.3 | XP_238186 | NM_005104 | NP_005095 | 36_5_2_6-rE | BD078987 SEQ ID NO: 67 from U.S. Pat. No. 6,777,177 | 294276 | 6046 |
| Brd3/Wdr5 | Bromodomain-containing 3/ WD repeat domain 5 | 3p12 | 9q34 | XP_342398 XP_342397 | NM_007371/ NM_017588 NM_052821 | NP_031397/ NP_060058 NP_438172 | 1A_rE | AR228036, BD069386 SEQ ID NO: 29 from U.S. Pat. No. 6,448,000 | 362093 | 8019/ 11091 |
| C9orf119+/ Golga2- | gene of unknown function Golgi autoantigen, Golgin subfamily a, 2 | 3p11 | 9q34.13 | NW_047652 NM_022596 | XM_372143 BC029911 NM_004486 | XP_372143 AAH29911 NP_004477 | 6_3_6_2E-rE | BD078967 SEQ ID NO: 47 from U.S. Pat. No. 6,177,177 | 375757 64528 | 375757 2801 |

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| C10orf3 | chromosome 10 open reading frame 3 | 1q54 | 10q23.33 | XP_220034 | NM_018131 | NP_060601 | 14_24#6-rE L24_5-3-rE L192A3E-rE 6b52-rE | AR228054 BD069404 SEQ ID NO: 47 from U.S. Pat. No. 6,448,000; BD078938 SEQ ID NO: 88 from U.S. Pat. No. 6,777,177 BD078978 SEQ ID NO: 58 from U.S. Pat. No. 6,777,177 AR228049 BD069399 SEQ ID NO: 42 from U.S. Pat. No. 6,448,000 | 55165 | 55165 |
| Cald1 | caldesmon 1 | 4q22 | 7q33 | NM_013146 | NM_004342 NM_033138 NM_033139 NM_033140 NM_033157 | NP_004333 NP_149129 NP_149130 NP_149131 NP_149347 | 191E3E-rE | BD078958 SEQ ID NO: 38 from U.S. Pat. No. 6,777,177 | 25687 | 800 |
| Calm2 | calmodulin 2 (phosphorylase kinase, delta) | 6q11-q12 | 2p21 | NM_017326 | NM_001743 | NP_001734 | 32-3-2#1E/-rE | BD078921 SEQ ID NO: 1 from U.S. Pat. No. 6,777,177 | 50663 | 805 |
| Celsr2 | cadherin, EGF LAG seven-pass G-type receptor 2 | 4q11 | 1p21 | NW_047687 | NM_001408 | NP_001399 | 12_4b_9-rE | AR228032., SEQ ID NO: 25 from U.S. Pat. No. 6,448,000; AR228027 SEQ ID | 83465 | 1952 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Clr-f | killer cell lectin-like receptor F1 | 4q12 | N/A | XM_232399 | N/A | N/A | 36_7_1a-rE SCA9#14_rE | NO: 20 from U.S. Pat. No. 6,448,000 BD069377; BD069382 BD078982 SEQ ID NO: 62 from U.S. Pat. No. 6,777,177 AR228038 SEQ ID NO: 31 from U.S. Pat. No. 6,448,000 | 312745 | N/A |
| Copg2/ | coatomer protein complex, subunit gamma 2/ | 4q22 | 7q32 | NW_047355/ | NM_012133/ | NP_036265 | 36_5_2-19b_lac 12cx#11-rE | AR228051, SEQ ID NO: 44 | 301742 | 26958 |
| Tsga13 | testis specific gene A13-variegated monoallelic expression 1 | | | XP_231582 | NM_052933 | NP_443165 | | from U.S. Pat. No. 6,448,000; BD078955 SEQ ID NO: 35 from U.S. Pat. No. 6,777,177, BD078941, BD069401, BD078988 SEQ ID NO: 68 from U.S. Pat. No. 6,777,177, | 312203 | 114960 |
| Cstf2t | cleavage stimulation factor, 3' pre-RNA, subunit 2, 64 kDa | 1q52 | 10q11 | NW_047565 | NM_015235 | NP_056050 | 19_9BE_rE | BD078960 SEQ ID NO: 40 from U.S. Pat. No. 6,777,177, BD078958 SEQ ID | 309338 | 23283 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Csmd2 | CUB and sushi multiple domains 2 | 5q36 | 1p35.1-p34.3 | XP_232753 | NM_052896 | NP_443128 | L24_9_1-rE | NO: 38 from U.S. Pat. No. 6,777,177 BD079033 SEQ ID NO: 113 in U.S. Pat. No. 6,777,177 | 313040 | 114784 |
| Ctcf | CCCTC-binding factor (zinc finger protein) | 19q12 | 16q21-q22.3 | NP_114012 | NM_006565 | NP_006556 | 6BE72_rE | AR228009 BD069366 SEQ ID NO: 2 from U.S. Pat. No. 6,448,000; | 83726 | 10664 |
| Cut11/ | cut-like 1, CCAAT displacement protein | 12q12 | 7q22.1 | XP_341054 | NM_001913 NM_181500 NM_181552/ | NP_001904 NP_852477 NP_853530/ | 31_3_17_rE | BD079017 BD078994 SEQ ID NO: 74 | 116639/ | 1523 |
| Mylc2pl+ | (Drosophila) myosin light chain 2, precursor lymphocyte-specific | | | XP_344098 | NM_138403 | NP_612412 | | from U.S. Pat. No. 6,777,177 | 363900 | 93408 |
| Dlx2 | distal-less homeo box 2 similar to TES-1 homeobox | 3q21 | 2q32 | XP_230986 | NM_004405 | NP_004396 | L24_4_2BE_rE | BD079037 SEQ ID NO: 117 from U.S. Pat. No. 6,777,177 | 296499 | 1746 |
| DnajaI | DnaJ (Hsp40) homolog, subfamily A, member 1 | 5q22 | 9p13-p12 | NP_075223 | NM_001539 | NP_001530 | 10_46_4-Lac 12_3B#8-rE | BD078944 SEQ ID NO: 24 from U.S. Pat. No. 6,777,177 | 65028 | 3301 |
| Dre1 Also known as KLHL24 | Dre1 protein | 11q23 | 3q27.1 | NM_181473 | NM_017644 | NP_060114 | 10_4b_4-rE | AR228014, SEQ ID NO: 7 from U.S. Pat. No. 6,448,000; BD069364 BD078933 SEQ ID | 303803 | 54800 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| E2ig2 | Estrogen induced gene 2 | 1q32 | 11q13.3 | NP_057649 | NM_016565 | NP_057649 | L197B3E-rE for | NO: 13 from U.S. Pat. No. 6,777,177 BD078972 SEQ ID NO: 52 from U.S. Pat. No. 6,777,177 | | 51287 |
| Eif3s10 | Elongation initiation factor 3 subunit 10 | 1q55 | 10q26 | NW_047570 | NM_003750 | NP_003741 | 12PSA#6_rE | AR228011 BD069361 SEQ ID NO: 4 from U.S. Pat. No. 6,448,000 | 292148 | 8661 |
| Erbb2ip | Erbb2 interacting protein | 2q12 | 5q13.1 | XP_345149 | NM_018695 | NP_061165 | SCA9#14_rE ScB2#19-rE | AR228015 BD069365 SEQ ID NO: 8 from U.S. Pat. No. 6,448,000 | | 55914 |
| Ferl13 | fer-1-like protein 3, myoferlin | 1q53 | 10q24 | NW_047565 | NM_013451 NM_133337 | NP_038479 NP_579899 | 14_24_#6-rE 6b52-re | AR228049, BD069399 SEQ ID NO: 42 from U.S. Pat. No. 6,448,000 | | 26509 |
| Fkbp8 | FK506 binding protein 8, 38 kDa | 16p14 | 19p12 | XP_214316 | NM_012181 | NP_036313 | 31_3_15#1_Lac 31_3_15#1_rE 31_3_6_2-rE. | BD079018 BD078996 SEQ ID NO: 76 from U.S. Pat. No. 6,777,177; BD079016, BD078993 SEQ ID NO: 96 from U.S. Pat. No. 6,777,177 | | 23770 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Fusip1 | FUS interacting protein (serine-arginine rich) 1 | 5q36 | 1p36.11 | XP_342949 | NM_006625 NM_054016 | NP_006616 NP_473357 | L28ap-rE | BD079009 SEQ ID NO: 89 from U.S. Pat. No. 6,777,177 | 362630 | 10772 |
| Gas5 | Growth arrest specific 5 | 13q21 | 1q23.3 | U77829 | AK025846 AL110141 BC038733 | N/A | 10_4A_8_rE | AR228010 BD069360 SEQ ID NO: 3 from 6,448,000 | 81714 | 60674 |
| Gata4 | GATA binding protein 4 | 15p12 | 8p23.1-p22 | NW_047454 | NM_002052 | NP_002043 | 10_2A_3_12-rE 10_2A_3-rE | AR228023 SEQ ID NO: 16 from U.S. Pat. No. 6,448,000 BD069373; AR228024 SEQ ID NO: 17 from U.S. Pat. No. 6,448,000 | | 2626 |
| Grb2 | Growth factor receptor bound protein 2 | 10q32.2 | 17q24-q25 | NP_110473 | NM_002086 NM_203506.. | NP_002077 NP_987102. | 36_5_2_19a | In process | 81504 | 2885 |
| Gtf2e1/ | General transcription factor IIE, polypeptide 1, alpha 56 kDa; | 11q22 | 3q21-q24 | XP_221426 | NM_005513/ | NP_005504/ | L195B1E | BD078975 SEQ ID NO: 55 from U.S. Pat. No. 6,777,177 | | 2960 |
| Rabl3 | RAB, member of RAS oncogene family-like 3 | | 20q11.21 | XP_340993 | NM_173825 | NP_776186 | RA3_A-rE RA2#C_rE | | 360720 | 285282 |
| HM13 | histocompatibility (minor) 13, human gene from A549 cell library | 1q21 | 19q13.2 | | NM_030789. | NP_110416 | RA2_A-rE | | | 81502 |
| HNRPL | heterogeneous nuclear ribonucleoprotein L-human gene from A549 cell library | | | | NM_001533 | NP_001524 | | | | 3191 |
| Hoxc13 | Homeo box C13 | 7q36 | 12q13.3 | XP_345881 | NM_017410. | NP_059106 | L191B2E#3+_rE | BD078923 SEQ ID | 366995 | 3229 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Hp1-bp74 | heterochromatin protein 1, binding protein 74 | 5q36 | 1p36.13 | NM_199108 | NM_016287 | NP_057371 | 10_3bE | 6,777,177 AR228022; BD069372 SEQ ID NO: 15 from U.S. Pat. No. 6,448,000 | 313647 | 50809 |
| Hspc135+/ Mox2r | HSPC135 protein homologue/ Cd200 receptor 2 | 11q21 | 3q13.2 | XP_340986 NP_076443 | NM_014170/ NM_138806 NM_138939 NM_138940 NM_170780 | NP_054889/ NP_620161 NP_620385 NP_620386 NP_740750 | 14D#8 | AR228059 BD069409 SEQ ID NO: 52 from U.S. Pat. No. 6,448,000; | 360714/ | 29083 131450 |
| Id3 | Inhibitor of DNA binding 3, dominant negative helix-loop-helix protein | 5q36 | 1p36.13-p36.12 | NP_037190 | NM_002167 | NP_002158 | 21_5_8E-rE 21_5_7E-rE 21_5_9E-rE | BD078974 SEQ ID NO: 54 from U.S. Pat. No. 6,777,177, BD078924 SEQ ID NO: 122 from U.S. Pat. No. 6,777,177 | 25585 | 3399 |
| Igf2r | Insulin-like growth factor 2 receptor (IGF2R) | 1q11 | 6q26 | NW_047553 | NM_000876 | NP_000867 | L192B3E#13_rE | BD078980 SEQ ID NO: 60 from U.S. Pat. No. 6,777,177 | 25151 | 3482 |
| Jak1 | Tyrosine-protein kinase JAK1 | 5q33 | 1p32.3-p31.3 | XP_342873 | NM_002227 | NP_002218 | 18A_8_4E-rE | BD078969 BD079044 SEQ ID NO: 49 | 362552 | 3716 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Kif13b | guanylate kinase associated kinesin | 15p12 | 8p12 | XP_224288 | NM_015254 | NP_056069. | 194c4e-rE | U.S. Pat. No. 6,777,177 BD078976 SEQ ID NO: 56 from U.S. Pat. No. 6,777,177 | 305967 | 23303 |
| Klhl6 | kelch-like 6 | 11q23 | 3q27.3 | NW_047358 | NM_130446 | NP_569713 | 10_3b_2_rE 10_4b_4_rE | AR228020 BD069370 SEQ ID NO: 13 from U.S. Pat. No. 6,448,000; BD078933 SEQ ID NO: 13 from U.S. Pat. No. 6,777,177; AR228014 SEQ ID NO: 7 from U.S. Pat. No. 6,488,000 | | 89857 |
| Ki-67 | proliferation related antigen | 2q26 | 10q25 | XP_227096 | NM_002417 | NP_002408 | 12_4b#11_rE | AR228033., BD069383 SEQ ID NO: 26 from U.S. Pat. No. 6,488,000 | 310382 | 4288 |
| Lipc/ LOC363090 Human Genbank accession Nos. and Entrez Gene correspond to Lipc gene | lipase, member H glyceraldehyde-3-phosphate dehydrogenase (phosphorylating) | 8q24 | 15q21-q23 | NM_012597XP_343422 | NM_000236/ | NP_000227/ | 6BSA12_rE | AR228018, BD069368 SEQ ID NO: 11 from U.S. Pat. No. 6,448,000; AR228046 BD069396 SEQ ID NO: | 24538/ 363090 | 3990 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Madh7 | MAD, mothers against decapentaplegic homolog 7 (*Drosophila*) | 18q12.3 | 18q21.1 | NW_047516 | NM_005904 | NP_005895. | 14A7re | 39 from U.S. Pat. No. 6,448,000; BD078950 SEQ ID NO: 30 from U.S. Pat. No. 6,777,177 | | 4092 |
| IKBζ (MAIL) | Molecule possessing ankyrin repeats induced by lipopolysaccharide | 11q12 | 3p12-q12 | NW_047355 | NM_031419 NM_001005474 | NP_113607 NP_001005474 | 31_3_9_rE | BD079015 BD078992 SEQ ID NO: 95 from U.S. Pat. No. 6,777,177, | | 64332 |
| Map3k7ip1 | Mitogen-activated protein kinase kinase kinase 7 interacting protein 1 | 7q34 | 22q13.1 | NW_047780 | NM_006116 NM_153497 | NP_006107 NP_705717 | 34X24_126-rE | BD078985 SEQ ID NO: 65 from U.S. Pat. No. 6,777,177 | | 10454 |
| Mapt | Microtubule-associated protein TAU | 10q32.1 | 17q21.1 | NM_017212 | NM_005910 NM_016834 NM_016835 NM_016841 | NP_005901 NP_058518 NP_058519 NP_058525 | 12_3B#7 | AR228033, BD069383 SEQ ID NO: 26 from U.S. Pat. No. 6,448,000; | 360248 | 4137 |
| Mgat1 | mannosyl (alpha-1,3-)-glycoprotein beta-1,2-N-acetyl-glucosaminyl-transferase | 10q21 | 5q35 | NW_047334 | NM_002406 | NP_002397 | 14_7#2E__rE | AR228012, BD069362, SEQ ID NO: 5 from U.S. Pat. No. 6,448,000; BD079013 SEQ ID NO: 93 from U.S. Pat. No. 6,777,177 BD078952 SEQ ID NO: 32 | 81519 | 4245 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Mical2 | flavoprotein oxidoreductase | 1q33 | 11p15.3 | NP_872610 | NM_014632. | NP_055447 | 12C#A_rE | from U.S. Pat. No. 6,777,177; AR228031, BD069381 SEQ ID NO: 24 from U.S. Pat. No. 6,448,000; BD078931 SEQ ID NO: 11 form U.S. Pat. No. 6,777,177; | 365352 | 9645 |
| Ocil | osteoclast inhibitory lectin C-type | 4q32 | 12p13 | XP_342770 | NM_001004419 NM_001004420 NM_013269 | NP_001004419 NP_001004420 NP_037401 | 14XD#12E-rE 191E9E-rE | AR228081, SEQ ID NO: 74 from U.S. Pat. No. 6,448,000; BD079024; BD069431.; BD078961 SEQ ID NO: 41 from U.S. Pat. No. 6,777,177; BD078951 SEQ ID NO: 31 from U.S. Pat. No. 6,777,177; | 113937 | 29121 |
| OL16 [Asam in humans] | adipocyte specific protein 5 and splice variant ol-16 | 8q22 | 11q24.1 | NM_173154 | NM_024769 | NP_079045 | X236E1_T7 X236E1_T3 | | 286939 | 79827 |
| Numb | putative inhibitor of Notch signaling | 6q31 | 14q24.3 | XP_234394 | NM_003744 | NP_003735 | SCA7#5_rE | AR228078 SEQ ID NO: 71 from U.S. Pat. No. 6,448,000; | 29419 | 8650 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Pde4b-/ | phosphodiesterase 4B, cAMP-specific (phosphodiesterase E4 dunce homolog, Drosophila) | 5q32 | 1p31 | NP_058727 | NM_002600 | NP_002591 | 34X25_23_Lac | BD078990 SEQ ID NO: 70 from U.S. Pat. No. 6,777,177 | 24626 | 5142 |
| Pgy1-(Abcb1)/ | ATP-binding cassette, sub-family B (MDR/TAP), member 1 | 4q12 | 7q21.1 | NM_012623 | NM_000927 | NP_000918 | 34X23_3-rE | BD078989 SEQ ID NO: 69 from U.S. Pat. No. 6,777,177 | 24646 | 5243 |
| Prss11 | protease, serine, 11 (IGF binding) | 1q37 | 10q26.3 | NP_113909 | NM_002775 | NP_002766 | 12CXY#7_rE | BD069425 AR228075 SEQ ID NO: 68 from U.S. Pat. No. 6,448,000 | 65164 | 5654 |
| Psa | Aminopeptidase puromycin sensitive | 10q31 | 17q21 | NW-047338 | NM_006310 | NP_006301 | 8C5_6_rE | BD069403; AR228053 SEQ ID NO: 46 from U.S. Pat. No. 6,448,000 | 50558 | 9520 |
| Psma7 | proteasome (prosome, macropain) subunit, alpha type, 7 | 3q43 | 20q13.33 | XP_342599 | NM_002792 NM_152255 | NP_002783 NP_689468 | 12CX#11E_rE 35 5 1 4a-rE I | BD078983 SEQ ID NO: 62 from U.S. Pat. No. 6,777,177 | 29674 | 5688 |
| Pts | 6-pyruvoyl-tetrahydropterin synthase | 8q23 | 11q22.3-q23.3 | NP_058916 | NM_000317 | NP_000308 | 19D5E_rE | BD078942 SEQ ID NO: 22 from U.S. Pat. No. 6,777,177 | 29498 | 5805 |
| Rfp2 | ret finger protein 2 or Trim13 | 15p12 | 13q14 | NM_005798 | NM_005798 NM_052811 NM_213590 | NP_005789 NP_434698 NP_998755 | 1A_A549_6_rE | | | 10206 |
| Rps18 | S18 ribosomal protein, cytosolic, substrate for Ca2+/calmodulin- | 5q24 | 6p21.3 | XP_232915 | NM_022551 | NP_072045 | 12_4b#11_rE 12_4b#7_rE | AR228028 BD069378 SEQ ID NO: 21 | 298014 | 6222 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| | activated protein kinase II | | | | | | | from U.S. Pat. No. 6,448,000; | | |
| Rin2 | ras association (RalGDS/AF-6) domain containing protein JC265; RAB5 interacting protein 2 | 3q41 | 20p11 | XP_230647 | NM_018993 | NP_061866 | 12_3B#10-rE | AR228026 BD069376 SEQ ID NO: 19 from 6,448,000 | 311494 | 54453 |
| Rorl | Receptor tyrosine kinase-like orphan receptor 1 | 5q33 | 1p32-p31 | XP_238402 | NM_005012 | NP_005003 | 12_6B#6_rE | AR228030, BD069380 SEQ ID NO: 23 from U.S. Pat. No. 6,448,000 | 117094 | 4919 |
| Rraga | Ras-related GTP binding A | 5q32 | 9p21.3 | NP_446425 | NM_006570 | NP_006561 | L193A1E#A_rE | BD078977 SEQ ID NO: 57 from U.S. Pat. No. 6,777,177 | 117044 | 10670 |
| Ryk | Receptor-like tyrosine kinase | 8q32 | 3q22 | XP_343459 | NM_002958 | NP_002949 | 19-7ae_rE | BD078959 SEQ ID NO: 39 from U.S. Pat. No. 6,777,177 | 140585 | 6259 |
| S100a6/ | S100 calcium binding protein A6 (calcyclin)/ | 2q34 | 1q21 | NP_445937 | NM_014624/ | NP_055439/ | L25_10-Lac 18_3#3E-rE is SEQ ID NO: 6 and 3_2_4-rE is 61 and 110 from U.S. pat. No. 6,777,177 SEQ ID NO: 111 is L25-10-rE SEQ ID NO: 114 is 17-L25-27#7-rE | AR228013., SEQ ID NO: 6 from U.S. Pat. No. 6,777,177 BD069363, BD079030 SEQ ID NO: from U.S. Pat. Nos. 61 and 110 | 85247 | 6277 |
| S100a1 | S-100 protein, alpha chain | | | XP_215606 | NM_006271 | NP_006262 | SEQ ID NO: 109 is 3_2_13-rE SEQ ID NO: 115 is L21C1E-rE | 6,777,177 BD078981, BD079031 SEQ ID NO: 111 | 295214 | 6271 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| | | | | | | | | from U.S. Pat. No. 6,777,177, BD079034 SEQ ID NO: 114 from U.S. Pat. No. 6,777,177, BD079029 SEQ ID NO: 109 from U.S. Pat. No. 6,777,177, BD079035 SEQ ID NO: 115 from U.S. Pat. No. 6,777,177, | | |
| Scmh1 | sex comb on midleg homolog 1 (Drosophila) | 5q36 | 1p34 | XP_342901 | NM_012236 | NP_036368 | 38_17#2_rE | In process | | 22955 |
| Serp1 | Stress-associated endoplasmic reticulum protein 1 | 15q11 | 3q25.1 | NM_030835 | NM_014445 | NP_055260 | 191E8E_rE | BD078962 SEQ ID NO: 42 from U.S. Pat. No. 6,777,177 | 80881 | 27230 |
| Srp19 | signal recognition particle 19 kDa | 18p12 | 5q21-q22 | NW_047510 | NM_003135. | NP_003126 | 14C_2E_rE | BD078963 SEQ ID NO: 43 from U.S. Pat. No. 6,777,177, | 291685 | 6728 |
| Stmn1 | Stathmin, microtubule-depolymerizing protein | 8q31 | 1p36.1-p35 | XP_343442 | NM_005563 NM_203399 NM_203401 | NP_005554 NP_981944 NP_981946 | SCA#1_rE | AR228025, BD069375 SEQ ID NO: 18 from U.S. Pat. No. 6,448,000; | 363108 | 3925 |
| Tpm1 | tropomyosin 1 (alpha) | 8q24 | 15q22.1 | NW_047799 | NM_000366 | NP_000357 | 6BE60_rE | BD078934 SEQ ID NO: 14 | 24851 | 7168 |

TABLE I-continued

| GENE | Definition | Rat CHR | Human CHR | Rat Genbank Accession | Human Genbank Accession # for mRNA | Human GenBank Accession # for protein | Clone Designation | Genbank Accession # for Nucleic Acid Insert | Entrez Gene for Rat Gene | Entrez Gene for Human Gene |
|---|---|---|---|---|---|---|---|---|---|---|
| Trim52 | Tripartite motif-containing 52 | 15q22 | 5q35.3 | XM_224468 | NM_032765 | NP_116154 | L24_26_2A-rE L24_3_2B-rE L24_26_1-BL | from U.S. Pat. No. 6,777,177 BD079011 SEQ ID NO: 91 from U.S. Pat. No. 6,777,177; BD079005 SEQ ID NO: 85 from U.S. Pat. No. 6,777,177; BD079002 SEQ ID NO: 82 from U.S. Pat. No. 6,777,177 | 290458 | 84851 |
| Tsec-2+/Mthfd1 | tsec-2+/C1-tetrahydrofolate synthase- | 6q24 | 14q24 | NW_047761 NM_022508 | NM_005956 | NP_005947 | 36_5_2_196-rE 14D#18-rE | AR228055 BD069405 SEQ ID NO: 48 from U.S. Pat. No. 6,448,000, | 299152 64300 | 4522 |
| Ube1c | ubiquitin-activating enzyme E1C | 4q34 | 3p24.3-p13 | NP_476553 | NM_003968 NM_198195 NM_198197 | NP_003959 NP_937838 NP_937840 | 12_3B#2_rE | AR228029 BD069379 SEQ ID NO: 22 from 6,448,000, | 117553 | 9039 |
| Zfp207 | zinc finger protein 207 | 10q26 | 17q12 | XP_221231 | NM_003457 | NP_003448 | 31_3_5-rE | BD078995 SEQ ID NO: 75 from U.S. Pat. No. 6,777,177 | 303763 | 7756 |
| Znt7 | Zinc finger protein 7 | 7q34 | 8q24 | XP_235457 | NM_003416 | NP_003407 | 1bw_lac | | 315101 | 7553 |

TABLE 2

Classification of trapped genes according to function.
Trapped genes are listed by the official HUGO Gene Nomenclature Committee names, when available. Functional placement of genes or their products are determined by literature assignments. Some genes perform more than one cellular role, and are classified arbitrarily and others have undefined roles.

Transcription

Brd2
Brd3
Ctcf
E2f2
Gtf2e1
Hnrpl
Hoxc13
Hp1-bp74
Id3
Znf207
Zfp7

Translation

Cstf2
Eif3s10
Srp19

Cytoskeletal-Related

Anx3
Cald1
Calm2
Mapt
Ppm1a
Rps18
Stmn1
Tpm1
Kif13b

Apoptosis

Bcl2l
Cycs
IkB☐
Mical2
Rfp2

Membrane

Abca4
Csmd2
Celsr2
Erbb2ip
OL16
Pgy1
Rab13
Serp1

Metabolism

Gas5
Lipc
Mgat1
Pts

TABLE 2-continued

Classification of trapped genes according to function.
Trapped genes are listed by the official HUGO Gene Nomenclature Committee names, when available. Functional placement of genes or their products are determined by literature assignments. Some genes perform more than one cellular role, and are classified arbitrarily and others have undefined roles.

Signaling

E2ip2
Fusip1
Fkbp8
Gata4
Grb2
Jak1
Madh7
Map3k7ip1
Pde4b
Rraga
Ryk

Chaperonin

Dnaja1

Ubiquitination/Proteosome

Ube1c
Psma7

Vesicle/Trafficking

Anxa1
Anxa2
Atp6v0c
Copg2
Golga2
Hm13
Igf2r
Psa
Rin2
Rabl3
S100a6

Unassigned

Aptx
Clr-f
Dre1
Dlx2
Hspc135
Klhl6
Mox2r
Numb
Ocil
Ror1
Scmh1
Trim52
Wdr5

TABLE 3

| Gene Name: | ABCA4 | GenBank Accession No: | NM_000350 | | GI: | 4557875 |
|---|---|---|---|---|---|---|
| Organism: | Homo sapiens | Length: | 7318 | | ORF Region: | 82-6903 |
| Locus: | 24 | | | | ORF GC%: | 52.58 |
| Definition: | Blast database: Homo sapiens ATP-binding cassette, sub-family A (ABC1), member 4 (ABCA4), mRNA. | | | | | |
| Name | Start | Sense RNA Sequence 5'-3' | | Antisense RNA Sequence 5'-3' | Region | GC% |
| NM_000350_siRNA_458 | 458 | GGACAGAGCUACACACUCUU (SEQ ID NO: 1) | | AAGAGUGUAGCUCUGUCC (SEQ ID NO: 2) | ORF | 47.36842105 |
| NM_000350_siRNA_869 | 869 | GCCGUUCUCAAGGUAUCAA (SEQ ID NO: 3) | | UUGAUACCUUGAGAACGGC (SEQ ID NO: 4) | ORF | 47.36842105 |
| NM_000350_siRNA_880 | 880 | GGUAUCAAUCUGAGAUCUU (SEQ ID NO: 5) | | AAGAUCUCAGAUUGAUACC (SEQ ID NO: 6) | ORF | 36.84210526 |
| NM_000350_siRNA_1734 | 1734 | GGUAUUCCCUGACAUGUAU (SEQ ID NO: 7) | | AUACAUGUCAGGGAAUACC (SEQ ID NO: 8) | ORF | 42.10526316 |
| NM_000350_siRNA_1864 | 1864 | GCUGAUCCCUGGAAGAUU (SEQ ID NO: 9) | | AAUCUUCCACGGGAUCAGC (SEQ ID NO: 10) | ORF | 52.63157895 |
| Gene Name: | ANXA1 | GenBank Accession No: | NM_000700 | | GI: | 4502100 |
| Organism: | Homo sapiens | Length: | 1399 | | ORF Region: | 75-1115 |
| Locus: | 301 | | | | ORF GC% | 44.48 |
| Definition: | Blast database: Homo sapiens annexin A1 (ANXA1), mRNA. | | | | | |
| Name | Start | Sense RNA Sequence 5'-3' | | Antisense RNA Sequence 5'-3' | Region | GC% |
| NM_000700_siRNA_318 | 318 | GCAGCAUAUCUCCAGGAAA (SEQ ID NO: 11) | | UUUCCUGGAGAUAUGCUGC (SEQ ID NO: 12) | ORF | 47.36842105 |
| NM_000700_siRNA_609 | 609 | GCUUUGCUUUCUCUUGCUA (SEQ ID NO: 13) | | UAGCAAGAGAAAGCAAAGC (SEQ ID NO: 14) | ORF | 42.10526316 |
| NM_000700_siRNA_775 | 775 | GCAGAGUGUUUCAGAAAUA (SEQ ID NO: 15) | | UAUUUCUGAAACACUCUGC (SEQ ID NO: 16) | ORF | 36.84210526 |
| NM_000700_siRNA_942 | 942 | GGAACUCGCCAUAAGGCAU (SEQ ID NO: 17) | | AUGCCUUAUGGCGAGUUCC (SEQ ID NO: 18) | ORF | 52.63157895 |
| NM_000700_siRNA_1058 | 1058 | GGAUGAAACCAAAGGAGAU (SEQ ID NO: 19) | | AUCUCCUUUGGUUUCAUCC ((SEQ ID NO: 20) | ORF | 42.10526316 |

TABLE 3-continued

| Gene Name: | ANXA2 | GenBank Accession No. | NM_001002857 | | GI: | 50845385 |
|---|---|---|---|---|---|---|
| Organism: | Homo sapiens | Length: | 1644 | | ORF Region | 137-1156 |
| Locus: | 302 | Blast database: | Human | | ORF GC% | 48.14 |
| Definition: | | Homo sapiens annexin A2 (ANXA2), transcript variant 2, mRNA. | | | | |
| Name | Sense RNA Sequence 5'-3' | | Antisense RNA Sequence 5'-3' | | Region | GC% |
| NM_001002857_siRNA_844 | CCCUUAUGACAUGUUGGAA (SEQ ID NO: 21) | | UUCCAACAUGUCAUAAGGG (SEQ ID NO: 22) | | ORF | 42.10526316 |
| NM_001002857_siRNA_845 | CCUUAUGACAUGUUGGAAA (SEQ ID NO: 23) | | UUUCCAACAUGUCAUAAGG (SEQ ID NO: 24) | | ORF | 36.84210526 |
| NM_001002857_siRNA_1071 | GCAAGUCCCUGUACUAUUA (SEQ ID NO: 25) | | UAAUAGUACAGGGACUUGC (SEQ ID NO: 26) | | ORF | 42.10526316 |
| Gene Name: | ANXA2 | GenBank Accession No. | NM_001002858 | | GI: | 50845387 |
| Organism: | Homo sapiens | Length: | 1635 | | ORF Region: | 74-1147 |
| Locus: | 302 | Blast database: | Human | | ORF GC% | 48.89 |
| Definition: | | Homo sapiens annexin A5 (ANXA2), transcript variant 1, mRNA. | | | | |
| Name | Sense RNA Sequence 5'-3' | | Antisense RNA Sequence 5'-3' | | Region | GC% |
| NM_001002858_siRNA_835 | CCCUUAUGACAUGUUGGAA (SEQ ID NO: 27) | | UUCCAACAUGUCAUAAGGG (SEQ ID NO: 28) | | ORF | 42.10526316 |
| NM_001002858_siRNA_836 | CCUUAUGACAUGUUGGAAA (SEQ ID NO: 29) | | UUUCCAACAUGUCAUAAGG (SEQ ID NO: 30) | | ORF | 36.84210526 |
| NM_001002858_siRNA_1062 | GCAAGUCCCUGUACUAUUA (SEQ ID NO: 31) | | UAAUAGUACAGGGACUUGC (SEQ ID NO: 32) | | ORF | 42.10526316 |
| Gene Name: | ANXA2 | GenBank Accession No. | NM_004039 | | GI: | 50845389 |
| Organism: | Homo sapiens | Length: | 1563 | | ORF Region: | 56-1075 |
| Locus: | 302 | Blast database: | Human | | ORF GC% | 48.14 |
| Definition: | | Homo sapiens annexin A2 (ANXA2), transcript variant 3, mRNA. | | | | |
| Name | Sense RNA Sequence 5'-3' | | Antisense RNA Sequence 5'-3' | | Region | GC% |
| NM_004039_siRNA_763 | CCCUUAUGACAUGUUGGAA (SEQ ID NO: 33) | | UUCCAACAUGUCAUAAGGG (SEQ ID NO: 34) | | ORF | 42.10526316 |

TABLE 3-continued

| Name | Start | Sense RNA Sequence 5'-3' | Antisense RNA Sequence 5'-3' | Region | GC% |
|---|---|---|---|---|---|
| NM_004039_siRNA_764 | 764 | CCUAUGACAUGUUGGAAA (SEQ ID NO: 35) | UUUCCAACACUGUCAUAAGG (SEQ ID NO: 36) | ORF | 36.84210526 |
| NM_004039_siRNA_990 | 990 | GCAAGUCCCUGUACUAUUA (SEQ ID NO: 37) | UAAUAGUACAGGGACUUGC (SEQ ID NO: 38) | ORF | 42.10526316 |

Gene Name: ANXA3
GenBank Accession No. NM_005139
Organism: Homo sapiens
Length: 1339
GI: 4826642
Locus: 306
ORF Region: 47-1018
ORF GC%: 42.8
Definition: Blast database: Homo sapiens annexin A3 (ANXA3), mRNA.
Human

| Name | Start | Sense RNA Sequence 5'-3' | Antisense RNA Sequence 5'-3' | Region | GC% |
|---|---|---|---|---|---|
| NM_005139_siRNA_317 | 317 | CCAGCAGUCUUUGAUGCAA (SEQ ID NO: 39) | UUGCAUCAAAGACUGCUGG (SEQ ID NO: 40) | ORF | 47.36842105 |
| NM_005139_siRNA_332 | 332 | GCAAAGCAGCUAAAGAAAU (SEQ ID NO: 41) | AUUUCUUUAGCUGCUUUGC (SEQ ID NO: 42) | ORF | 36.84210526 |
| NM_005139_siRNA_405 | 405 | GGACAAGCAGGCAAAUGAA (SEQ ID NO: 43) | UUCAUUUGCCUGCUUGUCC (SEQ ID NO: 44) | ORF | 42.10526316 |
| NM_005139_siRNA_411 | 411 | GCAGGCAAAUGAAGGAUAU (SEQ ID NO: 45) | AUAUCCUUCAUUUGCCUGC (SEQ ID NO: 46) | ORF | 47.36842105 |
| NM_005139_siRNA_827 | 827 | GCCUUGAAGGGUAUUUGGAA (SEQ ID NO: 47) | UUCCAAUACCCUUCAAGGC (SEQ ID NO: 48) | ORF | 47.36842105 |

Gene Name: APTX
GenBank Accession No. NM_017692
Organism: Homo sapiens
Length: 2016
GI: 28329424
Locus: 54840
ORF Region: 605-1111
ORF GC%: 47.93
Definition: Blast database: Homo sapiens aprataxin (APTX), transcript variant 4, mRNA.
Human

| Name | Start | Sense RNA Sequence 5'-3' | Antisense RNA Sequence 5'-3' | Region | GC% |
|---|---|---|---|---|---|
| NM_017692_siRNA_956 | 956 | GCUGUGAUCGAGAUGGUAC (SEQ ID NO: 49) | GUACCAUCUCGAUCACAGC (SEQ ID NO: 50) | ORF | 52.63157895 |
| NM_017692_siRNA_983 | 983 | GGUAGAGUAACUGUCCGAG (SEQ ID NO: 51) | CUCGGACAGUUACUCUACC (SEQ ID NO: 52) | ORF | 52.63157895 |
| NM_017692_siRNA_1005 | 1005 | GGAUGCCUGACUCUUGAA (SEQ ID NO: 53) | UUCAAGAGCUCAGGCAUCC (SEQ ID NO: 54) | ORF | 52.63157895 |

TABLE 3-continued

| Gene Name: | APTX | GenBank Accession No. | NM_175069 | | GI: | 28329429 |
|---|---|---|---|---|---|---|
| Organism: | Homo sapiens | Length: | 2036 | | ORF Region: | 25-945 |
| Locus: | 54840 | Blast database: | Human | | ORF GC%: | 48.0 |
| Definition: | Homo sapiens aprataxin (APTX), transcript variant 2, mRNA. | | | | | |
| Name | Start | Sense RNA Sequence 5'-3' | | Antisense RNA Sequence 5'-3' | Region | GC% |
| NM_175069_siRNA_105 | 105 | GCACCAGCGAAUCAGACACUU (SEQ ID NO: 55) | | AAGUCUGAUUCGCUGGUGC (SEQ ID NO: 56) | ORF | 52.63157895 |
| NM_175069_siRNA_266 | 266 | GCAUUGACUCAGUCGUAAU (SEQ ID NO: 57) | | AUUACGACUGAGUCAAUGC (SEQ ID NO: 58) | ORF | 42.10526316 |
| NM_175069_siRNA_389 | 389 | GCCUGGAAACACACAGGAA (SEQ ID NO: 59) | | UUCCUGUGUGUUUCCAGGC (SEQ ID NO: 60) | ORF | 52.63157895 |
| NM_175069_siRNA_652 | 652 | CCAAAGGCCCGUUACCAUU (SEQ ID NO: 61) | | AAUGGUAACGGGCCUUUGG (SEQ ID NO: 62) | ORF | 52.63157895 |
| NM_175069_siRNA_720 | 720 | GGAACACCUUGAACUCCUU (SEQ ID NO: 63) | | AAGGAGUUCAAGGUGUUCC (SEQ ID NO: 64) | ORF | 47.36842105 |
| Gene Name: | APTX | GenBank Accession No. | NM_175071 | | GI: | 28329426 |
| Organism: | Homo sapiens | Length: | 1836 | | ORF Region: | 425-931 |
| Locus: | 54840 | Blast database: | Human | | ORF GC%: | 47.93 |
| Definition: | Homo sapiens aprataxin (APTX), transcript variant 5, mRNA. | | | | | |
| Name | Start | Sense RNA Sequence 5'-3' | | Antisense RNA Sequence 5'-3' | Region | GC% |
| NM_175071_siRNA_799 | 799 | GGCUGGUAGAGUAACUGUC (SEQ ID NO: 65) | | GACAGUUACUCUACCAGCC (SEQ ID NO: 66) | ORF | 52.63157895 |
| NM_175071_siRNA_803 | 803 | GGUAGAGUAACUGUCCGAG (SEQ ID NO: 67) | | CUCGGACAGUUACUCUACC (SEQ ID NO: 68) | ORF | 52.63157895 |
| NM_175071_siRNA_825 | 825 | GGAUGCCUGAGCUCUUGAA (SEQ ID NO: 69) | | UUCAAGAGCUCAGGCAUCC (SEQ ID NO: 70) | ORF | 52.63157895 |
| Gene Name: | APTX | GenBank Accession No. | NM_175072 | | GI: | 28329432 |
| Organism: | Homo sapiens | Length: | 2041 | | ORF Region: | 372-1136 |
| Locus: | 54840 | Blast database: | Human | | ORF GC%: | 47.98 |
| Definition: | Homo sapiens aprataxin (APTX), transcript variant 3, mRNA. | | | | | |

TABLE 3-continued

| Name | Start | Sense RNA Sequence 5'-3' | Antisense RNA Sequence 5'-3' | Region | GC% |
|---|---|---|---|---|---|
| NM_175072_siRNA_981 | 951 | GCUGUGAUCGAGAUGGUAC (SEQ ID NO: 71) | GUACCAUCUCGAUCACAGC (SEQ ID NO: 72) | ORF | 52.63157895 |
| NM_75072_siRNA_1030 | 1030 | GGAUGCCUGAGCUCUUGAA (SEQ ID NO: 73) | UUCAAGAGCUCAGGCAUCC (SEQ ID NO: 74) | ORF | 52.63157895 |
| NM_175072_siRNA_1094 | 1094 | UCCUCAGCUGAAAGAACAU (SEQ ID NO: 75) | AUGUUCUUUCAGCUGAGGA SE ID NO: 76 | ORF | 42.10526316 |

Gene Name: DNAJA1  GenBank Accession No.: NM_001539  GI: 49472820
Organism: Homo sapiens  Length: 1538  ORF Region: 184-1377
Locus: 3301  Blast database: Human  ORF GC%: 43.22
Definition: Homo sapiens DnaJ (Hsp40) homolog, subfamily A, member 1 (DNAJA1), mRNA.

| Name | Start | Sense RNA Sequence 5'-3' | Antisense RNA Sequence 5'-3' | Region | GC% |
|---|---|---|---|---|---|
| NM_001539_siRNA_642 | 642 | CCGAGGUACUGGAAUGCAA (SEQ ID NO: 77) | UUGCAUUCCAGUACCUCGG (SEQ ID NO: 78) | ORF | 52.63157895 |
| NM_001539_siRNA_646 | 646 | GGUACUGGAAUGCAAAUAA (SEQ ID NO: 79) | UUAUUUGCAUUCCAGUACC (SEQ ID NO: 80) | ORF | 36.84210526 |
| NM_001539_siRNA_682 | 682 | CCUGGAAUGGUUCAGCAAA (SEQ ID NO: 81) | UUUGCUGAACCAUUCCAGG (SEQ ID NO: 82) | ORF | 47.36842105 |
| NM_001539_siRNA_779 | 779 | GGAAGAUAGUUCGAGAGAA (SEQ ID NO: 83) | UUCUCUCGAACUAUCUUCC (SEQ ID NO: 84) | ORF | 42.10526316 |
| NM_001539_siRNA_840 | 840 | CCAGAGAUAACAUUCCAU (SEQ ID NO: 85) | AUGGAAUGUUAUCUCUCUGG (SEQ ID NO: 86) | ORF | 36.84210526 |

Gene Name: ATP6V0C  GenBank Accession No.: NM_001694  GI: 19913436
Organism: Homo sapiens  Length: 1126  ORF Region: 153-620
Locus: 527  Blast database: Human  ORF GC%: 63.47
Definition: Homo sapiens ATPase, H+ transporting, lysosomal 15kDa, V0 subunit c(ATP6V0C), mRNA.

| Name | Start | Sense RNA Sequence 5'-3' | Antisense RNA Sequence 5'-3' | Region | GC% |
|---|---|---|---|---|---|
| NM_001694_siRNA_388 | 388 | CCCUGAAUGACGACAUCAG (SEQ ID NO: 87) | CUGAUGUCGUCAUUCAGGG (SEQ ID NO: 88) | ORF | 52.63157895 |
| NM_001694_siRNA_529 | 529 | GACUAUUCGUGGGCAUGAU (SEQ ID NO: 89) | AUCAUGCCCACGAAUAGUC (SEQ ID NO: 90) | ORF | 47.36842105 |

TABLE 3-continued

| NM_001694_siRNA_535 | 535 | UCGUGGGCAUGAUCCUGAU (SEQ ID NO: 91) | AUCAGGAUCAUGCCCACGA (SEQ ID NO: 92) | ORF | 52.63157895 |
|---|---|---|---|---|---|
| Gene Name: | BCL2L1 | GenBank Accession No. | NM_001191 | GI: | 20336333 |
| Organism: | Homo sapiens | Length: | 2386 | ORF Region: | 367-879 |
| Locus: | Human | | | ORF GC%: | 57.12 |
| Definition: | Homo sapiens BCL2-like 1 (BCL2L1), nuclear gene encoding mitochondrial protein, transcript variant 2, mRNA. | | | | |
| Name | Start | Sense RNA Sequence 5'-3' | Antisense RNA Sequence 5'-3' | Region | GC% |
| NM_001191_siRNA_753 | 753 | GGAACUCUAUGGGAACAAU (SEQ ID NO: 93) | AUUGUUCCCAUAGAGUUCC (SEQ ID NO: 94) | ORF | 42.10526316 |
| NM_001191_siRNA_857 | 857 | GCUCACUCUUCAGUCGGAA (SEQ ID NO: 95) | UUCCGACUGAAGAGUGAGC (SEQ ID NO: 96) | ORF | 52.63157895 |
| NM_001191_siRNA_859 | 859 | UCACUCUUCAGUCGGAAAU (SEQ ID NO: 97) | AUUUCCGACUGAAGAGUGA (SEQ ID NO: 98) | ORF | 42.10526316 |
| Gene Name: | BCL2L1 | GenBank Accession No. | NM_138578 | GI: | IL20336334 |
| Organism: | Homo sapiens | Length: | 2575 | ORF Region: | 367-1068 |
| Locus: | Human | | | ORF GC%: | 56.84 |
| Definition: | Homo sapiens BCL2-like 1 (BCL2L1), nuclear gene encoding mitochondrial protein, transcript variant 1, mRNA. | | | | |
| Name | Start | Sense RNA Sequence 5'-3' | Antisense RNA Sequence 5'-3' | Region | GC% |
| NM_138578_siRNA_514 | 514 | GCCAUCAAUGGCAACCCAU (SEQ ID NO: 99) | AUGGGUUGCCAUUGAUGGC (SEQ ID NO: 100) | ORF | 52.63157895 |
| NM_138578_siRNA_676 | 676 | GCAUUCAGUGACCUGACAU (SEQ ID NO: 101) | AUGUCAGGUCACUGAAUGC (SEQ ID NO: 102) | ORF | 47.36842105 |
| NM_138578_siRNA_716 | 716 | GGACAGCAUAUCAGAGCUU (SEQ ID NO: 103) | AAGCUCUGAUAUGCUGUCC (SEQ ID NO: 104) | ORF | 47.36842105 |
| NM_138578_siRNA_818 | 818 | GCGUGGAAAGCGUAGACAA (SEQ ID NO: 105) | UUGUCUACGCUUUCCACGC (SEQ ID NO: 106) | ORF | 52.63157895 |
| NM_138578_siRNA_872 | 872 | GGAUGGCCACUUACCUGAA (SEQ ID NO: 107) | UUCAGGUAAGUGGCCAUCC (SEQ ID NO: 108) | ORF | 52.63157895 |
| Gene Name: | BRD2 | GenBank Accession No. | NM_005104 | GI: | 12408641 |
| Organism: | Homo sapiens | Length: | 4693 | ORF Region: | 1702-4107 |

TABLE 3-continued

| Locus: | 6046 | Blast database: | Human | ORF GC% | 49.26 |
|---|---|---|---|---|---|
| Definition: | | Homo sapiens bromodomain containing 2 (BRD2), mRNA. | | | |
| Name | Start | Sense RNA Sequence 5'-3' | Antisense RNA Sequence 5'-3' | Region | GC% |
| NM_005104_siRNA_1851 | 1851 | GGUGCCUGCUUUGCAACUU (SEQ ID NO: 109) | AAGUUGCAAAGCAGGCACC (SEQ ID NO: 110) | ORF | 52.63157895 |
| NM_005104_siRNA_2229 | 2229 | GGUUGCAUCAAUGCCACAA (SEQ ID NO: 111) | UUGUGGCAUUGAUGCAACC (SEQ ID NO: 112) | ORF | 47.36842105 |
| NM_005104_siRNA_2694 | 2694 | GCCUGACUCUCAGCAACAA (SEQ ID NO: 113) | UUGUUGCUGAGAGUCAGGC (SEQ ID NO: 114) | ORF | 52.63157895 |
| NM_005104_siRNA_2944 | 2944 | GCUCUGAUGUACGGCUUA (SEQ ID NO: 115) | UAAGCCGUACAUCAGCAGC (SEQ ID NO: 116) | ORF | 52.63157895 |
| NM_005104_siRNA_2969 | 2969 | CCAACUGCUAUAAGUACAA (SEQ ID NO: 117) | UUGUACUUAUAGCAGUUGG (SEQ ID NO: 118) | ORF | 36.84210526 |
| Gene Name: | BRD3 | GenBank Accession No. | NM_007371 | GI: | 12408642 |
| Organism: | Homo sapiens | Length: | 3085 | ORF Region: | 140-2320 |
| Locus: | 8019 | Blast database: | Human | ORF GC% | 55.03 |
| Definition: | | Homo sapiens bromodomain containing 3 (BRD3), mRNA. | | | |
| Name | Start | Sense RNA Sequence 5'-3' | Antisense RNA Sequence 5'-3' | Region | GC% |
| NM_007371_siRNA_1098 | 1098 | GGGAGAUGCUAUCCAAGAA (SEQ ID NO: 119) | UUCUUGGAUAGCAUCUCCC (SEQ ID NO: 120) | ORF | 47.36842105 |
| NM_007371_siRNA_1279 | 1279 | CCGGCUGAUGUUCUCGAAU (SEQ ID NO: 121) | AUUCGAGAACAUCAGCCGG (SEQ ID NO: 122) | ORF | 52.63157895 |
| NM_007371_siRNA_1921 | 1921 | GGUAGUGCACAUCUCCAA (SEQ ID NO: 123) | UUGGAUGAUGUGCACUACC (SEQ ID NO: 124) | ORF | 47.36842105 |
| NM_007371_siRNA_2017 | 2017 | GCGGGAACUGGAGAGAUAU (SEQ ID NO: 125) | AUAUCUCUCCAGUUCCCGC (SEQ ID NO: 126) | ORF | 52.63157895 |
| Gene Name: | WDR5 | GenBank Accession No. | NM_017588 | GI: | 61744459 |
| Organism: | Homo sapiens | Length: | 3163 | ORF Region: | 172-1176 |
| Locus: | 11091 | Blast database: | Human | ORF GC% | 48.96 |
| Definition: | | Homo sapiens WD repeat domain 5 (WDR5), transcript variant 1, mRNA. | | | |

TABLE 3-continued

| Name | Start | Sense RNA Sequence 5'-3' | Antisense RNA Sequence 5'-3' | Region | GC% |
|---|---|---|---|---|---|
| NM_017588_siRNA_424 | 424 | GGUCACAAGCUGGGAAUAU (SEQ ID NO: 127) | AUAUUCCCAGCUUGUGACC (SEQ ID NO: 128) | ORF | 47.36842105 |
| NM_017588_siRNA_452 | 452 | CCUGGUCGUCAGAUUCUAA (SEQ ID NO: 129) | UUAGAAUCUGACGACCAGG (SEQ ID NO: 130) | ORF | 47.36842105 |
| NM_017588_siRNA_1032 | 1032 | CCUUCAGACGAAAGAGAUU (SEQ ID NO: 131) | AAUCUCUUUCGUCUGAAGG (SEQ ID NO: 132) | ORF | 42.10526316 |

Gene Name: C9orf119  GenBank Accession No. XM_372143  GI: 51467631
Organism: Homo sapiens  Length: 884  ORF Region: 1-636
Locus: 375757  Blast database: Human  ORF GC%: 59.12
Definition: PREDICTED: Homo sapiens chromosome 9 open reading frame 119 (C9orf119), mRNA.

| Name | Start | Sense RNA Sequence 5'-3' | Antisense RNA Sequence 5'-3' | Region | GC% |
|---|---|---|---|---|---|
| XM_372143_siRNA_501 | 501 | GGACCACAUUACCCAGCUU (SEQ ID NO: 133) | AAGCUGGGUAAUGUGGUCC (SEQ ID NO: 134) | ORF | 52.63157895 |
| XM_372143_siRNA_512 | 512 | CCCAGCUUCACGAGUACAA (SEQ ID NO: 135) | UUGUACUCGUGAAGCUGGG (SEQ ID NO: 136) | ORF | 52.63157895 |
| XM_372143_siRNA_513 | 513 | CCAGCUUCACGAGUACAAU (SEQ ID NO: 137) | AUUGUACUCGUGAAGCUGG (SEQ ID NO: 138) | ORF | 47.36842105 |

Gene Name: GOLGA2  GenBank Accession No. NM_004486  GI: 47078236
Organism: Homo sapiens  Length: 4304  ORF Region: 50-3022
Locus: 2801  Blast database: Human  ORF GC%: 55.84
Definition: Homo sapiens golgi autoantigen, golgin subfamily a, 2 (GOLGA2), mRNA.

| Name | Start | Sense RNA Sequence 5'-3' | Antisense RNA Sequence 5'-3' | Region | GC% |
|---|---|---|---|---|---|
| NM_004486_siRNA_406 | 406 | CCAACAGCUCAAUGGUCUU (SEQ ID NO: 139) | AAGACCAUUGAGCUGUUGG (SEQ ID NO: 140) | ORF | 47.36842105 |
| NM_004486_siRNA_528 | 528 | CCAGCUAUGUAACAAACAA (SEQ ID NO: 141) | UUGUUUGUUACAUAGCUGG (SEQ ID NO: 142) | ORF | 36.84210526 |
| NM_004486_siRNA_655 | 655 | GCAGUUACAGGUUCACAUU (SEQ ID NO: 143) | AAUGUGAACCUGUACUGC (SEQ ID NO: 144) | ORF | 42.10526316 |

TABLE 3-continued

| Name | Start | Sense RNA Sequence 5'-3' | Antisense RNA Sequence 5'-3' | Region | GC% |
|---|---|---|---|---|---|
| NM_018131_siRNA_292 | 292 | CCAGAGUACCAAAGAUUU (SEQ ID NO: 145) | AAAUCUUUGGUACUCUGG (SEQ ID NO: 146) | ORF | 36.84210526 |
| NM_018131_siRNA_494 | 494 | GGAGAAGAUGCUUAUCAA (SEQ ID NO: 147) | UUGAUAAGCAUUCUUCUCC (SEQ ID NO: 148) | ORF | 36.84210526 |
| NM_018131_siRNA_551 | 551 | CCAACUGAAGGCCAGAUAU (SEQ ID NO: 149) | AUAUCUGGCCUUCAGUUGG (SEQ ID NO: 150) | ORF | 47.36842105 |
| NM_018131_siRNA_753 | 753 | CCAAACUGCUUCAACUCAU (SEQ ID NO: 151) | AUGAGUUGAAGCAGUUUGG (SEQ ID NO: 152) | ORF | 42.10526316 |

Gene Name: CALD1
Organism: Homo sapiens
Locus: GenBank Accession No. NM_033138 Length: 5233
Blast database: Human
GI: 44680104
ORF Region: 460-2841
ORF GC%: 37.41

Definition: Homo sapiens caldesmon 1 (CALD1), transcript variant 1, mRNA.

| Name | Start | Sense RNA Sequence 5'-3' | Antisense RNA Sequence 5'-3' | Region | GC% |
|---|---|---|---|---|---|
| NM_033138_siRNA_695 | 695 | CCAAGACACCACCACAA (SEQ ID NO: 153) | UUUGUGGUGGUGUCUUGG (SEQ ID NO: 154) | ORF | 47.36842105 |
| NM_033138_siRNA_826 | 826 | CCAACAAUAACAGAUGCAA (SEQ ID NO: 155) | UUGCAUCUGUUAUUGUUGG (SEQ ID NO: 156) | ORF | 36.84210526 |
| NM_033138_siRNA_926 | 926 | GCCAAGAAAGAUACGAGAU (SEQ ID NO: 157) | AUCUCGUAUCUUUCUUGGC (SEQ ID NO: 158) | ORF | 42.10526316 |
| NM_033138_siRNA_2638 | 2638 | GCAGCAGGCACCACCAAAUA (SEQ ID NO: 159) | UAUUUGGUGUGCCUGCUGC (SEQ ID NO: 160) | ORF | 52.63157895 |

Gene Name: CALM2
Organism: Homo sapiens
Locus: GenBank Accession No. NM_001743 Length: 1128
Blast database: Human
GI: 20428653
ORF Region: 69-518
ORF GC%: 39.12

Definition: Homo sapiens calmodulin 2 (phosphorylase kinase, delta) (CALM2), mRNA.

| Name | Start | Sense RNA Sequence 5'-3' | Antisense RNA Sequence 5'-3' | Region | GC% |
|---|---|---|---|---|---|
| NM_001743_siRNA_138 | 138 | GGUGAUGGAACUAUAACAA (SEQ ID NO: 159) | UUGUUAUAGUUCCAUCACC (SEQ ID NO: 160) | ORF | 36.84210526 |
| NM_001743_siRNA_328 | 328 | GAGAAGCAUUCCGUGUGUU (SEQ ID NO: 161) | AACACACGGAAUGCUUCUC (SEQ ID NO: 162) | ORF | 47.36842105 |

TABLE 3-continued

| Name | Start | Sense RNA Sequence 5'-3' | Antisense RNA Sequence 5'-3' | Region | GC% |
|---|---|---|---|---|---|
| NM_001743_siRNA_333 | 333 | GCAUUCCGUGUGUUUGAUA (SEQ ID NO: 163) | UAUCAACACACGGAAUGC (SEQ ID NO: 164) | ORF | 42.10526316 |

Gene Name: CELSR2
Organism: Homo sapiens
Locus: 1952
Blast database: GenBank Accession No. NM_001408
Length: 10531
GI: 13325063
ORF Region: 63-8834
ORF GC%: 60.9
Definition: Homo sapiens cadherin, EGF LAG seven-pass G-type receptor 2 (flamingo homolog, Drosophila) (CELSR2), mRNA.

| Name | Start | Sense RNA Sequence 5'-3' | Antisense RNA Sequence 5'-3' | Region | GC% |
|---|---|---|---|---|---|
| NM_001408_siRNA_1997 | 1997 | CCAGAUCACCAGUGGCAAU (SEQ ID NO: 165) | AUUGCCACUGGUGAUCUGG (SEQ ID NO: 166) | ORF | 52.63157895 |
| NM_001408_siRNA_2011 | 2011 | GCAUAUCUCGAAACCGCUU (SEQ ID NO: 167) | AAGCGGUUUCGAGAUAUGC (SEQ ID NO: 168) | ORF | 47.36842105 |
| NM_001408_siRNA_2950 | 2950 | GCAACAUCCCUGAGAGUCU (SEQ ID NO: 169) | AAGACUCUCAGGGAUGUUGC (SEQ ID NO: 170) | ORF | 52.63157895 |
| NM_001408_siRNA_4427 | 4427 | GCAGCUGAAAUACUACAAU (SEQ ID NO: 171) | AUUGUAGUAUUUCAGCUGC (SEQ ID NO: 172) | ORF | 36.84210526 |
| NM_001408_siRNA_5512 | 5512 | GCAGCUGUGAUCCAGGUUA (SEQ ID NO: 173) | UAACCUGGAUCACAGCUGC (SEQ ID NO: 174) | ORF | 52.63157895 |

Gene Name: COPG2
Organism: Homo sapiens
Locus: 26958
Blast database: GenBank Accession No. NM_012133
Length: 1703
GI: 66348036
ORF Region: 61-828
ORF GC%: 42.45
Definition: Homo sapiens coatomer protein complex, subunit gamma 2 (COPG2), mRNA.

| Name | Start | Sense RNA Sequence 5'-3' | Antisense RNA Sequence 5'-3' | Region | GC% |
|---|---|---|---|---|---|
| NM_012133_siRNA_97 | 97 | GGUAGUGGCUCCAAUCCUU (SEQ ID NO: 175) | AAGGAUUGGAGCCACUACC (SEQ ID NO: 176) | ORF | 52.63157895 |
| NM_012133_siRNA_147 | 147 | GGAGCUCGUAUAUUCAAU (SEQ ID NO: 177) | AUUGAAUAUACGAGCCUCC (SEQ ID NO: 178) | ORF | 42.10526316 |
| NM_012133_siRNA_232 | 232 | GGUGAACACUUUGGAACAA (SEQ ID NO: 179) | UUGUUCCAAAGUGUUCACC (SEQ ID NO: 180) | ORF | 42.10526316 |
| NM_012133_siRNA_380 | 380 | GCAGUCUGACUAAAGACAU (SEQ ID NO: 181) | AUGUCUUUAGUCAGACUGC (SEQ ID NO: 182) | ORF | 42.10526316 |

TABLE 3-continued

| Name | Start | Sense RNA Sequence 5'-3' | Antisense RNA Sequence 5'-3' | Region | GC% |
|---|---|---|---|---|---|
| NM_012133_siRNA_548 | 548 | CCCUGCACAUGAUGAAGAU (SEQ ID NO: 183) | AUCUUCAUCAUGUGCAGGG (SEQ ID NO: 184) | ORF | 47.36842105 |

Gene Name: TSGA13
Organism: Homo sapiens
Locus: 114960
Definition: Homo sapiens testis specific, 13 (TSGA13), mRNA.

GenBank Accession No. NM_052933
GI: 31377632
Length: 1700
ORF Region: 458-1285
Blast database: Human
ORF GC%: 46.02

| Name | Start | Sense RNA Sequence 5'-3' | Antisense RNA Sequence 5'-3' | Region | GC% |
|---|---|---|---|---|---|
| NM_052933_siRNA_1130 | 1130 | GCGAGUGAAAGGCCAAUUU (SEQ ID NO: 185) | AAAUGGCCUUUCACUCGC (SEQ ID NO: 186) | ORF | 47.36842105 |
| NM_052933_siRNA_1140 | 1140 | GGCCAAUUUCCAAAGUGAU (SEQ ID NO: 187) | AUCACUUUGGAAAUUGGCC (SEQ ID NO: 188) | ORF | 42.10526316 |
| NM_052933_siRNA_1141 | 1141 | GCCAAUUUCCAAAGUGAUA (SEQ ID NO: 189) | AAUCACUUUGGAAAUUGGC (SEQ ID NO: 190) | ORF | 36.84210526 |

Gene Name: CSTF2T
Organism: Homo sapiens
Locus: 23283
Definition: Homo sapiens cleavage stimulation factor, 3' pre-RNA, subunit 2, 64kDa, tau variant (CSTF2T), mRNA.

GenBank Accession No. NM_015235
GI: 46094083
Length: 4127
ORF Region: 47-1897
Blast database: Human
ORF GC%: 54.14

| Name | Start | Sense RNA Sequence 5'-3' | Antisense RNA Sequence 5'-3' | Region | GC% |
|---|---|---|---|---|---|
| NM_015235_siRNA_219 | 219 | GCUAUGGCUUCUGCGAAUA (SEQ ID NO: 191) | UAUUCGCGAAGCCAUAGC (SEQ ID NO: 192) | ORF | 47.36842105 |
| NM_015235_siRNA_340 | 340 | GGAGGAGUUAAAGAGCCUU (SEQ ID NO: 193) | AAGGCUCUUUAACUCCUCC (SEQ ID NO: 194) | ORF | 47.36842105 |
| NM_015235_siRNA_641 | 641 | CCACUGAUCCCAGGCAAAU (SEQ ID NO: 195) | AUUUGCCUGGGAUCAGUGG (SEQ ID NO: 196) | ORF | 52.63157895 |
| NM_015235_siRNA_1138 | 1138 | GCAUCAUGCCUCUGGUCAU (SEQ ID NO: 197) | AUGACCAGAGGCAUGAUGC (SEQ ID NO: 198) | ORF | 52.63157895 |
| NM_015235_siRNA_1167 | 1167 | GCCCUUCCUCACAUGAGAU (SEQ ID NO: 199) | AUCUCAUGUGAGGAAGGGC (SEQ ID NO: 200) | ORF | 52.63157895 |

TABLE 3-continued

| Gene Name: | CSMD2 | | | GenBank Accession No. | NM_052896 | | GI: | 38045884 |
|---|---|---|---|---|---|---|---|---|
| Organism: | Homo sapiens | | | Length: | 13113 | | ORF Region: | 30-10493 |
| Locus: | 114784 | | | Blast database: | Human | | ORF GC%: | 57.15 |
| Definition: | Homo sapiens CUB and Shushi multiple domains (CSMD2), mRNA. | | | | | | | |
| Name | Start | Sense RNA Sequence 5'-3' | | | Antisense RNA Sequence 5'-3' | | Region | GC% |
| NM_052896_siRNA_224 | 224 | GCUUGUGUUCCAGUCCUUU (SEQ ID NO: 201) | | | AAAGGACUGGAACACAAGC (SEQ ID NO: 202) | | ORF | 47.36842105 |
| NM_052896_siRNA_520 | 520 | GCUGCAACCUUGGCUUCUU (SEQ ID NO: 203) | | | AAGAAGCCAAGGUUGCAGC (SEQ ID NO: 204) | | ORF | 52.63157895 |
| NM_052896_siRNA_797 | 797 | GGAAGUCACUGGGACAGAA (SEQ ID NO: 205) | | | UUCUGUCCCAGUGACUUCC (SEQ ID NO: 206) | | ORF | 52.63157893 |
| NM_052896_siRNA_931 | 931 | CCCAAUACCAAGUCAAGAA (SEQ ID NO: 207) | | | UUCUUGACUUGGUAUUGGG (SEQ ID NO: 208) | | ORF | 42.10526316 |
| NM_052896_siRNA_938 | 938 | CCAAGUCAAGAAGCAAAUU (SEQ ID NO: 209) | | | AAUUUGCUUCUUGACUUGG (SEQ ID NO: 210) | | ORF | 36.84210526 |

| Gene Name: | CTCF | | | GenBank Accession No. | NM_006565 | | GI: | 62952500 |
|---|---|---|---|---|---|---|---|---|
| Organism: | Homo sapiens | | | Length: | 3797 | | ORF Region: | 291-2474 |
| Locus: | 10664 | | | Blast database: | Human | | ORF GC%: | 48.81 |
| Definition: | Homo sapiens CCCTC-binding factor (zinc finger protein) (CTCF), mRNA. | | | | | | | |
| Name | Start | Sense RNA Sequence 5'-3' | | | Antisense RNA Sequence 5'-3' | | Region | GC% |
| NM_006565_siRNA_812 | 812 | GGUGGAGACACUAGAACA (SEQ ID NO: 211) | | | UUGUUCUAGUGUCUCCACC (SEQ ID NO: 212) | | ORF | 47.36842105 |
| NM_006565_siRNA_1211 | 1211 | CCUCCUGAGGAAUCACCUU (SEQ ID NO: 213) | | | AAGGUGAUUCCUCAGGAGG (SEQ ID NO: 214) | | ORF | 52.63157895 |
| NM_006565_siRNA_1540 | 1540 | CCCAAAGUGUACCAUGAA (SEQ ID NO: 215) | | | UUCAUGGUACCACAUUUGGG (SEQ ID NO: 216) | | ORF | 47.36842105 |
| NM_006565_siRNA_1667 | 1667 | GCAUCCUAUAUUGAGCAA (SEQ ID NO: 217) | | | UUGCUCAAUAUAGGAAUGC (SEQ ID NO: 218) | | ORF | 36.84210526 |
| NM_006565_siRNA_2285 | 2285 | CCAGCCAACAGCAGCUAUCAUU (SEQ ID NO: 219) | | | AAUGAUGCUGUUGGCUGG (SEQ ID NO: 220) | | ORF | 47.36842105 |

TABLE 3-continued

| Gene Name: | CUTL1 | GenBank Accession No | NM_001913 | | GI: | 31652235 |
|---|---|---|---|---|---|---|
| Organism: | Homo sapiens | Length: | 2942 | | ORF Region: | 20-2056 |
| Locus: | | Blast database: | Human | | ORF GC%: | 55.38 |
| Definition: | Homo sapiens cut-like 1, CCAAT displacement protein (Drosophila) (CUTL1), transcript variant 2, mRNA. | | | | | |
| Name | Start | Sense RNA Sequence 5'-3' | | Antisense RNA Sequence 5'-3' | Region | GC% |
| NM_001913_siRNA_418 | 418 | GGAAGAAUACAACAAGGAA (SEQ ID NO: 221) | | UUCCUUGUUGUUAUUCUUCC (SEQ ID NO: 222) | ORF | 36.84210526 |
| NM_001913_siRNA_1357 | 1357 | GCAGGACCUGAGCAUCAUU (SEQ ID NO: 223) | | AAUGAUGCUCAGGUCCUGC (SEQ ID NO: 224) | ORF | 52.63157895 |
| NM_001913_siRNA_1507 | 1507 | CCAGGUGGAUUCACUGCUU (SEQ ID NO: 225) | | AAGCAGUGAAUCCACCUGG (SEQ ID NO: 226) | ORF | 52.63157895 |
| NM_001913_siRNA_1644 | 1644 | CCGACAACAUCAAGCUCUU (SEQ ID NO: 227) | | AAGAGCUUGAUGUUGUCGG (SEQ ID NO: 228) | ORF | 47.36842105 |
| NM_001913_siRNA_2002 | 2002 | GCACAAGUCCACGAGAAU (SEQ ID NO: 229) | | AUUCUCGUGGAACUUGUGC (SEQ ID NO: 230) | ORF | 47.36842105 |
| Gene Name: | MYLC2PL | GenBank Accession No. | NM_138403 | | GI: | 40286635 |
| Organism: | Homo sapiens | Length: | 681 | | ORF Region: | 1-681 |
| Locus: | 93408 | Blast database: | Human | | ORF GC%: | 54.78 |
| Definition: | Homo sapiens myosin light chain 2, precursor lymphocyte-specific (MYLC2PL), mRNA. | | | | | |
| Name | Start | Sense RNA Sequence 5'-3' | | Antisense RNA Sequence 5'-3' | Region | GC% |
| NM_138403_siRNA_321 | 321 | GGACUUGAGGGACACCUUU (SEQ ID NO: 231) | | AAAGGUGUCCCUCAAGUCC (SEQ ID NO: 232) | ORF | 52.63157895 |
| NM_138403_siRNA_350 | 350 | GCCGCAUCAUGAUGUCAAGAA (SEQ ID NO: 233) | | UUCUUGACAUUGAUGCGGC (SEQ ID NO: 234) | ORF | 47.36842105 |
| NM_138403_siRNA_473 | 473 | CCAUUCUCCACGCCUUCAA (SEQ ID NO: 235) | | UUGAAGGCGUGGAGAAUGG (SEQ ID NO: 236) | ORF | 52.63157895 |
| NM_138403_siRNA_588 | 588 | GCAGAUGUUUGCAGCGUUU (SEQ ID NO: 237) | | AAACGCUGCAAACAUCUGC (SEQ ID NO: 238) | ORF | 47.36842105 |

TABLE 3-continued

| Gene Name: | DLX2 | GenBank Accession No. | NM_004405 | | GI: | 6996003 |
|---|---|---|---|---|---|---|
| Organism: | Homo sapiens | Length: | 2091 | | ORF Region: | 1-987 |
| Locus: | 1746 | Blast database: | Human | | ORF GC%: | 61.81 |
| Definition: | Homo sapiens distal-less homeo box 2 (DLX2), mRNA. | | | | | |

| Name | Start | Sense RNA Sequence 5'-3' | Antisense RNA Sequence 5'-3' | Region | GC% |
|---|---|---|---|---|---|
| NM_004405_siRNA_676 | 676 | GCUUCCCACCUUGUGCUU (SEQ ID NO: 239) | AGGCACAAGGUGGAGAAGC (SEQ ID NO: 240) | ORF | 52.63157895 |

| Gene Name: | KLHL24 | GenBank Accession No. | NM_017644 | | GI: | 62865888 |
|---|---|---|---|---|---|---|
| Organism: | Homo sapiens | Length: | 7331 | | ORF Region: | 296-2098 |
| Locus: | 54800 | Blast database: | Human | | ORF GC%: | 42.55 |
| Definition: | Homo sapiens kelch-like 24 (Drosophila) (KLHL24), mRNA. | | | | | |

| Name | Start | Sense RNA Sequence 5'-3' | Antisense RNA Sequence 5'-3' | Region | GC% |
|---|---|---|---|---|---|
| NM_017644_siRNA_558 | 558 | GCAGCUACUUUCAGAGCUAU (SEQ ID NO: 241) | AUAGCUCUGAAGUAGCUGC (SEQ ID NO: 242) | ORF | 47.36842105 |
| NM_017644_siRNA_594 | 594 | GGGAAAGCCGAGAAAUGUU (SEQ ID NO: 243) | AACAUUUCUCCGCUUUCCC (SEQ ID NO: 244) | ORF | 47.36842105 |
| NM_017644_siRNA_778 | 778 | GCAACUUGAUCCUUGUAAU (SEQ ID NO: 245) | AUUACAAGGAUCAAGUUGC (SEQ ID NO: 246) | ORF | 36.84210526 |
| NM_017644_siRNA_811 | 811 | GCGCUUUGCUGAUACCCAU (SEQ ID NO: 247) | AUGGGUAUCAGCAAAGCGC (SEQ ID NO: 248) | ORF | 52.63157895 |
| NM_017644_siRNA_913 | 913 | GCUUGACAAAGAUGAACUU (SEQ ID NO: 249) | AAGUUCAUCUUUGUCAAGC (SEQ ID NO: 250) | ORF | 36.84210526 |
| NM_017644_siRNA_1679 | 1679 | GGACCUGAUGAUAUAACUU (SEQ ID NO: 251) | AAGUAUUAUCAUCAGGUCC (SEQ ID NO: 252) | ORF | 36.84210526 |

| Gene Name: | CHCHD8 aka E2IG2 | GenBank Accession No. | NM_016565 | | GI: | 46198303 |
|---|---|---|---|---|---|---|
| Organism: | Homo sapiens | Length: | 833 | | ORF Region: | 106-369 |
| Locus: | 51287 | Blast database: | Human | | ORF GC%: | 60.99 |
| Definition: | Homo sapiens coiled-coil-helix-coiled-coil-helix domain containing8 (CHCHD8), mRNA. | | | | | |

TABLE 3-continued

| Name | Start | Sense RNA Sequence 5'-3' | Antisense RNA Sequence 5'-3' | Region | GC% |
|---|---|---|---|---|---|
| NM_016565_siRNA_115 | 115 | UCAGUCCCUCAAGGCCAUA (SEQ ID NO: 256) | UAUGGGCCUUGAGGGACUGA (SEQ ID NO: 254) | ORF | 52.63157895 |
| NM_016565_siRNA_138 | 138 | GACCCAACGGGUGAAGAAA (SEQ ID NO: 255) | UUUCUUCACCCGUUGGGUC (SEQ ID NO: 256) | ORF | 52.63157895 |
| NM_016565_siRNA_140 | 140 | CCCAACGGGUGAAGAAAGA (SEQ ID NO: 257) | UCUUUCUUCACCCGUUGGG (SEQ ID NO: 258) | ORF | 52.63157895 |

Gene Name: EIF3S10  
Organism: Homo sapiens  
GenBank Accession No. NM_003750  
GI: 4503508  
Length: 5256  
ORF Region: 114-262  
Locus: 8661  
ORF GC%: 46.81  
Blast database: Human  
Definition: Homo sapiens eukaryotic translation initiation factor 3, subunit 10 theta, 150/170kDa (EIF3S10), mRNA.

| Name | Start | Sense RNA Sequence 5'-3' | Antisense RNA Sequence 5'-3' | Region | GC% |
|---|---|---|---|---|---|
| NM_003750_siRNA_298 | 298 | GCAAGAGCCACUUGGCAAA (SEQ IDN O: 259) | UUUGCCAAGUGGCUCUUGC (SEQ ID NO: 260) | ORF | 52.63157895 |
| NM_003750_siRNA_440 | 440 | GCAGAUGGUCUUAAGAUAUA (SEQ ID NO: 261) | UAUAUCUUAAGACCAUCUGC (SEQ ID NO: 262) | ORF | 36.84210526 |
| NM_003750_siRNA_626 | 626 | GCGCUGUACCAUGAUAUU (SEQ ID NO: 263) | AAUAUCAUGGUACAGGCGC (SEQ ID NO: 264) | ORF | 47.36842105 |
| NM_003750_siRNA_635 | 635 | CCAUGAUAUUGCCCAGCAA (SEQ ID NO: 265) | UUGCUGGGCAAUAUCAUGG (SEQ ID NO: 266) | ORF | 47.36842105 |
| NM_003750_siRNA_1328 | 1328 | GCGAGUCACAAAGGUUCUA (SEQ ID NO: 267) | UAGAACCUUUGUGACUCGC (SEQ ID NO: 268) | ORF | 47.36842105 |

Gene Name: ERBB2IP  
Organism: Homo sapiens  
GenBank Accession No. NM_018695  
GI: 56237019  
Length: 6916  
ORF Region: 309-4424  
Locus: 55914  
ORF GC%: 38.63  
Blast database: Human  
Definition: Homo sapiens erbb2 interacting protein (ERBB2IP), transcript variant 2, mRNA.

| Name | Start | Sense RNA Sequence 5'-3' | Antisense RNA Sequence 5'-3' | Region | GC% |
|---|---|---|---|---|---|
| NM_018695_siRNA_899 | 899 | GGAAGUGCCUGAAGUACUU (SEQ ID NO: 269) | AAGACUUCAGGCACUUCC (SEQ I DNO: 270) | ORF | 47.36842105 |
| NM_018695_siRNA_920 | 920 | GCAACUAAGUGGAUUGAAA (SEQ ID NO: 271) | UUUCAAUCCACUUAGUUGC (SEQ ID NO: 272) | ORF | 36.84210526 |

TABLE 3-continued

| Name | Start | Sense RNA Sequence 5'-3' | | Antisense RNA Sequence 5'-3' | | Region | GC% |
|---|---|---|---|---|---|---|---|
| NM_018695_siRNA_1106 | 1106 | GCAGUUCCUGAGACUAUU | (SEQ ID NO: 273) | AAUAGUCUCAGGAAGCUGC | (SEQ ID NO: 274) | ORF | 47.36842105 |
| NM_018695_siRNA_1598 | 1598 | GCCAAGGACUGAGGAUGUU | (SEQ ID NO: 275) | AACAUCCUCAGUCCUUGGC | (SEQ ID NO: 276) | ORF | 52.63157895 |
| NM_018695_siRNA_2568 | 2568 | GCUGAUGACACUCACAAAU | (SEQ ID NO: 277) | AUUUGUGAGUGUCAUCAGC | (SEQ ID NO: 278) | ORF | 42.10526316 |
| NM_018695_siRNA_3434 | 3434 | CCAUUUACAUCAGAGACUU | (SEQ ID NO: 279) | AAGUCUCUGAUGUAAAUGG | (SEQ ID NO: 280) | ORF | 36.84210526 |

Gene Name: FER1L3 GenBank Accession No. NM_013451 GI: 19718757
Organism: Homo sapi- Length: 6829 ORF Region: 89-6274
ens
Locus: 26509 Blast database: Human ORF GC%: 47.63
Definition: Homo sapiens fer-1-like 3, myoferlin (C. elegans) (FER1L3), transcript variant 1, mRNA.

| Name | Start | Sense RNA Sequence 5'-3' | | Antisense RNA Sequence 5'-3' | | Region | GC% |
|---|---|---|---|---|---|---|---|
| NM_013451_siRNA_1529 | 1529 | GCUGCAUAUAUACAGUAA | (SEQ ID NO: 281) | UUACUGUAUAUAUGCAGC | (SEQ ID NO: 282) | ORF | 36.84210526 |
| NM_013451_siRNA_1589 | 1589 | CCUGUUACCUGAAUCUUU | (SEQ ID NO: 283) | AAAGAUUCAGGUAACAAGG | (SEQ ID NO: 284) | ORF | 36.84210526 |
| NM_013451_siRNA_1747 | 1747 | GCUUGAGCCCAUUUCAAAU | (SEQ ID NO: 285) | AUUUGAAAUGGGCUCAAGC | (SEQ ID NO: 286) | ORF | 42.10526316 |
| NM_013451_siRNA_3081 | 3081 | CCAUUCCUCUGAUCAUAA | (SEQ ID NO: 287) | UUAUGAUCAGGAGGAUUGG | (SEQ ID NO: 288) | ORF | 42010526316 |
| NM_013451_siRNA_5017 | 5017 | CCGAUCCUUUCCCGCUUU | (SEQ ID NO: 289) | AAAGCGGGAAAGGAAUCGG | (SEQ ID NO: 290) | ORF | 52.63157895 |

Gene Name: FER1L3 GenBank Accession No. NM_133337 GI: 19718758
Organism: Homo sapi- Length: 6790 ORF Region: 89-6235
ens
Locus: 26509 Blast database: Human ORF GC%: 47.64
Definition: Homo sapiens fer-1-like 3, myoferlin (C. elegans) (FER1L3), transcript variant 2, mRNA.

| Name | Start | Sense RNA Sequence 5'-3' | | Antisense RNA Sequence 5'-3' | | Region | GC% |
|---|---|---|---|---|---|---|---|
| NM_133337_siRNA_1501 | 1501 | GGAAGUAAACACAGGAGAA | (SEQ ID NO: 291) | UUCUCCUGUGUUUACUUCC | (SEQ ID NO: 292) | ORF | 42.10526316 |

TABLE 3-continued

| Name | Start | Sense RNA Sequence 5'-3' | Antisense RNA Sequence 5'-3' | Region | GC% |
|---|---|---|---|---|---|
| NM_133337_siRNA_1550 | 1550 | CCUGUUACCUGAAUCUUU (SEQ ID NO: 293) | AAAGAUUCAGUUACAAGG (SEQ ID NO: 294) | ORF | 36.84210526 |
| NM_133337_siRNA_1708 | 1708 | GCUUGAGCCCAUUUCAAAU (SEQ ID NO: 295) | AUUUGAAAUGGGCUCAAGC (SEQ ID NO: 296) | ORF | 42.10526316 |
| NM_133337_siRNA_3042 | 3042 | CCAUCCUCCUGAUCAUAA (SEQ ID NO: 297) | UUAUGAUCAGGAGGAUGG (SEQ ID NO: 298) | ORF | 42.10526316 |

Gene Name: FKBP8  
GenBank Accession No. NM_012181  
GI: 52630439  
Organism: Homo sapiens  
Length: 1787  
ORF Region: 114-1355  
Locus: 23770  
Blast database: Human  
ORF GC%: 62.08  
Definition: Homo sapiens FK506 binding protein 8, 38kDa (FKBP8), mRNA.

| Name | Start | Sense RNA Sequence 5'-3' | Antisense RNA Sequence 5'-3' | Region | GC% |
|---|---|---|---|---|---|
| NM_012181_siRNA_855 | 855 | GCCAUCAAGGCUAUCACCU (SEQ ID NO: 299) | AGGGUGAUAGCCUUGAUGGC (SEQ ID NO: 300) | ORF | 52.63157895 |
| NM_012181_siRNA_916 | 916 | UCCUGCAGUUGAAGGUGAA (SEQ ID NO: 301) | UUCACCUUCAACUGCAGGA (SEQ ID NO: 302) | ORF | 47.36842105 |
| NM_012181_siRNA_1019 | 1019 | CCAGCCAGACAACAACAAG (SEQ ID NO: 303) | CUUGUUGUUGUCUGGCUGG (SEQ ID NO: 304) | ORF | 52.63157895 |
| NM_012181_siRNA_1022 | 1022 | GCCAGACAACAUCAAGGCU (SEQ ID NO: 305) | AGCCUUGAUGUUGUCUGGC (SEQ ID NO: 306) | ORF | 52.63157895 |
| NM_012181_siRNA_1141 | 1141 | UCCACGCAGAGCUCUCAAA (SEQ ID NO: 307) | UUUGAGAGCUCUGCUGUGGA (SEQ IDN O: 308) | ORF | 52.63157895 |

Gene Name: FUSIP1  
GenBank Accession No. NM_066625  
GI: 16905515  
Organism: Homo sapiens  
Length: 1842  
ORF Region: 77-628  
Locus: 10772  
Blast database: Human  
ORF GC%: 45.66  
Definition: Homo sapiens FUS interacting protein (serine/arginine-rich) 1(FUSIP1), transcript variant 1, mRNA.

| Name | Start | Sense RNA Sequence 5'-3' | Antisense RNA Sequence 5'-3' | Region | GC% |
|---|---|---|---|---|---|
| NM_006625_siRNA_157 | 157 | GCGUGAAUUUGGUCGUUAU (SEQ ID NO: 309) | AUAACGACCAAAUUCACGC (SEQ ID NO: 310) | ORF | 42.10526316 |
| NM_006625_siRNA_567 | 567 | GACCAAACUGCAGCUGGAA (SEQ ID NO: 311) | UUCCAGCUGCAGUUUGGUC (SEQ ID NO: 312) | ORF | 52.63157895 |

TABLE 3-continued

| Name | Start | Sense RNA Sequence 5'-3' | Antisense RNA Sequence 5'-3' | Region | GC% |
|---|---|---|---|---|---|
| NM_006625_siRNA_569 | 569 | CCAAACUGCAGCUGGAAUA (SEQ ID NO: 313) | UAUUCCAGCUGCUGGAGUUGG (SEQ ID NO: 314) | ORF | 47.36842105 |
| Gene Name: | FUSIP1 | GenBank Accession No. | NM_054016 | GI: | 16905516 |
| Organism: | Homo sapiens | Length: | 2924 | ORF Region: | 77-865 |
| Locus: | 10772 | Blast database: | Human | ORF GC% | 43.98 |
| Definition: | | Homo sapiens FUS interacting protein (serine/arginine-rich) 1(FUSIP1), transcript variant 2, mRNA. | | | |
| Name | Start | Sense RNA Sequence 5'-3' | Antisense RNA Sequence 5'-3' | Region | GC% |
| NM_054016_siRNA_157 | 157 | GCGUGAAUUUGGUCGUUAU (SEQ ID NO: 315) | AUAACGACCAAAUUCACGC (SEQ ID NO: 316) | ORF | 42.10526316 |
| NM_054016_siRNA_169 | 169 | UCGUUAUGGUCCUAUAGUU (SEQ ID NO: 317) | AACUAUAGGACCAUAACGA (SEQ ID NO: 318) | ORF | 36.84210526 |
| NM_054016_siRNA_220 | 220 | CCGUCCAAGAGAGAUUUGCU (SEQ ID NO: 319) | AGCAAAUCUCCUUGGACGG (SEQ ID NO: 320) | ORF | 52.63157895 |
| Gene Name: | | GenBank Accession No. | AK025846 | GI: | 10438485 |
| Organism: | Homo sapiens | Length: | 2388 | ORF Region: | |
| Locus: | | Blast database: | Human | ORF GC% | |
| Definition: | | Homo sapiens cDNA: FLJ22193 fis, clone HRC01108, gas5 mRNA | | | |
| Name | Start | Sense RNA Sequence 5'-3' | Antisense RNA Sequence 5'-3' | Region | GC% |
| AK025846_siRNA_246 | 246 | GCAGAUGUGCUUCAUGCAU (SEQ ID NO: 321) | AUGCAUGAAGCACAUCUGC (SEQ ID NO: 322) | | 47.36842105 |
| AK025846_siRNA_1968 | 1968 | GCUAUACCUUUGCUUCUUU (SEQ ID NO: 323) | AAAGAAGCAAAGGUAUAGC (SEQ ID NO: 324) | | 36.84210526 |
| AK025846_siRNA_2088 | 2088 | CCCAACUACUGUUUUCAGUU (SEQ ID NO: 325) | AACUGAAACAGUAGUUGGG (SEQ ID NO: 326) | | 42.10526316 |
| AK025846_siRNA_2287 | 2287 | CCAGGAGCUGGAAUACAAA (SEQ ID NO: 327) | UUUGUAUUCCAGCUCCUGG (SEQ ID NO: 328) | | 47.36842105 |
| AK025846_siRNA_2296 | 2296 | GGAAUACAAAUGAGGACUU (SEQ ID NO: 329) | AAGUCCUCAUUUGUAUUCC (SEQ ID NO: 330) | | 36.84210526 |

TABLE 3-continued

| Gene Name: | GATA4 | | GenBank Accession No. | NM_002052 | | GI: | 33188460 |
|---|---|---|---|---|---|---|---|
| Organism: | Homo sapiens | | Length: | 3372 | | ORF Region: | 519-1847 |
| Locus: | 2626 | | Blast database: | Human | | ORF GC%: | 68.78 |
| Definition: | | | Homo sapiens GATA binding protein 4 (GATA4), mRNA. | | | | |
| Name | Start | | Sense RNA Sequence 5'-3' | | | Antisense RNA Sequence 5'-3' | Region | GC% |
| NM_002052_siRNA_1158 | 1158 | | GGCAGAGAGUGUGUCAACU (SEQ ID NO: 331) | | | AGUUGACACACUCUCUGCC (SEQ ID NO: 332) | ORF | 52.63157895 |
| NM_002052_siRNA_1243 | 1243 | | GCCUCUACCAAGAUGAA (SEQ ID NO: 333) | | | UUCAUCUUGGUGUAGAGGC (SEQ ID NO: 334) | ORF | 47.36842105 |
| NM_002052_siRNA_1477 | 1477 | | GGAAGCCCAAGAACCUGAA (SEQ ID NO: 335) | | | UUCAGGUUCUUGGGGCUUCC (SEQ ID NO: 336) | ORF | 52.63157895 |
| NM_002052_siRNA_1482 | 1482 | | CCCAAGAACCUGAAUAAAU (SEQ ID NO: 337) | | | AUUUAUUCAGGUUCUUGGG (SEQ ID NO: 338) | ORF | 36.84210526 |
| Gene Name: | GRB2 | | GenBank Accession No. | NM_002086 | | GI: | 45359857 |
| Organism: | Homo sapiens | | Length: | 3317 | | ORF Region: | 358-1011 |
| Locus: | 2885 | | Blast database: | Human | | ORF GC%: | 50.77 |
| Definition: | | | Homo sapiens growth factor receptor-bound protein 2 (GRB2), transcript variant 1, mRNA. | | | | |
| Name | Start | | Sense RNA Sequence 5'-3' | | | Antisense RNA Sequence 5'-3' | Region | GC% |
| NM_002086_siRNA_365 | 365 | | CCAUCGCCAAAUAUGACUU (SEQ ID NO: 339) | | | AAGUCAUAUUUGGCGAUGG (SEQ ID NO: 340) | ORF | 42.10526316 |
| NM_002086_siRNA_464 | 464 | | GGUACAAGGCAGAGCUUAA (SEQ ID NO: 341) | | | UUAAGCUCUGCCUUGUACC (SEQ ID NO: 342) | ORF | 47.36842105 |
| NM_002086_siRNA_494 | 494 | | GCUUCAUUCCCAAGAACUA (SEQ ID NO: 343) | | | UAGUUCUUGGGAAUGAAGC (SEQ ID NO: 344) | ORF | 42.10526316 |
| NM_002086_siRNA_779 | 779 | | CCAGAAACCAGCAGAUAUU (SEQ ID NO: 345) | | | AAUAUCUGCUGGUUUCUGG (SEQ ID NO: 346) | ORF | 42.10526316 |
| NM_002086_siRNA_840 | 840 | | CCAGGCCCUCUUUGACUUU (SEQ ID NO: 347) | | | AAAGUCAAAGAGGGCCUGG (SEQ ID NO: 348) | ORF | 52.63157895 |

TABLE 3-continued

| Gene Name: | GTF2E1 | GenBank Accession No. | NM_005513 | | GI: | 5031726 |
|---|---|---|---|---|---|---|
| Organism: | Homo sapiens | Length: | 2969 | | ORF Region: | 55-1374 |
| Locus | | Blast database: | Human | | ORF GC%: | 47.88 |
| Definition: | Homo sapiens general transcription factor IIE, polypeptide 1 (alphasubunit, 56kD) (GTF2E1), mRNA. | | | | | |
| Name | Start | Sense RNA Sequence 5'-3' | | Antisense RNA Sequence 5'-3' | Region | GC% |
| NM_005513_siRNA_198 | 198 | GCUGAGCUGCUCAAGUUU (SEQ ID NO: 349) | | AAACUGAGCAGCUCCAGC (SEQ ID NO: 350) | ORF | 52.63157895 |
| NM_005513_siRNA_378 | 378 | CCACAUGAGAAGAAGAAUU (SEQ ID NO: 351) | | AAUUCUUCUUCUCAUGUGG (SEQ ID NO: 352) | ORF | 36.84210526 |
| NM_005513_siRNA_885 | 885 | GCCUAUUUGGUUGAGAGAA (SEQ ID NO: 353) | | UUCUCUCAACCAAAUAGGC (SEQ ID NO: 354) | ORF | 42.10526316 |
| NM_005513_siRNA_950 | 950 | GCAUAGAUAUGGACCCAUU (SEQ ID NO: 355) | | AAUGCCGUCCAUAUCUAUGC (SEQ ID NO: 356) | ORF | 42.10526316 |
| NM_005513_siRNA_1349 | 1349 | GCAUGUUUGAGGACCUCUU (SEQ ID NO: 357) | | AAGAGGUCCUCAAACAUGC (SEQ ID NO: 358) | ORF | 47.36842105 |
| Gene Name: | RABL3 | GenBank Accession No. | NM_173825 | | GI: | 62751416 |
| Organism: | Homo sapiens | Length: | 3449 | | ORF Region: | 31-741 |
| Locus | 283282 | Blast database: | Human | | ORF GC%: | 43.75 |
| Definition: | Homo sapiens RAB, member of RAS oncogene family-like 3 (RABL3), mRNA. | | | | | |
| Name | Start | Sense RNA Sequence 5'-3' | | Antisense RNA Sequence 5'-3' | Region | GC% |
| NM_173825_siRNA_47 | 47 | GGGUGAAGGUACUGGUGUU (SEQ ID NO: 359) | | AACACCAGUACCUUCACCC (SEQ ID NO: 360) | ORF | 52.63157895 |
| NM_173825_siRNA_266 | 266 | GCACAAGAGCAGUAUUCUA (SEQ ID NO: 361) | | UAGAAUACUGCUCUUGUGC (SEQ ID NO: 362) | ORF | 42.10526316 |
| NM_173825_siRNA_467 | 467 | GGACUAAACUGGACCAGAU (SEQ ID NO: 363) | | AUCUGGUCCAGUUUAGUCC (SEQ ID NO: 364) | ORF | 47.36842105 |
| NM_173825_siRNA_528 | 528 | CCUGGCUGAGGAUUUCAAU (SEQ ID NO: 365) | | AUUGAAAUCCUCAGCCAGG (SEQ ID NO: 366) | ORF | 47.36842105 |

TABLE 3-continued

| Gene Name: | HM13 | GenBank Accession No. | NM_030789 | | GI: | 30581114 |
|---|---|---|---|---|---|---|
| Organism: | Homo sapiens | Length: | 1604 | | ORF Region: | 115-1248 |
| Locus: | 81502 | Blast database: | Human | | ORF GC%: | 54.77 |
| Definition: | Homo sapiens histocompatibility (minor) 13 (HM13), transcript variant, mRNA. | | | | | |

| Name | Start | Sense RNA Sequence 5'-3' | Antisense RNA Sequence 5'-3' | Region | GC% |
|---|---|---|---|---|---|
| NM_030789_siRNA_293 | 293 | GCAAGAAUGCUUCAGACAU (SEQ ID NO: 367) | AUGUCUGAAGCAUUCUUGC (SEQ ID NO: 368) | ORF | 42.10526316 |
| NM_030789_siRNA_420 | 420 | CCUCCUGCUGUCCAUGUAU (SEQ ID NO: 369) | AUACAUGGACAGCAGGAGG (SEQ ID NO: 370) | ORF | 52.63157895 |
| NM_030789_siRNA_645 | 645 | GCUGAGGAAGCACUGGAUU (SEQ ID NO: 371) | AAUCCAGUGCUUCCUCAGC (SEQ ID NO: 372) | ORF | 52.63157895 |
| NM_030789_siRNA_870 | 870 | CCUCGAAGCAAACACUUU (SEQ ID NO: 373) | AAAGUGUUUGCUUCGAGG (SEQ ID NO: 374) | ORF | 42.10526316 |
| NM_030789_siRNA_1155 | 1155 | GGAGUCAAAUCCUAAGGAU (SEQ ID NO: 375) | AUCCUUAGGAUUUGACUCC (SEQ ID NO: 376) | ORF | 42.10526316 |

| Gene Name: | HNRPL | GenBank Accession No. | NM_001533 | | GI: | 52632382 |
|---|---|---|---|---|---|---|
| Organism: | Homo sapiens | Length: | 2129 | | ORF Region: | 12-1781 |
| Locus: | 3191 | Blast database: | Human | | ORF GC%: | 51.53 |
| Definition: | Homo sapiens heterogeneous nuclear ribonucleoprotein L (HNRPL), transcript variant 1, mRNA. | | | | | |

| Name | Start | Sense RNA Sequence 5'-3' | Antisense RNA Sequence 5'-3' | Region | GC% |
|---|---|---|---|---|---|
| NM_001533_siRNA_480 | 480 | GCAGCCGACAACCAAAUAU (SEQ ID NO: 377) | AUAUUUGGUUGUCGGCUGC (SEQ ID NO: 378) | ORF | 47.36842105 |
| NM_001533_siRNA_716 | 716 | GGUGGAAUUUGACCUCAGUU (SEQ ID NO: 379) | AACUGAGUCAAAUUCCACC (SEQ ID NO: 380) | ORF | 42.10526316 |
| NM_001533_siRNA_719 | 719 | GGAAUUUGACUCAGUUCAA (SEQ ID NO: 381) | UUGAACUGAGUCAAAUUCC (SEQ ID NO: 382) | ORF | 36.84210526 |
| NM_001533_siRNA_793 | 793 | GCACUCUGAAGAUCGAAUA (SEQ ID NO: 383) | UAUUCGAUCUUCAGAGUGC (SEQ ID NO: 384) | ORF | 42.10526316 |

TABLE 3-continued

| Gene Name: | HOXC13 | GenBank Accession No. | NM_017410 | | GI: | 24497535 |
|---|---|---|---|---|---|---|
| Organism: | Homo sapiens | Length: | 2435 | | ORF Region: | 116-1108 |
| Locus: | 3229 | Blast database: | Human | | ORF GC%: | 62.34 |
| Definition: | Homo sapiens homeo box C13 (HOXC13), mRNA. | | | | | |

| Name | Start | Sense RNA Sequence 5'-3' | Antisense RNA Sequence 5'-3' | Region | GC% |
|---|---|---|---|---|---|
| NM_017410_siRNA_154 | 154 | GAGCCUUAUGUACGUCUAU (SEQ ID NO: 385) | AUAGACGUACAUAAGGCUC (SEQ ID NO: 386) | ORF | 42.10526316 |
| NM_017410_siRNA_912 | 912 | CCUACACUAAGGUGCAGCU (SEQ ID NO: 387) | AGCUGCACCUUAGUGUAGG (SEQ ID NO: 388) | ORF | 52.63157895 |
| NM_017410_siRNA_1066 | 1066 | GGUGGUCAGCAAAUCGAAA (SEQ ID NO: 389) | UUUCGAUUUGCUGACCACC (SEQ ID NO: 390) | ORF | 47.36842105 |
| NM_017410_siRNA_1074 | 1074 | GCAAAUCGAAAGCGCCUCA (SEQ ID NO: 391) | UGAGGCGCUUUCGAUUUGC (SEQ ID NO: 392) | ORF | 52.63157895 |

| Gene Name: | HP1BP3 | GenBank Accession No. | NM_016287 | | GI: | 56676329 |
|---|---|---|---|---|---|---|
| Organism: | Homo sapiens | Length: | 1855 | | ORF Region: | 101-1762 |
| Locus: | 50809 | Blast database: | Human | | ORF GC%: | 47.24 |
| Definition: | Homo sapiens heterochromatin protein 1, binding protein 3 (HP1BP3), mRNA also known as HP1-BP74 | | | | | |

| Name | Start | Sense RNA Sequence 5'-3' | Antisense RNA Sequence 5'-3' | Region | GC% |
|---|---|---|---|---|---|
| NM_016287_siRNA_576 | 576 | CCAAGAUGGAUGCAAUCUU (SEQ ID NO: 393) | AAGAUUGCAUCCAUCUUGG (SEQ ID NO: 394) | ORF | 42.10526316 |
| NM_016287_siRNA_990 | 990 | GGCCUCAGCUGUUGAAGAA (SEQ ID NO: 395) | UUCUUCAACAGCUGAGGCC (SEQ ID NO: 396) | ORF | 52.63157895 |
| NM_016287_siRNA_1112 | 1112 | GGUGGAAGCCUGAUGGAAU (SEQ ID NO: 397) | AUUCCAUCAGGCUUCCACC (SEQ ID NO: 398) | ORF | 52.63157895 |

| Gene Name: | HSPC135 | GenBank Accession No. | NM_014170 | | GI: | 56549684 |
|---|---|---|---|---|---|---|
| Organism: | Homo sapiens | Length: | 1364 | | ORF Region: | 48-902 |
| Locus: | 29083 | Blast database: | Human | | ORF GC%: | 46.91 |
| Definition: | Homo sapiens HSPC135 protein (HSPC135), transcript variant 1, mRNA. | | | | | |

TABLE 3-continued

| Name | Start | Sense RNA Sequence 5'-3' | Antisense RNA Sequence 5'-3' | Region | GC% |
|---|---|---|---|---|---|
| NM_014170_siRNA_533 | 533 | GGUGGACAUGCCAGUUAU (SEQ ID NO: 399) | AUAACCUGGCAUGUCCACC (SEQ ID NO: 400) | ORF | 52.63157895 |
| NM_014170_siRNA_638 | 638 | GGAUAGCGUUGUUGGAAUU (SEQ ID NO: 401) | AAUUCCAACAACGCUAUCC (SEQ ID NO: 402) | ORF | 42.10526316 |
| NM_014170_siRNA_849 | 849 | GGAAUCCACCUGUUGAGAU (SEQ ID NO: 403) | AUCUCAACAGGUGGAUUCC (SEQ ID NO: 404) | ORF | 47.36842105 |
| NM_014170_siRNA_854 | 854 | CCACCUGUUGAGAUGCUUU (SEQ ID NO: 405) | AAAGCAUCUCAACAGGUGG (SEQ ID NO: 406) | ORF | 47.36842105 |

Gene Name: CD200R1  
GenBank Accession No. NM_138806  
GI: 41327722  
Organism: Homo sapiens  
Length: 2272  
ORF Region: 234-1280  
Locus: 131450  
Blast database: Human  
ORF GC%: 43.18  
Definition: Homo sapiens CD200 receptor 1 (CD200R1), transcript variant 1, mRNA.

| Name | Start | Sense RNA Sequence 5'-3' | Antisense RNA Sequence 5'-3' | Region | GC% |
|---|---|---|---|---|---|
| NM_138806_siRNA_341 | 341 | GCAAACUAGCAAGGAGAAU (SEQ ID NO: 407) | AUUCUCCUUGCUAGUUUGC (SEQ ID NO: 408) | ORF | 42.10526316 |
| NM_138806_siRNA_429 | 429 | GCAGAAGUUAACACUUCAU (SEQ ID NO: 409) | AUGAAGUGUUAACUUCUGC (SEQ ID NO: 410) | ORF | 36.84210526 |
| NM_138806_siRNA_462 | 462 | GCUACAAAUGCUGUGCUUU (SEQ ID NO: 411) | AAAGCACAGCAUUUGUAGC (SEQ ID NO: 412) | ORF | 42.10526316 |
| NM_138806_siRNA_590 | 590 | GGAAACCAACUGUACUGAU (SEQ ID NO: 413) | AUCAGUACAGUUGGUUUCC (SEQ ID NO: 414) | ORF | 42.10526316 |
| NM_138806_siRNA_869 | 869 | GCAAGAAAUACUGGAGCAAU (SEQ ID NO: 415) | AUUGCUCCAGUAUUCUUGC (SEQ ID NO: 416) | ORF | 42.10526316 |
| NM_138806_siRNA_1230 | 1230 | GCAUCUGAGGCAUUACAAA (SEQ ID NO: 417) | UUUGUAAUGCCUCAGAUGC (SEQ ID NO: 418) | ORF | 42.10526316 |

Gene Name: ID3  
GenBank Accession No. NM_002167  
GI: 32171181  
Organism: Homo sapiens  
Length: 1203  
ORF Region: 368-727  
Locus: 3399  
Blast database: Human  
ORF GC%: 64.17  
Definition: Homo sapiens inhibitor of DNA binding 3, dominant negative helix-loop-helix protein (ID3), mRNA.

TABLE 3-continued

| Name | Start | Sense RNA Sequence 5'-3' | Antisense RNA Sequence 5'-3' | Region | GC% |
|---|---|---|---|---|---|
| NM_002167_siRNA_561 | 561 | GCCAGGUGGAAAUCCUACA (SEQ ID NO: 419) | UGUAGGAUUUCCACCUGGC (SEQ ID NO: 420) | ORF | 52.63157895 |
| NM_002167_siRNA_580 | 580 | GCGCUCACUCGACUACAUU (SEQ ID NO: 421) | AAUGUAGUCGAUGAGCGCGC (SEQ ID NO: 422) | ORF | 52.63157895 |
| NM_002167_siRNA_680 | 680 | GCUCCGGAACUUGUCAUCU (SEQ ID NO: 423) | AGAUGACAAGUUCCGGAGC (SEQ ID NO: 424) | ORF | 52.63157895 |

Gene Name: IGF2R  
Organism: Homo sapiens  
Locus: 3482  
Definition: Homo sapiens insulin-like growth factor 2 receptor (IGF2R), mRNA.

GenBank Accession No. NM_000876  
Length: 9090  
Blast database: Human

GI: 4504610  
ORF Region: 148-7623  
ORF GC%: 52.23

| Name | Start | Sense RNA Sequence 5'-3' | Antisense RNA Sequence 5'-3' | Region | GC% |
|---|---|---|---|---|---|
| NM_000876_siRNA_461 | 461 | CCAGAUCUCCUUGGAAUU (SEQ ID NO: 425) | AAUUCCAGGAGAGAUCUGG (SEQ ID NO: 426) | ORF | 47.36842105 |
| NM_000876_siRNA_558 | 558 | CCUGGGAACUCCUGAAUUU (SEQ ID NO: 427) | AAAUUCAGGAGUUCCCAGG (SEQ ID NO: 428) | ORF | 47.36842105 |
| NM_000876_siRNA_649 | 649 | GCAAAUAAGGAGGUGCCAU (SEQ ID NO: 429) | AUGGCACCUCCUUAUUUGC (SEQ ID NO: 430) | ORF | 47.36842105 |
| NM_000876_siRNA_1146 | 1146 | GCAGCAGGAUGUCUCCAUA (SEQ ID NO: 431) | UAUGGAGACAUCCUGCUGC (SEQ ID NO: 432) | ORF | 52.63157895 |
| NM_000876_siRNA_1927 | 1927 | GCACCAGUGUUGAGAGACUU (SEQ ID NO: 433) | AAGUUCUCAACACUGGUGC (SEQ ID NO: 434) | ORF | 47.36842105 |
| NM_000876_siRNA_2092 | 2092 | GCCUAUAAAGUUGAGACAA (SEQ ID NO: 435) | UUGUCUCAACUUUAUAGGC (SEQ ID NO: 436) | ORF | 36.84210526 |
| NM_000876_siRNA_2735 | 2735 | GCAGCCUCCUUCUGGAAUA (SEQ ID NO: 437) | UAUUCCAGAAGGAGGCUGC (SEQ ID NO: 438) | ORF | 52.63157895 |
| NM_000876_siRNA_3901 | 3901 | GCUGGCGAAUACACUUAUU (SEQ ID NO: 439) | AAUAAGUGUAUUCGCCAGC (SEQ ID NO: 440) | ORF | 42.10526316 |
| NM_000876_siRNA_6587 | 6587 | GCUUCAGCCUCGGAGAUAU (SEQ ID NO: 441) | AUAUCUCCGAGGCUGAAGC (SEQ ID NO: 442) | ORF | 52.63157895 |
| NM_000876_siRNA_6849 | 6849 | GGAUAAGACCAAGUCUGUU (SEQ ID NO: 443) | AACAGACUUGGUCUUAUCC (SEQ ID NO: 444) | ORF | 42.10526316 |

TABLE 3-continued

| Gene Name: | JAK1 | | GenBank Accession No. | NM_002227 | | GI: | 4504802 |
|---|---|---|---|---|---|---|---|
| Organism: | Homo sapiens | | Length: 3541 | | | ORF Region: | 76-3504 |
| Locus: | 3716 | | | | | ORF GC%: | 47.54 |
| Definition: | | | Blast database: Human | | | | |
| | | | Homo sapiens Janus kinase 1 (a protein tyrosine kinase) (JAK1), mRNA. | | | | |

| Name | Start | Sense RNA Sequence 5'-3' | | Antisense RNA Sequence 5'-3' | | Region | GC% |
|---|---|---|---|---|---|---|---|
| NM_002227_siRNA_297 | 297 | GCUCUGGUAUGCUCCAAAU (SEQ ID NO: 445) | | AUUUGGAGCAUACCAGAGC (SEQ ID NO: 446) | | ORF | 47.36842105 |
| NM_002227_siRNA_320 | 320 | CCAUCACCGUUGAUGACAA (SEQ ID NO: 447) | | UUGUCAUCAACGGUGAUGG (SEQ ID NO: 448) | | ORF | 47.36842105 |
| NM_002227_siRNA_380 | 380 | CCAAUUGGCAUGGAACCAA (SEQ ID NO: 449) | | UUGGUUCCAUGCCAAUUGG (SEQ ID NO: 450) | | ORF | 47.36842105 |
| NM_002227_siRNA_387 | 387 | GCAUGGAACCAACGACAAU (SEQ ID NO: 451) | | AUUGUCGUUGGUUCCAUGC (SEQ ID NO: 452) | | ORF | 47.36842105 |
| NM_002227_siRNA_621 | 621 | CCUGGCCAUCUCACACUAU (SEQ ID NO: 453) | | AUAGUGUGAGAUGGCCAGG (SEQ ID NO: 454) | | ORF | 52.63157895 |
| NM_002227_siRNA_626 | 626 | CCAUCUCACACUAUGCCAU (SEQ ID NO: 455) | | AUGGCAUAGUGUGAGAUGG (SEQ ID NO: 456) | | ORF | 47.36842105 |
| NM_002227_siRNA_1511 | 1511 | CCCAGAAGCAGUUCAAGAA (SEQ ID NO: 457) | | UUCUUGAACUGCUUCUGGG (SEQ ID NO: 458) | | ORF | 47.36842105 |
| NM_002227_siRNA_1701 | 1701 | GCUGGUGGCUACUAAGAAA (SEQ ID NO: 459) | | UUUCUUAGUAGCCACCAGC (SEQ ID NO: 460) | | ORF | 47.36842105 |
| NM_002227_siRNA_1814 | 1814 | GCACGAGAACACACACUCA (SEQ ID NO: 461) | | UAGAGUGUGUGUUCUCGUGC (SEQ ID NO: 462) | | ORF | 47.36842105 |
| NM_002227_siRNA_2022 | 2022 | GGAGAAUAUCAUGGUGGAA (SEQ ID NO: 463) | | UUCCACCAUGAUAUUCUCC (SEQ ID NO: 464) | | ORF | 42.10526316 |

| Gene Name: | KIF13B | | GenBank Accession No. | NM_016254 | | GI: | 46852171 |
|---|---|---|---|---|---|---|---|
| Organism: | Homo sapiens | | Length: 8796 | | | ORF Region: | 91-5571 |
| Locus: | 23303 | | | | | ORF GC%: | 52.64 |
| Definition: | | | Blast database: Human | | | | |
| | | | Homo sapiens kinesin family member 13B (KIF13B), mRNA. | | | | |

| Name | Start | Sense RNA Sequence 5'-3' | | Antisense RNA Sequence 5'-3' | | Region | GC% |
|---|---|---|---|---|---|---|---|
| NM_015254_siRNA_141 | 141 | GCGAGAGACUGACUUGCAU (SEQ ID NO: 465) | | AUGCAAGUCAGUCUCUCCGC (SEQ ID NO: 466) | | ORF | 52.63157895 |
| NM_015254_siRNA_631 | 631 | CCUUAUGUCGACGGACUUU (SEQ ID NO: 467) | | AAAGUCCGUCGACAUAAGG (SEQ ID NO: 468) | | ORF | 47.36842105 |
| NM_015254_siRNA_1374 | 1374 | GCUUGAGAGUCUUGGAAUA (SEQ ID NO: 469) | | UAUUCCAAGACUCUCAAGC (SEQ ID NO: 470) | | ORF | 42.10526316 |
| NM_015254_siRNA_1473 | 1473 | GCUUCUGGUGUACUAUUUA (SEQ ID NO: 471) | | UAAAUAGUACACCAGAAGC (SEQ ID NO: 472) | | ORF | 36.84210526 |
| NM_015254_siRNA_4479 | 4479 | GCUCCUCAAGUCUCUCUUU (SEQ ID NO: 473) | | AAAGAGAGACUUGAGGAGC (SEQ ID NO: 474) | | ORF | 47.36842105 |

TABLE 3-continued

| Gene Name: | MKI67 | GenBank Accession No. | NM_002417 | | GI: | 19923216 |
|---|---|---|---|---|---|---|
| Organism: | Homo sapiens | Length: | 12515 | | ORF Region: | 197-9967 |
| Locus: | 4288 | Blast database: | Human | | ORF GC%: | 47.35 |
| Definition: | Homo sapiens antigen identified by monoclonal antibody Ki-67(MKI67), mRNA. | | | | | |

| Name | Start | Sense RNA Sequence 5'-3' | | Antisense RNA Sequence 5'-3' | Region | GC% |
|---|---|---|---|---|---|---|
| NM_002417_siRNA_727 | 727 | GGGAACAACUAAUGUUCAU (SEQ ID NO: 475) | | AUGAACAUUAGUUGUUCCC (SEQ ID NO: 476) | ORF | 36.84210526 |
| NM_002417_siRNA_1913 | 1913 | GCACAAAGCUUGGUUAUAA (SEQ ID NO: 477) | | UUAUAACCAAGCUUUGUGC (SEQ ID NO: 478) | ORF | 36.84210526 |
| NM_002417_siRNA_3621 | 3621 | GCACAAAGCAAUGGCCUAA (SEQ ID NO: 479) | | UUAGGCCAUUGCUUUGUGC (SEQ ID NO: 480) | ORF | 47.36842105 |
| NM_002417_siRNA_6317 | 6317 | GCGUUUAAGGAAUCUGCAA (SEQ ID NO: 481) | | UUGCAGAUUCCUUAAACGC (SEQ ID NO: 482) | ORF | 42.10526316 |
| NM_002417_siRNA_8846 | 8846 | GCAUUUAAGCAACCUGCAA (SEQ ID NO: 483) | | UUGCAGGUUGCUUAAAUGC (SEQ ID NO: 484) | ORF | 42.10526316 |
| NM_002417_siRNA_9505 | 9505 | GCAAAUAACUGAGGUCUUU (SEQ ID NO: 485) | | AAAGACCUCAGUUAUUUGC (SEQ ID NO: 486) | ORF | 36.84210526 |

| Gene Name: | LIPC | GenBank Accession No. | NM_000236 | | GI: | 4557722 |
|---|---|---|---|---|---|---|
| Organism: | Homo sapiens | Length: | 1603 | | ORF Region: | 58-1557 |
| Locus: | 3990 | Blast database: | Human | | ORF GC%: | 52.34 |
| Definition: | Homo sapiens lipase, hepatic (LIPC), mRNA. | | | | | |

| Name | Start | Sense RNA Sequence 5'-3' | | Antisense RNA Sequence 5'-3' | Region | GC% |
|---|---|---|---|---|---|---|
| NM_000236_siRNA_122 | 122 | CCCUGGACAAAGCCUGAA (SEQ ID NO: 487) | | UUCAGGCUUUGUCCAGGG (SEQ ID NO: 488) | ORF | 52.63157895 |
| NM_000236_siRNA_646 | 646 | GGACCUUUGUUUGAGGGAA (SEQ ID NO: 489) | | UUCCCUCAAACAAAGGUCC (SEQ ID NO: 490) | ORF | 47.36842105 |
| NM_000236_siRNA_767 | 767 | CCAUAGGACACUAUGACUU (SEQ ID NO: 491) | | AAGUCAUAGUGUCCUAUGG (SEQ ID NO: 492) | ORF | 42.10526316 |
| NM_000236_siRNA_1058 | 1058 | GCAAGAGCAAGAGGCUCUU (SEQ ID NO: 493) | | AAGAGCCUCUUGCUCUUGC (SEQ ID NO: 494) | ORF | 52.63157895 |
| NM_000236_siRNA_1229 | 1229 | GCAAAGGAAUUGCUAGUAA (SEQ ID NO: 495) | | UUACUAGCAAUUCCUUUGC (SEQ ID NO: 496) | ORF | 36.84210526 |

| Gene Name: | NFKBIZ | GenBank Accession: | NM_031419 | | GI: | 53832022 |
|---|---|---|---|---|---|---|
| Organism: | Homo sapiens | Length: | 3983 | | ORF Region: | 116-2272 |
| Locus: | 64332 | Blast database: | Human | | ORF GC%: | 53.0 |
| Definition: | Homo sapiens nuclear factor of kappa light polypeptide gene enhancer in B-cells inhibitor, zeta (NFKBIZ), transcript variant 1, mRNA (MAIL) | | | | | |

TABLE 3-continued

| Name | Start | Sense RNA Sequence 5'-3' | Antisense RNA Sequence 5'-3' | Region | GC% |
|---|---|---|---|---|---|
| NM_031419_siRNA_490 | 490 | GCACAUCCGAAGUCAUAAA (SEQ ID NO: 497) | UUUAUGACUUCGGAUGUGC (SEQ ID NO: 498) | ORF | 42.10526316 |
| NM_031419_siRNA_616 | 616 | GCCCGAUUCGUUGUCUGAU (SEQ ID NO: 499) | AUCAGACAACGAAUCGGGC (SEQ ID NO: 500) | ORF | 52.63157895 |
| NM_031419_siRNA_965 | 965 | GCUUCCCUGUACCAGUAUU (SEQ ID NO: 501) | AAUACUGGUACAGGGAAGC (SEQ ID NO: 502) | ORF | 47.36842105 |
| NM_031419_siRNA_1175 | 1175 | GCUAAUCCCAUGCAGACUU (SEQ ID NO: 503) | AAGUCUGCAUGGGAUUAGC (SEQ ID NO: 504) | ORF | 47.36842105 |
| NM_031419_siRNA_1494 | 1494 | CCUAUGUUCUUGCAAGAAA (SEQ ID NO: 505) | UUUCUUGCAAGAACAUAGG (SEQ ID NO: 506) | ORF | 36.84210526 |
| NM_031419_siRNA_1520 | 1520 | GCACUUCACAUGCUGGAUA (SEQ ID NO: 507) | UAUCCAGCAUGUGAAGUGC (SEQ ID NO: 508) | ORF | 47.36842105 |
| NM_031419_siRNA_1801 | 1801 | CCACAAUGCUGUGGUCCAU (SEQ ID NO: 509) | AUGGACCACAGCAUUGUGG (SEQ ID NO: 510) | ORF | 52.63157895 |
| NM_031419_siRNA_1816 | 1816 | CCAUGAACUCCAGAGAAAU (SEQ ID NO: 511) | AUUUCUCUGGAGUUCAUGG (SEQ ID NO: 512) | ORF | 42.10526316 |
| NM_031419_siRNA_1840 | 1840 | GCCUCAUUCACCUGAAGUU (SEQ ID NO: 513) | AACUUCAGGUGAAUGAGGC (SEQ ID NO: 514) | ORF | 47.36842105 |
| NM_031419_siRNA_2092 | 2092 | GCAGUAUCGUUGACACAA (SEQ ID NO: 515) | UUGUGUCAACCGAUACUGC (SEQ ID NO: 516) | ORF | 47.36842105 |

Gene Name: NFKBIZ  GenBank Accession No. NM_001005474  GI: 53832023
Organism: Homo sapiens
Locus: 64332  Length: 3782  ORF Region: 260-2116  ORF GC%: 49.49
Blast database: Human
Definition: Homo sapiens nuclear factor of kappa light polypedtide geneenhancer in B-cells inhibitor, zeta (NFKBIZ), transcript variant 2, mRNA.

| Name | Start | Sense RNA Sequence 5'-3' | Antisense RNA Sequence 5'-3' | Region | GC% |
|---|---|---|---|---|---|
| NM_001005474_siRNA_334 | 334 | GCACAUCCGAAGUCAUAAA (SEQ ID NO: 517) | UUUAUGACUUCGGAUGUGC (SEQ ID NO: 518) | ORF | 42.10526316 |
| NM_001005474_siRNA_460 | 460 | GCCCGAUUCGUUGUCUGAU (SEQ ID NO: 519) | AUCAGACAACGAAUCGGGC (SEQ ID NO: 520) | ORF | 52.63157895 |
| NM_001005474_siRNA_809 | 809 | GCUUCCCUGUACCAGUAUU (SEQ ID NO: 521) | AAUACUGGUACAGGGAAGC (SEQ ID NO: 522) | ORF | 47.36842105 |
| NM_001005474_siRNA_1019 | 1019 | GCUAAUCCCAUGCAGACUU (SEQ ID NO: 523) | AAGUCUGCAUGGGAUUAGC (SEQ ID NO: 524) | ORF | 47.36842105 |
| NM_001005474_siRNA_1338 | 1338 | CCUAUGUUCUUGCAAGAAA (SEQ ID NO: 525) | UUUCUUGCAAGAACAUAGG (SEQ ID NO: 526) | ORF | 36.84210526 |
| NM_001005474_siRNA_1364 | 1364 | GCACUUCACAUGCUGGAUA (SEQ ID NO: 527) | UAUCCAGCAUGUGAAGUGC (SEQ ID NO: 528) | ORF | 47.36842105 |
| NM_001005474_siRNA_1645 | 1645 | CCACAAUGCUGUGGUCCAU (SEQ ID NO: 529) | AUGGACCACAGCAUUGUGG (SEQ ID NO: 530) | ORF | 52.63157895 |
| NM_001005474_siRNA_1660 | 1660 | CCAUGAACUCCAGAGAAAU (SEQ ID NO: 531) | AUUUCUCUGGAGUUCAUGG (SEQ ID NO: 532) | ORF | 42.10526316 |
| NM_001005474_siRNA_1684 | 1684 | GCCUCAUUCACCUGAAGUU (SEQ ID NO: 533) | AACUUCAGGUGAAUGAGGC (SEQ ID NO: 534) | ORF | 47.36842105 |

TABLE 3-continued

| Name | Start | Sense RNA Sequence 5'-3' | | Antisense RNA Sequence 5'-3' | | Region | GC% |
|---|---|---|---|---|---|---|---|
| NM_001005474_siRNA_1936 | 1936 | GCAGUAUCGGUUGACACAA (SEQ ID NO: 535) | | UUGUGUCAACCGAUACUGC (SEQ ID NO: 536) | | ORF | 47.36842105 |

Gene Name: MAP3K7IP1    GenBank Accession No. NM_006116    GI: 47717114
Organism: Homo sapiens    Length: 3240    ORF Region: 50-1564
Locus: 10454    Blast database: Human    ORF GC%: 60.73
Definition: Homo sapiens mitogen-activated protein kinase kinase 7 interacting protein 1 (MAP3K7IP1), transcript variant alpha, mRNA.
Sequence: NM_006116

| Name | Start | Sense RNA Sequence 5'-3' | Antisense RNA Sequence 5'-3' | Region | GC% |
|---|---|---|---|---|---|
| NM_006116_siRNA_219 | 219 | GGAGUGAGAACAACUGCUU (SEQ ID NO: 537) | AAGCAGUUGUUCUCACUCC (SEQ ID NO: 538) | ORF | 47.36842105 |
| NM_006116_siRNA_267 | 267 | GCAACCGAGUGACCAACUU (SEQ ID NO: 539) | AAGUUGGUCACUCGGUUGC (SEQ ID NO: 540) | ORF | 52.63157895 |
| NM_006116_siRNA_831 | 831 | CCAAGUCCAAACCAAUCAU (SEQ ID NO: 543) | AUGAUUGGUUUGGACUUGG (SEQ ID NO: 544) | ORF | 42.10526316 |

Gene Name: MAP3K7IP1    GenBank Accession No. NM_153497    GI: 47717113
Organism: Homo sapiens    Length: 1994    ORF Region: 51-1438
Locus: 10454    Blast database: Human    ORF GC%: 60.12
Definition: Homo sapiens mitogen-activated protein kinase kinase 7 interacting protein 1 (MAP3K7IP1), transcript variant beta, mRNA.

| Name | Start | Sense RNA Sequence 5'-3' | Antisense RNA Sequence 5'-3' | Region | GC% |
|---|---|---|---|---|---|
| NM_153497_siRNA_219 | 219 | GGAGUGAGAACAACUGCUU (SEQ ID NO: 545) | AAGCAGUUGUUCUCACUCC (SEQ ID NO: 546) | ORF | 47.36842105 |
| NM_153497_siRNA_267 | 267 | GCAACCGAGUGACCAACUU (SEQ ID NO: 547) | AAGUUGGUCACUCGGUUGC (SEQ ID NO: 548) | ORF | 52.63157895 |
| NM_153497_siRNA_685 | 685 | GGAUGAGCUCUUCCGUCUU (SEQ ID NO: 549) | AAGACGGAAGAGCUCCAUCC (SEQ ID NO: 550) | ORF | 52.63157895 |
| NM_153497_siRNA_831 | 831 | CCAAGUCCAAACCAAUCAU (SEQ ID NO: 551) | AUGAUUGGUUUGGACUUGG (SEQ ID NO: 552) | ORF | 42.10526316 |

Gene Name: MAPT    GenBank Accession No. NM_005910    GI: 6754637
Organism: Homo sapiens    Length: 2796    ORF Region: 237-1562
Locus: 4137    Blast database: Human    ORF GC%: 58.68
Definition: Homo sapiens microtubule-associated protein tau (MAPT), transcript variant 2, mRNA.

TABLE 3-continued

| Name | Start | Sense RNA Sequence 5'-3' | Antisense RNA Sequence 5'-3' | Region | GC% |
|---|---|---|---|---|---|
| NM_005910_siRNA_1054 | 1054 | GGAAGGUGCAGAUAAUUAA (SEQ ID NO: 553) | UUAAUUAUCUGCACCUUCC (SEQ ID NO: 554) | ORF | 36.84210526 |
| NM_005910_siRNA_1147 | 1147 | GCAGUGUGCAAAUAGUCUA (SEQ ID NO: 555) | UAGACUAUUUGCACACUGC (SEQ ID NO: 556) | ORF | 42.10526316 |
| NM_005910_siRNA_1192 | 1192 | CCUCCAAGUGGCUCAUU (SEQ ID NO: 557) | AAUGAGCCACACUUGGAGG (SEQ ID NO: 558) | ORF | 52.63157895 |
| Gene Name: | MAPT | GenBank Accession No. | NM_016834 | GI: | 8400710 |
| Organism: | Homo sapiens | Length: | 2622 | ORF Region: | 237-1388 |
| Locus: | 4137 | Blast database: | Human | ORF GC% | 58.43 |
| Definition: | | | Homo sapiens microtubule-associated protein tau (MAPT), transcript variant 3, mRNA. | | |

| Name | Start | Sense RNA Sequence 5'-3' | Antisense RNA Sequence 5'-3' | Region | GC% |
|---|---|---|---|---|---|
| NM_016834_siRNA_877 | 877 | GCGGGAAGGUGCAGAUAAU (SEQ ID NO: 559) | AUUAUCUGCACCUUCCCGC (SEQ ID NO: 560) | ORF | 52.63157895 |
| NM_016834_siRNA_973 | 973 | GCAGUGUGCAAAUAGUCUA (SEQ ID NO: 561) | UAGACUAUUUGCACACUGC (SEQ ID NO: 562) | ORF | 42.10526316 |
| NM_016834_siRNA_1018 | 1018 | CCUCCAAGUGGCUCAUU (SEQ ID NO: 563) | AAUGAGCCACACUUGGAGG (SEQ ID NO: 564) | ORF | 52.63157895 |
| Gene Name: | MAPT | GenBank Accession No. | NM_016836 | GI: | 8400712 |
| Organism: | Homo sapiens | Length: | 3747 | ORF Region: | 237-2513 |
| Locus: | 4137 | Blast database: | Human | ORF GC% | 60.52 |
| Definition: | | | Homo sapiens microtubule-associated protein tau (MAPT), transcript variant 1, mRNA. | | |

| Name | Start | Sense RNA Sequence 5'-3' | Antisense RNA Sequence 5'-3' | Region | GC% |
|---|---|---|---|---|---|
| NM_016835_siRNA_250 | 250 | GCCAGGAGUUCGAAGUGAU (SEQ ID NO: 565) | AUCACUUCGAACUCCUGGC (SEQ ID NO: 566) | ORF | 52.63157895 |
| NM_016835_siRNA_797 | 797 | GCUCAAGCACCAGCUUCUA (SEQ ID NO: 567) | UAGAAGCUGGUGCUUGAGC (SEQ ID NO: 568) | ORF | 52.63157895 |
| NM_016835_siRNA_1413 | 1413 | GCCAAGACAUCCACACGUU (SEQ ID NO: 569) | AACGUGUGGAUGUCUUGGC (SEQ ID NO: 570) | ORF | 52.63157895 |
| NM_016835_siRNA_2098 | 2098 | GCAGUGUGCAAAUAGUCUA (SEQ ID NO: 571) | UAGACUAUUUGCACACUGC (SEQ ID NO: 572) | ORF | 42.10526316 |
| Gene Name: | MGAT1 | GenBank Accession No. | NM_002406 | GI: | 6031182 |
| Organism: | Homo sapiens | Length: | 2937 | ORF Region: | 497-1834 |
| Locus: | 4245 | Blast database: | Human | ORF GC% | 65.1 |
| Definition: | | | Homo sapiens mannosyl (alpha-1,3-)-glycoprotein beta-1,2-N-acetylglucosaminyltransferase (MGAT1), mRNA. | | |

TABLE 3-continued

| Name | Start | Sense RNA Sequence 5'-3' | Antisense RNA Sequence 5'-3' | Region | GC% |
|---|---|---|---|---|---|
| NM_002406_siRNA_541 | 541 | CCUCUUUGUGGCCUUGGAAU (SEQ ID NO: 573) | AUUCCAGGCCACAAAGAGG (SEQ ID NO: 574) | ORF | 52.63157895 |
| NM_002406_siRNA_1026 | 1026 | GCAAGUUCCAGGGCUACUA (SEQ ID NO: 575) | UAGUAGCCCUGGAACUUGC (SEQ ID NO: 576) | ORF | 52.63157895 |
| NM_002406_siRNA_1668 | 1668 | GGGACAGCUUCAAGGCUUU (SEQ ID NO: 577) | AAAGCCUUGAAGCUGUCCC (SEQ ID NO: 578) | ORF | 52.63157895 |

Gene Name: MICAL2  
Organism: Homo sapiens  
GenBank Accession No.: NM_014632  
Length: 3934  
Blast database: Human  
Locus: 9645  
ORF Region: 289-3663  
ORF GC%: 53.75  
GI: 41281417  
Definition: Homo sapiens microtubule associated monoxygenase, calponin and LIM domain containing 2 (MICAL2), mRNA.

| Name | Start | Sense RNA Sequence 5'-3' | Antisense RNA Sequence 5'-3' | Region | GC% |
|---|---|---|---|---|---|
| NM_014632_siRNA_372 | 372 | CCUCCAGGCCUUCAACAUU (SEQ ID NO: 579) | AAUGUUGAAGGCCUGGAGG (SEQ ID NO: 580) | ORF | 52.63157895 |
| NM_014632_siRNA_473 | 473 | CCAAAGCCCUGUGGUACAA (SEQ ID NO: 581) | UUGUACCACAGGGCUUUGG (SEQ ID NO: 582) | ORF | 52.63157895 |
| NM_014632_siRNA_585 | 585 | GCGCACUGCCAUUGAACUU (SEQ ID NO: 583) | AAGUUCAAUGGCAGUGCGC (SEQ ID NO: 584) | ORF | 52.63157895 |
| NM_014632_siRNA_746 | 746 | CCAUCGACCAUAUACAGUAU (SEQ ID NO: 585) | AUACUGUAUAUGGUCGAUGG (SEQ ID NO: 586) | ORF | 42.10526316 |
| NM_014632_siRNA_753 | 753 | CCAUAUCAGUAUUCCGCCAA (SEQ ID NO: 587) | UUGGCGAAUACUGAUAUGG (SEQ ID NO: 588) | ORF | 42.10526316 |
| NM_014632_siRNA_912 | 912 | CCAUUCUCUCGUCGGAGUUU (SEQ ID NO: 589) | AAACUCCGACAGAGAAUGG (SEQ ID NO: 590) | ORF | 47.36842105 |
| NM_014632_siRNA_1136 | 1136 | GCAUAGAUCUUGAGAACAU (SEQ ID NO: 591) | AUGUUCUCAAGAUCUAUGC (SEQ ID NO: 592) | ORF | 36.84210526 |
| NM_014632_siRNA_1338 | 1338 | GCUGCCAUUCCUUUAGACUUU (SEQ ID NO: 593) | AAAGUCUAAAGGAUGGCAGC (SEQ ID NO: 594) | ORF | 47.36842105 |
| NM_014632_siRNA_2402 | 2402 | GCAGUAAGGAAGGUGGAAA (SEQ ID NO: 595) | UUUCCACCUUCCUUACUGC (SEQ ID NO: 596) | ORF | 47.36842105 |
| NM_014632_siRNA_3111 | 3111 | CCAUUUGAGAACAGUGCAU (SEQ ID NO: 597) | AUGCACUGUUCUCAAAUGG (SEQ ID NO: 598) | ORF | 42.10526316 |

Gene Name: CLEC2D  
Organism: Homo sapiens  
GenBank Accession No.: NM_001004419  
Length: 1821  
Blast database: Human  
Locus: 29121  
ORF Region: 23-607  
ORF GC%: 41.71  
GI: 52426781  
Definition: Homo sapiens C-type lectin domain family 2, member D (CLEC2D), transcript variant 2, mRNA. (OCIL)

| Name | Start | Sense RNA Sequence 5'-3' | Antisense RNA Sequence 5'-3' | Region | GC% |
|---|---|---|---|---|---|
| NM_001004419_siRNA_506 | 506 | GCCAACUUGUAUGUUGCAA (SEQ ID NO: 599) | UUGCAACAUACAAGUUGGC (SEQ ID NO: 600) | ORF | 42.10526316 |

TABLE 3-continued

| Name | Start | Sense RNA Sequence 5'-3' | Antisense RNA Sequence 5'-3' | Region | GC% |
|---|---|---|---|---|---|
| NM_001004419_siRNA_507 | 507 | CCAACUGUAUGUUGCAAA (SEQ ID NO: 601) | UUUGCAACAUACAAGUUGG (SEQ ID NO: 602) | ORF | 36.84210526 |
| NM_001004419_siRNA_551 | 551 | CCAAGACCUGUCAUGGUUU (SEQ ID NO: 603) | AAACCAUGACAGGUCUUGG (SEQ ID NO: 604) | ORF | 47.36842105 |
| NM_001004419_siRNA_582 | 582 | GCAGAGAGUGUGCCUAUU (SEQ ID NO: 605) | AAUAGGCACACUCUCCUGC (SEQ ID NO: 606) | ORF | 52.63157895 |

Gene Name: CLEC2D  GenBank Accession No. NM_001004420  GI: 52426783
Organism: Homo sapiens  Length: 1814  ORF Region: 23-391
Locus: 29121  Blast database: Human  ORF GC% 40.11
Definition: Homo sapiens C-type lectin domain family 2, member D (CLEC2D), transcript variant 3, mRNA. (OCIL)

| Name | Start | Sense RNA Sequence 5'-3' | Antisense RNA Sequence 5'-3' | Region | GC% |
|---|---|---|---|---|---|
| NM_013269_siRNA_402 | 402 | GCCCAUCUGAUCACUGGAU (SEQ ID NO: 613) | AUCCAGUGAUCAGAUGGGC (SEQ ID NO: 614) | ORF | 52.63157895 |
| NM_013269_siRNA_441 | 441 | GCCAACCAUGGAAAUGGAU (SEQ ID NO: 615) | AUCCAUUUCCAUGGUUGGC (SEQ ID NO: 616) | ORF | 47.36842105 |
| NM_013269_siRNA_500 | 500 | GCAGAGAGUGUGCCUAUU (SEQ ID NO: 617) | AAUAGGCACACUCUCCUGC (SEQ ID NO: 618) | ORF | 52.63157895 |
| NM_013269_siRNA_561 | 561 | GGAAGUGGAUUUGUUCCAA (SEQ ID NO: 619) | UUGGAACAAAUCCACUUCC (SEQ ID NO: 620) | ORF | 42.10526316 |

Gene Name: ASAM  GenBank Accession No. NM_024769  GI: 41393588
Organism: Homo sapiens  Length: 2645  ORF Region: 360-1481
Locus: 79827  Blast database: Human  ORF GC% 51.61
Definition: Homo sapiens adipocyte-specific adhesion molecule (ASAM), mRNA.

| Name | Start | Sense RNA Sequence 5'-3' | Antisense RNA Sequence 5'-3' | Region | GC% |
|---|---|---|---|---|---|
| NM_024769_siRNA_391 | 391 | CCUACUAUGUUGGACCUU (SEQ ID NO: 621) | AAGGUCCAACAUAGUAGG (SEQ ID NO: 622) | ORF | 42.10526316 |
| NM_024769_siRNA_682 | 682 | GGUACACCUGUAAGGUUAA (SEQ ID NO: 623) | UUAACCUUACAGGUGUACC (SEQ ID NO: 624) | ORF | 42.10526316 |
| NM_024769_siRNA_780 | 780 | GGAGAGCUGACAGAAGGAA (SEQ ID NO: 625) | UUCCUUCUGUCAGCUCUCC (SEQ ID NO: 626) | ORF | 52.63157895 |
| NM_024769_siRNA_1022 | 1022 | GCGAGUAACUGUACAGUAU (SEQ ID NO: 627) | AUACUGUACAGUUAUCCGC (SEQ ID NO: 628) | ORF | 42.10526316 |
| NM_024769_siRNA_1406 | 1406 | CCAUGCUAAUCUGACCAAA (SEQ ID NO: 629) | UUUGGUCAGAUUAGCAUGG (SEQ ID NO: 630) | ORF | 42.10526316 |

Gene Name: NUMB  GenBank Accession No. NM_003744  GI: 54144623
Organism: Homo sapiens  Length: 3614  ORF Region: 321-2243

TABLE 3-continued

| Locus: | 8650 | | | | |
|---|---|---|---|---|---|
| Blast database: | Human | | | | |
| Definition: | Homo sapiens numb homolog (Drosophila) (NUMB), transcript variant 3, mRNA. | | | | |
| Name | Start | Sense RNA Sequence 5'-3' | Antisense RNA Sequence 5'-3' | Region | ORF GC% |
| NM_003744_siRNA_700 | 700 | GCUGGAUCUGUCACUGCUU (SEQ ID NO: 631) | AAGCAGUGACAGAUCCAGC (SEQ ID NO: 632) | ORF | 52.63157895 |
| NM_003744_siRNA_864 | 864 | GGAUCAUUCCGUGUCACAA (SEQ ID NO: 633) | UUGUGACACGGAAUGAUCC (SEQ ID NO: 634) | ORF | 47.36842105 |
| NM_003744_siRNA_1139 | 1139 | CCAGAAGAUGACAUCCCUUU (SEQ ID NO: 635) | AAAGGGUGACAUCUUCUGG (SEQ ID NO: 636) | ORF | 47.36842105 |
| NM_003744_siRNA_1402 | 1402 | CCUUCCAUGUGCUUGCUAA (SEQ ID NO: 637) | UUAGCAAGCACAUGGAAGG (SEQ ID NO: 638) | ORF | 47.36842105 |
| NM_003744_siRNA_1615 | 1615 | GGUUAGAAGAGGUGUCUAA (SEQ ID NO: 639) | UUAGACACCUCUUCUAACC (SEQ ID NO: 640) | ORF | 42.10526316 |
| NM_003744_siRNA_1999 | 1999 | CCACCAGUCCCUUCUUUAA (SEQ ID NO: 641) | UUAAAGAAGGGACUGGUGG (SEQ ID NO: 642) | ORF | 47.36842105 |

| Gene Name: | PDE4B | | | | |
|---|---|---|---|---|---|
| Organism: | Homo sapiens | | GenBank Accession No. | NM_002600 | GI: 32171240 |
| Locus: | 5142 | | Length: 3186 | | ORF Region: 139-2349 |
| Blast database: | Human | | | | |
| Definition: | Homo sapiens phosphodiesterase 4B, cAMP-specific (phosphodiesteraseE4 dunce homolog, Drosophila) (PDE4B), mRNA. | | | | |
| Name | Start | Sense RNA Sequence 5'-3' | Antisense RNA Sequence 5'-3' | Region | ORF GC% 46.32 |
| NM_002600_siRNA_218 | 218 | CCUACAGUUCUUCCAGUAA (SEQ ID NO: 643) | UUACUGGAAGAACUGUAGG (SEQ ID NO: 644) | ORF | 42.10526316 |
| NM_002600_siRNA_527 | 527 | GCAGAGAGUCAUUUCUCUA (SEQ ID NO: 645) | UAGAGAAAUGACUCUCUGC (SEQ ID NO: 646) | ORF | 42.10526316 |
| NM_002600_siRNA_945 | 945 | CCAGGUGUCUGAAUACAUU (SEQ ID NO: 647) | AAUGUAUUCAGACACCUGG (SEQ ID NO: 648) | ORF | 42.10526316 |
| NM_002600_siRNA_1499 | 1499 | CCAAUCAGUUUCUCAUCAA (SEQ ID NO: 649) | UUGAUGAGAAACUGAUUGG (SEQ ID NO: 650) | ORF | 36.84210526 |
| NM_002600_siRNA_1763 | 1763 | GCGUCUUCUCCUAGACAA (SEQ ID NO: 651) | UUGUCUAGGAGAAGACGC (SEQ ID NO: 652) | ORF | 47.36842105 |
| NM_002600_siRNA_2050 | 2050 | GCUCAGGACAUUCUCGAUA (SEQ ID NO: 653) | UAUCGAGAAUGUCCUGAGC (SEQ ID NO: 654) | ORF | 47.36842105 |

| Gene Name: | ABCB1 | | | | |
|---|---|---|---|---|---|
| Organism: | Homo sapiens | | GenBank Accession No. | NM_000927 | GI: 42741658 |
| Locus: | 5243 | | Length: 4872 | | ORF Region: 419-4261 |
| Blast database: | Human | | | | |
| Definition: | Homo sapiens ATP-binding cassette, sub-family B (MDR/TAP), member 1 (ABCB1), mRNA. | | | | ORF GC% 43.69 |

TABLE 3-continued

| Name | Start | Sense RNA Sequence 5'-3' | Antisense RNA Sequence 5'-3' | Region | GC% |
|---|---|---|---|---|---|
| NM_000927_siRNA_761 | 761 | GCCUAUAUUACAGUGGAA (SEQ ID NO: 655) | UUCCACUGUAAUAUAGGC (SEQ ID NO: 656) | ORF | 36.84210526 |
| NM_000927_siRNA_1330 | 1330 | GCUGAUCUAUGCAUCUUAU (SEQ ID NO: 657) | AUAAGAUGCAUAGAUCAGC (SEQ ID NO: 658) | ORF | 36.84210526 |
| NM_000927_siRNA_1470 | 1470 | GCAUUGAAGCAUUUGCAAA (SEQ ID NO: 659) | UUUGCAAAUGCUUCAAUGC (SEQ ID NO: 660) | ORF | 36.84210526 |
| NM_000927_siRNA_1732 | 1732 | GCUGAUGCAGAGGCUCUAU (SEQ ID NO: 661) | AUAGAGCCUCUGCAUCAGC (SEQ ID NO: 662) | ORF | 52.63157895 |
| NM_000927_siRNA_2309 | 2309 | GCAGAAAUGAAGUUGAAU (SEQ ID NO: 663) | AUUCACUUCAUUUCCUGC (SEQ ID NO: 664) | ORF | 36.84210526 |
| NM_000927_siRNA_2815 | 2815 | GGAUGUAGUUGGUUUGAU (SEQ ID NO: 665) | AUCAAACCAACUACAUCC (SEQ ID NO: 666) | ORF | 42.10526316 |
| NM_000927_siRNA_3915 | 3915 | GCACUAAGUAGGAGACAA (SEQ ID NO: 667) | UUGUCUCCUACUUUAGUGC (SEQ ID NO: 668) | ORF | 42.10526316 |

Gene Name: HTRA1  
Organism: Homo sapiens  
GenBank Accession No. NM_002775  
Length: 2133  
GI: 73747816  
ORF Region: 113-1555

Locus: 5654  
Blast database: Human  
ORF GC%: 59.26

Definition: Homo sapiens HtrA serine peptidase 1 (HTRA1), mRNA. (PRSS11)

| Name | Start | Sense RNA Sequence 5'-3' | Antisense RNA Sequence 5'-3' | Region | GC% |
|---|---|---|---|---|---|
| NM_002775_siRNA_597 | 597 | CCAACAGUUUGCGCCAUAA (SEQ ID NO: 669) | UUAUGGCGCAAACUGUUGG (SEQ ID NO: 670) | ORF | 47.36842105 |
| NM_002775_siRNA_716 | 716 | GCUACUGGGUCUGGGUUUA (SEQ ID NO: 671) | UAAACCCAGACCCACUAGC (SEQ ID NO: 672) | ORF | 52.63157895 |
| NM_002775_siRNA_1073 | 1073 | GCCAUCAUCAACUAUGGAA (SEQ ID NO: 673) | UUCCAUAGUUGAUGAUGGC (SEQ ID NO: 674) | ORF | 42.10526316 |
| NM_002775_siRNA_1114 | 1114 | CCUGGACGUGGAAGUGAUU (SEQ ID NO: 675) | AAUCACUUCACCGUCCAGG (SEQ ID NO: 676) | ORF | 52.63157895 |
| NM_002775_siRNA_1535 | 1535 | CCCGAAGAAAUUGACCCAU (SEQ ID NO: 677) | AUGGGUCAAUUUCUUCGGG (SEQ ID NO: 678) | ORF | 47.36842105 |

Gene Name: NPEPPS  
Organism: Homo sapiens  
GenBank Accession No. NM_006310  
Length: 4177  
GI: 15451906  
ORF Region: 196-2823

Locus: 9520  
Blast database: Human  
ORF GC%: 44.79

Definition: Homo sapiens aminopeptidase puromycin sensitive (NPEPPS), mRNA.  
Sequence: NM_006310

| Name | Start | Sense RNA Sequence 5'-3' | Antisense RNA Sequence 5'-3' | Region | GC% |
|---|---|---|---|---|---|
| NM_006310_siRNA_1939 | 1939 | GCUCGAGCUGGAAUCAUUA (SEQ ID NO: 679) | UAAUGAUUCCAGCUCGAGC (SEQ ID NO: 680) | ORF | 47.36842105 |

TABLE 3-continued

| Name | Sense RNA Sequence 5'-3' | Antisense RNA Sequence 5'-3' |
|---|---|---|
| NM_006310_siRNA_2539 | GCUGCUUGGAAAUUCAUAA (SEQ ID NO: 681) | UUAUGAAUUUCCAAGCAGC (SEQ ID NO: 682) ORF 36.84210526 |
| NM_006310_siRNA_2622 | GCUAUCAGUUGAGGGAUUU (SEQ ID NO: 683) | AAAUCCCUCAACUGAUAGC (SEQ ID NO: 684) ORF 42.10526316 |

Gene Name: PSMA7  GenBank Accession No. NM_002792  GI: 23110945
Organism: Homo sapiens  Length: 984  ORF Region: 116-862
Locus: 5688  Blast database: Human  ORF GC% 50.47
Definition: Homo sapiens proteasome (prosome, macropain) subunit, alpha type, 7(PSMA7), transcript variant 1, mRNA.

| Name | Sense RNA Sequence 5'-3' | Antisense RNA Sequence 5'-3' | Region | GC% |
|---|---|---|---|---|
| NM_002792_siRNA_266 | GCCAAACUGCAGGAUGAAA (SEQ ID NO: 685) | UUUCAUCCUGCAGUUUGGC (SEQ ID NO: 686) | ORF | 47.36842105 |
| NM_002792_siRNA_300 | UCUGUGGCUUUGGAUGACAA (SEQ ID NO: 687) | UGUGUCAUCCAAAGCACAGA (SEQ ID NO: 688) | ORF | 42.10526316 |
| NM_002792_siRNA_348 | CCGAUGCAAGGAUAGUCAU (SEQ ID NO: 689) | AUGACUAUCCUUGCAUCGG (SEQ ID NO: 690) | ORF | 47.36842105 |

Gene Name: PTS  GenBank Accession No. NM_000317  GI: 4506330
Organism: Homo sapiens  Length: 921  ORF Region: 69-506
Locus: 5805  Blast database: Human  ORF GC% 43.16
Definition: Homo sapiens 6-pyruvoyltetrahydropterin synthase (PTS), mRNA.

| Name | Sense RNA Sequence 5'-3' | Antisense RNA Sequence 5'-3' | Region | GC% |
|---|---|---|---|---|
| NM_000317_siRNA_137 | CCACCGAUUGUACAGUAAA (SEQ ID NO: 691) | UUUACUGUACAAUCGGUGG (SEQ ID NO: 692) | ORF | 42.10526316 |
| NM_000317_siRNA_275 | GGUUAUGAAUCUGGCUGAU (SEQ ID NO: 693) | AUCAGCCAGAUUCAUAACC (SEQ ID NO: 694) | ORF | 42.10526316 |
| NM_000317_siRNA_413 | GGACAACCUCCAGAAAGUU (SEQ ID NO: 695) | AACUUUCUGGAGGUUGUCC (SEQ ID NO: 696) | ORF | 47.36842105 |

Gene Name: RIN2  GenBank Accession No. NM_018993  GI: 35493905
Organism: Homo sapiens  Length: 4529  ORF Region: 37-2724
Locus: 54453  Blast database: Human  ORF GC% 55.92
Definition: Homo sapiens Ras and Rab interactor 2 (RIN2), mRNA.

| Name | Sense RNA Sequence 5'-3' | Antisense RNA Sequence 5'-3' | Region | GC% |
|---|---|---|---|---|
| NM_018993_siRNA_471 | GGAAUUUGCCAUAAAAGGAA (SEQ ID NO: 697) | UUCCUUUAUGGCAAAUUCC (SEQ ID NO: 698) | ORF | 36.84210526 |

TABLE 3-continued

| Name | Start | Sense RNA Sequence 5'-3' | Antisense RNA Sequence 5'-3' | Region | GC% |
|---|---|---|---|---|---|
| NM_018993_siRNA_569 | 569 | GCAGGGAUGUUCUACCAUU (SEQ ID NO: 699) | AAUGGUAGAACAUCCCUGC (SEQ ID NO: 700) | ORF | 47.36842105 |
| NM_018993_siRNA_1034 | 1034 | GCAUGCCAGAAACAGUCAA (SEQ ID NO: 701) | UUGACUGUUUCUGGCAUGC (SEQ ID NO: 702) | ORF | 47.36842105 |
| NM_018993_siRNA_1376 | 1376 | GCAUGCCUCUGUUUGGCUA (SEQ ID NO: 703) | UAGCCAAACAGAGGCAUGC (SEQ ID NO: 704) | ORF | 52.63157895 |
| NM_018993_siRNA_2236 | 2236 | GGAGGCUAUAUACUUGACAA (SEQ ID NO: 705) | UUGUCAAGUAUAUAGCCUCC (SEQ ID NO: 706) | ORF | 42.10526316 |

Gene Name: ROR1  GenBank Accession No. NM_005012  GI: 4826867
Organism: Homo sapiens  Length: 3358  ORF Region: 376-3189
Locus: Blast database: Human  ORF GC%: 47.45
Definition: Homo sapiens receptor tyrosine kinase-like orphan receptor 1 (ROR1), mRNA.

| Name | Start | Sense RNA Sequence 5'-3' | Antisense RNA Sequence 5'-3' | Region | GC% |
|---|---|---|---|---|---|
| NM_005012_siRNA_932 | 932 | CCGUCUAUAUGGAGUCUUU (SEQ ID NO: 707) | AAAGACUCCAUAUAGACGG (SEQ ID NO: 708) | ORF | 42.10526316 |
| NM_005012_siRNA_1543 | 1543 | GCUUCGAUUCAAAGGAUU (SEQ ID NO: 709) | AAUCCUUUGAAUCGCAAGC (SEQ ID NO: 710) | ORF | 42.10526316 |
| NM_005012_siRNA_1920 | 1920 | GCAAUGGAUGGAAUUUCAA (SEQ ID NO: 711) | UUGAAAUUCCAUCCAUUGC (SEQ ID NO: 712) | ORF | 36.84210526 |
| NM_005012_siRNA_2817 | 2817 | GCGAUUCAUUCCCAUCAAU (SEQ ID NO: 713) | AUUGAUGGGAAUGAAUCGC (SEQ ID NO: 714) | ORF | 42.10526316 |
| NM_005012_siRNA_3031 | 3031 | CCACACAUGUCAAUUCCAA (SEQ ID NO: 715) | UUGGAAUUGACAUGUGUGG (SEQ ID NO: 716) | ORF | 42.10526316 |

Organism: Homo sapiens  Length: 10670  ORG Region: 287-1228
Locus: Blast database: Human  ORF GC%: 51.39
Definition: Homo sapiens Ras-related GTP binding A (RRAGA), mRNA.

| Name | Start | Sense RNA Sequence 5'-3' | Antisense RNA Sequence 5'-3' | Region | GC% |
|---|---|---|---|---|---|
| NM_006570_siRNA_351 | 351 | GCAUGAGGUCGAUAAUCUU (SEQ ID NO: 717) | AAGAUUAUCGACCUCAUGC (SEQ ID NO: 718) | ORF | 42.1052316 |
| NM_006570_siRNA_510 | 510 | CCAGCCAGCGAGACAAUAU (SEQ ID NO: 719) | AUAUUGUCUCCGCUGGCUGG (SEQ ID NO: 720) | ORF | 52.63157895 |
| NM_006570_siRNA_673 | 673 | GGAUCUGGUUCAGGAGGAU (SEQ ID NO: 721) | AUCCUCCUGAACCAGAUCC (SEQ ID NO: 722) | ORF | 52.63157895 |
| NM_006570_siRNA_1056 | 1056 | CCAACUUCGCUGCUUUCAU (SEQ ID NO: 723) | AUGAAAGCAGCGAAGUUGG (SEQ ID NO: 724) | ORF | 47.36842105 |

Gene Name: RYK  GenBank Accession No. NM_002958  GI: 54607017
Organism: Homo sapiens  Length: 2951  ORF Region: 91-1914

TABLE 3-continued

| Locus: | 6259 | Blast database: | Human | | ORF GC% | 42.38 |
|---|---|---|---|---|---|---|
| Definition: | | *Homo sapiens* RYK receptor-like tyrosine kinase (RYK), transcript variant 2, mRNA. | | | | |
| Name | Start | Sense RNA Sequence 5'-3' | | Antisense RNA Sequence 5'-3' | Region | GC% |
| NM_002958_siRNA_558 | 558 | GCUUCCUGUACUGGCAAA (SEQ ID NO: 725) | | UUUGCCAGUACAGGAAAGC (SEQ ID NO: 726) | ORF | 47.36842105 |
| NM_002958_siRNA_748 | 748 | GCAGUCCAACCACUUCUA (SEQ ID NO: 727) | | UAGAAGUGGUUGGAGCUGC (SEQ ID NO: 728) | ORF | 52.63157895 |
| NM_002958_siRNA_1367 | 1367 | GCAAGUUAGUAGAGCCAA (SEQ ID NO: 729) | | UUGGCCUCUACUAACUUGC (SEQ ID NO: 730) | ORF | 47.36842105 |
| NM_002958_siRNA_1413 | 1413 | CCUGUACACAUGGCUAUU (SEQ ID NO: 731) | | AAUAGCCAUGUGUACCAGG (SEQ ID NO: 732) | ORF | 47.36842105 |
| NM_002958_siRNA_1779 | 1779 | GCCAUCAACUGUCCUGAU (SEQ ID NO: 733) | | AUCAGGACAGUUGAUUGGC (SEQ ID NO: 734) | ORF | 47.36842105 |
| Gene Name: | S100A6 | GenBank Accession No. | NM_014624 | | GI: | 52352807 |
| Organism: | *Homo sapiens* | Length: | 683 | | ORF Region: | 315-587 |
| Locus: | 6277 | Blast database: | Human | | ORF GC% | 56.05 |
| Definition: | | *Homo sapiens* S100 calcium binding protein A6 (calcyclin) (S100A6), mRNA. | | | | |
| Name | Start | Sense RNA Sequence 5'-3' | | Antisense RNA Sequence 5'-3' | Region | GC% |
| NM_014624_siRNA_455 | 455 | GCUGCAGGAUGCUGAAAUU (SEQ ID NO: 735) | | AAUUUCAGCAUCCUGCAGC (SEQ ID NO: 736) | ORF | 47.36842105 |
| NM_014624_siRNA_474 | 474 | GCAAGGCUGAUCGAAGACU (SEQ ID NO: 737) | | AGUCUUCGAUCAGCCUUGC (SEQ ID NO: 738) | ORF | 52.63157895 |
| NM_014624_siRNA_479 | 479 | GCUGAUGGAAGACUUGGAC (SEQ ID NO: 739) | | GUCCAAGUCUUCCAUCAGC (SEQ ID NO: 740) | ORF | 52.63157895 |
| Gene Name: | S100A1 | GenBank Accession No. | NM_006271 | | GI: | 5454031 |
| Organism: | *Homo sapiens* | Length: | 607 | | ORF Region: | 114-398 |
| Locus: | 6271 | Blast database: | Human | | ORF GC% | 55.44 |
| Definition: | | *Homo sapiens* S100 calcium binding protein A1 (S100A1), mRNA. | | | | |
| Name | Start | Sense RNA Sequence 5'-3' | | Antisense RNA Sequence 5'-3' | Region | GC% |
| NM_006271_siRNA_136 | 136 | CGAUGGAGACCCUCAUCAA (SEQ ID NO: 741) | | UUGAUGAGGGUCUCCAUCG (SEQ ID NO: 742) | ORF | 52.63157895 |
| NM_006271_siRNA_137 | 137 | GAUGGAGACCCUCAUCAAC (SEQ ID NO: 743) | | GUUGAUGAGGGUCUCCAUC (SEQ ID NO: 744) | ORF | 52.63157895 |
| Gene Name: | SCMH1 | GenBank Accession No. | NM_012236 | | GI: | 16912641 |
| Organism: | *Homo sapiens* | Length: | 3250 | | ORF Region: | 485-2260 |

TABLE 3-continued

| Locus: | 22955 | | | | |
|---|---|---|---|---|---|
| Definition: | Blast database: | | Human | | |
| | *Homo sapiens* sex comb on midleg homolog 1 (Drosophila) (SCMH1), transcript variant 2, mRNA. | | | | |
| Name | Start | Sense RNA Sequence 5'-3' | | Antisense RNA Sequence 5'-3' | ORF GC% 54.79 |
| NM_012236_siRNA_876 | 876 | GGAAGAAACCCUCAUUUCAU (SEQ ID NO: 745) | | AUGAAAUGAGGGUUCUUCC (SEQ ID NO: 746) | ORF 42.10526316 |
| NM_012236_siRNA_1632 | 1632 | GGGACAGCAUACCCUUCAA (SEQ ID NO:747) | | UUGAGGGUAUGCUGUUCCC (SEQ ID NO: 748) | ORF 52.63157895 |
| NM_012236_siRNA_1743 | 1743 | CCUUUACACAGACUCACUU (SEQ ID NO:749) | | AAGUGAGUCUGUGUAAAGG (SEQ ID NO: 750) | ORF 42.10526316 |
| NM_012236_siRNA_1804 | 1804 | CCUACCAGGUGAAACCUUU (SEQ ID NO: 751) | | AAAGGUUUCACCUGGUAGG (SEQ ID NO: 752) | ORF 47.36842105 |
| Gene Name: | SERP1 | GenBank Accession No. | | NM_014445 | GI: 19923408 |
| Organism: | *Homo sapiens* | Length: | | 2488 | ORF Region: 316-516 |
| Definition: | Blast database; | | Human | | ORF GC% 50.25 |
| | *Homo sapiens* stress-associated endoplasmic reticulum protein 1 (SERP1), mRNA. | | | | |
| Name | Start | Sense RNA Sequence 5'-3' | | Antisense RNA Sequence 5'-3' | Region GC% |
| NM_014445_siRNA_323 | 323 | CCAAGCAAAGGAUCCGUAU (SEQ ID NO: 753) | | AUACGGAUCCUUUGCUUGG (SEQ ID NO: 754) | ORF 47.36842105 |
| NM_014445_siRNA_434 | 434 | CCUGGUUAUUGGCUCUCUU (SEQ ID NO: 755) | | AAGAGAGCCAAUAACCAGG (SEQ ID NO: 756) | ORF 47.36842105 |
| NM_014445_siRNA_437 | 437 | GGUUAUUGGCUCUCUUCAU (SEQ ID NO: 757) | | AUGAAGAGAGCCAAUAACC (SEQ ID NO: 758) | ORF 42.10526316 |
| Gene Name: | SRP19 | GenBank Accession No. | | NM_003135 | GI: 4507212 |
| Organism: | *Homo sapiens* | Length: | | 894 | ORF Region: 82-516 |
| Definition: | Blast database; | | Human | | ORF GC% 41.38 |
| | *Homo sapiens* signal recognition particle 19kDa (SRP19), mRNA. | | | | |
| Name | Start | Sense RNA Sequence 5'-3' | | Antisense RNA Sequence 5'-3' | Region GC% |
| NM_003135_siRNA_110 | 110 | CCGACCAGGACAGGUUUAU (SEQ ID NO: 759) | | AUAAACCUGUCCUGGUCGG (SEQ ID NO: 760) | ORF 52.63157895 |
| NM_003135_siRNA_244 | 244 | GCAGUUGGACUUAACGUAU (SEQ ID NO: 761) | | AUACGUUAAGUCCAACUGC (SEQ ID NO: 762) | ORF 42.10526316 |
| NM_003135_siRNA_454 | 454 | GCUGACCAAAGUCUUCAAC (SEQ ID NO: 763) | | GUUGAAGACUUUGGUCAGC (SEQ ID NO: 764) | ORF 47.36842105 |
| Gene Name: | TPM1 | GenBank Accession No. | | NM_000366 | GI: 63252894 |
| Organism: | *Homo sapiens* | Length: | | 1294 | ORF Region: 192-1046 |

TABLE 3-continued

| Locus: | 7168 | Blast database: | Human | ORF GC% | 50.77 |
|---|---|---|---|---|---|
| Definition: | | Homo sapiens tropomyosin 1 (alpha) (TPM1), transcript variant 5, mRNA. | | | |
| Name | Start | Sense RNA Sequence 5'-3' | Antisense RNA Sequence 5'-3' | Region | GC% |
| NM_000366_siRNA_688 | 688 | CCCGUAAGCUGGUCAUCAU (SEQ ID NO 765) | AUGAUGACCAGCUUACGGG (SEQ ID NO: 766) | ORF | 52.63157895 |
| NM_000366_siRNA_915 | 915 | GCGGAGAGGUCAGUAACUA (SEQ ID NO: 767) | UAGUUACUGACCUCUCCGC (SEQ ID NO: 768) | ORF | 52.63157895 |
| NM_000366_siRNA_1020 | 1020 | GCUCUCAACCAUAUGACUU (SEQ ID NO: 769) | AAGUCAUAUGGUUGAGAGC (SEQ ID NO: 770) | ORF | 42.10526316 |
| Gene Name: | TRIM52 | GenBank Accession No. | NM_032765 | GI: | 34147443 |
| Organism: | Homo sapiens | Length: | 2244 | ORF Region: | 306-1199 |
| Locus: | 84851 | Blast database: | Human | ORF GC% | 48.77 |
| Definition: | | Homo sapiens tripartite motif-containing 52 (TRIM52), mRNA. | | | |
| Name | Start | Sense RNA Sequence 5'-3' | Antisense RNA Sequence 5'-3' | Region | GC% |
| NM_032765_siRNA_1115 | 1115 | CCAGGAAAUAAAGUUGGAA (SEQ ID NO: 771) | UUCCAACUUUAUUUCCUGG (SEQ ID NO: 772) | ORF | 36.84210526 |
| NM_032765_siRNA_1142 | 1142 | GGUGGGAAUACUUCAGAUA (SEQ ID NO: 773) | UAUCUGAAGUAUUCCCACC (SEQ ID NO: 774) | ORF | 42.10526316 |
| NM_032765_siRNA_1145 | 1145 | GGGAAUACUUCAGAUAGAG (SEQ ID NO: 775) | CUCUAUCUGAAGUAUUCCC (SEQ ID NO: 776) | ORF | 42.10526316 |
| NM_032765_siRNA_1171 | 1171 | GCAUUCACAGCAAGGCCUA (SEQ ID NO: 777) | UAGGCCUUGCUGUGAAUGC (SEQ ID NO: 778) | ORF | 52.63157895 |
| Gene Name: | MTHFD1 | GenBank Accession No. | NM_005956 | GI: | 13699867 |
| Organism: | Homo sapiens | Length: | 3110 | ORF Region: | 54-2861 |
| Locus: | 4522 | Blast database: | Human | ORF GC% | 49.11 |
| Definition: | | | | | |
| Sequence: | NM_005956 | | | | |
| Name | Start | Sense RNA Sequence 5'-3' | Antisense RNA Sequence 5'-3' | Region | GC% |
| NM_005956_siRNA_184 | 184 | GCAACAGAGAUGAUCCAA (SEQ ID NO: 779) | UUGGAAUCAUCUCUGUUGC (SEQ ID NO: 780) | ORF | 42.10526316 |
| NM_005956_siRNA_696 | 696 | GCAACUGGUCAGCCUGAAA (SEQ ID NO: 781) | UUUCAGGCUGACCAGUUGC (SEQ ID NO: 782) | ORF | 52.63157895 |
| NM_005956_siRNA_1429 | 1429 | CCAUUGAUGCUCGGAUAUU (SEQ ID NO: 783) | AAUAUCCGAGCAUCAAUGG (SEQ ID NO: 784) | ORF | 42.10526316 |

TABLE 3-continued

| Name | Start | Sense RNA Sequence 5'-3' | Antisense RNA Sequence 5'-3' | Region | GC% |
|---|---|---|---|---|---|
| NM_005956_siRNA_1780 | 1780 | CCACUUCUCUAGAGAGACAU (SEQ ID NO: 785) | AUGUCUUCUAGAGAAGUGG (SEQ ID NO: 786) | ORF | 42.10526316 |
| NM_005956_siRNA_2482 | 2482 | GCAGCUUCCAGCUCCUUUA (SEQ ID NO: 787) | UAAAGGAGCUGGAAGCUGC (SEQ ID NO: 788) | ORF | 52.63157895 |

Gene Name: UBE1C
GenBank Accession No.: NM_003966
GI: 38045941
Organism: Homo sapiens
Length: 2136
ORF Region: 21-1412
Locus: 9039
Blast database: Human
ORF GC%: 42.25
Definition:
Sequence: NM_003968

| Name | Start | Sense RNA Sequence 5'-3' | Antisense RNA Sequence 5'-3' | Region | GC% |
|---|---|---|---|---|---|
| NM_003968_siRNA_133 | 133 | GGAACCAUGUAAAGAAGUU (SEQ ID NO: 789) | AACUUCUUUACAUUGGUUCC (SEQ ID NO: 790) | ORF | 36.84210526 |
| NM_003968_siRNA_393 | 393 | GCUGAAGUGCUGCAGAAU (SEQ ID NO: 791) | AUUCUGCAGCAACUUCAGC (SEQ ID NO: 792) | ORF | 47.36842105 |
| NM_003968_siRNA_594 | 594 | CCAAGCUCCAUUGUCCCUU (SEQ ID NO: 793) | AAGGGACAAUGGAGCUUGG (SEQ ID NO: 794) | ORF | 52.63157895 |
| NM_003968_siRNA_1023 | 1023 | GCAUACAUUCCCUGAAUA (SEQ ID NO: 795) | UAUUCAAGGGAAUGUAUGC (SEQ ID NO: 796) | ORF | 36.84210526 |
| NM_003968_siRNA_1197 | 1197 | GCUUCUGCAAAUGAAAU (SEQ ID NO: 797) | AUUUCAUUUGCAGAGAAGC (SEQ ID NO: 798) | ORF | 36.84210526 |

Gene Name: UBE1C
GenBank Accession No.: NM_198195
GI: 3805943
Organism: Homo sapiens
Length: 2094
ORF Region: 21-1370
Locus: 9039
Blast database: Human
ORF GC%: 42.08
Definition:
Sequence: NM_198195

| Name | Start | Sense RNA Sequence 5'-3' | Antisense RNA Sequence 5'-3' | Region | GC% |
|---|---|---|---|---|---|
| NM_198195_siRNA_35 | 35 | GGAGCCAAUGGCUGUGAU (SEQ ID NO: 799) | AUCAACAGCCAUUGGCUCC (SEQ ID NO: 800) | ORF | 52.63157895 |
| NM_198195_siRNA_91 | 91 | GGAACCAUGUAAAGAAGUU (SEQ ID NO: 801) | AACUUCUUUACAUUGGUUCC (SEQ ID NO: 802) | ORF | 36.84210526 |
| NM_198195_siRNA_351 | 351 | GCUGAAGUGCUGCAGAAU (SEQ ID NO: 803) | AUUCUGCAGCAACUUCAGC (SEQ ID NO: 804) | ORF | 47.36842105 |
| NM_198195_siRNA_552 | 552 | CCAAGCUCCAUUGUCCCUU (SEQ ID NO: 805) | AAGGGACAAUGGAGCUUGG (SEQ ID NO: 806) | ORF | 52.63157895 |
| NM_198195_siRNA_981 | 981 | GCAUACAUUCCCUGAAUA (SEQ ID NO: 807) | UAUUCAAGGGAAUGUAUGC (SEQ ID NO: 808) | ORF | 36.84210526 |
| NM_198195_siRNA_1155 | 1155 | GCUUCUGCAAAUGAAAU (SEQ ID NO: 809) | AUUUCAUUUGCAGAGAAGC (SEQ ID NO: 810) | ORF | 36.84210526 |

TABLE 3-continued

| Gene Name: | UBE1C | GenBank Accession No. | NM_198197 | GI: | 38045945 |
|---|---|---|---|---|---|
| Organism: | Homo sapiens | Length: | 2015 | ORF Region: | 200-1291 |
| Locus: | 9039 | Blast database: | Human | ORF GC% | 40.39 |
| Definition: | | | | | |
| Sequence: | NM_98197 | | | | |

| Name | Start | Sense RNA Sequence 5'-3' | Antisense RNA Sequence 5'-3' | Region | GC% |
|---|---|---|---|---|---|
| NM_198197_siRNA_272 | 272 | GCUGAAGUUGCUGCAGAAU (SEQ ID NO: 809) | AUUCUGCAGCAACUUCAGC (SEQ ID NO: 810) | ORF | 47.36842105 |
| NM_198197_siRNA_473 | 473 | CCAAGCUCCAUUGUCCCUU (SEQ ID NO: 811) | AAGGGACAAUGGAGCUUGG (SEQ ID NO: 812) | ORF | 52.63157895 |
| NM_198197_siRNA_902 | 902 | GCAUACAUUCCCUUGAAUA (SEQ ID NO: 813) | UAUUCAAGGGAAUGUAUGC (SEQ ID NO: 814) | ORF | 36.84210526 |
| NM_198197_siRNA_1076 | 1076 | GCUUCUCUGCAAAUGAAAU (SEQ ID NO: 815) | AUUUCAUUUGCAGAGAAGC (SEQ ID NO: 816) | ORF | 36.84210526 |

| Gene Name: | ZNF207 | GenBank Accession No. | NM_003457 | GI: | 75750493 |
|---|---|---|---|---|---|
| Organism: | Homo sapiens | Length: | 2348 | ORF Region: | 204-1640 |
| Locus: | 7756 | Blast database: | Human | ORF GC% | 48.3 |
| Definition: | | | | | |
| Sequence: | NM_003457 | | | | |

| Name | Start | Sense RNA Sequence 5'-3' | Antisense RNA Sequence 5'-3' | Region | GC% |
|---|---|---|---|---|---|
| NM_003457_siRNA_747 | 747 | CCACCUGGAAUGAUGCCAA (SEQ ID NO: 817) | UUGGCAUCAUUCCAGGUGG (SEQ ID NO: 818) | ORF | 52.63157895 |
| NM_003457_siRNA_888 | 888 | GCGCCAGGUAUUCUUAAUA (SEQ ID NO: 819) | UAUUAAGAAUACCUGGCGC (SEQ ID NO: 820) | ORF | 42.10526316 |
| NM_003457_siRNA_1014 | 1014 | GCUUCAUCCAAUUCAGAAA (SEQ ID NO: 821) | UUUCUGAAUUGGAUGAAGC (SEQ ID NO: 822) | ORF | 36.84210526 |
| NM_003457_siRNA_1230 | 1230 | CCAGCGGCUUCAAUAACAA (SEQ ID NO: 823) | UUGUUAUUGAAGCCGCUGG (SEQ ID NO: 824) | ORF | 47.36842105 |
| NM_003457_siRNA_1257 | 1257 | GCUACACUUACAACACUA (SEQ ID NO: 825) | UAGUUGUUGUAAGUGUAGC (SEQ ID NO: 826) | ORF | 36.84210526 |

| Gene Name: | ZNF7 | GenBank Accession No. | NM_003416 | GI: | 4508034 |
|---|---|---|---|---|---|
| Organism: | Homo sapiens | Length: | 2351 | ORF Region: | 239-2299 |
| Locus: | 7553 | Blast database: | Human | ORF GC% | 48.62 |

TABLE 3-continued

Definition:

Sequence: NM_003416

| Name | Start | Sense RNA Sequence 5'-3' | Antisense RNA Sequence 5'-3' | Region | GC% |
|---|---|---|---|---|---|
| NM_003416_stealth_1839 | 1839 | UCAGUAUGAGCACCAGCUUACAAU (SEQ ID NO: 827) | AUUGUAAGCUGUGCUCAUACUGA (SEQ ID NO: 828) | ORF | 40 |
| NM_003416_stealth_1843 | 1843 | GCACACAGCUUACAAUACAUCAAAG (SEQ ID NO: 829) | CUUUGAUGUAUUGUAAGCUGUGUGC (SEQ ID NO: 830) | ORF | 36 |
| NM_003416_stealth_1848 | 1848 | GCACACAGCUUACAAUACAUCAAAG (SEQ ID NO: 831) | CUUUGAUGUAUUGUAAGCUGUGUGC (SEQ ID NO: 832) | ORF | 40 |
| NM_003416_stealth_2089 | 2089 | AGGGUCCACCUUUGUGAGCCGUAAA (SEQ ID NO: 833) | UUUACGGCUCACAAAGGUGGACCCU (SEQ ID NO: 834) | ORF | 52 |
| NM_003146_stealth_2163 | 2163 | UAUUUAGGUGGCGUUCACACCUAAU (SEQ ID NO: 835) | AUUAGGUGUGAACGCCACCUAAAUA (SEQ ID NO: 836) | ORF | 40 |

REFERENCES

1. Op De Beeck A, Caillet-Fauquet P: Viruses and the cell cycle. *Prog Cell Cycle Res* 1997, 3:1-19.
2. Dermody T S, Nibert M L, Wetzel J D, Tong X, Fields B N: Cells and viruses with mutations affecting viral entry are selected during persistent infections of L cells with mammalian reoviruses. *J Virol* 1993, 67(4):2055-2063.
3. Taterka J, Sutcliffe M, Rubin D H: Selective reovirus infection of murine hepatocarcinoma cells during cell division. A model of viral liver infection. *J Clin Invest* 1994, 94(1):353-360.
4. Sheng J, Organ E L, Hao C, Wells K S, Ruley H E, Rubin D H: Mutations in the IGF-II pathway that confer resistance to lytic reovirus infection. *BMC Cell Biol* 2004, 5(1):32.
5. Hansen J, Floss T, Van Sloun P, Fuchtbauer E M, Vauti F, Arnold H H, Schnutgen F, Wurst W, von Melchner H, Ruiz P: A large-scale, gene-driven mutagenesis approach for the functional analysis of the mouse genome. *Proc Natl Acad Sci USA* 2003, 100(17):9918-9922.
6. Hicks G G, Shi E G, Li X M, Li C H, Pawlak M, Ruley H E: Functional genomics in mice by tagged sequence mutagenesis. *Nat Genet* 1997, 16(4):338-344.
7. Salminen M, Meyer B I, Gruss P: Efficient poly A trap approach allows the capture of genes specifically active in differentiated embryonic stem cells and in mouse embryos. *Dev Dyn* 1998, 212(2):326-333.
8. Stryke D, Kawamoto M, Huang C C, Johns S J, King L A, Harper C A, Meng E C, Lee R E, Yee A, L'Italien L et al: BayGenomics: a resource of insertional mutations in mouse embryonic stem cells. *Nucleic Acids Res* 2003, 31(1):278-281.
9. Wiles M V, Vauti F, Otte J, Fuchtbauer E M, Ruiz P, Fuchtbauer A, Arnold H H, Lehrach H, Metz T, von Melchner H et al: Establishment of a gene-trap sequence tag library to generate mutant mice from embryonic stem cells. *Nat Genet*. 2000, 24(1):13-14.
10. Zambrowicz B P, Friedrich G A, Buxton E C, Lilleberg S I, Person C, Sands A T: Disruption and sequence identification of 2,000 genes in mouse embryonic stem cells. *Nature* 1998, 392(6676):608-611.
11. Osipovich A B, White-Grindley E K, Hicks G G, Roshon M J, Shaffer C, Moore J H, H.E. R: Activation of cryptic 3' splice sites within introns of cellular genes following gene entrapment. *Nucleic Acids Res* 2004, in press.
12. De Ceuninck F, Poiraudeau S, Pagano M, Tsagris L, Blanchard O, Willeput J, Corvol M: Inhibition of chondrocyte cathepsin B and L activities by insulin-like growth factor-II (IGF-II) and its Ser29 variant in vitro: possible role of the mannose 6-phosphate/IGF-II receptor. *Mol Cell Endocrinol* 1995, 113(2):205-213.
13. Martinez C G, Guinea R, Benavente J, Carrasco L: The entry of reovirus into L cells is dependent on vacuolar proton-ATPase activity. *J Virol* 1996, 70(1):576-579.
14. Guinea R, Carrasco L: Requirement for vacuolar proton-ATPase activity during entry of influenza virus into cells. *J Virol* 1995, 69(4):2306-2312.
15. Brunetti C R, Burke R L, Kornfeld S, Gregory W, Masiarz F R, Dingwell K S, Johnson D C: Herpes simplex virus glycoprotein D acquires mannose 6-phosphate residues and binds to mannose 6-phosphate receptors. *J Biol Chem* 1994, 269(25):17067-17074.
16. Zeng F Y, Gerke V, Gabius H J: Identification of annexin II, annexin VI and glyceraldehyde-3-phosphate dehydrogenase as calcyclin-binding proteins in bovine heart. *Int J Biochem* 1993, 25(7):1019-1027.
17. Lee K H, Na D S, Kim J W: Calcium-dependent interaction of annexin I with annexin II and mapping of the interaction sites. *FEBS Lett* 1999, 442(2-3):143-146.
18. Filipek A, Wojda U, Lesniak W: Interaction of calcyclin and its cyanogen bromide fragments with annexin II and glyceraldehyde 3-phosphate dehydrogenase. *Int J Biochem Cell Biol* 1995, 27(11):1123-1131.
19. Pietropaolo R L, Compton T: Direct interaction between human cytomegalovirus glycoprotein B and cellular annexin II. *J Virol* 1997, 71(12):9803-9807.
20. Golitsina N L, Kordowska J, Wang C L, Lehrer S S: Ca2+-dependent binding of calcyclin to muscle tropomyosin. *Biochem Biophys Res Commun* 1996, 220(2):360-365.
21. Hida K, Wada J, Zhang H, Hiragushi K, Tsuchiyama Y, Shikata K, Makino H: Identification of genes specifically expressed in the accumulated visceral adipose tissue of OLETF rats. *J Lipid Res* 2000, 41(10):1615-1622.
22. Katoh M: IGSF11 gene, frequently up-regulated in intestinal-type gastric cancer, encodes adhesion molecule homologous to CXADR, FLJ22415 and ESAM. *Int J Oncol* 2003, 23(2):525-531.
23. Barton E S, Forrest J C, Connolly J L, Chappell J D, Liu Y, Schnell F J, Nusrat A, Parkos C A, Dermody T S: Junction adhesion molecule is a receptor for reovirus. *Cell* 2001, 104(3):441-451.
24. Weiner H L, Powers M L, Fields B N: Absolute linkage of virulence and central nervous system cell tropism of reoviruses to viral hemagglutinin. *J Infect Dis* 1980, 141(5): 609-616.
25. Rubin D H, Wetzel J D, Williams W V, Cohen J A, Dworkin C, Dermody T S: Binding of type 3 reovirus by a domain of the sigma 1 protein important for hemagglutination leads to infection of murine erythroleukemia cells. *J Clin Invest* 1992, 90(6):2536-2542.
26. Sizova D V, Kolupaeva V G, Pestova T V, Shatsky I N, Hellen C U: Specific interaction of eukaryotic translation initiation factor 3 with the 5' nontranslated regions of hepatitis C virus and classical swine fever virus RNAs. *J Virol* 1998, 72(6):4775-4782.
27. McGregor F, Phelan A, Dunlop J, Clements J B: Regulation of herpes simplex virus poly (A) site usage and the action of immediate-early protein IE63 in the early-late switch. *J Virol* 1996, 70(3):1931-1940.
28. Pitha P M, Au W C, Lowther W, Juang Y T, Schafer S L, Burysek L, Hiscott J, Moore P A: Role of the interferon regulatory factors (IRFs) in virus-mediated signaling and regulation of cell growth. *Biochimie* 1998, 80(8-9):651-658.
29. Hawiger J: Innate immunity and inflammation: a transcriptional paradigm. *Immunol Res* 2001, 23(2-3):99-109.
30. Lau J F, Horvath C M: Mechanisms of Type I interferon cell signaling and STAT-mediated transcriptional responses. *Mt Sinai J Med* 2002, 69(3):156-168.
31. Werner-Felmayer G, Werner E R, Fuchs D, Hausen A, Reibnegger G, Schmidt K, Weiss G, Wachter H: Pteridine biosynthesis in human endothelial cells. Impact on nitric oxide-mediated formation of cyclic GMP. *J Biol Chem* 1993, 268(3): 1842-1846.
32. Reiss C S, Komatsu T: Does nitric oxide play a critical role in viral infections? *J Virol* 1998, 72(6):4547-4551.
33. Pertile T L, Karaca K, Sharma J M, Walser M M: An antiviral effect of nitric oxide: inhibition of reovirus replication. *Avian Dis* 1996, 40(2):342-348.
34. Takekawa M, Maeda T, Saito H: Protein phosphatase 2Calpha inhibits the human stress-responsive p38 and JNK MAPK pathways. *Embo J* 1998, 17(16):4744-4752.

35. Rousse S, Lallemand F, Montarras D, Pinset C, Mazars A, Prunier C, Atfi A, Dubois C: Transforming growth factor-beta inhibition of insulin-like growth factor-binding protein-5 synthesis in skeletal muscle cells involves a c-Jun N-terminal kinase-dependent pathway. *J Biol Chem* 2001, 276(50):46961-46967.

36. Uchida K, Suzuki H, Ohashi T, Nitta K, Yumura W, Nihei H: Involvement of MAP kinase cascades in Smad7 transcriptional regulation. *Biochem Biophys Res Commun* 2001, 289(2):376-381.

37. Arsura M, Panta G R, Bilyeu J D, Cavin L G, Sovak M A, Oliver A A, Factor V, Heuchel R, Mercurio F, Thorgeirsson S S et al: Transient activation of NF-kappaB through a TAK1/IKK kinase pathway by TGF-beta1 inhibits AP-1/SMAD signaling and apoptosis: implications in liver tumor formation. *Oncogene* 2003, 22(3):412-425.

38. Amir R E, Iwai K, Ciechanover A: The NEDD8 pathway is essential for SCF(beta-TrCP)-mediated ubiquitination and processing of the NF-kappa B precursor p105. *J Biol Chem* 2002, 277(26):23253-23259.

39. Tanaka K, Kawakami T, Tateishi K, Yashiroda H, Chiba T: Control of IkappaBalpha proteolysis by the ubiquitin-proteasome pathway. *Biochimie* 2001, 83(3-4):351-356.

40. Sakurai H, Shigemori N, Hasegawa K, Sugita T: TGF-beta-activated kinase 1 stimulates NF-kappa B activation by an NF-kappa B-inducing kinase-independent mechanism. *Biochem Biophys Res Commun* 1998, 243(2):545-549.

41. Shibuya H, Yamaguchi K, Shirakabe K, Tonegawa A, Gotoh Y, Ueno N, Irie K, Nishida E, Matsumoto K: TAB1: an activator of the TAK1 MAPKKK in TGF-beta signal transduction. *Science* 1996, 272(5265):1179-1182.

42. Bhat N R, Shen Q, Fan F: TAK1-mediated induction of nitric oxide synthase gene expression in glial cells. *J Neurochem* 2003, 87(1):238-247.

43. Yanagisawa M, Nakashima K, Takeda K, Ochiai W, Takizawa T, Ueno M, Takizawa M, Shibuya H, Taga T: Inhibition of BMP2-induced, TAK1 kinase-mediated neurite outgrowth by Smad6 and Smad7. *Genes Cells* 2001, 6(12): 1091-1099.

44. Asano K, Vornlocher H P, Richter-Cook N J, Merrick W C, Hinnebusch A G, Hershey J W: Structure of cDNAs encoding human eukaryotic initiation factor 3 subunits. Possible roles in RNA binding and macromolecular assembly. *J Biol Chem* 1997, 272(43):27042-27052.

45. Higaki S, Gebhardt B M, Lukiw W J, Thompson H W, Hill J M: Effect of immunosuppression on gene expression in the HSV-1 latently infected mouse trigeminal ganglion. *Invest Opthalmol Vis Sci* 2002, 43(6): 1862-1869.

46. Spear B T, Longley T, Moulder S, Wang S L, Peterson M L: A sensitive lacZ-based expression vector for analyzing transcriptional control elements in eukaryotic cells. *DNA Cell Biol* 1995, 14(7):635-642.

47. Pier G B, Grout M, Zaidi T, Meluleni G, Mueschenborn S S, Banting G, Ratcliff R, Evans M J, Colledge W H: *Salmonella typhi* uses CFTR to enter intestinal epithelial cells. *Nature* 1998, 393(6680):79-82.

48. Perkins M E, Wu T W, Le Blancq S M: Cyclosporin analogs inhibit in vitro growth of *Cryptosporidium parvum*. *Antimicrob Agents Chemother* 1998, 42(4):843-848.

49. Clarke P, Tyler K L: Reovirus-induced apoptosis: A minireview. *Apoptosis* 2003, 8(2):141-150.

50. Richardson-Burns S M, Tyler K L: Regional differences in viral growth and central nervous system injury correlate with apoptosis. *J Virol* 2004, 78(10):5466-5475.

51. Clarke P, Meintzer S M, Widmann C, Johnson G L, Tyler K L: Reovirus infection activates JNK and the JNK-dependent transcription factor c-Jun. *J Virol* 2001, 75(23):11275-11283.

52. Clarke P, Meintzer S M, Moffitt L A, Tyler K L: Two distinct phases of virus-induced nuclear factor kappa B regulation enhance tumor necrosis factor-related apoptosis-inducing ligand-mediated apoptosis in virus-infected cells. *J Biol Chem* 2003, 278(20):18092-18100.

53. Bender F C, Whitbeck J C, Ponce de Leon M, Lou H, Eisenberg R J, Cohen G H: Specific association of glycoprotein B with lipid rafts during herpes simplex virus entry. *J Virol* 2003, 77(17):9542-9552.

54. Zhou G, Avitabile E, Campadelli-Fiume G, Roizman B: The domains of glycoprotein D required to block apoptosis induced by herpes simplex virus 1 are largely distinct from those involved in cell-cell fusion and binding to nectin1. *J Virol* 2003, 77(6):3759-3767.

55. Schelling J R, Gentry D J, Dubyak G R: Annexin II inhibition of G protein-regulated inositol trisphosphate formation in rat aortic smooth muscle. *Am J Physiol* 1996, 270(4 Pt 2):F682-690.

56. Babiychuk E B, Monastyrskaya K, Burkhard F C, Wray S, Draeger A: Modulating signaling events in smooth muscle: cleavage of annexin 2 abolishes its binding to lipid rafts. *Faseb J* 2002, 16(10):1177-1184.

57. Pittis M G, Muzzolin L, Giulianini P G, Garcia R C: *Mycobacteria*-containing phagosomes associate less annexins I, VI, VII and XI, but not II, concomitantly with a diminished phagolysosomal fusion. *Eur J Cell Biol* 2003, 82(1):9-17.

58. Brunetti C R, Dingwell K S, Wale C, Graham F L, Johnson D C: Herpes simplex virus gD and virions accumulate in endosomes by mannose 6-phosphate-dependent and -independent mechanisms. *J Virol* 1998, 72(4):3330-3339.

59. Rubin D H, Kornstein M J, Anderson A O: Reovirus serotype 1 intestinal infection: a novel replicative cycle with ileal disease. *J Virol* 1985, 53(2):391-398.

60. Ahmed R, Canning W M, Kauffman R S, Sharpe A H, Hallum J V, Fields B N: Role of the host cell in persistent viral infection: coevolution of L cells and reovirus during persistent infection. *Cell* 1981, 25(2):325-332.

61. Altschul S F, Madden T L, Schaffer A A, Zhang J, Zhang Z, Miller W, Lipman D J: Gapped BLAST and PSI-BLAST: a new generation of protein database search programs. *Nucleic Acids Res* 1997, 25(17):3389-3402.

62. Raynor C M, Wright J F, Waisman D M, Pryzdial E L: Annexin II enhances cytomegalovirus binding and fusion to phospholipid membranes. *Biochemistry* 1999, 38(16): 5089-5095.

63. Glomb-Reinmund S, Kielian M: The role of low pH and disulfide shuffling in the entry and fusion of Semliki Forest virus and Sindbis virus. *Virology* 1998, 248(2):372-381.

64. Roberts P C, Kipperman T, Compans R W: Vesicular stomatitis virus G protein acquires pH-independent fusion activity during transport in a polarized endometrial cell line. *J Virol* 1999, 73(12):10447-10457.

65. Luo T, Douglas J L, Livingston R L, Garcia J V: Infectivity enhancement by HIV-1 Nef is dependent on the pathway of virus entry: implications for HIV-based gene transfer systems. *Virology* 1998, 241(2):224-233.

66. Platt G M, Simpson G R, Mittnacht S, Schulz T F: Latent nuclear antigen of Kaposi's sarcoma-associated herpesvirus interacts with RING3, a homolog of the *Drosophila* female sterile homeotic (fsh) gene. *J Virol* 1999, 73(12): 9789-9795.

67. Koffa M D, Graham S V, Takagaki Y, Manley J L, Clements J B: The human papillomavirus type 16 negative regulatory RNA element interacts with three proteins that act at different posttranscriptional levels. *Proc Natl Acad Sci USA* 2000, 97(9):4677-4682.

68. Hirose Y, Manley J L: Creatine phosphate, not ATP, is required for 3' end cleavage of mammalian pre-mRNA in vitro. *J Biol Chem* 1997, 272(47):29636-29642.

69. Hansen J, Etchison D, Hershey J W, Ehrenfeld E: Association of cap-binding protein with eucaryotic initiation factor 3 in initiation factor preparations from uninfected and poliovirus-infected HeLa cells. *J Virol* 1982, 42(1):200-207.

70. Kieft J S, Zhou K, Jubin R, Murray M G, Lau J Y, Doudna J A: The hepatitis C virus internal ribosome entry site adopts an ion-dependent tertiary fold. *J Mol Biol* 1999, 292(3):513-529.

71. Briggs C J, Ott D E, Coren L V, Oroszlan S, Tozser J: Comparison of the effect of FK506 and cyclosporin A on virus production in H9 cells chronically and newly infected by HIV-1. *Arch Virol* 1999, 144(11):2151-2160.

72. Kanopka A, Muhlemann O, Petersen-Mahrt S, Estmer C, Ohrmalm C, Akusjarvi G: Regulation of adenovirus alternative RNA splicing by dephosphorylation of SR proteins. *Nature* 1998, 393(6681):185-187.

73. Tan S L, Nakao H, He Y, Vijaysri S, Neddermann P, Jacobs B L, Mayer B J, Katze M G: NS5A, a nonstructural protein of hepatitis C virus, binds growth factor receptor-bound protein 2 adaptor protein in a Src homology 3 domain/ligand-dependent manner and perturbs mitogenic signaling. *Proc Natl Acad Sci USA* 1999, 96(10):5533-5538.

74. Korkaya H, Jameel S, Gupta D, Tyagi S, Kumar R, Zafrullah M, Mazumdar M, Lal S K, Xiaofang L, Sehgal D et al: The ORF3 protein of hepatitis E virus binds to Src homology 3 domains and activates MAPK. *J Biol Chem* 2001, 276(45):42389-42400.

75. Scaplehorn N, Holmstrom A, Moreau V, Frischknecht F, Reckmann I, Way M: Grb2 and Nck act cooperatively to promote actin-based motility of vaccinia virus. *Curr Biol* 2002, 12(9):740-745.

76. Finkelstein L D, Ney P A, Liu Q P, Paulson R F, Correll P H: Sf-Stk kinase activity and the Grb2 binding site are required for Epo-independent growth of primary erythroblasts infected with Friend virus. *Oncogene* 2002, 21(22):3562-3570.

77. Huh J R, Park J M, Kim M, Carlson B A, Hatfield D L, Lee B J: Recruitment of TBP or TFIIB to a promoter proximal position leads to stimulation of RNA polymerase II transcription without activator proteins both in vivo and in vitro. *Biochem Biophys Res Commun* 1999, 256(1):45-51.

78. Zhou M, Kashanchi F, Jiang H, Ge H, Brady J N: Phosphorylation of the RAP74 subunit of TFIIF correlates with Tat-activated transcription of the HIV-1 long terminal repeat. *Virology* 2000, 268(2):452-460.

79. Kim H, Lee Y H, Won J, Yun Y: Through induction of juxtaposition and tyrosine kinase activity of Jak1, X-gene product of hepatitis B virus stimulates Ras and the transcriptional activation through AP-1, NF-kappaB, and SRE enhancers. *Biochem Biophys Res Commun* 2001, 286(5):886-894.

80. Breslin J J, Mork I, Smith M K, Vogel L K, Hemmila E M, Bonavia A, Talbot P J, Sjostrom H, Noren O, Holmes K V: Human coronavirus 229E: receptor binding domain and neutralization by soluble receptor at 37 degrees C. *J Virol* 2003, 77(7):4435-4438.

81. Li Y, Kang J, Horwitz M S: Interaction of an adenovirus 14.7-kilodalton protein inhibitor of tumor necrosis factor alpha cytolysis with a new member of the GTPase superfamily of signal transducers. *J Virol* 1997, 71(2):1576-1582.

82. Hugle T, Fehrmann F, Bieck E, Kohara M, Krausslich H G, Rice C M, Blum H E, Moradpour D: The hepatitis C virus nonstructural protein 4B is an integral endoplasmic reticulum membrane protein. *Virology* 2001, 284(1):70-81.

83. Bonatti S, Migliaccio G, Blobel G, Walter P: Role of signal recognition particle in the membrane assembly of Sindbis viral glycoproteins. *Eur J Biochem* 1984, 140(3):499-502.

84. Melancon P, Garoff H: Reinitiation of translocation in the Semliki Forest virus structural polyprotein: identification of the signal for the E1 glycoprotein. *Embo J* 1986, 5(7):1551-1560.

85. Emans N, Gorvel J P, Walter C, Gerke V, Kellner R, Griffiths G, Gruenberg J: Annexin II is a major component of fasogenic endosomal vesicles. *J Cell Biol* 1993, 120(6):1357-1369.

86. Fiedler K, Kellner R, Simons K: Mapping the protein composition of trans-Golgi network (TGN)-derived carrier vesicles from polarized MDCK cells. *Electrophoresis* 1997, 18(14):2613-2619.

87. Nezu J, Motojima K, Tamura H, Ohkuma S: Molecular cloning of a rat liver cDNA encoding the 16 kDa subunit of vacuolar H(+)-ATPases: organellar and tissue distribution of 16 kDa proteolipids. *J Biochem (Tokyo)* 1992, 112(2):212-219.

88. Orci L, Perrelet A, Rothman J E: Vesicles on strings: morphological evidence for processive transport within the Golgi stack. *Proc Natl Acad Sci USA* 1998, 95(5):2279-2283.

89. Nakamura N, Lowe M, Levine T P, Rabouille C, Warren G: The vesicle docking protein p115 binds GM130, a cis-Golgi matrix protein, in a mitotically regulated manner. *Cell* 1997, 89(3):445-455.

90. Okutsu T, Kuroiwa Y, Kagitani F, Kai M, Aisaka K, Tsutsumi O, Kaneko Y, Yokomori K, Surani M A, Kohda T et al: Expression and imprinting status of human PEG8/IGF2AS, a paternally expressed antisense transcript from the IGF2 locus, in Wilms' tumors. *J Biochem (Tokyo)* 2000, 127(3):475-483.

91. Kumar R, Yang J, Larsen R D, Stanley P: Cloning and expression of N-acetylglucosaminyltransferase I, the medial Golgi transferase that initiates complex N-linked carbohydrate formation. *Proc Natl Acad Sci USA* 1990, 87(24):9948-9952.

92. Nilsson T, Rabouille C, Hui N, Watson R, Warren G: The role of the membrane-spanning domain and stalk region of N-acetylglucosaminyltransferase I in retention, kin recognition and structural maintenance of the Golgi apparatus in HeLa cells. *J Cell Sci* 1996, 109(Pt 7):1975-1989.

93. Nilsson T, Slusarewicz P, Hoe M H, Warren G: Kin recognition. A model for the retention of Golgi enzymes. *FEBS Lett* 1993, 330(1):1-4.

94. Yang W, Pepperkok R, Bender P, Kreis T E, Storrie B: Modification of the cytoplasmic domain affects the subcellular localization of Golgi glycosyl-transferases. *Eur J Cell Biol* 1996, 71(1):53-61.

95. Hirst J, Futter C E, Hopkins C R: The kinetics of mannose 6-phosphate receptor trafficking in the endocytic pathway in HEp-2 cells: the receptor enters and rapidly leaves multivesicular endosomes without accumulating in a prelysosomal compartment. *Mol Biol Cell* 1998, 9(4):809-816.

96. Sheng Q, Denis D, Ratnofsky M, Roberts T M, DeCaprio J A, Schaffhausen B: The DnaJ domain of polyomavirus large T antigen is required to regulate Rb family tumor suppressor function. *J Virol* 1997, 71(12):9410-9416.

What is claimed is:

1. An in vitro method of identifying an antiviral agent comprising:
   a) administering the agent to a cell containing a cellular heterogeneous nuclear ribonucleoprotein L gene;
   b) contacting the cell with a virus;
   c) detecting the level of viral infection; and
   d) associating the level of viral infection with the level of expression of heterogeneous nuclear ribonucleoprotein L or the activity of heterogeneous nuclear ribonucleoprotein L, a decrease or elimination of viral infection associated with a decrease or elimination of gene expression or activity, or a decrease or elimination of both gene expression and activity, as compared to control cells, indicating that the agent is an antiviral agent.

2. The method of claim 1, wherein the activity of heterogeneous nuclear ribonucleoprotein L is measured via binding assay.

* * * * *

SEQUENCE LISTING

<160> NUMBER OF SEQ ID NOS: 842

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence; note: = Synthetic Construct

<400> SEQUENCE: 1
ggacagagcu acacaucuu                                           19

<210> SEQ ID NO 2
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 2
aagaugugua gcucugucc                                           19

<210> SEQ ID NO 3
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 3
gccguucuca agguaucaa                                           19

<210> SEQ ID NO 4
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 4
uugauaccuu gagaacggc                                           19

<210> SEQ ID NO 5
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 5
gguaucaauc ugagaucuu                                           19

<210> SEQ ID NO 6
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 6
aagaucucag auugauacc                                        19

<210> SEQ ID NO 7
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 7
gguauucccu gacauguau                                        19

<210> SEQ ID NO 8
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 8
auacauguca gggaauacc                                        19

<210> SEQ ID NO 9
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 9
gcugaucccg uggaagauu                                        19

<210> SEQ ID NO 10
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 10
aaucuuccac gggaucagc                                        19

<210> SEQ ID NO 11
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 11
gcagcauauc uccaggaaa                                        19

<210> SEQ ID NO 12
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 12
uuuccuggag auaugcugc                                        19

```
<210> SEQ ID NO 13
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 13
gcuuugcuuu cucuugcua                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 14
uagcaagaga aagcaaagc                                                  19

<210> SEQ ID NO 15
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 15
gcagaguguu ucagaaaua                                                  19

<210> SEQ ID NO 16
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 16
uauuucugaa acacucugc                                                  19

<210> SEQ ID NO 17
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 17
ggaacucgcc auaaggcau                                                  19

<210> SEQ ID NO 18
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 18
augccuuaug gcgaguucc                                                  19

<210> SEQ ID NO 19
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 19
ggaugaaacc aaaggagau                                                  19

<210> SEQ ID NO 20
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 20
aucuccuuug guuucaucc                                                  19

<210> SEQ ID NO 21
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 21
cccuuaugac auguuggaa                                                  19

<210> SEQ ID NO 22
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 22
uuccaacaug ucauaaggg                                                  19

<210> SEQ ID NO 23
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 23
ccuuaugaca uguuggaaa                                                  19

<210> SEQ ID NO 24
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 24
uuuccaacau gucauaagg                                                  19

<210> SEQ ID NO 25
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 25
gcaagucccu guacuauua                                                       19

<210> SEQ ID NO 26
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 26
uaauaguaca gggacuugc                                                       19

<210> SEQ ID NO 27
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 27
cccuuaugac auguuggaa                                                       19

<210> SEQ ID NO 28
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 28
uuccaacaug ucauaaggg                                                       19

<210> SEQ ID NO 29
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 29
ccuuaugaca uguuggaaa                                                       19

<210> SEQ ID NO 30
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 30
uuuccaacau gucauaagg                                                       19

<210> SEQ ID NO 31
<211> LENGTH: 19
<212> TYPE: RNA
<213> ORGANISM: Artificial Sequence
<220> FEATURE:
```

```
<223> OTHER INFORMATION: Description of Artficial Sequence note: =
      Synthetic Construct

<400> SEQUENCE: 31
gcaagucccu guacuauua                                                  19

<210> SEQ ID NO 32
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 32
uaauaguaca gggacuugc                                                  19

<210> SEQ ID NO 33
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 33
cccuuaugac auguuggaa                                                  19

<210> SEQ ID NO 34
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 34
uuccaacaug ucauaaggg                                                  19

<210> SEQ ID NO 35
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 35
ccuuaugaca uguuggaaa                                                  19

<210> SEQ ID NO 36
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 36
uuuccaacau gucauaagg                                                  19

<210> SEQ ID NO 37
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

```
<400> SEQUENCE: 37
gcaagucccu guacuauua                                              19

<210> SEQ ID NO 38
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 38
uaauaguaca gggacuugc                                              19

<210> SEQ ID NO 39
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 39
ccagcagucu uugaugcaa                                              19

<210> SEQ ID NO 40
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 40
uugcaucaaa gacugcugg                                              19

<210> SEQ ID NO 41
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 41
gcaaagcagc uaaagaaau                                              19

<210> SEQ ID NO 42
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 42
auuucuuuag cugcuuugc                                              19

<210> SEQ ID NO 43
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 43
```
ggacaagcag gcaaaugaa                                                    19

<210> SEQ ID NO 44
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 44
uucauuugcc ugcuugucc                                                    19

<210> SEQ ID NO 45
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 45
gcaggcaaau gaaggauau                                                    19

<210> SEQ ID NO 46
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 46
auauccuuca uuugccugc                                                    19

<210> SEQ ID NO 47
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 47
gccuugaagg guauuggaa                                                    19

<210> SEQ ID NO 48
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 48
uuccaauacc cuucaaggc                                                    19

<210> SEQ ID NO 49
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 49
gcugugaucg agaugguac                                                    19

```
<210> SEQ ID NO 50
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 50
guaccaucuc gaucacagc                                                    19

<210> SEQ ID NO 51
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 51
gguagaguaa cuguccgag                                                    19

<210> SEQ ID NO 52
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 52
cucggacagu uacucuacc                                                    19

<210> SEQ ID NO 53
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 53
ggaugccuga gcucuugaa                                                    19

<210> SEQ ID NO 54
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 54
uucaagagcu caggcaucc                                                    19

<210> SEQ ID NO 55
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 55
gcaccagcga aucagacuu                                                    19
```

-continued

```
<210> SEQ ID NO 56
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 56
aagucugauu cgcuggugc                                                       19

<210> SEQ ID NO 57
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 57
gcauugacuc agucguaau                                                       19

<210> SEQ ID NO 58
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 58
auuacgacug agucaaugc                                                       19

<210> SEQ ID NO 59
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 59
gccuggaaac acacaggaa                                                       19

<210> SEQ ID NO 60
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 60
uuccugugug uuuccaggc                                                       19

<210> SEQ ID NO 61
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 61
ccaaaggccc guuaccauu                                                       19

<210> SEQ ID NO 62
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 62
aaugguaacg ggccuuugg                                                  19

<210> SEQ ID NO 63
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 63
ggaacaccuu gaacuccuu                                                  19

<210> SEQ ID NO 64
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 64
aaggaguuca agguguucc                                                  19

<210> SEQ ID NO 65
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 65
ggcugguaga guaacuguc                                                  19

<210> SEQ ID NO 66
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 66
gacaguuacu cuaccagcc                                                  19

<210> SEQ ID NO 67
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 67
gguagaguaa cuguccgag                                                  19

<210> SEQ ID NO 68
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 68
cucggacagu uacucuacc                                                19

<210> SEQ ID NO 69
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 69
ggaugccuga gcucuugaa                                                19

<210> SEQ ID NO 70
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 70
uucaagagcu caggcaucc                                                19

<210> SEQ ID NO 71
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 71
gcugugaucg agauggauc                                                19

<210> SEQ ID NO 72
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 72
guaccaucuc gaucacagc                                                19

<210> SEQ ID NO 73
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 73
ggaugccuga gcucuugaa                                                19

<210> SEQ ID NO 74
<211> LENGTH: 19
<212> TYPE: RNA
<213> ORGANISM: Artificial Sequence
<220> FEATURE:
<223> OTHER INFORMATION: Description of Artficial Sequence note: =
```

Synthetic Construct

<400> SEQUENCE: 74
uucaagagcu caggcaucc                                          19

<210> SEQ ID NO 75
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 75
uccucagcug aaagaacau                                          19

<210> SEQ ID NO 76
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 76
auguucuuuc agcugagga                                          19

<210> SEQ ID NO 77
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 77
ccgagguacu ggaaugcaa                                          19

<210> SEQ ID NO 78
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 78
uugcauucca guaccucgg                                          19

<210> SEQ ID NO 79
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 79
gguacuggaa ugcaaauaa                                          19

<210> SEQ ID NO 80
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 80
uuauuugcau uccaguacc                                          19

<210> SEQ ID NO 81
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 81
ccuggaaugg uucagcaaa                                          19

<210> SEQ ID NO 82
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 82
uuugcugaac cauuccagg                                          19

<210> SEQ ID NO 83
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 83
ggaagauagu ucgagagaa                                          19

<210> SEQ ID NO 84
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 84
uucucucgaa cuaucuucc                                          19

<210> SEQ ID NO 85
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 85
ccagaagaua acauuccau                                          19

<210> SEQ ID NO 86
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 86
```
auggaauguu aucuucugg                                              19

<210> SEQ ID NO 87
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 87
cccugaauga cgacaucag                                              19

<210> SEQ ID NO 88
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 88
cugaugucgu cauucaggg                                              19

<210> SEQ ID NO 89
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 89
gacuauucgu gggcaugau                                              19

<210> SEQ ID NO 90
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 90
aucaugccca cgaauaguc                                              19

<210> SEQ ID NO 91
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 91
ucgugggcau gauccugau                                              19

<210> SEQ ID NO 92
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 92
aucaggauca ugcccacga                                              19

```
<210> SEQ ID NO 93
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 93
ggaacucuau gggaacaau                                                    19

<210> SEQ ID NO 94
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 94
auuguuccca uagaguucc                                                    19

<210> SEQ ID NO 95
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 95
gcucacucuu cagucggaa                                                    19

<210> SEQ ID NO 96
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 96
uuccgacuga agagugagc                                                    19

<210> SEQ ID NO 97
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 97
ucacucuuca gucggaaau                                                    19

<210> SEQ ID NO 98
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 98
auuuccgacu gaagaguga                                                    19

<210> SEQ ID NO 99
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 99
gccaucaaug gcaacccau                                                      19

<210> SEQ ID NO 100
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 100
auggguugcc auugauggc                                                      19

<210> SEQ ID NO 101
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 101
gcauucagug accugacau                                                      19

<210> SEQ ID NO 102
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 102
augucagguc acugaaugc                                                      19

<210> SEQ ID NO 103
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 103
ggacagcaua ucagagcuu                                                      19

<210> SEQ ID NO 104
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 104
aagcucugau augcugucc                                                      19

<210> SEQ ID NO 105
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 105
gcguggaaag cguagacaa                                                    19

<210> SEQ ID NO 106
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 106
uugucuacgc uuccacgc                                                     19

<210> SEQ ID NO 107
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 107
ggauggccac uuaccugaa                                                    19

<210> SEQ ID NO 108
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 108
uucagguaag uggccaucc                                                    19

<210> SEQ ID NO 109
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 109
ggugccugcu uugcaacuu                                                    19

<210> SEQ ID NO 110
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 110
aaguugcaaa gcaggcacc                                                    19

<210> SEQ ID NO 111
<211> LENGTH: 19
<212> TYPE: RNA
<213> ORGANISM: Artificial Sequence
<220> FEATURE:
```

```
<223> OTHER INFORMATION: Description of Artficial Sequence note: =
      Synthetic Construct

<400> SEQUENCE: 111
gguugcauca augccacaa                                                   19

<210> SEQ ID NO 112
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 112
uuguggcauu gaugcaacc                                                   19

<210> SEQ ID NO 113
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 113
gccugacucu cagcaacaa                                                   19

<210> SEQ ID NO 114
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 114
uuguugcuga gagucaggc                                                   19

<210> SEQ ID NO 115
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 115
gcugcugaug uacggcuua                                                   19

<210> SEQ ID NO 116
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 116
uaagccguac aucagcagc                                                   19

<210> SEQ ID NO 117
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

```
<400> SEQUENCE: 117
ccaacugcua uaaguacaa                                                     19

<210> SEQ ID NO 118
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 118
uuguacuuau agcaguugg                                                     19

<210> SEQ ID NO 119
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 119
gggagaugcu auccaagaa                                                     19

<210> SEQ ID NO 120
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 120
uucuuggaua gcaucuccc                                                     19

<210> SEQ ID NO 121
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 121
ccggcugaug uucucgaau                                                     19

<210> SEQ ID NO 122
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 122
auucgagaac aucagccgg                                                     19

<210> SEQ ID NO 123
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 123
```
gguagugcac aucauccaa                                                    19

<210> SEQ ID NO 124
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 124
uuggaugaug ugcacuacc                                                    19

<210> SEQ ID NO 125
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 125
gcgggaacug gagagauau                                                    19

<210> SEQ ID NO 126
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 126
auaucucucc aguucccgc                                                    19

<210> SEQ ID NO 127
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 127
ggucacaagc ugggaauau                                                    19

<210> SEQ ID NO 128
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 128
auauucccag cuugugacc                                                    19

<210> SEQ ID NO 129
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 129
ccuggucguc agauucuaa                                                    19

```
<210> SEQ ID NO 130
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 130
uuagaaucug acgaccagg                                                   19

<210> SEQ ID NO 131
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 131
ccuucagacg aaagagauu                                                   19

<210> SEQ ID NO 132
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 132
aaucucuuuc gucugaagg                                                   19

<210> SEQ ID NO 133
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 133
ggaccacauu acccagcuu                                                   19

<210> SEQ ID NO 134
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 134
aagcugggua auggucc                                                     19

<210> SEQ ID NO 135
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 135
cccagcuuca cgaguacaa                                                   19
```

-continued

```
<210> SEQ ID NO 136
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 136
uuguacucgu gaagcuggg                                                       19

<210> SEQ ID NO 137
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 137
ccagcuucac gaguacaau                                                       19

<210> SEQ ID NO 138
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 138
auuguacucg ugaagcugg                                                       19

<210> SEQ ID NO 139
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 139
ccaacagcuc aauggucuu                                                       19

<210> SEQ ID NO 140
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 140
aagaccauug agcuguugg                                                       19

<210> SEQ ID NO 141
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 141
ccagcuaugu aacaaacaa                                                       19

<210> SEQ ID NO 142
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 142
uuguuuguua cauagcugg                                                   19

<210> SEQ ID NO 143
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 143
gcaguuacag guucacauu                                                   19

<210> SEQ ID NO 144
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 144
aaugugaacc uguaacugc                                                   19

<210> SEQ ID NO 145
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 145
ccagaaguac caaagauuu                                                   19

<210> SEQ ID NO 146
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 146
aaaucuuugg uacuucugg                                                   19

<210> SEQ ID NO 147
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 147
ggagaagaau gcuuaucaa                                                   19

<210> SEQ ID NO 148
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 148
uugauaagca uucuucucc                                                    19

<210> SEQ ID NO 149
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 149
ccaacugaag gccagauau                                                    19

<210> SEQ ID NO 150
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 150
auaucuggcc uucaguugg                                                    19

<210> SEQ ID NO 151
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 151
ccaaacugcu ucaacucau                                                    19

<210> SEQ ID NO 152
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 152
augaguugaa gcaguuugg                                                    19

<210> SEQ ID NO 153
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 153
ccaacaauaa cagaugcaa                                                    19

<210> SEQ ID NO 154
<211> LENGTH: 19
<212> TYPE: RNA
<213> ORGANISM: Artificial Sequence
<220> FEATURE:
<223> OTHER INFORMATION: Description of Artficial Sequence note: =
```

-continued

Synthetic Construct

<400> SEQUENCE: 154
uugcaucugu uauuguugg                                                19

<210> SEQ ID NO 155
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 155
gccaagaaag auacgagau                                                19

<210> SEQ ID NO 156
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 156
aucucguauc uuucuuggc                                                19

<210> SEQ ID NO 157
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 157
gcagcaggca caccaaaua                                                19

<210> SEQ ID NO 158
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 158
uauuuggugu gccugcugc                                                19

<210> SEQ ID NO 159
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 159
ggugauggaa cuauaacaa                                                19

<210> SEQ ID NO 160
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 160
uuguuauagu uccaucacc                                              19

<210> SEQ ID NO 161
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 161
gagaagcauu ccguguguu                                              19

<210> SEQ ID NO 162
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 162
aacacacgga augcuucuc                                              19

<210> SEQ ID NO 163
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 163 gcauccgug uguuugaua                                               19

<210> SEQ ID NO 164
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 164
uaucaaacac acggaaugc                                              19

<210> SEQ ID NO 165
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 165
ccagaucacc aguggcaau                                              19

<210> SEQ ID NO 166
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 166
```

| | |
|---|---|
| auugccacug gugaucugg | 19 |

<210> SEQ ID NO 167
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 167

| | |
|---|---|
| gcaauacucg aaaccgcuu | 19 |

<210> SEQ ID NO 168
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 168

| | |
|---|---|
| aagcgguuuc gaguauugc | 19 |

<210> SEQ ID NO 169
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 169

| | |
|---|---|
| gcaacauccc ugaggucuu | 19 |

<210> SEQ ID NO 170
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 170

| | |
|---|---|
| aagaccucag ggauguugc | 19 |

<210> SEQ ID NO 171
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 171

| | |
|---|---|
| gcagcugaaa uacuacaau | 19 |

<210> SEQ ID NO 172
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 172

| | |
|---|---|
| auuguaguau uucagcugc | 19 |

<210> SEQ ID NO 173
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 173
gcagcuguga uccagguua                                               19

<210> SEQ ID NO 174
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 174
uaaccuggau cacagcugc                                               19

<210> SEQ ID NO 175
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 175
gguaguggcu ccaauccuu                                               19

<210> SEQ ID NO 176
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 176
aaggauugga gccacuacc                                               19

<210> SEQ ID NO 177
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 177
ggaggcucgu auauucaau                                               19

<210> SEQ ID NO 178
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 178
auugaauaua cgagccucc                                               19

<210> SEQ ID NO 179

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 179
ggugaacacu uuggaacaa                                                      19

<210> SEQ ID NO 180
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 180
uuguuccaaa guguucacc                                                      19

<210> SEQ ID NO 181
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 181
gcagucugac uaaagacau                                                      19

<210> SEQ ID NO 182
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 182
augucuuuag ucagacugc                                                      19

<210> SEQ ID NO 183
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 183
cccugcacau gaugaagau                                                      19

<210> SEQ ID NO 184
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 184
aucuucauca ugugcaggg                                                      19

<210> SEQ ID NO 185
<211> LENGTH: 19
<212> TYPE: RNA
```

-continued

<213> ORGANISM: Artificial Sequence
<220> FEATURE:
<223> OTHER INFORMATION: Description of Artficial Sequence note: =
      Synthetic Construct

<400> SEQUENCE: 185
gcgagugaaa ggccaauuu                                                        19

<210> SEQ ID NO 186
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 186
aaauuggccu uucacucgc                                                        19

<210> SEQ ID NO 187
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 187
ggccaauuuc caaagugau                                                        19

<210> SEQ ID NO 188
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 188
aucacuuugg aaauuggcc                                                        19

<210> SEQ ID NO 189
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 189
gccaauuucc aaagugauu                                                        19

<210> SEQ ID NO 190
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 190
aaucacuuug gaaauuggc                                                        19

<210> SEQ ID NO 191
<211> LENGTH: 19
<212> TYPE: RNA
<213> ORGANISM: Artificial Sequence
<220> FEATURE:

-continued

<223> OTHER INFORMATION: Description of Artficial Sequence note: =
     Synthetic Construct

<400> SEQUENCE: 191
gcuauggcuu cugcgaaua                                              19

<210> SEQ ID NO 192
<211> LENGTH: 19
<212> TYPE: RNA
<213> ORGANISM: Artificial Sequence
<220> FEATURE:
<223> OTHER INFORMATION: Description of Artficial Sequence note: =
     Synthetic Construct

<400> SEQUENCE: 192
uauucgcaga agccauagc                                              19

<210> SEQ ID NO 193
<211> LENGTH: 19
<212> TYPE: RNA
<213> ORGANISM: Artificial Sequence
<220> FEATURE:
<223> OTHER INFORMATION: Description of Artficial Sequence note: =
     Synthetic Construct

<400> SEQUENCE: 193
ggaggaguua aagagccuu                                              19

<210> SEQ ID NO 194
<211> LENGTH: 19
<212> TYPE: RNA
<213> ORGANISM: Artificial Sequence
<220> FEATURE:
<223> OTHER INFORMATION: Description of Artficial Sequence note: =
     Synthetic Construct

<400> SEQUENCE: 194
aaggcucuuu aacuccucc                                              19

<210> SEQ ID NO 195
<211> LENGTH: 19
<212> TYPE: RNA
<213> ORGANISM: Artificial Sequence
<220> FEATURE:
<223> OTHER INFORMATION: Description of Artficial Sequence note: =
     Synthetic Construct

<400> SEQUENCE: 195
ccacugaucc caggcaaau                                              19

<210> SEQ ID NO 196
<211> LENGTH: 19
<212> TYPE: RNA
<213> ORGANISM: Artificial Sequence
<220> FEATURE:
<223> OTHER INFORMATION: Description of Artficial Sequence note: =
     Synthetic Construct

<400> SEQUENCE: 196
auuugccugg gaucagugg                                              19

<210> SEQ ID NO 197
<211> LENGTH: 19
<212> TYPE: RNA
<213> ORGANISM: Artificial Sequence
<220> FEATURE:
<223> OTHER INFORMATION: Description of Artficial Sequence note: =
     Synthetic Construct -continued

```
<400> SEQUENCE: 197
gcaucaugcc ucggucau                                           19

<210> SEQ ID NO 198
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 198
augaccagag gcaugaugc                                          19

<210> SEQ ID NO 199
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 199
gcccuuccuc acaugagau                                          19

<210> SEQ ID NO 200
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 200
aucucaugug aggaagggc                                          19

<210> SEQ ID NO 201
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 201
gcuuguguuc caguccuuu                                          19

<210> SEQ ID NO 202
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 202
aaaggacugg aacacaagc                                          19

<210> SEQ ID NO 203
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 203
```

```
gcugcaaccu uggcuucuu                                              19
```

<210> SEQ ID NO 204
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 204

```
aagaagccaa gguugcagc                                              19
```

<210> SEQ ID NO 205
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 205

```
ggaagucacu gggacagaa                                              19
```

<210> SEQ ID NO 206
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 206

```
uucuguccca gugacuucc                                              19
```

<210> SEQ ID NO 207
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 207

```
cccaauacca agucaagaa                                              19
```

<210> SEQ ID NO 208
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 208

```
uucuugacuu gguauuggg                                              19
```

<210> SEQ ID NO 209
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 209

```
ccaagucaag aagcaaauu                                              19
```

<210> SEQ ID NO 210
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 210
aauuugcuuc uugacuugg                                                  19

<210> SEQ ID NO 211
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 211
gguggagaca cuagaacaa                                                  19

<210> SEQ ID NO 212
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 212
uuguucuagu gucuccacc                                                  19

<210> SEQ ID NO 213
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 213
ccuccugagg aaucaccuu                                                  19

<210> SEQ ID NO 214
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 214
aaggugauuc cucaggagg                                                  19

<210> SEQ ID NO 215
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 215
cccaaagugg uaccaugaa                                                  19

<210> SEQ ID NO 216
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 216
uucaugguac cacuuuggg                                              19

<210> SEQ ID NO 217
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 217
gcauuccuau auugagcaa                                              19

<210> SEQ ID NO 218
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 218
uugcucaaua uaggaaugc                                              19

<210> SEQ ID NO 219
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 219
ccagccaaca gcuaucauu                                              19

<210> SEQ ID NO 220
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 220
aaugauagcu guuggcugg                                              19

<210> SEQ ID NO 221
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 221
ggaagaauac aacaaggaa                                              19

<210> SEQ ID NO 222
<211> LENGTH: 19

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 222 uccuuguug uauucuucc                                                      19

<210> SEQ ID NO 223
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 223
gcaggaccug agcaucauu                                                     19

<210> SEQ ID NO 224
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 224
aaugaugcuc agguccugc                                                     19

<210> SEQ ID NO 225
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 225
ccagguggau ucacugcuu                                                     19

<210> SEQ ID NO 226
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 226
aagcagugaa uccaccugg                                                     19

<210> SEQ ID NO 227
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 227
ccgacaacau caagcucuu                                                     19

<210> SEQ ID NO 228
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 228
aagagcuuga uguugucgg                                                        19

<210> SEQ ID NO 229
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 229
gcacaaguuc cacgagaau                                                        19

<210> SEQ ID NO 230
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 230
auucucgugg aacuugugc                                                        19

<210> SEQ ID NO 231
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 231
ggacuugagg gacaccuuu                                                        19

<210> SEQ ID NO 232
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 232
aaaggugucc cucaagucc                                                        19

<210> SEQ ID NO 233
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 233
gccgcaucaa ugucaagaa                                                        19

<210> SEQ ID NO 234
<211> LENGTH: 19
<212> TYPE: RNA
<213> ORGANISM: Artificial Sequence
<220> FEATURE:
<223> OTHER INFORMATION: Description of Artficial Sequence note: =
```

-continued

Synthetic Construct

<400> SEQUENCE: 234
uucuugacau ugaugcggc					19

<210> SEQ ID NO 235
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 235
ccauucucca cgccuucaa					19

<210> SEQ ID NO 236
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 236
uugaaggcgu ggagaaugg					19

<210> SEQ ID NO 237
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 237
gcagauguuu gcagcguuu					19

<210> SEQ ID NO 238
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 238
aaacgcugca aacaucugc					19

<210> SEQ ID NO 239
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 239
gcuucuccac cuugugcuu					19

<210> SEQ ID NO 240
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct -continued

```
<400> SEQUENCE: 240
aagcacaagg uggagaagc                                              19

<210> SEQ ID NO 241
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 241
gcagcuacuu cagagcuau                                              19

<210> SEQ ID NO 242
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 242
auagcucuga aguagcugc                                              19

<210> SEQ ID NO 243
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 243
gggaaagccg agaaauguu                                              19

<210> SEQ ID NO 244
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 244
aacauuucuc ggcuuuccc                                              19

<210> SEQ ID NO 245
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 245
gcaacuugau ccuuguaau                                              19

<210> SEQ ID NO 246
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 246
```
auuacaagga ucaaguugc                                                    19

<210> SEQ ID NO 247
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 247
gcgcuuugcu gauacccau                                                    19

<210> SEQ ID NO 248
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 248
auggguauca gcaaagcgc                                                    19

<210> SEQ ID NO 249
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 249
gcuugacaaa gaugaacuu                                                    19

<210> SEQ ID NO 250
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 250
aaguucaucu uugucaagc                                                    19

<210> SEQ ID NO 251
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 251
ggaccugaug auaauacuu                                                    19

<210> SEQ ID NO 252
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 252
aaguauuauc aucaggucc                                                    19

```
<210> SEQ ID NO 253
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 253 ucaguccuc aaggccaua                                                    19

<210> SEQ ID NO 254
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 254
uauggccuug agggacuga                                                   19

<210> SEQ ID NO 255
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 255
gacccaacgg gugaagaaa                                                   19

<210> SEQ ID NO 256
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 256
uuucuucacc cguuggguc                                                   19

<210> SEQ ID NO 257
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 257
cccaacgggu gaagaaaga                                                   19

<210> SEQ ID NO 258
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 258
ucuuucuuca cccguuggg                                                   19

<210> SEQ ID NO 259
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 259
gcaagagcca cuuggcaaa                                             19

<210> SEQ ID NO 260
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 260
uuugccaagu ggcucuugc                                             19

<210> SEQ ID NO 261
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 261
gcagaugguc uuagauaua                                             19

<210> SEQ ID NO 262
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 262
uauaucuaag accaucugc                                             19

<210> SEQ ID NO 263
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 263
gcgccuguac caugauauu                                             19

<210> SEQ ID NO 264
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 264
aauaucaugg uacaggcgc                                             19

<210> SEQ ID NO 265
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 265
ccaugauauu gcccagcaa                                                    19

<210> SEQ ID NO 266
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 266
uugcugggca auaucaugg                                                    19

<210> SEQ ID NO 267
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 267
gcgagucaca aagguucua                                                    19

<210> SEQ ID NO 268
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 268
uagaaccuuu gugacucgc                                                    19

<210> SEQ ID NO 269
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 269
ggaagugccu gaaguacuu                                                    19

<210> SEQ ID NO 270
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 270
aaguacuuca ggcacuucc                                                    19

<210> SEQ ID NO 271
<211> LENGTH: 19
<212> TYPE: RNA
<213> ORGANISM: Artificial Sequence
<220> FEATURE:
```

```
<223> OTHER INFORMATION: Description of Artficial Sequence note: =
      Synthetic Construct

<400> SEQUENCE: 271
gcaacuaagu ggauugaaa                                                   19

<210> SEQ ID NO 272
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 272
uuucaaucca cuuaguugc                                                   19

<210> SEQ ID NO 273
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 273
gcagcuuccu gagacuauu                                                   19

<210> SEQ ID NO 274
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 274
aauagucuca ggaagcugc                                                   19

<210> SEQ ID NO 275
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 275
gccaaggacu gaggauguu                                                   19

<210> SEQ ID NO 276
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 276
aacauccuca guccuuggc                                                   19

<210> SEQ ID NO 277
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

```
<400> SEQUENCE: 277
gcugaugaca cucacaaau                                              19

<210> SEQ ID NO 278
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 278
auuugugagu gcaucagc                                               19

<210> SEQ ID NO 279
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 279
ccauuuacau cagagacuu                                              19

<210> SEQ ID NO 280
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 280
aagucucuga uguaaaugg                                              19

<210> SEQ ID NO 281
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 281
gcugcaucau auacaguaa                                              19

<210> SEQ ID NO 282
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 282
uuacuguaua ugaugcagc                                              19

<210> SEQ ID NO 283
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 283
```

```
ccuuguuacc ugaaucuuu                                              19

<210> SEQ ID NO 284
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 284
aaagauucag guaacaagg                                              19

<210> SEQ ID NO 285
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 285
gcuugagccc auuucaaau                                              19

<210> SEQ ID NO 286
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 286
auuugaaaug ggcucaagc                                              19

<210> SEQ ID NO 287
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 287 ccauccucc ugaucauaa                                               19

<210> SEQ ID NO 288
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 288
uuaugaucag gaggaaugg                                              19

<210> SEQ ID NO 289
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 289
ccgauuccuu ucccgcuuu                                              19
```

```
<210> SEQ ID NO 290
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 290
aaagcgggaa aggaaucgg                                                  19

<210> SEQ ID NO 291
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 291
ggaaguaaac acaggagaa                                                  19

<210> SEQ ID NO 292
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 292
uucuccugug uuuacuucc                                                  19

<210> SEQ ID NO 293
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 293
ccuuguuacc ugaaucuuu                                                  19

<210> SEQ ID NO 294
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 294
aaagauucag guaacaagg                                                  19

<210> SEQ ID NO 295
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 295
gcuugagccc auuucaaau                                                  19
```

```
<210> SEQ ID NO 296
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 296
auuugaaaug ggcucaagc                                                    19

<210> SEQ ID NO 297
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 297 ccauccucc ugaucauaa                                                     19

<210> SEQ ID NO 298
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 298
uuaugaucag gaggaaugg                                                    19

<210> SEQ ID NO 299
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 299
gccaucaagg cuaucaccu                                                    19

<210> SEQ ID NO 300
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 300
aggugauagc cuugauggc                                                    19

<210> SEQ ID NO 301
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 301
uccugcaguu gaaggugaa                                                    19

<210> SEQ ID NO 302
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 302
uucaccuuca acugcagga                                                19

<210> SEQ ID NO 303
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 303
ccagccagac aacaucaag                                                19

<210> SEQ ID NO 304
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 304
cuugauguug ucggcugg                                                 19

<210> SEQ ID NO 305
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 305
gccagacaac aucaaggcu                                                19

<210> SEQ ID NO 306
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 306
agccuugaug uugucuggc                                                19

<210> SEQ ID NO 307
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 307
uccacgcaga gcucucaaa                                                19

<210> SEQ ID NO 308
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 308
uuugagagcu cugcgugga                                                   19

<210> SEQ ID NO 309
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 309
gcgugaauuu ggucguuau                                                   19

<210> SEQ ID NO 310
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 310
auaacgacca aauucacgc                                                   19

<210> SEQ ID NO 311
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 311
gaccaaacug cagcuggaa                                                   19

<210> SEQ ID NO 312
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 312
uuccagcugc aguugguc                                                    19

<210> SEQ ID NO 313
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 313
ccaaacugca gcuggaaua                                                   19

<210> SEQ ID NO 314
<211> LENGTH: 19
<212> TYPE: RNA
<213> ORGANISM: Artificial Sequence
<220> FEATURE:
<223> OTHER INFORMATION: Description of Artficial Sequence note: =
```

```
                                    Synthetic Construct

<400> SEQUENCE: 314
uauuccagcu gcaguuugg                                                    19

<210> SEQ ID NO 315
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 315
gcgugaauuu ggucguuau                                                    19

<210> SEQ ID NO 316
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 316
auaacgacca aauucacgc                                                    19

<210> SEQ ID NO 317
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 317
ucguuauggu ccuauaguu                                                    19

<210> SEQ ID NO 318
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 318
aacuauagga ccauaacga                                                    19

<210> SEQ ID NO 319
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 319
ccguccaaga ggauuugcu                                                    19

<210> SEQ ID NO 320
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

```
<400> SEQUENCE: 320
agcaaauccu cuuggacgg                                                    19

<210> SEQ ID NO 321
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 321
gcagaugugc uucaugcau                                                    19

<210> SEQ ID NO 322
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 322
augcaugaag cacaucugc                                                    19

<210> SEQ ID NO 323
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 323
gcuauaccuu ugcuucuuu                                                    19

<210> SEQ ID NO 324
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 324
aaagaagcaa agguauagc                                                    19

<210> SEQ ID NO 325
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 325
cccaacuacu guuucaguu                                                    19

<210> SEQ ID NO 326
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 326
```

-continued aacugaaaca guaguuggg                                              19

<210> SEQ ID NO 327
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 327
ccaggagcug gaauacaaa                                              19

<210> SEQ ID NO 328
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 328
uuuguauucc agcuccugg                                              19

<210> SEQ ID NO 329
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 329
ggaauacaaa ugaggacuu                                              19

<210> SEQ ID NO 330
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 330
aaguccucau uuguauucc                                              19

<210> SEQ ID NO 331
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 331
ggcagagagu gugucaacu                                              19

<210> SEQ ID NO 332
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 332
aguugacaca cucucugcc                                              19

```
<210> SEQ ID NO 333
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 333
gccucuacca caagaugaa                                                   19

<210> SEQ ID NO 334
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 334
uucaucuugu gguagaggc                                                   19

<210> SEQ ID NO 335
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 335
ggaagcccaa gaaccugaa                                                   19

<210> SEQ ID NO 336
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 336
uucagguucu ugggcuucc                                                   19

<210> SEQ ID NO 337
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 337
cccaagaacc ugaauaaau                                                   19

<210> SEQ ID NO 338
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 338
auuuauucag guucuuggg                                                   19

<210> SEQ ID NO 339
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 339
ccaucgccaa auaugacuu                                                19

<210> SEQ ID NO 340
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 340
aagucauauu uggcgaugg                                                19

<210> SEQ ID NO 341
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 341
gguacaaggc agagcuuaa                                                19

<210> SEQ ID NO 342
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 342
uuaagcucug ccuuguacc                                                19

<210> SEQ ID NO 343
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 343
gcuucauucc caagaacua                                                19

<210> SEQ ID NO 344
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 344
uaguucuugg gaaugaagc                                                19

<210> SEQ ID NO 345
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 345
ccagaaacca gcagauauu                                                    19

<210> SEQ ID NO 346
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 346
aauaucugcu gguuucugg                                                    19

<210> SEQ ID NO 347
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 347
ccaggcccuc uuugacuuu                                                    19

<210> SEQ ID NO 348
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 348
aaagucaaag agggccugg                                                    19

<210> SEQ ID NO 349
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 349
gcuggagcug cucaaguuu                                                    19

<210> SEQ ID NO 350
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 350
aaacuugagc agcuccagc                                                    19

<210> SEQ ID NO 351
<211> LENGTH: 19
<212> TYPE: RNA
<213> ORGANISM: Artificial Sequence
<220> FEATURE:
```

<223> OTHER INFORMATION: Description of Artficial Sequence note: =
      Synthetic Construct

<400> SEQUENCE: 351
ccacaugaga agaagaauu                                                      19

<210> SEQ ID NO 352
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 352 aaucuucuu cucaugugg                                                       19

<210> SEQ ID NO 353
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 353
gccuauuugg uugagagaa                                                      19

<210> SEQ ID NO 354
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 354
uucucucaac caaauaggc                                                      19

<210> SEQ ID NO 355
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 355
gcauagauau ggacgcauu                                                      19

<210> SEQ ID NO 356
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 356
aaugcgucca uaucuaugc                                                      19

<210> SEQ ID NO 357
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 357
gcauguuuga ggaccucuu                                                  19

<210> SEQ ID NO 358
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 358
aagagguccu caaacaugc                                                  19

<210> SEQ ID NO 359
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 359
gggugaaggu acugguguu                                                  19

<210> SEQ ID NO 360
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 360
aacaccagua ccuucaccc                                                  19

<210> SEQ ID NO 361
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 361
gcacaagagc aguauucua                                                  19

<210> SEQ ID NO 362
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 362
uagaauacug cucuugugc                                                  19

<210> SEQ ID NO 363
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 363
```

```
ggacuaaacu ggaccagau                                               19
```

<210> SEQ ID NO 364
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 364

```
aucuggucca guuuagucc                                               19
```

<210> SEQ ID NO 365
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 365

```
ccuggcugag gauuucaau                                               19
```

<210> SEQ ID NO 366
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 366

```
auugaaaucc ucagccagg                                               19
```

<210> SEQ ID NO 367
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 367

```
gcaagaaugc uucagacau                                               19
```

<210> SEQ ID NO 368
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 368

```
augucugaag cauucuugc                                               19
```

<210> SEQ ID NO 369
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 369

```
ccuccugcug uccauguau                                               19
```

```
<210> SEQ ID NO 370
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 370
auacauggac agcaggagg                                                  19

<210> SEQ ID NO 371
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 371
gcugaggaag cacuggauu                                                  19

<210> SEQ ID NO 372
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 372
aauccagugc uuccucagc                                                  19

<210> SEQ ID NO 373
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 373
ccucgaagca aacaacuuu                                                  19

<210> SEQ ID NO 374
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 374
aaaguuguuu gcuucgagg                                                  19

<210> SEQ ID NO 375
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 375
ggagucaaau ccuaaggau                                                  19
```

```
<210> SEQ ID NO 376
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 376
auccuuagga uuugacucc                                                    19

<210> SEQ ID NO 377
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 377
gcagccgaca accaaauau                                                    19

<210> SEQ ID NO 378
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 378 auauugguu gucggcugc                                                     19

<210> SEQ ID NO 379
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 379
gguggaauuu gacucaguu                                                    19

<210> SEQ ID NO 380
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 380
aacugaguca aauuccacc                                                    19

<210> SEQ ID NO 381
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 381
ggaauuugac ucaguucaa                                                    19

<210> SEQ ID NO 382
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 382
uugaacugag ucaaauucc                                                      19

<210> SEQ ID NO 383
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 383
gcacucugaa gaucgaaua                                                      19

<210> SEQ ID NO 384
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 384
uauucgaucu ucagagugc                                                      19

<210> SEQ ID NO 385
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 385
gagccuuaug uacgucuau                                                      19

<210> SEQ ID NO 386
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 386
auagacguac auaaggcuc                                                      19

<210> SEQ ID NO 387
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 387
ccuacacuaa ggugcagcu                                                      19

<210> SEQ ID NO 388
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 388
agcugcaccu uaguguagg                                                        19

<210> SEQ ID NO 389
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 389
gguggucagc aaaucgaaa                                                        19

<210> SEQ ID NO 390
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 390
uuucgauuug cugaccacc                                                        19

<210> SEQ ID NO 391
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 391
gcaaaucgaa agcgccuca                                                        19

<210> SEQ ID NO 392
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 392
ugaggcgcuu ucgauuugc                                                        19

<210> SEQ ID NO 393
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 393
ccaagaugga ugcaaucuu                                                        19

<210> SEQ ID NO 394
<211> LENGTH: 19
<212> TYPE: RNA
<213> ORGANISM: Artificial Sequence
<220> FEATURE:
<223> OTHER INFORMATION: Description of Artficial Sequence note: =
```

Synthetic Construct

<400> SEQUENCE: 394
aagauugcau ccaucuugg                                              19

<210> SEQ ID NO 395
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 395
ggccucagcu guugaagaa                                              19

<210> SEQ ID NO 396
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 396
uucuucaaca gcugaggcc                                              19

<210> SEQ ID NO 397
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 397
gguggaagcc ugauggaau                                              19

<210> SEQ ID NO 398
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 398
auuccaucag gcuuccacc                                              19

<210> SEQ ID NO 399
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 399
gguggacaug ccagguuau                                              19

<210> SEQ ID NO 400
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 400
auaaccuggc auguccacc                                              19

<210> SEQ ID NO 401
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 401
ggauagcguu guuggaauu                                              19

<210> SEQ ID NO 402
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 402
aauuccaaca acgcuaucc                                              19

<210> SEQ ID NO 403
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 403
ggaauccacc uguugagau                                              19

<210> SEQ ID NO 404
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 404
aucucaacag guggauucc                                              19

<210> SEQ ID NO 405
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 405
ccaccuguug agaugcuuu                                              19

<210> SEQ ID NO 406
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 406
```

-continued aaagcaucuc aacaggugg                                        19

<210> SEQ ID NO 407
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 407
gcaaacuagc aaggagaau                                        19

<210> SEQ ID NO 408
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 408
auucuccuug cuaguuugc                                        19

<210> SEQ ID NO 409
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 409
gcagaaguua acacuucau                                        19

<210> SEQ ID NO 410
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 410
augaaguguu aacuucugc                                        19

<210> SEQ ID NO 411
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 411
gcuacaaaug cugugcuuu                                        19

<210> SEQ ID NO 412
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 412
aaagcacagc auuuguagc                                        19

<210> SEQ ID NO 413
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 413
ggaaaccaac uguacugau                                               19

<210> SEQ ID NO 414
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 414
aucaguacag uugguuucc                                               19

<210> SEQ ID NO 415
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 415
gcaagaauac uggagcaau                                               19

<210> SEQ ID NO 416
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 416
auugcuccag uauucuugc                                               19

<210> SEQ ID NO 417
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 417
gcaucugagg cauuacaaa                                               19

<210> SEQ ID NO 418
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 418
uuuguaaugc cucagaugc                                               19

<210> SEQ ID NO 419

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 419
gccaggugga aauccuaca                                                  19

<210> SEQ ID NO 420
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 420
uguaggauuu ccaccuggc                                                  19

<210> SEQ ID NO 421
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 421
gcgcgucauc gacuacauu                                                  19

<210> SEQ ID NO 422
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 422
aauguagucg augacgcgc                                                  19

<210> SEQ ID NO 423
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 423
gcuccggaac uugucaucu                                                  19

<210> SEQ ID NO 424
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 424
agaugacaag uuccggagc                                                  19

<210> SEQ ID NO 425
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 425
ccagaucucu ccuggaauu                                                19

<210> SEQ ID NO 426
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 426
aauuccagga gagaucugg                                                19

<210> SEQ ID NO 427
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 427
ccugggaacu ccugaauuu                                                19

<210> SEQ ID NO 428
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 428
aaauucagga guucccagg                                                19

<210> SEQ ID NO 429
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 429
gcaaauaagg aggugccau                                                19

<210> SEQ ID NO 430
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 430
auggcaccuc cuuauuugc                                                19

<210> SEQ ID NO 431
<211> LENGTH: 19
<212> TYPE: RNA
<213> ORGANISM: Artificial Sequence
<220> FEATURE:
```

```
<223> OTHER INFORMATION: Description of Artficial Sequence note: =
      Synthetic Construct

<400> SEQUENCE: 431
gcagcaggau gucuccaua                                                   19

<210> SEQ ID NO 432
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 432
uauggagaca uccugcugc                                                   19

<210> SEQ ID NO 433
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 433
gcaccagugu ugagaacuu                                                   19

<210> SEQ ID NO 434
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 434
aaguucucaa cacuggugc                                                   19

<210> SEQ ID NO 435
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 435
gccuauaaag uugagacaa                                                   19

<210> SEQ ID NO 436
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 436
uugucucaac uuuauaggc                                                   19

<210> SEQ ID NO 437
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

<400> SEQUENCE: 437
gcagccuccu ucuggaaua                                                    19

<210> SEQ ID NO 438
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 438
uauuccagaa ggaggcugc                                                    19

<210> SEQ ID NO 439
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 439
gcuggcgaau acacuuauu                                                    19

<210> SEQ ID NO 440
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 440
aauaagugua uucgccagc                                                    19

<210> SEQ ID NO 441
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 441
gcuucagccu cggagauau                                                    19

<210> SEQ ID NO 442
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 442
auaucuccga ggcugaagc                                                    19

<210> SEQ ID NO 443
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 443

-continued ggauaagacc aagucuguu                                                19

<210> SEQ ID NO 444
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 444
aacagacuug gucuuaucc                                                19

<210> SEQ ID NO 445
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 445
gcucugguau gcuccaaau                                                19

<210> SEQ ID NO 446
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 446
auuuggagca uaccagagc                                                19

<210> SEQ ID NO 447
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 447
ccaucaccgu ugaugacaa                                                19

<210> SEQ ID NO 448
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 448
uugucaucaa cggugaugg                                                19

<210> SEQ ID NO 449
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 449
ccaauuggca uggaaccaa                                                19

```
<210> SEQ ID NO 450
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 450
uugguuccau gccaauugg                                                  19

<210> SEQ ID NO 451
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 451
gcauggaacc aacgacaau                                                  19

<210> SEQ ID NO 452
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 452
auugucguug guuccaugc                                                  19

<210> SEQ ID NO 453
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 453
ccuggccauc ucacacuau                                                  19

<210> SEQ ID NO 454
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 454
auagugugag auggccagg                                                  19

<210> SEQ ID NO 455
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 455
ccaucucaca cuaugccau                                                  19
```

-continued

<210> SEQ ID NO 456
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 456
auggcauagu gugagaugg                     19

<210> SEQ ID NO 457
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 457
cccagaagca guucaagaa                     19

<210> SEQ ID NO 458
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 458
uucuugaacu gcuucuggg                     19

<210> SEQ ID NO 459
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 459
gcugguggcu acuaagaaa                     19

<210> SEQ ID NO 460
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 460
uuucuuagua gccaccagc                     19

<210> SEQ ID NO 461
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 461
gcacgagaac acacaucua                     19

<210> SEQ ID NO 462
<211> LENGTH: 19

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 462
uagaugugug uucucgugc                                                 19

<210> SEQ ID NO 463
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 463
ggagaauauc augguggaa                                                 19

<210> SEQ ID NO 464
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 464
uuccaccaug auauucucc                                                 19

<210> SEQ ID NO 465
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 465
gcgagagacu gacuugcau                                                 19

<210> SEQ ID NO 466
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 466
augcaaguca gucucucgc                                                 19

<210> SEQ ID NO 467
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 467
ccuuaugucg acggacuuu                                                 19

<210> SEQ ID NO 468
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 468
aaaguccguc gacauaagg                                                   19

<210> SEQ ID NO 469
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 469
gcuugagagu cuuggaaua                                                   19

<210> SEQ ID NO 470
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 470
uauuccaaga cucucaagc                                                   19

<210> SEQ ID NO 471
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 471
gcuucuggug uacuauuua                                                   19

<210> SEQ ID NO 472
<211> LENGTH: 18
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 472
aaauaguaca ccagaagc                                                    18

<210> SEQ ID NO 473
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 473
gcuccucaag ucucucuuu                                                   19

<210> SEQ ID NO 474
<211> LENGTH: 19
<212> TYPE: RNA
<213> ORGANISM: Artificial Sequence
<220> FEATURE:
<223> OTHER INFORMATION: Description of Artficial Sequence note: =
```

-continued

Synthetic Construct

<400> SEQUENCE: 474
aaagagagac uugaggagc					19

<210> SEQ ID NO 475
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 475
gggaacaacu aauguucau					19

<210> SEQ ID NO 476
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 476
augaacauua guuguuccc					19

<210> SEQ ID NO 477
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 477
gcacaaagcu ugguuauaa					19

<210> SEQ ID NO 478
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 478
uuauaaccaa gcuuugugc					19

<210> SEQ ID NO 479
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 479
gcacaaagca auggccuaa					19

<210> SEQ ID NO 480
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 480
uuaggccauu gcuuugugc                                              19

<210> SEQ ID NO 481
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 481
gcguuuaagg aaucugcaa                                              19

<210> SEQ ID NO 482
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 482
uugcagauuc cuuaaacgc                                              19

<210> SEQ ID NO 483
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 483
gcauuuaagc aaccugcaa                                              19

<210> SEQ ID NO 484
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 484
uugcagguug cuuaaaugc                                              19

<210> SEQ ID NO 485
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 485
gcaaauaacu gaggucuuu                                              19

<210> SEQ ID NO 486
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 486
```
aaagaccuca guuauuugc                                                19

<210> SEQ ID NO 487
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 487
cccuuggaca aagccugaa                                                19

<210> SEQ ID NO 488
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 488
uucaggcuuu guccaaggg                                                19

<210> SEQ ID NO 489
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 489
ggaccuuugu uugagggaa                                                19

<210> SEQ ID NO 490
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 490 uuccccucaaa caaaggucc                                               19

<210> SEQ ID NO 491
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 491
ccauaggaca cuaugacuu                                                19

<210> SEQ ID NO 492
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 492
aagucauagu guccuaugg                                                19

```
<210> SEQ ID NO 493
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 493
gcaagagcaa gaggcucuu                                                   19

<210> SEQ ID NO 494
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 494
aagagccucu ugcucuugc                                                   19

<210> SEQ ID NO 495
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 495
gcaaaggaau ugcuaguaa                                                   19

<210> SEQ ID NO 496
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 496
uuacuagcaa uuccuuugc                                                   19

<210> SEQ ID NO 497
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 497
gcacauccga agucauaaa                                                   19

<210> SEQ ID NO 498
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 498
uuuaugacuu cggaugugc                                                   19

<210> SEQ ID NO 499
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 499
gcccgauucg uugucugau                                                       19

<210> SEQ ID NO 500
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 500
aucagacaac gaaucgggc                                                       19

<210> SEQ ID NO 501
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 501
gcuucccugu accaguauu                                                       19

<210> SEQ ID NO 502
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 502
aauacuggua cagggaagc                                                       19

<210> SEQ ID NO 503
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 503
gcuaauccca ugcagacuu                                                       19

<210> SEQ ID NO 504
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 504
aagucugcau gggauuagc                                                       19

<210> SEQ ID NO 505
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 505
ccuauguucu ugcaagaaa                                                    19

<210> SEQ ID NO 506
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 506
uuucuugcaa gaacauagg                                                    19

<210> SEQ ID NO 507
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 507
gcacuucaca ugcuggaua                                                    19

<210> SEQ ID NO 508
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 508
uauccagcau gugaagugc                                                    19

<210> SEQ ID NO 509
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 509
ccacaaugcu gugguccau                                                    19

<210> SEQ ID NO 510
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 510
auggaccaca gcauugugg                                                    19

<210> SEQ ID NO 511
<211> LENGTH: 19
<212> TYPE: RNA
<213> ORGANISM: Artificial Sequence
<220> FEATURE:
```

<223> OTHER INFORMATION: Description of Artficial Sequence note: =
      Synthetic Construct

<400> SEQUENCE: 511
ccaugaacuc cagagaaau                                                      19

<210> SEQ ID NO 512
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 512
auuucucugg aguucaugg                                                      19

<210> SEQ ID NO 513
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 513
gccucauuca ccugaaguu                                                      19

<210> SEQ ID NO 514
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 514
aacuucaggu gaaugaggc                                                      19

<210> SEQ ID NO 515
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 515
gcaguaucgg uugacacaa                                                      19

<210> SEQ ID NO 516
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 516
uugugucaac cgauacugc                                                      19

<210> SEQ ID NO 517
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 517
gcacauccga agucauaaa                                              19

<210> SEQ ID NO 518
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 518
uuuaugacuu cggaugugc                                              19

<210> SEQ ID NO 519
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 519
gcccgauucg uugucugau                                              19

<210> SEQ ID NO 520
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 520
aucagacaac gaaucgggc                                              19

<210> SEQ ID NO 521
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 521
gcuucccugu accaguauu                                              19

<210> SEQ ID NO 522
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 522
aauacuggua cagggaagc                                              19

<210> SEQ ID NO 523
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 523
```
gcuaauccca ugcagacuu                                              19

<210> SEQ ID NO 524
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 524
aagucugcau gggauuagc                                              19

<210> SEQ ID NO 525
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 525
ccuauguucu ugcaagaaa                                              19

<210> SEQ ID NO 526
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 526
uuucuugcaa gaacauagg                                              19

<210> SEQ ID NO 527
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 527
gcacuucaca ugcuggaua                                              19

<210> SEQ ID NO 528
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 528
uauccagcau gugaagugc                                              19

<210> SEQ ID NO 529
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 529
ccacaaugcu gugguccau                                              19

```
<210> SEQ ID NO 530
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 530
auggaccaca gcauugugg                                              19

<210> SEQ ID NO 531
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 531
ccaugaacuc cagagaaau                                              19

<210> SEQ ID NO 532
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 532
auuucucugg aguucaugg                                              19

<210> SEQ ID NO 533
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 533
gccucauuca ccugaaguu                                              19

<210> SEQ ID NO 534
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 534
aacuucaggu gaaugaggc                                              19

<210> SEQ ID NO 535
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 535
gcaguaucgg uugacacaa                                              19
```

```
<210> SEQ ID NO 536
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 536
uugugucaac cgauacugc                                                19

<210> SEQ ID NO 537
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 537
ggagugagaa caacugcuu                                                19

<210> SEQ ID NO 538
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 538
aagcaguugu ucucacucc                                                19

<210> SEQ ID NO 539
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 539
gcaaccgagu gaccaacuu                                                19

<210> SEQ ID NO 540
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 540
aaguugguca cucgguugc                                                19

<210> SEQ ID NO 541
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 541
ggaugagcuc uuccgucuu                                                19

<210> SEQ ID NO 542
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 542
aagacggaag agcucaucc                                                    19

<210> SEQ ID NO 543
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 543
ccaaguccaa accaaucau                                                    19

<210> SEQ ID NO 544
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 544
augauugguu uggacuugg                                                    19

<210> SEQ ID NO 545
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 545
ggagugagaa caacugcuu                                                    19

<210> SEQ ID NO 546
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 546
aagcaguugu ucucacucc                                                    19

<210> SEQ ID NO 547
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 547
gcaaccgagu gaccaacuu                                                    19

<210> SEQ ID NO 548
<211> LENGTH: 19
<212> TYPE: RNA
<213> ORGANISM: Artificial Sequence
```

```
-continued

<220> FEATURE:
<223> OTHER INFORMATION: Description of Artficial Sequence note: =
      Synthetic Construct

<400> SEQUENCE: 548
aaguugguca cucgguugc                                                19

<210> SEQ ID NO 549
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 549
ggaugagcuc uuccgucuu                                                19

<210> SEQ ID NO 550
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 550
aagacggaag agcucaucc                                                19

<210> SEQ ID NO 551
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 551
ccaaguccaa accaaucau                                                19

<210> SEQ ID NO 552
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 552
augauugguu uggacuugg                                                19

<210> SEQ ID NO 553
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 553
ggaaggugca gauaauuaa                                                19

<210> SEQ ID NO 554
<211> LENGTH: 19
<212> TYPE: RNA
<213> ORGANISM: Artificial Sequence
<220> FEATURE:
<223> OTHER INFORMATION: Description of Artficial Sequence note: =
```

-continued

Synthetic Construct

<400> SEQUENCE: 554
uuaauuaucu gcaccuucc                                               19

<210> SEQ ID NO 555
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 555
gcagugugca aauagucua                                               19

<210> SEQ ID NO 556
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 556
uagacuauuu gcacacugc                                               19

<210> SEQ ID NO 557
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 557
ccuccaagug uggcucauu                                               19

<210> SEQ ID NO 558
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 558
aaugagccac acuuggagg                                               19

<210> SEQ ID NO 559
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 559
gcgggaaggu gcagauaau                                               19

<210> SEQ ID NO 560
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 560
auuaucugca ccuucccgc                                                  19

<210> SEQ ID NO 561
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 561
gcagugugca aauagucua                                                  19

<210> SEQ ID NO 562
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 562
uagacuauuu gcacacugc                                                  19

<210> SEQ ID NO 563
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 563
ccuccaagug uggcucauu                                                  19

<210> SEQ ID NO 564
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 564
aaugagccac acuuggagg                                                  19

<210> SEQ ID NO 565
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 565
gccaggaguu cgaagugau                                                  19

<210> SEQ ID NO 566
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 566
```
aucacuucga acuccuggc                                                      19

<210> SEQ ID NO 567
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 567
gcucaagcac cagcuucua                                                      19

<210> SEQ ID NO 568
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 568
uagaagcugg ugcuugagc                                                      19

<210> SEQ ID NO 569
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 569
gccaagacau ccacacguu                                                      19

<210> SEQ ID NO 570
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 570
aacgugugga ugucuuggc                                                      19

<210> SEQ ID NO 571
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 571
gcagugugca aauagucua                                                      19

<210> SEQ ID NO 572
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 572
uagacuauuu gcacacugc                                                      19

```
<210> SEQ ID NO 573
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 573
ccucuuugug gccuggaau                                                    19

<210> SEQ ID NO 574
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 574
auuccaggcc acaaagagg                                                    19

<210> SEQ ID NO 575
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 575
gcaaguucca gggcuacua                                                    19

<210> SEQ ID NO 576
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 576
uaguagcccu ggaacuugc                                                    19

<210> SEQ ID NO 577
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 577
gggacagcuu caaggcuuu                                                    19

<210> SEQ ID NO 578
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 578
aaagccuuga agcuguccc                                                    19

<210> SEQ ID NO 579
```

<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 579
ccuccaggcc uucaacauu                                              19

<210> SEQ ID NO 580
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 580
aauguugaag gccuggagg                                              19

<210> SEQ ID NO 581
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 581
ccaaagcccu gugguacaa                                              19

<210> SEQ ID NO 582
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 582
uuguaccaca gggcuuugg                                              19

<210> SEQ ID NO 583
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 583
gcgcacugcc auugaacuu                                              19

<210> SEQ ID NO 584
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 584
aaguucaaug gcagugcgc                                              19

<210> SEQ ID NO 585
<211> LENGTH: 19
<212> TYPE: RNA

<213> ORGANISM: Artificial Sequence
<220> FEATURE:
<223> OTHER INFORMATION: Description of Artficial Sequence note: =
      Synthetic Construct

<400> SEQUENCE: 585
ccaucgacca uaucaguau                                                19

<210> SEQ ID NO 586
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 586
auacugauau ggucgaugg                                                19

<210> SEQ ID NO 587
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 587
ccauaucagu auucgccaa                                                19

<210> SEQ ID NO 588
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 588
uuggcgaaua cugauaugg                                                19

<210> SEQ ID NO 589
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 589
ccauucucug ucggaguuu                                                19

<210> SEQ ID NO 590
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 590
aaacuccgac agagaaugg                                                19

<210> SEQ ID NO 591
<211> LENGTH: 19
<212> TYPE: RNA
<213> ORGANISM: Artificial Sequence
<220> FEATURE:

```
<223> OTHER INFORMATION: Description of Artficial Sequence note: =
      Synthetic Construct

<400> SEQUENCE: 591
gcauagaucu ugagaacau                                              19

<210> SEQ ID NO 592
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 592
auguucucaa gaucuaugc                                              19

<210> SEQ ID NO 593
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 593
gcugccaucc uuagacuuu                                              19

<210> SEQ ID NO 594
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 594
aaagucuaag gauggcagc                                              19

<210> SEQ ID NO 595
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 595
gcaguaagga agguggaaa                                              19

<210> SEQ ID NO 596
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 596
uuuccaccuu ccuuacugc                                              19

<210> SEQ ID NO 597
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

```
<400> SEQUENCE: 597
ccauuugaga acagugcau                                              19

<210> SEQ ID NO 598
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 598
augcacuguu cucaaaugg                                              19

<210> SEQ ID NO 599
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 599
gccaacuugu auguugcaa                                              19

<210> SEQ ID NO 600
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 600
uugcaacaua caaguuggc                                              19

<210> SEQ ID NO 601
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 601
ccaacuugua uguugcaaa                                              19

<210> SEQ ID NO 602
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 602
uuugcaacau acaaguugg                                              19

<210> SEQ ID NO 603
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 603
```
ccaagaccug ucaugguuu                               19

<210> SEQ ID NO 604
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 604
aaaccaugac aggucuugg                               19

<210> SEQ ID NO 605
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 605
gcaggagagu gugccuauu                               19

<210> SEQ ID NO 606
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 606
aauaggcaca cucuccugc                               19

<210> SEQ ID NO 607
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 607
ccaucugaau ugccugcaa                               19

<210> SEQ ID NO 608
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 608
uugcaggcaa uucagaugg                               19

<210> SEQ ID NO 609
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 609
gcugcuuuaa gcgcaauaa                               19

```
<210> SEQ ID NO 610
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 610
uuauugcgcu uaaagcagc                                                19

<210> SEQ ID NO 611
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 611
gccaucagua ugucuucaa                                                19

<210> SEQ ID NO 612
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 612
uugaagacau acugauggc                                                19

<210> SEQ ID NO 613
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 613
gcccaucuga ucacuggau                                                19

<210> SEQ ID NO 614
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 614
auccagugau cagaugggc                                                19

<210> SEQ ID NO 615
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 615
gccaaccaug gaaauggau                                                19
```

```
<210> SEQ ID NO 616
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 616
auccauuccc auggutuggc                                                      19

<210> SEQ ID NO 617
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 617
gcaggagagu gugccuauu                                                       19

<210> SEQ ID NO 618
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 618
aauaggcaca cucuccugc                                                       19

<210> SEQ ID NO 619
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 619
ggaaguggau uuguuccaa                                                       19

<210> SEQ ID NO 620
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 620
uuggaacaaa uccacuucc                                                       19

<210> SEQ ID NO 621
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 621
ccuacuaugu uggaaccuu                                                       19

<210> SEQ ID NO 622
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 622
aagguuccaa cauaguagg                                                  19

<210> SEQ ID NO 623
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 623
gguacaccug uaagguuaa                                                  19

<210> SEQ ID NO 624
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 624
uuaaccuuac agguguacc                                                  19

<210> SEQ ID NO 625
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 625
ggagagcuga cagaaggaa                                                  19

<210> SEQ ID NO 626
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 626
uuccuucugu cagcucucc                                                  19

<210> SEQ ID NO 627
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 627
gcgaguaacu guacaguau                                                  19

<210> SEQ ID NO 628
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 628
auacuguaca guuacucgc                                                    19

<210> SEQ ID NO 629
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 629
ccaugcuaau cugaccaaa                                                    19

<210> SEQ ID NO 630
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 630
uuuggucaga uuagcaugg                                                    19

<210> SEQ ID NO 631
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 631
gcuggaucug ucacugcuu                                                    19

<210> SEQ ID NO 632
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 632
aagcagugac agauccagc                                                    19

<210> SEQ ID NO 633
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 633
ggaucauucc gugucacaa                                                    19

<210> SEQ ID NO 634
<211> LENGTH: 19
<212> TYPE: RNA
<213> ORGANISM: Artificial Sequence
<220> FEATURE:
<223> OTHER INFORMATION: Description of Artficial Sequence note: =
```

Synthetic Construct

<400> SEQUENCE: 634
uugugacacg gaaugaucc                                                    19

<210> SEQ ID NO 635
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 635
ccagaagaug ucacccuuu                                                    19

<210> SEQ ID NO 636
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 636
aaagggugac aucuucugg                                                    19

<210> SEQ ID NO 637
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 637
ccuuccaugu gcuugcuaa                                                    19

<210> SEQ ID NO 638
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 638
uuagcaagca cauggaagg                                                    19

<210> SEQ ID NO 639
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 639
gguuagaaga ggugucuaa                                                    19

<210> SEQ ID NO 640
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 640
uuagacaccu cuucuaacc                                              19

<210> SEQ ID NO 641
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 641
ccaccagucc cuucuuuaa                                              19

<210> SEQ ID NO 642
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 642
uuaaagaagg gacuggugg                                              19

<210> SEQ ID NO 643
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 643
ccuacaguuc uuccaguaa                                              19

<210> SEQ ID NO 644
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 644
uuacuggaag aacuguagg                                              19

<210> SEQ ID NO 645
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 645
gcagagaguc auuucucua                                              19

<210> SEQ ID NO 646
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 646
```
uagagaaaug acucucugc                            19

<210> SEQ ID NO 647
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 647
ccaggugucu gaauacauu                            19

<210> SEQ ID NO 648
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 648
aauguauuca gacaccugg                            19

<210> SEQ ID NO 649
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 649
ccaaucaguu ucucaucaa                            19

<210> SEQ ID NO 650
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 650
uugaugagaa acugauugg                            19

<210> SEQ ID NO 651
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 651
gcguucuucu ccuagacaa                            19

<210> SEQ ID NO 652
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 652
uugucuagga gaagaacgc                            19

<210> SEQ ID NO 653
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 653
gcucaggaca uucucgaua                                                  19

<210> SEQ ID NO 654
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 654
uaucgagaau guccugagc                                                  19

<210> SEQ ID NO 655
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 655
gccuauuauu acaguggaa                                                  19

<210> SEQ ID NO 656
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 656
uuccacugua auaauaggc                                                  19

<210> SEQ ID NO 657
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 657
gcugaucuau gcaucuuau                                                  19

<210> SEQ ID NO 658
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 658
auaagaugca uagaucagc                                                  19

<210> SEQ ID NO 659

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 659
gcauugaagc auuugcaaa                                                  19

<210> SEQ ID NO 660
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 660
uuugcaaaug cuucaaugc                                                  19

<210> SEQ ID NO 661
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 661
gcugaugcag aggcucuau                                                  19

<210> SEQ ID NO 662
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 662
auagagccuc ugcaucagc                                                  19

<210> SEQ ID NO 663
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 663
gcaggaaaug aaguugaau                                                  19

<210> SEQ ID NO 664
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 664
auucaacuuc auuuccugc                                                  19

<210> SEQ ID NO 665
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 665
ggaugugagu ugguuugau                                              19

<210> SEQ ID NO 666
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 666
aucaaaccaa cucacaucc                                              19

<210> SEQ ID NO 667
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 667
gcacuaaagu aggagacaa                                              19

<210> SEQ ID NO 668
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 668
uugucuccua cuuuagugc                                              19

<210> SEQ ID NO 669
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 669
ccaacaguuu gcgccauaa                                              19

<210> SEQ ID NO 670
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 670
uuauggcgca aacuguugg                                              19

<210> SEQ ID NO 671
<211> LENGTH: 19
<212> TYPE: RNA
<213> ORGANISM: Artificial Sequence
<220> FEATURE:
```

<223> OTHER INFORMATION: Description of Artficial Sequence note: =
      Synthetic Construct

<400> SEQUENCE: 671
gcuagugggu cuggguuua                                                    19

<210> SEQ ID NO 672
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 672
uaaacccaga cccacuagc                                                    19

<210> SEQ ID NO 673
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 673
gccaucauca acuauggaa                                                    19

<210> SEQ ID NO 674
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 674
uuccauaguu gaugauggc                                                    19

<210> SEQ ID NO 675
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 675
ccuggacggu gaagugauu                                                    19

<210> SEQ ID NO 676
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 676
aaucacuuca ccguccagg                                                    19

<210> SEQ ID NO 677
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 677
cccgaagaaa uugacccau                                                    19

<210> SEQ ID NO 678
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 678
augggucaau uucuucggg                                                    19

<210> SEQ ID NO 679
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 679
gcucgagcug gaaucauua                                                    19

<210> SEQ ID NO 680
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 680
uaaugauucc agcucgagc                                                    19

<210> SEQ ID NO 681
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 681
gcugcuugga aauucauaa                                                    19

<210> SEQ ID NO 682
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 682
uuaugaauuu ccaagcagc                                                    19

<210> SEQ ID NO 683
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 683

```
gcuaucaguu gagggauuu                                              19

<210> SEQ ID NO 684
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 684
gccaaacugc aggaugaaa                                              19

<210> SEQ ID NO 685
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 685
uuucauccug caguuuggc                                              19

<210> SEQ ID NO 686
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 686
ucugugcuuu ggaugacaa                                              19

<210> SEQ ID NO 687
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 687
uugucaucca aagcacaga                                              19

<210> SEQ ID NO 688
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 688
ccgaugcaag gauagucau                                              19

<210> SEQ ID NO 689
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 689
augacuaucc uugcaucgg                                              19
```

<210> SEQ ID NO 690
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 690
aaaucccuca acugauagc                                                  19

<210> SEQ ID NO 691
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 691
ccaccgauug uacaguaaa                                                  19

<210> SEQ ID NO 692
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 692
uuuacuguac aaucggugg                                                  19

<210> SEQ ID NO 693
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 693
gguuaugaau cuggcugau                                                  19

<210> SEQ ID NO 694
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 694
aucagccaga uucauaacc                                                  19

<210> SEQ ID NO 695
<211> LENGTH: 19
<212> TYPE: RNA
<213> ORGANISM: Artificial Sequence
<220> FEATURE:
<223> OTHER INFORMATION: Description of Artficial Sequence note: = Synthetic Construct

<400> SEQUENCE: 695
ggacaaccuc cagaaaguu                                                  19

```
<210> SEQ ID NO 696
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 696
aacuuucugg agguugucc                                                  19

<210> SEQ ID NO 697
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 697
ggaauuugcc auaaaggaa                                                  19

<210> SEQ ID NO 698
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 698
uuccuuuaug gcaaauucc                                                  19

<210> SEQ ID NO 699
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 699
gcagggaugu ucuaccauu                                                  19

<210> SEQ ID NO 700
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 700
aaugguagaa caucccugc                                                  19

<210> SEQ ID NO 701
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 701
gcaugccaga aacagucaa                                                  19

<210> SEQ ID NO 702
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 702
uugacuguuu cuggcaugc                                                  19

<210> SEQ ID NO 703
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 703
gcaugccucu guuuggcua                                                  19

<210> SEQ ID NO 704
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 704
uagccaaaca gaggcaugc                                                  19

<210> SEQ ID NO 705
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 705
ggaggcuauu acuugacaa                                                  19

<210> SEQ ID NO 706
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 706
uugucaagua auagccucc                                                  19

<210> SEQ ID NO 707
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 707
ccgucuauau ggagucuuu                                                  19

<210> SEQ ID NO 708
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 708
aaagacucca uauagacgg                                                      19

<210> SEQ ID NO 709
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 709
gcuugcgauu caaaggauu                                                      19

<210> SEQ ID NO 710
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 710
aauccuuuga aucgcaagc                                                      19

<210> SEQ ID NO 711
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 711
gcaauggaug gaauuucaa                                                      19

<210> SEQ ID NO 712
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 712
uugaaauucc auccauugc                                                      19

<210> SEQ ID NO 713
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 713
gcgauucauu cccaucaau                                                      19

<210> SEQ ID NO 714
<211> LENGTH: 19
<212> TYPE: RNA
<213> ORGANISM: Artificial Sequence
<220> FEATURE:
<223> OTHER INFORMATION: Description of Artficial Sequence note: =
```

-continued

Synthetic Construct

<400> SEQUENCE: 714
auugauggga augaaucgc                                                19

<210> SEQ ID NO 715
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 715
ccacacaugu caauuccaa                                                19

<210> SEQ ID NO 716
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 716
uuggaauuga caugugugg                                                19

<210> SEQ ID NO 717
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 717
gcaugagguc gauaaucuu                                                19

<210> SEQ ID NO 718
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 718
aagauuaucg accucaugc                                                19

<210> SEQ ID NO 719
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 719
ccagccagcg agacaauau                                                19

<210> SEQ ID NO 720
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 720
auauugucuc gcuggcugg                                         19

<210> SEQ ID NO 721
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 721
ggaucugguu caggaggau                                         19

<210> SEQ ID NO 722
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 722
auccuccuga accagaucc                                         19

<210> SEQ ID NO 723
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 723
ccaacuucgc ugcuuucau                                         19

<210> SEQ ID NO 724
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 724
augaaagcag cgaaguugg                                         19

<210> SEQ ID NO 725
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 725 gcuuccugu acuggcaaa                                          19

<210> SEQ ID NO 726
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 726
```
uuugccagua caggaaagc                                        19

<210> SEQ ID NO 727
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 727
gcagcuccaa ccacuucua                                        19

<210> SEQ ID NO 728
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 728
uagaaguggu uggagcugc                                        19

<210> SEQ ID NO 729
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 729
gcaaguuagu agaggccaa                                        19

<210> SEQ ID NO 730
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 730
uuggccucua cuaacuugc                                        19

<210> SEQ ID NO 731
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 731
ccugguacac auggcuauu                                        19

<210> SEQ ID NO 732
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 732
aauagccaug uguaccagg                                        19

```
<210> SEQ ID NO 733
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 733
gccaaucaac uguccugau                                                    19

<210> SEQ ID NO 734
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 734
aucaggacag uugauuggc                                                    19

<210> SEQ ID NO 735
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 735
gcugcaggau gcugaaauu                                                    19

<210> SEQ ID NO 736
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 736
aauuucagca uccugcagc                                                    19

<210> SEQ ID NO 737
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 737
gcaaggcuga uggaagacu                                                    19

<210> SEQ ID NO 738
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 738
agucuuccau cagccuugc                                                    19

<210> SEQ ID NO 739
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 739
gcugauggaa gacuuggac                                                   19

<210> SEQ ID NO 740
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 740
guccaagucu uccaucagc                                                   19

<210> SEQ ID NO 741
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 741
cgauggagac ccucaucaa                                                   19

<210> SEQ ID NO 742
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 742
uugaugaggg ucuccaucg                                                   19

<210> SEQ ID NO 743
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 743
gauggagacc cucaucaac                                                   19

<210> SEQ ID NO 744
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 744
guugaugagg gucuccauc                                                   19

<210> SEQ ID NO 745
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 745
ggaagaaccc ucauuucau                                                 19

<210> SEQ ID NO 746
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 746
augaaaugag gguucuucc                                                 19

<210> SEQ ID NO 747
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 747
gggaacagca uacccucaa                                                 19

<210> SEQ ID NO 748
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 748
uugaggguau gcuguuccc                                                 19

<210> SEQ ID NO 749
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 749
ccuuuacaca gacucacuu                                                 19

<210> SEQ ID NO 750
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 750
aagugagucu guguaaagg                                                 19

<210> SEQ ID NO 751
<211> LENGTH: 19
<212> TYPE: RNA
<213> ORGANISM: Artificial Sequence
<220> FEATURE:
```

```
<223> OTHER INFORMATION: Description of Artficial Sequence note: =
      Synthetic Construct

<400> SEQUENCE: 751
ccuaccaggu gaaaccuuu                                                    19

<210> SEQ ID NO 752
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 752
aaagguuuca ccugguagg                                                    19

<210> SEQ ID NO 753
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 753
ccaagcaaag gauccguau                                                    19

<210> SEQ ID NO 754
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 754
auacggaucc uuugcuugg                                                    19

<210> SEQ ID NO 755
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 755
ccugguuauu ggcucucuu                                                    19

<210> SEQ ID NO 756
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 756
aagagagcca auaaccagg                                                    19

<210> SEQ ID NO 757
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct
```

-continued

```
<400> SEQUENCE: 757
gguuauuggc ucucuucau                                                  19

<210> SEQ ID NO 758
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 758
augaagagag ccaauaacc                                                  19

<210> SEQ ID NO 759
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 759
ccgaccagga cagguuuau                                                  19

<210> SEQ ID NO 760
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 760
auaaaccugu ccggucgg                                                   19

<210> SEQ ID NO 761
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 761
gcaguuggac uuaacguau                                                  19

<210> SEQ ID NO 762
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 762
auacguuaag uccaacugc                                                  19

<210> SEQ ID NO 763
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 763
```
gcugaccaaa gucuucaac                                               19

<210> SEQ ID NO 764
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 764
guugaagacu uuggucagc                                               19

<210> SEQ ID NO 765
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 765
cccguaagcu ggucaucau                                               19

<210> SEQ ID NO 766
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 766
augaugacca gcuuacggg                                               19

<210> SEQ ID NO 767
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 767
gcggagaggu caguaacua                                               19

<210> SEQ ID NO 768
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 768
uaguuacuga ccucuccgc                                               19

<210> SEQ ID NO 769
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 769
gcucucaacg auaugacuu                                               19

```
<210> SEQ ID NO 770
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 770
aagucauauc guugagagc                                                    19

<210> SEQ ID NO 771
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 771
ccaggaaaua aaguuggaa                                                    19

<210> SEQ ID NO 772
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 772
uuccaacuuu auuuccugg                                                    19

<210> SEQ ID NO 773
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 773
ggugggaaua cuucagaua                                                    19

<210> SEQ ID NO 774
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 774
uaucugaagu auucccacc                                                    19

<210> SEQ ID NO 775
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 775
gggaauacuu cagauagag                                                    19
```

```
<210> SEQ ID NO 776
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 776
cucuaucuga aguauuccc                                              19

<210> SEQ ID NO 777
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 777
gcauucacag caaggccua                                              19

<210> SEQ ID NO 778
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 778
uaggccuugc ugugaaugc                                              19

<210> SEQ ID NO 779
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 779
gcaacagaga ugauuccaa                                              19

<210> SEQ ID NO 780
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 780
uuggaaucau cucuguugc                                              19

<210> SEQ ID NO 781
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 781
gcaacugguc agccugaaa                                              19

<210> SEQ ID NO 782
<211> LENGTH: 19
```

```
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 782
uuucaggcug accaguugc                                                  19

<210> SEQ ID NO 783
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 783
ccauugaugc ucggauauu                                                  19

<210> SEQ ID NO 784
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 784
aauauccgag caucaaugg                                                  19

<210> SEQ ID NO 785
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 785
ccacuucucu agaagacau                                                  19

<210> SEQ ID NO 786
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 786
augucuucua gagaagugg                                                  19

<210> SEQ ID NO 787
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 787
gcagcuucca gcuccuuua                                                  19

<210> SEQ ID NO 788
<211> LENGTH: 19
<212> TYPE: RNA
<213> ORGANISM: Artificial Sequence
```

```
<220> FEATURE:
<223> OTHER INFORMATION: Description of Artficial Sequence note: =
      Synthetic Construct

<400> SEQUENCE: 788
uaaaggagcu ggaagcugc                                               19

<210> SEQ ID NO 789
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 789
ggaaccaugu aaagaaguu                                               19

<210> SEQ ID NO 790
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 790
aacuucuuua caugguucc                                               19

<210> SEQ ID NO 791
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 791
gcugaaguug cugcagaau                                               19

<210> SEQ ID NO 792
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 792
auucugcagc aacuucagc                                               19

<210> SEQ ID NO 793
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 793
ccaagcucca uugucccuu                                               19

<210> SEQ ID NO 794
<211> LENGTH: 19
<212> TYPE: RNA
<213> ORGANISM: Artificial Sequence
<220> FEATURE:
<223> OTHER INFORMATION: Description of Artficial Sequence note: =
```

-continued

Synthetic Construct

<400> SEQUENCE: 794
aagggacaau ggagcuugg					19

<210> SEQ ID NO 795
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 795
gcauacauuc ccugaaua					19

<210> SEQ ID NO 796
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 796
uauucaaggg aauguaugc					19

<210> SEQ ID NO 797
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 797
gcuucucugc aaaugaaau					19

<210> SEQ ID NO 798
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 798
auuucauuug cagagaagc					19

<210> SEQ ID NO 799
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 799
ggagccaaug gcuguugau					19

<210> SEQ ID NO 800
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

```
<400> SEQUENCE: 800
aucaacagcc auuggcucc                                              19

<210> SEQ ID NO 801
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 801
ggaaccaugu aaagaaguu                                              19

<210> SEQ ID NO 802
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 802
aacuucuuua caugguucc                                              19

<210> SEQ ID NO 803
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 803
gcugaaguug cugcagaau                                              19

<210> SEQ ID NO 804
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 804
auucugcagc aacuucagc                                              19

<210> SEQ ID NO 805
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 805
ccaagcucca uugucccuu                                              19

<210> SEQ ID NO 806
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 806
```
aagggacaau ggagcuugg            19

<210> SEQ ID NO 807
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 807
gcauacauuc ccugaaua             19

<210> SEQ ID NO 808
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 808
uauucaaggg aauguaugc            19

<210> SEQ ID NO 809
<211> LENGTH: 34
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 809
gcuucucugc aaauggcuga aguugcugca gaau            34

<210> SEQ ID NO 810
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 810
auucugcagc aacuucagc            19

<210> SEQ ID NO 811
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 811
ccaagcucca uugucccuu            19

<210> SEQ ID NO 812
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 812
aagggacaau ggagcuugg            19

```
<210> SEQ ID NO 813
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 813
gcauacauuc ccugaaua                                                        19

<210> SEQ ID NO 814
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 814
uauucaaggg aauguaugc                                                       19

<210> SEQ ID NO 815
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 815
gcuucucugc aaaugaaau                                                       19

<210> SEQ ID NO 816
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 816
auuucauuug cagagaagc                                                       19

<210> SEQ ID NO 817
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 817
ccaccuggaa ugaugccaa                                                       19

<210> SEQ ID NO 818
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 818
uuggcaucau uccaggugg                                                       19

<210> SEQ ID NO 819
```

```
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 819
gcgccaggua uucuuaaua                                                   19

<210> SEQ ID NO 820
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 820
uauuaagaau accuggcgc                                                   19

<210> SEQ ID NO 821
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 821
gcuucaucca auucagaaa                                                   19

<210> SEQ ID NO 822
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 822
uuucugaauu ggaugaagc                                                   19

<210> SEQ ID NO 823
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 823
ccagcggcuu caauaacaa                                                   19

<210> SEQ ID NO 824
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 824
uuguuauuga agccgcugg                                                   19

<210> SEQ ID NO 825
<211> LENGTH: 19
<212> TYPE: RNA
```

```
<213> ORGANISM: Artificial Sequence
<220> FEATURE:
<223> OTHER INFORMATION: Description of Artficial Sequence note: =
      Synthetic Construct

<400> SEQUENCE: 825
gcuacacuua caacaacua                                                    19

<210> SEQ ID NO 826
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 826
uaguuguugu aaguguagc                                                    19

<210> SEQ ID NO 827
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 827
ucaguaugag cacacagcuu acaau                                             25

<210> SEQ ID NO 828
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 828
auuguaagcu gugugcucau acuga                                             25

<210> SEQ ID NO 829
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 829
uaugagcaca cagcuuacaa uacau                                             25

<210> SEQ ID NO 830
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 830
auguauugua agcugugugc ucaua                                             25

<210> SEQ ID NO 831
<211> LENGTH: 25
<212> TYPE: RNA
<213> ORGANISM: Artificial Sequence
<220> FEATURE:
```

```
<223> OTHER INFORMATION: Description of Artficial Sequence note: =
      Synthetic Construct

<400> SEQUENCE: 831
gcacacagcu uacaauacau caaag                                                25

<210> SEQ ID NO 832
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 832
cuuugaugua uuguaagcug ugugc                                                25

<210> SEQ ID NO 833
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 833
aggguccacc uuugugagcc guaaa                                                25

<210> SEQ ID NO 834
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 834
uuuacggcuc acaaaggugg acccu                                                25

<210> SEQ ID NO 835
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 835
uauuuaggug gcguucacac cuaau                                                25

<210> SEQ ID NO 836
<211> LENGTH: 25
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 836
auuaggugug aacgccaccu aaaua                                                25

<210> SEQ ID NO 837
<211> LENGTH: 47
<212> TYPE: DNA
<213> ORGANISM: Artificial Sequence
<220> FEATURE:
<223> OTHER INFORMATION: Description of Artficial Sequence note: =
      Synthetic Construct
```

```
<400> SEQUENCE: 837
caccgccaga agtaccaaag atttcgaaaa atctttggta cttctgg        47

<210> SEQ ID NO 838
<211> LENGTH: 47
<212> TYPE: DNA
<213> ORGANISM: Artificial Sequence
<220> FEATURE:
<223> OTHER INFORMATION: Description of Artficial Sequence note: =
      Synthetic Construct

<400> SEQUENCE: 838
aaaaccagaa gtaccaaaga tttttcgaaa tctttggtac ttctggc        47

<210> SEQ ID NO 839
<211> LENGTH: 47
<212> TYPE: DNA
<213> ORGANISM: Artificial Sequence
<220> FEATURE:
<223> OTHER INFORMATION: Description of Artficial Sequence note: =
      Synthetic Construct

<400> SEQUENCE: 839
caccgccaga agtaccaaag atttcgaaaa atctttggta cttctgg        47

<210> SEQ ID NO 840
<211> LENGTH: 47
<212> TYPE: DNA
<213> ORGANISM: Artificial Sequence
<220> FEATURE:
<223> OTHER INFORMATION: Description of Artficial Sequence note: =
      Synthetic Construct

<400> SEQUENCE: 840
cggtcttcat ggtttctaaa gcttttttaga aaccatgaag accaaaa       47

<210> SEQ ID NO 841
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 841
ccaagacaac caccacaaa                                       19

<210> SEQ ID NO 842
<211> LENGTH: 19
<212> TYPE: RNA
<213> ORGANISM: Artificial Sequence
<220> FEATURE:
<223> OTHER INFORMATION: Description of Artficial Sequence note: =
      Synthetic Construct

<400> SEQUENCE: 842
uuuguggugg uugucuugg                                       19
```